US007723496B2

(12) United States Patent
Ishii et al.

(10) Patent No.: US 7,723,496 B2
(45) Date of Patent: May 25, 2010

(54) PREVENTIVES/REMEDIES FOR CANCER

(75) Inventors: Takafumi Ishii, Hyogo (JP); Koji Yamamoto, Ibaraki (JP); Eiji Sunahara, Ibaraki (JP); Shuji Sato, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 549 days.

(21) Appl. No.: 10/525,105

(22) PCT Filed: Aug. 20, 2003

(86) PCT No.: PCT/JP03/10532

§ 371 (c)(1),
(2), (4) Date: Oct. 25, 2005

(87) PCT Pub. No.: WO2004/018678

PCT Pub. Date: Mar. 4, 2004

(65) Prior Publication Data

US 2006/0134117 A1 Jun. 22, 2006

(30) Foreign Application Priority Data

Aug. 21, 2002 (JP) ............................ 2002-240830
Dec. 13, 2002 (JP) ............................ 2002-363108

(51) Int. Cl.
*C07H 21/04* (2006.01)
*C12N 15/00* (2006.01)
*C12P 15/00* (2006.01)

(52) U.S. Cl. .................... 536/23.1; 435/69.1; 435/71.1

(58) Field of Classification Search ...................... None
See application file for complete search history.

(56) References Cited

U.S. PATENT DOCUMENTS 5,928,884 A * 7/1999 Croce et al. ................ 435/7.23
6,964,868 B1 * 11/2005 Williams et al. ............ 435/325

FOREIGN PATENT DOCUMENTS

| | | | |
|---|---|---|---|
| EP | 1 270 745 | A2 | 1/2003 |
| WO | WO 98/37199 | | 8/1998 |
| WO | WO/99/38972 | * | 5/1999 |
| WO | WO 00/35937 | | 6/2000 |
| WO | WO 0129921 | | 4/2001 |
| WO | WO 01/70979 | A1 | 9/2001 |
| WO | WO 01/74836 | A1 | 10/2001 |
| WO | WO 03/000113 | A1 | 1/2003 |

OTHER PUBLICATIONS

Genebank access No. T50605.*
Agrawal et al. Molecular Medicine Today, 2000, vol. 6, p. 72-81.*
Opalinska et al. Nature Reviews Drug Discovery, 2002, vol. 1, p. 503-514.*
Jen et al. Stem Cells 2000, vol. 18, p. 307-319.*
GeneBank (EST) Accession No. BQ68095 submitted Apr. 2002 and search result.*
Search result.*
Database—Abstract—XP002353459 Accession No. AL359557.
Database—Abstract—XP002353460 Accession No. AB046803.
Database—Abstract—XP002353461 Accession No. Q86VZ8 (2003).
Database—Abstract—XP002353462 Accession No. AAH52168 (2001).
Database—Abstract—XP002353463 Accession No. AX118987.
Oh-hashi, et al., "Cloning and Characterization of a Novel GRP78-binding Protein in the Rat Brain," The Journal of Biological Chemistry 278:10531-10537 (2003).
Valesky et al., "Noninvasive Dynamic Fluorescence Imaging of Human Melanomas Reveals that Targeted Inhibition of bFGF or FGFR-1 in Melanoma Cells Blocks Tumor Growth by Apoptosis", Molecular Medicine 8(2): 103-112 (2002).
Koller, et al., "Use of a Chemically Modified Antisense Oligonucleotide Library to Identify and Validate Eg5 (Kinesin-Like 1) as a Target for Antineoplastic Drug Development", Cancer Res (2006) 66(4):2059-2066.
Kamiyama et al., "VEGF receptor antisense therapy inhibits angiogenesis and peritoneal dissemination of human gastric cancer in nude mice", Cancer Gene Therapy (2002) 9, 197-201.
Supplemental Partial European Search Report dated Feb. 24, 2006 in EP 03792750.
Database—Abstract—XP002364033 Accession No. AEA00601.
Database—Abstract—XP002364034 Accession No. AEA00679.
Database—Abstract—XP002364035 Accession No. Q86W97.
Database—Abstract—XP002364036 Accession No. Q9NWY0.
Database—Abstract—XP002364037 Accession No. Q9H8K3.
Database—Abstract—XP002364038 Accession No. ADL61921.
Database—Abstract—XP002364039 Accession No. AAB95440.
Database—Abstract—XP002364040 Accession No. Q9HCI9.
Database—Abstract—XP002364041 Accession No. AK000546.
Database—Abstract—XP002364042 Accession No. AAA78411.

(Continued)

*Primary Examiner*—Larry R. Helms
*Assistant Examiner*—Lei Yao
(74) *Attorney, Agent, or Firm*—Edwards Angell Palmer & Dodge LLP; David G. Conlin; Mark D. Russett

(57) ABSTRACT

A compound inhibiting the activity of a protein comprising the same or substantially the same amino acid sequence as the amino acid sequence represented by SEQ ID NO: 1, SEQ ID NO: 4, SEQ ID NO: 7, SEQ ID NO: 10, SEQ ID NO: 15, SEQ ID NO: 17, SEQ ID NO: 20, SEQ ID NO: 22, SEQ ID NO: 25 or SEQ ID NO: 27, or a salt thereof; a compound inhibiting the expression of a gene of the protein; an antisense polynucleotide containing the entire or part of a base sequence complementary or substantially complementary to a base sequence of a polynucleotide encoding the protein or its partial peptide; an antibody to the protein or its partial peptide, etc. are useful as prophylactic/therapeutic agents for cancer, etc., apoptosis promoters for cancer cells, and the like.

9 Claims, 6 Drawing Sheets

OTHER PUBLICATIONS

Shuukan Igaku no Ayumi (weekly magazine "Advances in Medicine"), 2001, vol. 199, No. 9, pp. 613-617.
Bunshi Saibou Chiryo (Molecular Cell Therapy), 2000, vol. 1, No. 4, pp. 395-400.
Housha-sen Seibutsu Kenkyu (Radiation Biology Research Communications), 2001, vol. 36, No. 4, pp. 317-330.
Japanese Office Action dated Aug. 4, 2009 in corresponding Japanese patent application No. 2003-296081 (with English translation).

* cited by examiner

PREVENTIVES/REMEDIES FOR CANCER

CROSS-REFERENCES TO RELATED APPLICATIONS

This application is the 35 U.S.C. 371 national stage of PCT application PCT/JP2003/010532, filed Aug. 20, 2003, which claims benefit of Japanese applications 2002-240830, filed Aug. 21, 2002, and 2002-363108, filed Dec. 13, 2002. The entire disclosures of all these applications is incorporated herein by reference.

TECHNICAL FIELD

The present invention relates to novel proteins and prophylactic/therapeutic agents and diagnostic agents for a cancer, and so on.

BACKGROUND ART

Recent advance in microarray/oligonucleotide array technology has enabled exhaustive analysis of gene expression. It is predicted that a cancer could also be assessed for its pathological conditions by microarray profiling data for the gene. Actually in leukemia, it is reportedly possible to classify leukemia by gene expression profiles. By clarifying the gene expression profile of each cancerous tissue and accumulating its classification, it is considered possible to predict response to a particular cancer therapy or discover a novel drug development target protein for a particular cancer. Specifically, where enhanced expression of a certain protein is observed in a certain cancer, it becomes possible to induce an anti-tumor activity in patients newly diagnosed to be antigen positive, by means of (i) reducing its expression level, (ii) suppressing its function, (iii) eliciting immune response of host to the protein, etc. At the same time, patients diagnosed to be antigen negative can immediately switch over to another cancer therapy, assuming to eliminate any concern of imposing a superfluous burden on patients. As such, it is expected that the expression profile analysis would greatly contribute to molecular diagnosis of a cancer and development of molecular target-based drugs.

Meanwhile, FLJ20539 gene (GenBank Accession No. AK000546) is a gene cloned from a library derived from the human gastric cancer cell line KATOIII and encodes a protein consisting of 774 amino acids (GenBank Accession No. BAA91245). The FLJ13515 gene (GenBank Accession No. AK023577) is a gene cloned from a human placenta-derived library and encodes a protein consisting of 639 amino acids (GenBank Accession No. BAB14613). This protein has an amino acid sequence corresponding to the 136-774 amino acid sequence of a protein encoded by the FLJ20539 gene, in which the amino acid at position 440 is replaced from glutamic acid to lysine. Furthermore, a mouse gene (GenBank Accession No. BC006896) showing homology to these 2 human genes is cloned from a mouse breast cancer tissue-derived library and encoded by a protein consisting of 1018 amino acids (GenBank Accession No. AAH06896). This mouse gene has homology of about 83% in the base sequence and about 86% in the amino acid sequence, to the FLJ13515 gene.

A safe drug capable of targeting the molecule specifically expressed in cancer cells to induce growth inhibition of the cancer cells has been earnestly desired.

DISCLOSURE OF THE INVENTION

The present inventors have made extensive investigations to solve the foregoing problem and as a result, have found genes, expression of which is markedly enhanced in cancer tissues. Based on this finding, the inventors have continued further studies and come to accomplish the present invention.

That is, the present invention provides the following features and so on.

(1) A protein comprising the same or substantially the same amino acid sequence as the amino acid sequence represented by SEQ ID NO: 4, SEQ ID NO: 7, SEQ ID NO: 15, SEQ ID NO: 17, SEQ ID NO: 20, SEQ ID NO: 22, SEQ ID NO: 25 or SEQ ID NO: 27, or a salt thereof.

(2) A protein consisting of the amino acid sequence represented by SEQ ID NO: 15, SEQ ID NO: 17, SEQ ID NO: 20, SEQ ID NO: 22, SEQ ID NO: 25 or SEQ ID NO: 27, or a salt thereof.

(3) A partial peptide of the protein according to (1), or a salt thereof.

(4) A polynucleotide comprising a polynucleotide encoding the protein according to (1), or a partial peptide thereof.

(5) The polynucleotide according to (4), which is a DNA.

(6) The polynucleotide according to (5), which contains a base sequence represented by SEQ ID NO: 5, SEQ ID NO: 8, SEQ ID NO: 16, SEQ ID NO: 18, SEQ ID NO: 21, SEQ ID NO: 23, SEQ ID NO: 26 or SEQ ID NO: 28.

(7) A polynucleotide consisting of a base sequence represented by SEQ ID NO: 16, SEQ ID NO: 18, SEQ ID NO: 21, SEQ ID NO: 23, SEQ ID NO: 26 or SEQ ID NO: 28.

(8) A recombinant vector comprising the polynucleotide according to (4).

(9) A transformant transformed by the recombinant vector according to (8).

(10) A method of manufacturing the protein according to (1), its partial peptide, or a salt thereof, which comprises culturing the transformant according to (9), and producing/accumulating the protein according to (1) or its partial peptide.

(11) A pharmaceutical comprising the protein according to (1), its partial peptide, or a salt thereof.

(12) A pharmaceutical comprising the polynucleotide according to (4).

(13) A diagnostic agent comprising the polynucleotide according to (4).

(14) An antibody to the protein according to (1), the partial peptide, or a salt thereof.

(14a) The antibody according to (14), which has a prophylactic/therapeutic effect on a cancer.

(14b) The antibody according to (14), which has an apoptosis promoting activity.

(14c) The antibody according to (14), which has an apoptosis promoting activity in cancer cell.

(15) A pharmaceutical comprising the antibody according to (14).

(16) A diagnostic agent comprising the antibody according to (14).

(17) An antisense polynucleotide comprising the entire or part of a base sequence complementary or substantially complementary to a base sequence of the polynucleotide according to (4).

(18) A pharmaceutical comprising the antisense polynucleotide according to (17).

(19) A method of quantifying the protein according to (1), which comprises using the antibody according to (14).

(20) A method for diagnosis of a disease associated with the function of the protein according to (1), which comprises using the quantifying method according to (19).

(21) A method of screening a compound or its salt inhibiting the activity of the protein according to (1), which comprises using the protein according to (1), the partial peptide, or a salt thereof.

(22) A kit for screening a compound or its salt inhibiting the activity of the protein according to (1), comprising the protein according to (1), the partial peptide, or a salt thereof.

(23) A compound or its salt inhibiting the activity of the protein according to (1), which is obtainable by using the screening method according to (21) or the screening kit according to (22).

(24) A method of screening a compound or its salt inhibiting the expression of a gene for the protein according to (1), which comprises using the polynucleotide according to (4).

(25) A kit for screening a compound or its salt inhibiting the expression of a gene for the protein according to (1), comprising the polynucleotide according to (4).

(26) A compound or its salt inhibiting the expression of a gene for the protein according to (1), which is obtainable by using the screening method according to (24) or the screening kit according to (25).

(27) A pharmaceutical comprising the compound according to (23) or (26), or a salt thereof.

(28) An antisense polynucleotide comprising the entire or part of a base sequence complementary or substantially complementary to a base sequence of a polynucleotide encoding a protein comprising the same or substantially the same amino acid sequence as the amino acid sequence represented by SEQ ID NO: 1 or SEQ ID NO: 10, or a partial peptide thereof.

(29) A pharmaceutical comprising the antisense polynucleotide according to (28).

(30) A diagnostic agent comprising the antisense polynucleotide according to (28).

(31) An antibody to a protein comprising the same or substantially the same amino acid sequence as the amino acid sequence represented by SEQ ID NO: 1 or SEQ ID NO: 10, its partial peptide, or a salt thereof.

(32) A pharmaceutical comprising the antibody according to (31).

(33) A diagnostic agent comprising the antibody according to (31).

(34) A diagnostic agent comprising a polynucleotide encoding a protein comprising the same or substantially the same amino acid sequence as the amino acid sequence represented by SEQ ID NO: 1 or SEQ ID NO: 10, or a partial peptide thereof.

(35) The pharmaceutical according to (11), (12), (15), (18), (27), (29) or (32), which is a prophylactic/therapeutic agent for a cancer.

(35a) The pharmaceutical according to (35), wherein the cancer is colon cancer, breast cancer, lung cancer, prostate cancer, esophageal cancer, gastric cancer, liver cancer, biliary tract cancer, spleen cancer, renal cancer, bladder cancer, uterine cancer, testicular cancer, thyroid cancer, pancreatic cancer, brain tumor or blood tumor.

(35b) The pharmaceutical according to (32), which is a prophylactic/therapeutic agent for breast cancer or lung cancer.

(36) The diagnostic agent according to (13), (16), (30), (33) or (34), which is a diagnostic agent for a cancer.

(36a) The diagnostic agent according to (36), wherein the cancer is colon cancer, breast cancer, lung cancer, prostate cancer, esophageal cancer, gastric cancer, liver cancer, biliary tract cancer, spleen cancer, renal cancer, bladder cancer, uterine cancer, testicular cancer, thyroid cancer, pancreatic cancer, brain tumor or blood tumor.

(37) A prophylactic/therapeutic agent for a cancer, comprising a compound or its salt inhibiting the activity of a protein comprising the same or substantially the same amino acid sequence as the amino acid sequence represented by SEQ ID NO: 1, SEQ ID NO: 4, SEQ ID NO: 7, SEQ ID NO: 10, SEQ ID NO: 15, SEQ ID NO: 17, SEQ ID NO: 20, SEQ ID NO: 22, SEQ ID NO: 25 or SEQ ID NO: 27, or its partial peptide, or a salt thereof.

(38) A prophylactic/therapeutic agent for a cancer, comprising a compound or its salt inhibiting the expression of a gene for a protein comprising the same or substantially the same amino acid sequence as the amino acid sequence represented by SEQ ID NO: 1, SEQ ID NO: 4, SEQ ID NO: 7, SEQ ID NO:10, SEQ ID NO: 15, SEQ ID NO: 17, SEQ ID NO: 20, SEQ ID NO: 22, SEQ ID NO: 25 or SEQ ID NO: 27, or its partial peptide, or a salt thereof.

(39) A method of screening a prophylactic/therapeutic agent for a cancer, which comprises using a protein comprising the same or substantially the same amino acid sequence as the amino acid sequence represented by SEQ ID NO: 1, SEQ ID NO: 4, SEQ ID NO: 7, SEQ ID NO: 10, SEQ ID NO: 15, SEQ ID NO: 17, SEQ ID NO: 20, SEQ ID NO: 22, SEQ ID NO: 25 or SEQ ID NO: 27, or its partial peptide, or a salt thereof.

(40) A kit for screening a prophylactic/therapeutic agent for a cancer, comprising a protein comprising the same or substantially the same amino acid sequence as the amino acid sequence represented by SEQ ID NO: 1, SEQ ID NO: 4, SEQ ID NO: 7, SEQ ID NO: 10, SEQ ID NO: 15, SEQ ID NO: 17, SEQ ID NO: 20, SEQ ID NO: 22, SEQ ID NO: 25 or SEQ ID NO: 27, or its partial peptide, or a salt thereof.

(41) A prophylactic/therapeutic agent for a cancer, which is obtainable by using the screening method according to (39) or the screening kit according to (40).

(42) A method of screening a prophylactic/therapeutic agent for a cancer, which comprises using a polynucleotide encoding a protein comprising the same or substantially the same amino acid sequence as the amino acid sequence represented by SEQ ID NO: 1, SEQ ID NO: 4, SEQ ID NO: 7, SEQ ID NO: 10, SEQ ID NO: 15, SEQ ID NO: 17, SEQ ID NO: 20, SEQ ID NO: 22, SEQ ID NO: 25 or SEQ ID NO: 27, or a partial peptide thereof.

(43) A kit for screening a prophylactic/therapeutic agent for a cancer, comprising a polynucleotide encoding a protein comprising the same or substantially the same amino acid sequence as the amino acid sequence represented by SEQ ID NO: 1, SEQ ID NO: 4, SEQ ID NO: 7, SEQ ID NO: 10, SEQ ID NO: 15, SEQ ID NO: 17, SEQ ID NO: 20, SEQ ID NO: 22, SEQ ID NO: 25 or SEQ ID NO: 27, or a partial peptide thereof.

(44) A prophylactic/therapeutic agent for a cancer, which is obtainable by using the screening method according to (42) or the screening kit according to (43).

(45) The pharmaceutical according to (11), (12), (15), (18), (27), (29) or (32), which is an apoptosis promoter.

(45a) The pharmaceutical according to (11), (12), (15), (18), (27), (29) or (32), which is an apoptosis promoter for a cancer cell.

(46) A method of screening an apoptosis promoter, which comprises using a protein comprising the same or substantially the same amino acid sequence as the amino acid sequence represented by SEQ ID NO: 1, SEQ ID NO: 4, SEQ ID NO: 7, SEQ ID NO: 10, SEQ ID NO: 15, SEQ ID NO: 17, SEQ ID NO: 20, SEQ ID NO: 22, SEQ ID NO: 25 or SEQ ID NO: 27, or its partial peptide, or a salt thereof.

(47) A method of screening an apoptosis promoter, which comprises using a polynucleotide encoding a protein comprising the same or substantially the same amino acid sequence as the amino acid sequence represented by SEQ ID NO: 1, SEQ ID NO: 4, SEQ ID NO: 7, SEQ ID NO: 10, SEQ ID NO: 15, SEQ ID NO: 17, SEQ ID NO: 20, SEQ ID NO: 22, SEQ ID NO: 25 or SEQ ID NO: 27, or a partial peptide thereof.

(48) A method of preventing/treating a cancer, which comprises administering to a mammal an effective dose of (i) the antibody of (14) or (31), (ii) a compound or its salt inhibiting the activity of a protein comprising the same or substantially the same amino acid sequence as the amino acid sequence represented by SEQ ID NO: 1, SEQ ID NO: 4, SEQ ID NO: 7, SEQ ID NO: 10, SEQ ID NO: 15, SEQ ID NO: 17, SEQ ID NO: 20, SEQ ID NO: 22, SEQ ID NO: 25 or SEQ ID NO: 27, or its partial peptide, or a salt thereof, or (iii) a compound or its salt inhibiting the expression of a gene for the protein.

(49) A method of preventing/treating a cancer, which comprises inhibiting the activity of a protein comprising the same or substantially the same amino acid sequence as the amino acid sequence represented by SEQ ID NO: 1, SEQ ID NO: 4, SEQ ID NO: 7, SEQ ID NO: 10, SEQ ID NO: 15, SEQ ID NO: 17, SEQ ID NO: 20, SEQ ID NO: 22, SEQ ID NO: 25 or SEQ ID NO: 27, its partial protein, or a salt thereof, or inhibiting the expression of a gene for the protein.

(50) Use of (i) the antibody of (14) or (31), (ii) a compound or its salt inhibiting the activity of a protein comprising the same or substantially the same amino acid sequence as the amino acid sequence represented by SEQ ID NO: 1, SEQ ID NO: 4, SEQ ID NO: 7, SEQ ID NO: 10, SEQ ID NO: 15, SEQ ID NO: 17, SEQ ID.NO: 20, SEQ ID NO: 22, SEQ ID NO: 25 or SEQ ID NO: 27, or its partial peptide, or a salt thereof, or (iii) a compound or its salt inhibiting the expression of a gene for the protein, to manufacture a prophylactic/therapeutic agent for a cancer.

BEST MODE FOR CARRYING OUT THE INVENTION

Figure 1:
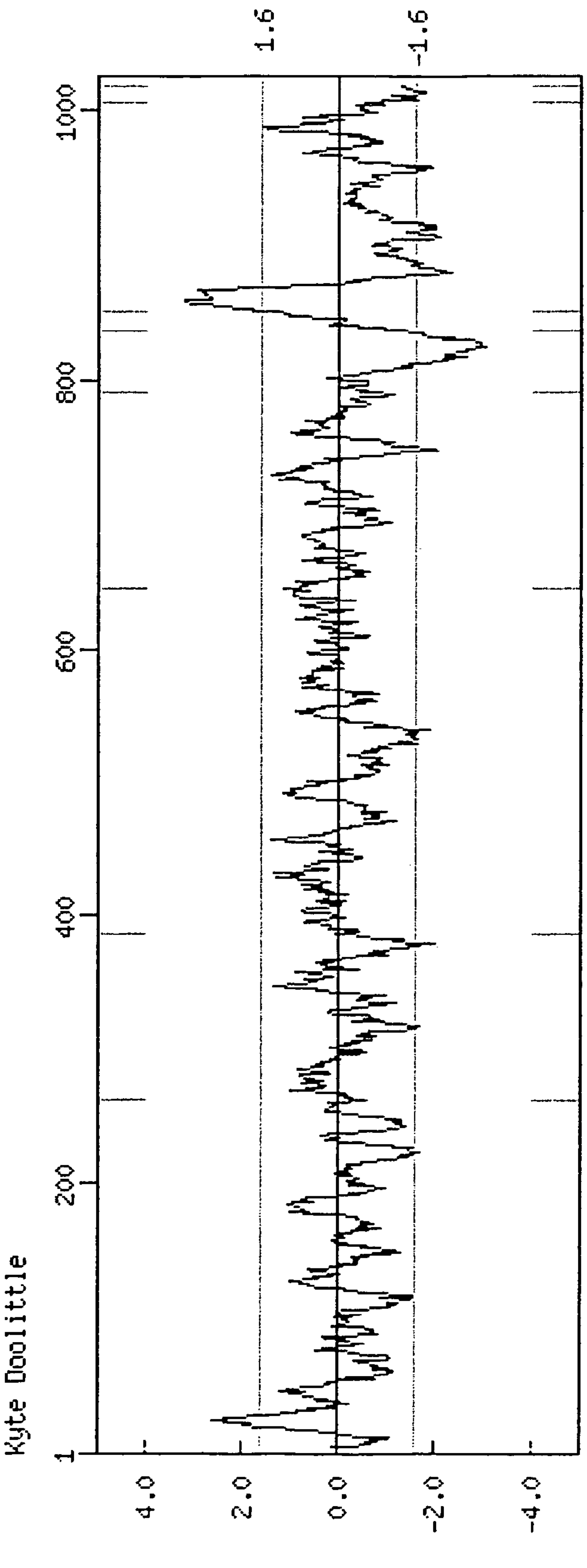
FIG. 1 is a graph illustrating the hydrophobic plot of TACT427-A.
Figure 2:
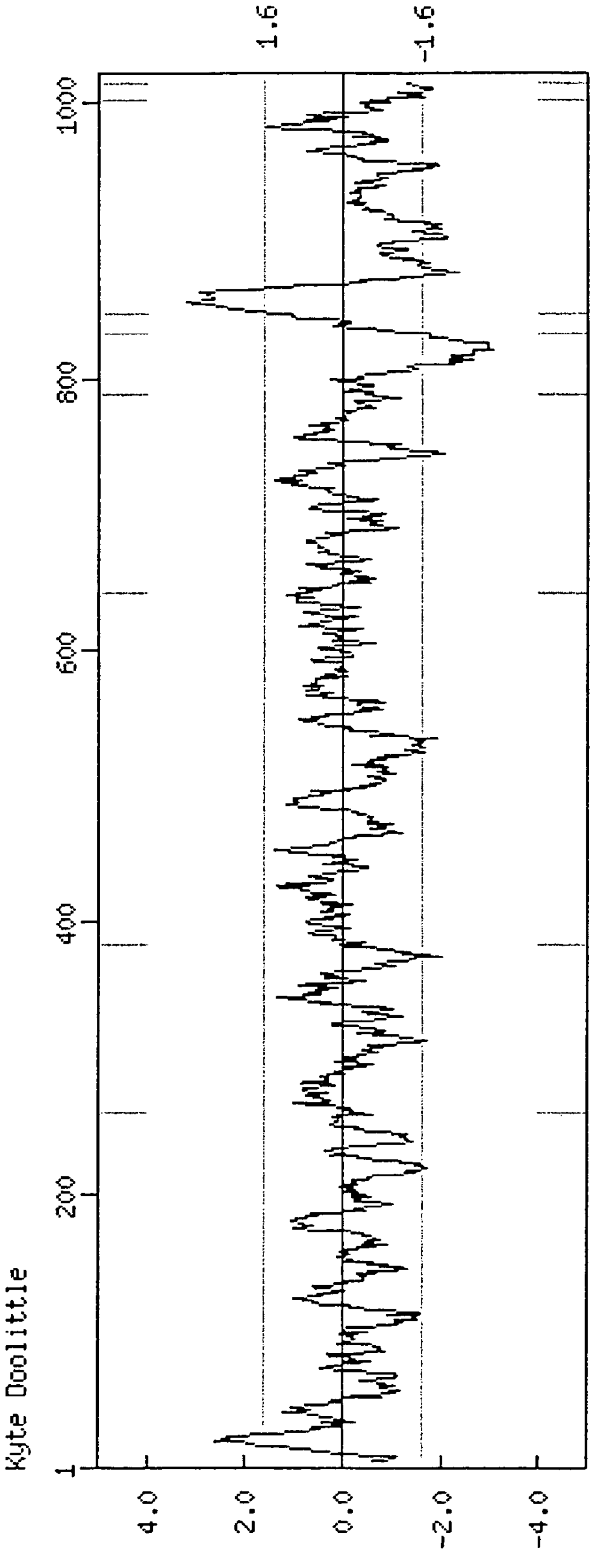
FIG. 2 is a graph illustrating the hydrophobic plot of TACT427-A2.
Figure 3:
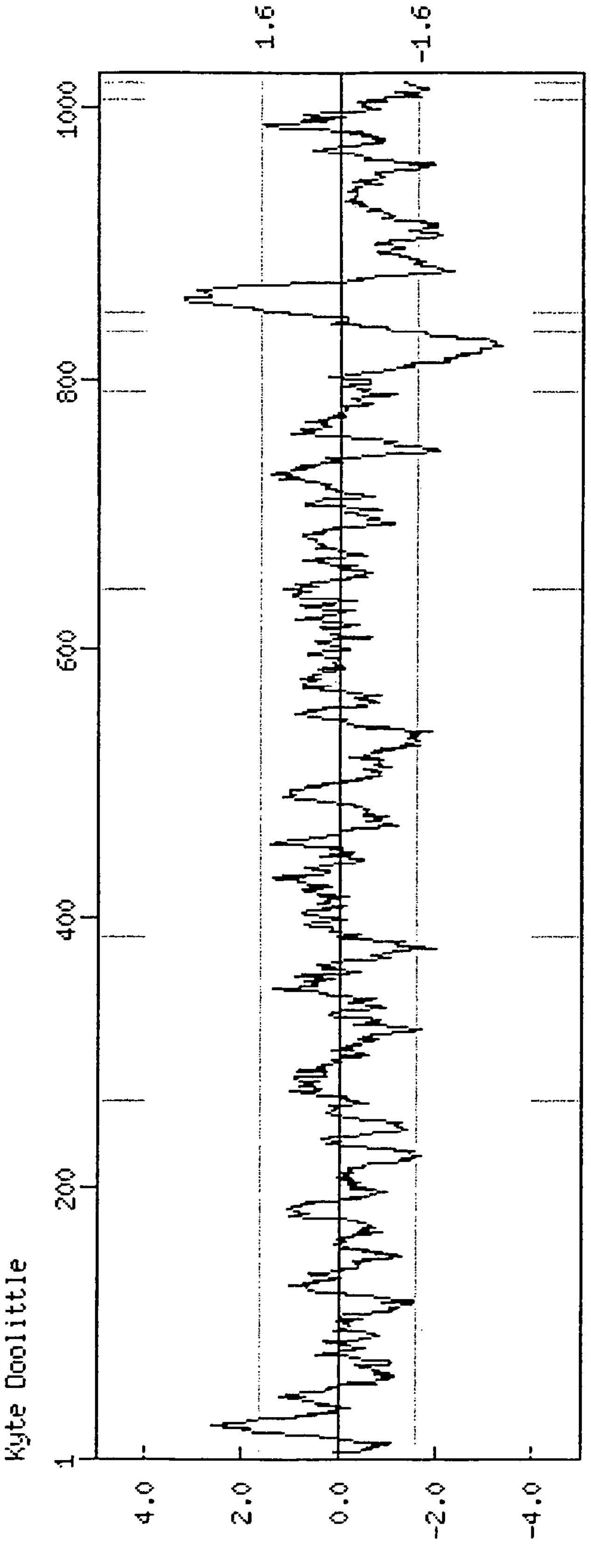
FIG. 3 is a graph illustrating the hydrophobic plot of TACT427-B.
Figure 4:
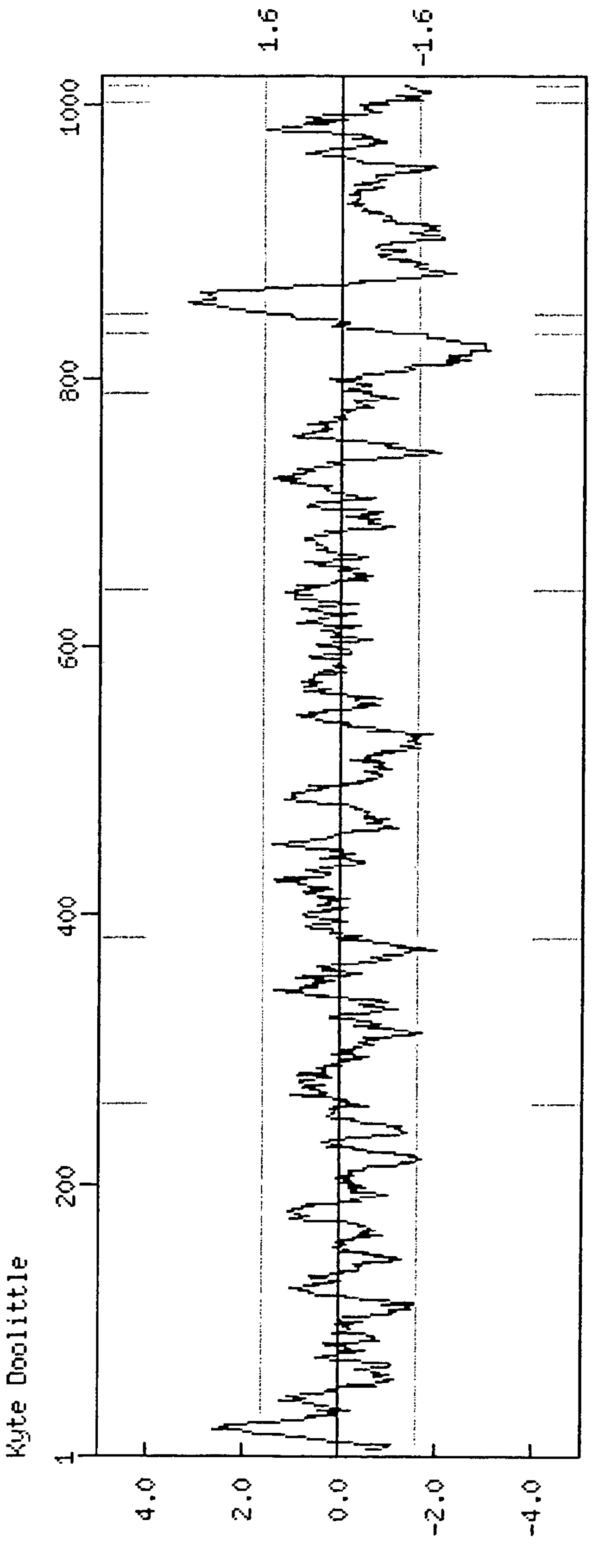
FIG. 4 is a graph illustrating the hydrophobic plot of TACT427-2B.

The protein comprising the same or substantially the same amino acid sequence as the amino acid sequence represented by SEQ ID NO: 1, SEQ ID NO: 4, SEQ ID NO: 7, SEQ ID NO: 10, SEQ ID NO: 15, SEQ ID NO: 17, SEQ ID NO: 20, SEQ ID NO: 22, SEQ ID NO: 25 or SEQ ID NO: 27 used in the present invention (hereinafter these proteins are referred to as the protein of the present invention or sometimes as the protein used in the present invention) may be any protein derived from any cells of human and warm-blooded animals (e.g., guinea pig, rat, mouse, fowl, rabbit, swine, sheep, bovine, monkey, etc.) such as hepatocytes, splenocytes, nerve cells, glial cells, β cells of pancreas, bone marrow cells, mesangial cells, Langerhans' cells, epidermic cells, epithelial cells, goblet cells, endothelial cells, smooth muscle cells, fibroblasts, fibrocytes, myocytes, fat cells, immune cells (e.g., macrophages, T cells, B cells, natural killer cells, mast cells, neutrophils, basophils, eosinophils, monocytes), megakaryocytes, synovial cells, chondrocytes, bone cells, osteoblasts, osteoclasts, mammary gland cells, hepatocytes or interstitial cells; or the corresponding precursor cells, stem cells, cancer cells, etc.; or any tissues where such cells are present, such as brain or any of brain regions (e.g., olfactory bulb, amygdaloid nucleus, basal ganglia, hippocampus, thalamus, hypothalamus, cerebral cortex, medulla oblongata, cerebellum), spinal cord, hypophysis, stomach, pancreas, kidney, liver, gonad, thyroid, gall-bladder, bone marrow, adrenal gland, skin, muscle, lung, gastrointestinal tract (e.g., large intestine and small intestine), blood vessel, heart, thymus, spleen, submandibular gland, peripheral blood, prostate, testis, ovary, placenta, uterus, bone, joint, skeletal muscle, etc.; the proteins may also be synthetic proteins.

The amino acid sequence comprising substantially the same amino acid sequence as that represented by SEQ ID NO: 1 includes amino acid sequences having at least about 70% homology, preferably at least about 80% homology, more preferably at least about 90% homology and most preferably at least about 95% homology, to the amino acid sequence shown by SEQ ID NO: 1; etc.

Preferred examples of the protein comprising substantially the same amino acid sequence as the amino acid sequence represented by SEQ ID NO: 1 include proteins comprising substantially the same amino acid sequence as the amino acid sequence represented by SEQ ID NO: 1 and having a property substantially equivalent to that of the protein containing the amino acid sequence represented by SEQ ID NO: 1, etc.

The amino acid sequence comprising substantially the same amino acid sequence as that represented by SEQ ID NO: 4 includes amino acid sequences having at least about 70% homology, preferably at least about 80% homology, more preferably at least about 90% homology and most preferably at least about 95% homology, to the amino acid sequence shown by SEQ ID NO: 4; etc. For example, there are amino acid sequences having at least about 70% homology, preferably at least about 80% homology, more preferably at least about 90% homology and most preferably at least about 95% homology, to the 47-296 amino acid sequence in the amino acid sequence represented by SEQ ID NO: 4; etc.

Preferred examples of the protein comprising substantially the same amino acid sequence as the amino acid sequence represented by SEQ ID NO: 4 include proteins comprising substantially the same amino acid sequence as the amino acid sequence represented by SEQ ID NO: 4 and having a property substantially equivalent to that of the protein comprising the amino acid sequence represented by SEQ ID NO: 4, etc.

The amino acid sequence comprising substantially the same amino acid sequence as that represented by SEQ ID NO: 7 includes amino acid sequences having at least about 70% homology, preferably at least about 80% homology, more preferably at least about 90% homology and most preferably at least about 95% homology, to the amino acid sequence shown by SEQ ID NO: 7; etc. For example, there are amino acid sequences having at least about 70% homology, preferably at least about 80% homology, more preferably at least about 90% homology and most preferably at least about 95% homology, to the 577-594 amino acid sequence in the amino acid sequence represented by SEQ ID NO: 7; etc.

Preferred examples of the protein comprising substantially the same amino acid sequence as the amino acid sequence represented by SEQ ID NO: 7 include proteins comprising substantially the same amino acid sequence as the amino acid sequence represented by SEQ ID NO: 7 and having a property substantially equivalent to that of the protein comprising the amino acid sequence represented by SEQ ID NO: 7, etc.

The amino acid sequence comprising substantially the same amino acid sequence as that represented by SEQ ID NO: 10 includes amino acid sequences having at least about 70% homology, preferably at least about 80% homology, more preferably at least about 90% homology and most preferably at least about 95% homology, to the amino acid sequence shown by SEQ ID NO: 10; etc.

Preferred examples of the protein comprising substantially the same amino acid sequence as the amino acid sequence represented by SEQ ID NO: 10 include proteins comprising substantially the same amino acid sequence as the amino acid sequence represented by SEQ ID NO: 10 and having a property substantially equivalent to that of the protein containing the amino acid sequence represented by SEQ ID NO: 10, etc.

The amino acid sequence comprising substantially the same amino acid sequence as that represented by SEQ ID NO: 15 includes amino acid sequences having at least about 70% homology, preferably at least about 80% homology, more preferably at least about 90% homology and most preferably at least about 95% homology, to the amino acid sequence shown by SEQ ID NO: 15; etc. For example, there are amino acid sequences having at least about 70% homology, preferably at least about 80% homology, more preferably at least about 90% homology and most preferably at least about 95% homology, to the 47-296 amino acid sequence in the amino acid sequence represented by SEQ ID NO: 15; etc.

Preferred examples of the protein comprising substantially the same amino acid sequence as the amino acid sequence represented by SEQ ID NO: 15 include proteins comprising substantially the same amino acid sequence as the amino acid sequence represented by SEQ ID NO: 15 and having a property substantially equivalent to that of the protein comprising the amino acid sequence represented by SEQ ID NO: 15, etc.

The amino acid sequence comprising substantially the same amino acid sequence as that represented by SEQ ID NO: 17 includes amino acid sequences having at least about 70% homology, preferably at least about 80% homology, more preferably at least about 90% homology and most preferably at least about 95% homology, to the amino acid sequence shown by SEQ ID NO: 17; etc. For example, there are amino acid sequences having at least about 70% homology, preferably at least about 80% homology, more preferably at least about 90% homology and most preferably at least about 95% homology, to the 43-292 amino acid sequence in the amino acid sequence represented by SEQ ID NO: 17; etc.

Preferred examples of the protein comprising substantially the same amino acid sequence as the amino acid sequence represented by SEQ ID NO: 17 include proteins comprising substantially the same amino acid sequence as the amino acid sequence represented by SEQ ID NO: 17 and having a property substantially equivalent to that of the protein comprising the amino acid sequence represented by SEQ ID NO:17, etc.

The amino acid sequence comprising substantially the same amino acid sequence as that represented by SEQ ID NO: 20 includes amino acid sequences having at least about 70% homology, preferably at least about 80% homology, more preferably at least about 90% homology and most preferably at least about 95% homology, to the amino acid sequence shown by SEQ ID NO: 20; etc. For example, there are amino acid sequences having at least about 70% homology, preferably at least about 80% homology, more preferably at least about 90% homology and most preferably at least about 95% homology, to the 47-296 amino acid sequence in the amino acid sequence represented by SEQ ID NO: 20; etc.

Preferred examples of the protein comprising substantially the same amino acid sequence as the amino acid sequence represented by SEQ ID NO: 20 include proteins comprising substantially the same amino acid sequence as the amino acid sequence represented by SEQ ID NO: 20 and having a property substantially equivalent to that of the protein comprising the amino acid sequence represented by SEQ ID NO: 20, etc.

The amino acid sequence comprising substantially the same amino acid sequence as that represented by SEQ ID NO: 22 includes amino acid sequences having at least about 70% homology, preferably at least about 80% homology, more preferably at least about 90% homology and most preferably at least about 95% homology, to the amino acid sequence shown by SEQ ID NO: 22; etc. For example, there are amino acid sequences having at least about 70% homology, preferably at least about 80% homology, more preferably at least about 90% homology and most preferably at least about 95% homology, to the 43-292 amino acid sequence in the amino acid sequence represented by SEQ ID NO: 22; etc.

Preferred examples of the protein comprising substantially the same amino acid sequence as the amino acid sequence represented by SEQ ID NO: 22 include proteins comprising substantially the same amino acid sequence as the amino acid sequence represented by SEQ ID NO: 22 and having a property substantially equivalent to that of the protein comprising the amino acid sequence represented by SEQ ID NO: 22, etc.

The amino acid sequence comprising substantially the same amino acid sequence as that represented by SEQ ID NO: 25 includes amino acid sequences having at least about 70% homology, preferably at least about 80% homology, more preferably at least about 90% homology and most preferably at least about 95% homology, to the amino acid sequence shown by SEQ ID NO: 25; etc. For example, there are amino acid sequences having at least about 70% homology, preferably at least about 80% homology, more preferably at least about 90% homology and most preferably at least about 95% homology, to the 47-296 amino acid sequence in the amino acid sequence represented by SEQ ID NO: 25; etc.

Preferred examples of the protein comprising substantially the same amino acid sequence as the amino acid sequence represented by SEQ ID NO: 25 include proteins comprising substantially the same amino acid sequence as the amino acid sequence represented by SEQ ID NO: 25 and having a property substantially equivalent to that of the protein comprising the amino acid sequence represented by SEQ ID NO: 25, etc.

The amino acid sequence comprising substantially the same amino acid sequence as that represented by SEQ ID NO: 27 includes amino acid sequences having at least about 70% homology, preferably at least about 80% homology, more preferably at least about 90% homology and most preferably at least about 95% homology, to the amino acid sequence shown by SEQ ID NO: 27; etc. For example, there are amino acid sequences having at least about 70% homology, preferably at least about 80% homology, more preferably at least about 90% homology and most preferably at least about 95% homology, to the 43-292 amino acid sequence in the amino acid sequence represented by SEQ ID NO: 27; etc.

Preferred examples of the protein comprising substantially the same amino acid sequence as the amino acid sequence represented by SEQ ID NO: 27 include proteins comprising substantially the same amino acid sequence as the amino acid sequence represented by SEQ ID NO: 27 and having a property substantially equivalent to that of the protein comprising the amino acid sequence represented by SEQ ID NO: 27, etc.

Homology of the amino acid sequences can be measured under the following conditions (an expectation value=10; gaps are allowed; matrix=BLOSUM62; filtering =OFF)

using a homology scoring algorithm NCBI BLAST (National Center for Biotechnology Information Basic Local Alignment Search Tool).

As the substantially equivalent properties, there is, for example, a chloroperoxidase activity, or the like. The substantially equivalent is used to mean that the nature of these properties is equivalent in terms of quality (e.g., physiologically or pharmacologically). Thus, the chloroperoxidase activity is preferably equivalent (e.g., about 0.01 to 100 times, preferably about 0.1 to 10 times, more preferably 0.5 to 2 times), but differences in degree such as a level of these activities, quantitative factors such as a molecular weight of the protein may be present and allowable.

The chloroperoxidase activity can be determined by publicly known methods with modifications. For example, the activity can be assayed by the method described in Journal of Biological Chemistry (J. Biol. Chem.), 241, 1763-1768 (1966), etc.

Examples of the protein used in the present invention include so-called muteins such as proteins having (i) the amino acid sequence represented by SEQ ID NO: 1, SEQ ID NO: 4, SEQ ID NO: 7, SEQ ID NO: 10, SEQ ID NO: 15, SEQ ID NO: 17, SEQ ID NO: 20, SEQ ID NO: 22, SEQ ID NO: 25 or SEQ ID NO: 27, of which at least 1 or 2 (e.g., about 1 to about 100, preferably about 1 to about 30, more preferably about 1 to about 10 and most preferably several (1 to 5)) amino acids are deleted; (ii) the amino acid sequence represented by SEQ ID NO: 1, SEQ ID NO: 4, SEQ ID NO: 7, SEQ ID NO: 10, SEQ ID NO: 15, SEQ ID NO: 17, SEQ ID NO: 20, SEQ ID NO: 22, SEQ ID NO: 25 or SEQ ID NO: 27, to which at least 1 or 2 (e.g., about 1 to about 100, preferably about 1 to about 30, more preferably about 1 to about 10 and most preferably several (1 to 5)) amino acids are added; (iii) the amino acid sequence represented by SEQ ID NO: 1, SEQ ID NO: 4, SEQ ID NO: 7, SEQ ID NO: 10, SEQ ID NO: 15, SEQ ID NO: 17, SEQ ID NO: 20, SEQ ID NO: 22, SEQ ID NO: 25 or SEQ ID NO: 27, in which at least 1 or 2 (e.g., about 1 to about 100, preferably about 1 to about 30, more preferably about 1 to about 10 and most preferably several (1 to 5)) amino acids are inserted; (iv) the amino acid sequence represented by SEQ ID NO: 1, SEQ ID NO: 4, SEQ ID NO: 7, SEQ ID NO: 10, SEQ ID NO: 15, SEQ ID NO: 17, SEQ ID NO: 20, SEQ ID NO: 22, SEQ ID NO: 25 or SEQ ID NO: 27, in which at least 1 or 2 (e.g., about 1 to about 100, preferably about 1 to about 30, more preferably about 1 to about 10 and most preferably several (1 to 5)) amino acids are substituted by other amino acids; or (v) a combination of these amino acid sequences, which is so-called mutein; and the like.

Where the amino acid sequence is inserted, deleted or substituted as described above, the position of its insertion, deletion or substitution is not particularly limited.

Throughout the specification, the proteins are represented in accordance with the conventional way of describing proteins, that is, the N-terminus (amino terminus) at the left hand and the C-terminus (carboxyl terminus) at the right hand. In the protein used in the present invention including the protein comprising the amino acid sequence represented by SEQ ID NO: 1, the C-terminus may be in any form of a carboxyl group (—COOH), a carboxylate (—$COO^-$), an amide (—$CONH_2$) And an ester (—COOR).

Herein, examples of the ester group shown by R include a $C_{1-6}$ alkyl group such as methyl, ethyl, n-propyl, isopropyl, n-butyl, etc.; a $C_{3-8}$ cycloalkyl group such as cyclopentyl, cyclohexyl, etc.; a $C_{6-12}$ aryl group such as phenyl, α-naphthyl, etc.; a $C_{7-14}$ aralkyl such as a phenyl-$C_{1-2}$ alkyl group, e.g., benzyl, phenethyl, etc.; an α-naphthyl-$C_{1-2}$ alkyl group such as α-naphthylmethyl, etc.; pivaloyloxymethyl and the like.

Where the protein used in the present invention contains a carboxyl group (or a carboxylate) at a position other than the C-terminus, the carboxyl group may be amidated or esterified and such an amide or ester is also included within the protein of the present invention. Examples of the ester group in this case may be the C-terminal esters described above, etc.

Furthermore, examples of the protein used in the present invention include variants wherein the amino group at the N-terminal amino acid residues (e.g., methionine residue) is protected with a protecting group (e.g., a $C_{1-6}$ acyl group such as a $C_{1-6}$ alkanoyl group, e.g., formyl group, acetyl group, etc.); those wherein the N-terminal region is cleaved in vivo and the glutamyl group thus formed is pyroglutaminated; those wherein a substituent (e.g., —OH, —SH, amino group, imidazole group, indole group, guanidino group, etc.) on the side chain of an amino acid in the molecule is protected with a suitable protecting group (e.g., a $C_{1-6}$ acyl group such as a $C_{1-6}$ alkanoyl group, e.g., formyl group, acetyl group, etc.), or conjugated proteins such as glycoproteins having sugar chains; etc.

Specific examples of the protein used in the present invention are a protein comprising the amino acid sequence represented by SEQ ID NO: 1, a protein comprising the amino acid sequence represented by SEQ ID NO: 4, a protein comprising the amino acid sequence represented by SEQ ID NO: 7, a protein comprising the amino acid sequence represented by SEQ ID NO: 10, a protein comprising the amino acid sequence represented by SEQ ID NO: 15, a protein comprising the amino acid sequence represented by SEQ ID NO: 17, a protein comprising the amino acid sequence represented by SEQ ID NO: 20, a protein comprising the amino acid sequence represented by SEQ ID NO: 22, a protein comprising the amino acid sequence represented by SEQ ID NO: 25, a protein comprising the amino acid sequence represented by SEQ ID NO: 27, and the like.

The partial peptide of the protein used in the present invention may be any peptide as long as it is a partial peptide of the protein used in the present invention described above and preferably has the property equivalent to that of the protein used in the present invention described above.

For example, there are used peptides containing, e.g., at least 20, preferably at least 50, more preferably at least 70, much more preferably at least 100, and most preferably at least 200 amino acids in the constituent amino acid sequence of the protein used in the present invention, etc.

The partial peptide used in the present invention may be peptides containing the amino acid sequence, of which at least 1 or 2 (preferably about 1 to about 10 and more preferably several (1 to 5)) amino acids may be deleted; peptides, to which at least 1 or 2 (preferably about 1 to about 20, more preferably about 1 to about 10 and most preferably several (1 to 5)) amino acids may be added; peptides, in which at least 1 or 2 (preferably about 1 to about 20, more preferably about 1 to about 10 and most preferably several (1 to 5)) amino acids may be inserted; or peptides, in which at least 1 or 2 (preferably about 1 to about 10, more preferably several and most preferably about 1 to about 5) amino acids may be substituted by other amino acids.

In the partial peptide used in the present invention, the C-terminus may be in any form of a carboxyl group (—COOH), a carboxylate (—$COO^-$), an amide (—$CONH_2$) or an ester (—COOR).

Furthermore, the partial peptide used in the present invention includes variants having a carboxyl group (or a carboxylate) at a position other than the C-terminus, those wherein the amino group at the N-terminal amino acid residues (e.g., methionine residue) is protected with a protecting group; those wherein the N-terminal region is cleaved in vivo and the glutamyl group thus formed is pyroglutaminated; those wherein a substituent on the side chain of an amino acid in the molecule is protected with a suitable protecting group, or conjugated proteins such as so-called glycoproteins having sugar chains; etc., as in the protein of the present invention described above.

The partial peptide used in the present invention may also be used as an antigen for producing antibodies.

As salts of the protein or partial peptide used in the present invention, salts with physiologically acceptable acids (e.g., inorganic acids or organic acids) or bases (e.g., alkali metal salts) may be employed, preferably in the form of physiologically acceptable acid addition salts. Examples of such salts include salts with inorganic acids (e.g., hydrochloric acid, phosphoric acid, hydrobromic acid, sulfuric acid), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid) And the like.

The protein or partial peptide used in the present invention or salts thereof may be manufactured by publicly known methods used to purify a protein from human or warm-blooded animal cells or tissues described above. Alternatively, they may also be manufactured by culturing transformants containing DNAs encoding these proteins. Furthermore, they may also be manufactured by a modification of the methods for peptide synthesis, which will be later described.

Where these proteins are manufactured from human or mammalian tissues or cells, human or non-human mammalian tissues or cells are homogenized, extracted with an acid or the like, and the extract is purified and isolated by a combination of chromatography techniques such as reverse phase chromatography, ion exchange chromatography, and the like.

To synthesize the protein or partial peptide used in the present invention or its salts, or amides thereof, commercially available resins that are used for protein synthesis may be used. Examples of such resins include chloromethyl resin, hydroxymethyl resin, benzhydrylamine resin, aminomethyl resin, 4-benzyloxybenzyl alcohol resin, 4-methylbenzhydrylamine resin, PAM resin, 4-hydroxymethylmethylphenyl acetamidomethyl resin, polyacrylamide resin, 4-(2',4'-dimethoxyphenyl-hydroxymethyl)phenoxy resin, 4-(2',4'-dimethoxyphenyl-Fmoc-aminoethyl) phenoxy resin, etc. Using these resins, amino acids, in which α-amino groups and functional groups on the side chains are appropriately protected, are condensed on the resin in accordance with the sequence of the objective protein according to various condensation methods publicly known in the art. At the end of the reaction, the protein or partial peptide is excised from the resin and at the same time, the protecting groups are removed. Then, intramolecular disulfide bond-forming reaction is performed in a highly diluted solution to obtain the objective protein or partial peptide, or amides thereof.

For condensation of the protected amino acids described above, a variety of activation reagents for protein synthesis may be used, and carbodiimides are particularly employed. Examples of such carbodiimides include DCC, N,N'-diisopropylcarbodiimide, N-ethyl-N'-(3-dimethylaminopropyl) carbodiimide, etc. For activation by these reagents, the protected amino acids in combination with a racemization inhibitor (e.g., HOBt, HOOBt) are added directly to the resin, or the protected amino acids are previously activated in the form of symmetric acid anhydrides, HOBt esters or HOOBt esters, followed by adding the thus activated protected amino acids to the resin.

Solvents suitable for use to activate the protected amino acids or condense with the resin may be appropriately chosen from solvents that are known to be usable for protein condensation reactions. Examples of such solvents are acid amides such as N,N-dimethylformamide, N,N-dimethylacetamide, N-methylpyrrolidone, etc.; halogenated hydrocarbons such as methylene chloride, chloroform, etc.; alcohols such as trifluoroethanol, etc.; sulfoxides such as dimethylsulfoxide, etc.; ethers such as pyridine, dioxane, tetrahydrofuran, etc.; nitrites such as acetonitrile, propionitrile, etc.; esters such as methyl acetate, ethyl acetate, etc.; and appropriate mixtures of these solvents. The reaction temperature is appropriately chosen from the range known to be applicable to protein binding reactions and is usually selected in the range of approximately −20° C. to 50° C. The activated amino acid derivatives are used generally in an excess of 1.5 to 4 times. The condensation is examined using the ninhydrin reaction; when the condensation is insufficient, the condensation can be completed by repeating the condensation reaction without removal of the protecting groups. When the condensation is yet insufficient even after repeating the reaction, unreacted amino acids are acetylated with acetic anhydride or acetylimidazole to avoid any possible effect on the subsequent reaction.

Examples of the protecting groups used to protect the starting amino groups include Z, Boc, t-pentyloxycarbonyl, isobornyloxycarbonyl, 4-methoxybenzyloxycarbonyl, Cl-Z, Br-Z, adamantyloxycarbonyl, trifluoroacetyl, phthaloyl, formyl, 2-nitrophenylsulphenyl, diphenylphosphinothioyl, Fmoc, etc.

A carboxyl group can be protected by, e.g., alkyl esterification (linear, branched or cyclic alkyl esterification of, e.g., methyl, ethyl, propyl, butyl, t-butyl, cyclopentyl, cyclohexyl, cycloheptyl, cyclooctyl, 2-adamantyl, etc.), aralkyl esterification (e.g., benzyl ester, 4-nitrobenzyl ester, 4-methoxybenzyl ester, 4-chlorobenzyl ester, benzhydryl ester, etc.), phenacyl esterification, benzyloxycarbonyl hydrazidation, t-butoxycarbonyl hydrazidation, trityl hydrazidation, or the like.

The hydroxyl group of serine can be protected through, for example, its esterification or etherification. Examples of groups appropriately used for the esterification include a lower ($C_{1-6}$) alkanoyl group, such as acetyl group, an aroyl group such as benzoyl group, and a group derived from carbonic acid such as benzyloxycarbonyl group, ethoxycarbonyl group, etc. Examples of a group appropriately used for the etherification include benzyl group, tetrahydropyranyl group, t-butyl group, etc.

Examples of groups for protecting the phenolic hydroxyl group of tyrosine include Bzl, $C_{12}$-Bzl, 2-nitrobenzyl, Br-Z, t-butyl, etc.

Examples of groups used to protect the imidazole moiety of histidine include Tos, 4-methoxy-2,3,6-trimethylbenzenesulfonyl, DNP, benzyloxymethyl, Bum, Boc, Trt, Fmoc, etc.

Examples of the activated carboxyl groups in the starting material include the corresponding acid anhydrides, azides, activated esters [esters with alcohols (e.g., pentachlorophenol, 2,4,5-trichlorophenol, 2,4-dinitrophenol, cyanomethyl alcohol, p-nitrophenol, HONB, N-hydroxysuccimide, N-hydroxyphthalimide, HOBt)]. As the amino acids in which the amino groups are activated in the starting material, the corresponding phosphoric amides are employed.

To eliminate (split off) the protecting groups, there are used catalytic reduction under hydrogen gas flow in the presence of a catalyst such as Pd-black or Pd-carbon; an acid treatment with anhydrous hydrogen fluoride, methanesulfonic acid, trifluoromethanesulfonic acid, trifluoroacetic acid, or a mixture solution of these acids; a treatment with a base such as diisopropylethylamine, triethylamine, piperidine or piperazine; reduction with sodium in liquid ammonia, etc. The elimination of the protecting group by the acid treatment described above is carried out generally at a temperature of approximately −20° C. to 40° C. In the acid treatment, it is efficient to add a cation scavenger such as anisole, phenol, thioanisole, m-cresol, p-cresol, dimethylsulfide, 1,4-butanedithiol, 1,2-ethanedithiol, etc. Furthermore, 2,4-dinitrophenyl group known as the protecting group for the imidazole of histidine is removed by a treatment with thiophenol. Formyl group used as the protecting group of the indole of tryptophan is eliminated by the aforesaid acid treatment in the presence of 1,2-ethanedithiol, 1,4-butanedithiol, etc. as well as by a treatment with an alkali such as a dilute sodium hydroxide solution, dilute ammonia, etc.

Protection of functional groups that should not be involved in the reaction of the starting materials, protecting groups, elimination of the protecting groups and activation of functional groups involved in the reaction may be appropriately selected from publicly known groups and publicly known means.

In another method for obtaining the amides of the desired protein or partial peptide, for example, the α-carboxyl group of the carboxy terminal amino acid is first protected by amidation; the peptide (protein) chain is then extended from the amino group side to a desired length. Subsequently, a protein or partial peptide, in which only the protecting group of the N-terminal α-amino group of the peptide chain has been eliminated, and a protein or partial peptide, in which only the protecting group of the C-terminal carboxyl group has been eliminated, are manufactured. The two proteins or peptides are condensed in a mixture of the solvents described above. The details of the condensation reaction are the same as described above. After the protected protein or peptide obtained by the condensation is purified, all the protecting groups are eliminated by the method described above to give the desired crude protein or peptide. This crude protein or peptide is purified by various known purification means. Lyophilization of the major fraction gives the amide of the desired protein or peptide.

To prepare the esterified protein or peptide, for example, the α-carboxyl group of the carboxy terminal amino acid is condensed with a desired alcohol to prepare the amino acid ester, which is followed by procedures similar to the preparation of the amidated protein or peptide above to give the desired esterified protein or peptide.

The partial peptide used in the present invention or salts thereof can be manufactured by publicly known methods for peptide synthesis, or by cleaving the protein used in the present invention with an appropriate peptidase. For the methods for peptide synthesis, for example, either solid phase synthesis or liquid phase synthesis may be used. That is, the partial peptide or amino acids that can construct the partial peptide used in the present invention are condensed with the remaining part. Where the product contains protecting groups, these protecting groups are removed to give the desired peptide. Publicly known methods for condensation and elimination of the protecting groups are described in (i) to (v) below.

(i) M. Bodanszky & M. A. Ondetti: Peptide Synthesis, Interscience Publishers, New York (1966)

(ii) Schroeder & Luebke: The Peptide, Academic Press, New York (1965)

(iii) Nobuo Izumiya, et al.: Peptide Gosei-no-Kiso to Jikken (Basics and experiments of peptide synthesis), published by Maruzen Co. (1975)

(iv) Haruaki Yajima & Shunpei Sakakibara: Seikagaku Jikken Koza (Biochemical Experiment) 1, Tanpakushitsu no Kagaku (Chemistry of Proteins) IV, 205 (1977)

(v) Haruaki Yajima ed.: Zoku Iyakuhin no Kaihatsu (A sequel to Development of Pharmaceuticals), Vol. 14, Peptide Synthesis, published by Hirokawa Shoten After completion of the reaction, the product may be purified and isolated by a combination of conventional purification methods such as solvent extraction, distillation, column chromatography, liquid chromatography and recrystallization to give the partial peptide used in the present invention. When the partial peptide obtained by the above methods is in a free form, the partial peptide can be converted into an appropriate salt by a publicly known method or its modification; when the partial peptide is obtained in a salt form, it can be converted into a free form or other different salt form by a publicly known method or its modification.

The polynucleotide encoding the protein used in the present invention may be any polynucleotide so long as it contains the base sequence encoding the protein used in the present invention described above. Preferably, the polynucleotide is a DNA. The DNA may also be any one of genomic DNA, genomic DNA library, cDNA derived from the cells or tissues described above, cDNA library derived from the cells or tissues described above and synthetic DNA.

The vector used for the library may be any of bacteriophage, plasmid, cosmid, phagemid and the like. In addition, the DNA can be amplified by reverse transcriptase polymerase chain reaction (hereinafter abbreviated as RT-PCR) with total RNA or mRNA fraction prepared from the above-described cells or tissues.

Examples of the DNA encoding the protein used in the present invention may be any one of:

(i) a DNA comprising the base sequence represented by SEQ ID NO: 2, or a DNA comprising a base sequence hybridizable to the base sequence represented by SEQ ID NO: 2 under high stringent conditions and encoding a protein which has the properties of substantially the same nature as those of the protein comprising the amino acid sequence represented by SEQ ID NO: 1 described above, (ii) a DNA comprising the base sequence represented by SEQ ID NO: 5, or a DNA comprising a base sequence hybridizable to the base sequence represented by SEQ ID NO: 5 under high stringent conditions and encoding a protein which has the properties of substantially the same nature as those of the protein comprising the amino acid sequence represented by SEQ ID NO: 4 described above, (iii) a DNA comprising the base sequence represented by SEQ ID NO: 8, or a DNA comprising a base sequence hybridizable to the base sequence represented by SEQ ID NO: 8 under high stringent conditions and encoding a protein which has the properties of substantially the same nature as those of the protein comprising the amino acid sequence represented by SEQ ID NO: 7 described above, (iv) a DNA comprising the base sequence represented by SEQ ID NO: 11, or a DNA comprising a base sequence hybridizable to the base sequence represented by SEQ ID NO: 11 under high stringent conditions and encoding a protein which has the properties of substantially the same nature as those of the protein comprising the amino acid sequence represented by SEQ ID NO: 10 described above, (v) a DNA comprising the base sequence represented by SEQ ID NO: 16, or a DNA comprising a base sequence hybridizable to the base sequence represented by SEQ ID NO: 16 under high stringent conditions and encoding a protein which has the properties of substantially the same nature as those of the protein comprising the amino acid sequence represented by SEQ ID NO: 15 described above, (vi) a DNA comprising the base sequence represented by SEQ ID NO: 18, or a DNA comprising a base sequence hybridizable to the base sequence represented by SEQ ID NO: 18 under high stringent conditions and encoding a protein which has the properties of substantially the same nature as those of the protein comprising the amino acid sequence represented by SEQ ID NO: 17 described above, (vii) a DNA comprising the base sequence represented by SEQ ID NO: 21, or a DNA comprising a base sequence hybridizable to the base sequence represented by SEQ ID NO: 21 under high stringent conditions and encoding a protein which has the properties of substantially the same nature as those of the protein comprising the amino acid sequence represented by SEQ ID NO: 20 described above, (viii) a DNA comprising the base sequence represented by SEQ ID NO: 23, or a DNA comprising a base sequence hybridizable to the base sequence represented by SEQ ID NO: 23 under high stringent conditions and encoding a protein which has the properties of substantially the same nature as those of the protein comprising the amino acid sequence represented by SEQ ID NO: 22 described above, (ix) a DNA comprising the base sequence represented by SEQ ID NO: 26, or a DNA comprising a base sequence hybridizable to the base sequence represented by SEQ ID NO: 26 under high stringent conditions and encoding a protein which has the properties of substantially the same nature as those of the protein comprising the amino acid sequence represented by SEQ ID NO: 25 described above, and (x) a DNA comprising the base sequence represented by SEQ ID NO: 28, or a DNA comprising a base sequence hybridizable to the base sequence represented by SEQ ID NO: 28 under high stringent conditions and encoding a protein which has the properties of substantially the same nature as those of the protein comprising the amino acid sequence represented by SEQ ID NO: 27 described above.

As the DNA that is hybridizable to the base sequence represented by SEQ ID NO: 2 under high stringent conditions, there are employed, for example, DNAs comprising base sequences having at least about 70% homology, preferably at least about 80% homology, more preferably at least about 90% homology and most preferably at least about 95% homology, to the base sequence represented by SEQ ID NO: 2; and the like.

As the DNA that is hybridizable to the base sequence represented by SEQ ID NO: 5 under high stringent conditions, there are employed, for example, DNAs comprising base sequences having at least about 70% homology, preferably at least about 80% homology, more preferably at least about 90% homology and most preferably at least about 95% homology, to the base sequence represented by SEQ ID NO: 5; and the like. There are also employed, for example, DNAs comprising base sequences having at least about 70% homology, preferably at least about 80% homology, more preferably at least about 90% homology and most preferably at least about 95% homology, to the 139-888 base sequence of the base sequence represented by SEQ ID NO: 5, etc.

As the DNA that is hybridizable to the base sequence represented by SEQ ID NO: 8 under high stringent conditions, there are employed, for example, DNAs comprising base sequences having at least about 70% homology, preferably at least about 80% homology, more preferably at least about 90% homology and most preferably at least about 95% homology, to the base sequence represented by SEQ ID NO: 8; and the like. There are also employed, for example, DNAs comprising base sequences having at least about 70% homology, preferably at least about 80% homology, more preferably at least about 90% homology and most preferably at least about 95% homology, to the 1728-1782 base sequence of the base sequence represented by SEQ ID NO: 8, etc.

As the DNA that is hybridizable to the base sequence represented by SEQ ID NO: 11 under high stringent conditions, there are employed, for example, DNAs comprising base sequences having at least about 70% homology, preferably at least about 80% homology, more preferably at least about 90% homology and most preferably at least about 95% homology, to the base sequence represented by SEQ ID NO: 11; and the like.

As the DNA that is hybridizable to the base sequence represented by SEQ ID NO: 16 under high stringent conditions, there are employed, for example, DNAs comprising base sequences having at least about 70% homology, preferably at least about 80% homology, more preferably at least about 90% homology and most preferably at least about 95% homology, to the base sequence represented by SEQ ID NO: 16; and the like.

As the DNA that is hybridizable to the base sequence represented by SEQ ID NO: 18 under high stringent conditions, there are employed, for example, DNAs comprising base sequences having at least about 70% homology, preferably at least about 80% homology, more preferably at least about 90% homology and most preferably at least about 95% homology, to the base sequence represented by SEQ ID NO: 18; and the like.

As the DNA that is hybridizable to the base sequence represented by SEQ ID NO: 21 under high stringent conditions, there are employed, for example, DNAs comprising base sequences having at least about 70% homology, preferably at least about 80% homology, more preferably at least about 90% homology and most preferably at least about 95% homology, to the base sequence represented by SEQ ID NO: 21; and the like.

As the DNA that is hybridizable to the base sequence represented by SEQ ID NO: 23 under high stringent conditions, there are employed, for example, DNAs comprising base sequences having at least about 70% homology, preferably at least about 80% homology, more preferably at least about 90% homology and most preferably at least about 95% homology, to the base sequence represented by SEQ ID NO: 23; and the like.

As the DNA that is hybridizable to the base sequence represented by SEQ ID NO: 26 under high stringent conditions, there are employed, for example, DNAs comprising base sequences having at least about 70% homology, preferably at least about 80% homology, more preferably at least about 90% homology and most preferably at least about 95% homology, to the base sequence represented by SEQ ID NO: 26; and the like.

As the DNA that is hybridizable to the base sequence represented by SEQ ID NO: 28 under high stringent conditions, there are employed, for example, DNAs comprising base sequences having at least about 70% homology, preferably at least about 80% homology, more preferably at least about 90% homology and most preferably at least about 95% homology, to the base sequence represented by SEQ ID NO: 28; and the like.

Homology of the base sequences can be measured under the following conditions (Expectation value=10; gaps are allowed; filtering =ON; match score=1; mismatch score=−3)

using a homology scoring algorithm NCBI BLAST (National Center for Biotechnology Information Basic Local Alignment Search Tool).

The hybridization can be carried out by publicly known methods or by modifications thereof, for example, by the method described in Molecular Cloning, 2nd ed. (J. Sambrook et al., Cold Spring Harbor Lab. Press, 1989). A commercially available library can also be used according to the instructions of the attached manufacturer's protocol. The hybridization can be carried out preferably under high stringent conditions.

The high stringent conditions used herein are, for example, those in a sodium concentration at about 19 to 40 mM, preferably about 19 to 20 mM at a temperature of about 50 to 70° C., preferably about 60 to 65° C. In particular, hybridization conditions in a sodium concentration at about 19 mM at a temperature of about 65° C. are most preferred.

More specifically, there are employed:

(i) a DNA comprising the base sequence represented by SEQ ID NO: 2, a DNA comprising the base sequence represented by SEQ ID NO: 3, etc. as the DNA encoding the protein comprising the amino acid sequence represented by SEQ ID NO: 1;

(ii) a DNA comprising the base sequence represented by SEQ ID NO: 5, a DNA comprising the base sequence represented by SEQ ID NO: 6, etc. as the DNA encoding the protein comprising the amino acid sequence represented by SEQ ID NO: 4;

(iii) a DNA comprising the base sequence represented by SEQ ID NO: 8, a DNA comprising the base sequence represented by SEQ ID NO: 9, etc. as the DNA encoding the protein comprising the amino acid sequence represented by SEQ ID NO: 7;

(iv) a DNA comprising the base sequence represented by SEQ ID NO: 11, a DNA comprising the base sequence represented by SEQ ID NO: 12, etc. as the DNA encoding the protein comprising the amino acid sequence represented by SEQ ID NO: 10;

(v) a DNA comprising the base sequence represented by SEQ ID NO: 16, a DNA comprising the base sequence represented by SEQ ID NO: 19, etc. as the DNA encoding the protein comprising the amino acid sequence represented by SEQ ID NO: 15;

(vi) a DNA comprising the base sequence represented by SEQ ID NO: 18, a DNA comprising the base sequence represented by SEQ ID NO: 19, etc. as the DNA encoding the protein comprising the amino acid sequence represented by SEQ ID NO: 17;

(vii) a DNA comprising the base sequence represented by SEQ ID NO: 21, a DNA comprising the base sequence represented by SEQ ID NO: 24, etc. as the DNA encoding the protein comprising the amino acid sequence represented by SEQ ID NO: 20;

(viii) a DNA comprising the base sequence represented by SEQ ID NO: 23, a DNA comprising the base sequence represented by SEQ ID NO: 24, etc. as the DNA encoding the protein comprising the amino acid sequence represented by SEQ ID NO: 22;

(ix) a DNA comprising the base sequence represented by SEQ ID NO: 26, a DNA comprising the base sequence represented by SEQ ID NO: 29, etc. as the DNA encoding the protein comprising the amino acid sequence represented by SEQ ID NO: 25; and, (x) a DNA comprising the base sequence represented by SEQ ID NO: 28, a DNA comprising the base sequence represented by SEQ ID NO: 29, etc. as the DNA encoding the protein comprising the amino acid sequence represented by SEQ ID NO: 27.

The polynucleotide (e.g., DNA) encoding the partial peptide used in the present invention may be any polynucleotide so long as it contains the base sequence encoding the partial peptide used in the present invention described above. The polynucleotide may also be any of genomic DNA, genomic DNA library, cDNA derived from the cells and tissues described above, cDNA library derived from the cells and tissues described above and synthetic DNA.

As the DNA encoding the partial peptide used in the present invention, there are employed, for example, a DNA comprising a part of the DNA having the base sequence represented by SEQ ID NO: 2, SEQ ID NO: 5, SEQ ID NO: 8, SEQ ID NO: 11, SEQ ID NO: 16, SEQ ID NO: 18, SEQ ID NO: 21, SEQ ID NO: 23, SEQ ID NO: 26 or SEQ ID NO: 28, or a DNA comprising a base sequence hybridizable to the base sequence represented by EQ ID NO: 2, SEQ ID NO: 5, SEQ ID NO: 8, SEQ ID NO: 11, SEQ ID NO: 16, SEQ ID NO: 18, SEQ ID NO: 21, SEQ ID NO: 23, SEQ ID NO: 26 or SEQ ID NO: 28 under high stringent conditions and comprising a part of DNA encoding a protein having the activities of substantially the same nature as those of the protein of the present invention, and the like.

The DNA hybridizable to the base sequence represented by SEQ ID NO: 2, SEQ ID NO: 5, SEQ ID NO: 8, SEQ ID NO: 11, SEQ ID NO: 16, SEQ ID NO: 18, SEQ ID NO: 21, SEQ ID NO: 23, SEQ ID NO: 26 or SEQ ID NO: 28 indicates the same meaning as described above.

Methods for the hybridization and the high stringent conditions that can be used are the same as those described above.

For cloning of DNAs that completely encode the protein or partial peptide used in the present invention (hereinafter sometimes merely referred to as the protein of the present invention in the description of cloning of DNAs encoding the protein and partial peptide and their expression), the DNA can be either amplified by PCR using synthetic DNA primers containing a part of the base sequence encoding the protein of the present invention, or the DNA inserted into an appropriate vector can be selected by hybridization with a labeled DNA fragment or synthetic DNA that encodes a part or entire region of the protein of the present invention. The hybridization can be carried out, for example, according to the method described in Molecular Cloning, 2nd (J. Sambrook et al., Cold Spring Harbor Lab. Press, 1989). Where the hybridization is carried out using commercially available library, the procedures may be conducted in accordance with the protocol described in the attached instructions.

Substitution of the base sequence of DNA can be effected by publicly known methods such as the ODA-LA PCR method, the Gapped duplex method, the Kunkel method, etc., or its modification, using PCR, a publicly known kit available as Mutan™-super Express Km (manufactured by Takara Shuzo Co., Ltd.) or Mutan™-K (manufactured by Takara Shuzo Co., Ltd.), etc.

The cloned DNA encoding the protein can be used as it is, depending upon purpose or, if desired, after digestion with a restriction enzyme or after addition of a linker thereto. The DNA may contain ATG as a translation initiation codon at the 5' end thereof and TAA, TGA or TAG as a translation termination codon at the 3' end thereof. These translation initiation and termination codons may also be added by using an appropriate synthetic DNA adapter.

The expression vector for the protein of the present invention can be manufactured, for example, by (a) excising the desired DNA fragment from the DNA encoding the protein of the present invention, and then (b) ligating the DNA fragment with an appropriate expression vector downstream a promoter in the vector.

Examples of the vector include plasmids derived form *E. coli* (e.g., pBR322, pBR325, pUC12, pUC13), plasmids derived from *Bacillus subtilis* (e.g., pUB110, pTP5, pC194), plasmids derived from yeast (e.g., pSH19, pSH15), bacteriophages such as λ phage, etc., animal viruses such as *retrovirus, vaccinia virus, baculovirus*, etc. as well as pA1-11, pXT1, pRc/CMV, pRc/RSV, pcDNA I/Neo, etc.

The promoter used in the present invention may be any promoter if it matches well with a host to be used for gene expression. In the case of using animal cells as the host, examples of the promoter include SRa promoter, SV40 promoter, LTR promoter, CMV promoter, HSV-TK promoter, etc.

Among them, it is preferred to use CMV (cytomegalovirus) promoter, SRa promoter, etc. Where the host is bacteria of the genus *Escherichia*, preferred examples of the promoter include trp promoter, lac promoter, recA promoter, $\lambda P_L$ promoter, lpp promoter, T7 promoter, etc. In the case of using bacteria of the genus *Bacillus* as the host, preferred example of the promoter are SPO1 promoter, SPO2 promoter, penP promoter, etc. When yeast is used as the host, preferred examples of the promoter are PHO5 promoter, PGK promoter, GAP promoter, ADH promoter, etc. When insect cells are used as the host, preferred examples of the promoter include polyhedrin prompter, P10 promoter, etc.

In addition to the foregoing examples, the expression vector may further optionally contain an enhancer, a splicing signal, a poly A addition signal, a selection marker, SV40 replication origin (hereinafter sometimes abbreviated as SV40ori), etc. Examples of the selection marker include dihydrofolate reductase (hereinafter sometimes abbreviated as dhfr) gene [methotrexate (MTX) resistance], ampicillin resistant gene (hereinafter sometimes abbreviated as $Amp^r$), neomycin resistant gene (hereinafter sometimes abbreviated as $Neo^r$, G418 resistance), etc. In particular, when dhfr gene is used as the selection marker using dhfr gene-deficient Chinese hamster cells, selection can also be made on a thymidine free medium.

If necessary, a signal sequence that matches with a host is added to the N-terminus of the protein of the present invention. Examples of the signal sequence that can be used are PhoA signal sequence, OmpA signal sequence, etc. when bacteria of the genus *Escherichia* is used as the host; α-amylase signal sequence, subtilisin signal sequence, etc. when bacteria of the genus *Bacillus* is used as the host; MFα signal sequence, SUC2 signal sequence, etc. when yeast is used as the host; and insulin signal sequence, α-interferon signal sequence, antibody molecule signal sequence, etc. when animal cells are used as the host, respectively.

Using the vector containing the DNA encoding the protein of the present invention thus constructed, transformants can be manufactured.

Examples of the host, which may be employed, are bacteria belonging to the genus *Escherichia*, bacteria belonging to the genus *Bacillus*, yeast, insect cells, insects, animal cells, etc.

Specific examples of the bacteria belonging to the genus *Escherichia* include *Escherichia coli* K12 DH1 [Proc. Natl. Acad. Sci. U.S.A., 60, 160 (1968)], JM103 [Nucleic Acids Research, 9, 309 (1981)], JA221 [Journal of Molecular Biology, 120, 517 (1978)], HB101 [Journal of Molecular Biology, 41, 459 (1969)], C600 [Genetics, 39, 440 (1954)], etc.

Examples of the bacteria belonging to the genus *Bacillus* include *Bacillus subtilis* M1114 [Gene, 24, 255 (1983)], 207-21 [Journal of Biochemistry, 95, 87 (1984)], etc.

Examples of yeast include *Saccharomyces cereviseae* AH22, $AH22R^-$, NA87-11A, DKD-5D, 20B-12, *Schizosaccharomyces pombe* NCYC1913, NCYC2036, *Pichia pastoris* KM71, etc.

Examples of insect cells include, for the virus AcNPV, *Spodoptera frugiperda* cell (Sf cell), MG1 cell derived from mid-intestine of *Trichoplusia ni*, High Five™ cell derived from egg of *Trichoplusia ni*, cells derived from *Mamestra brassicae*, cells derived from Estigmena acrea, etc.; and for the virus BmNPV, *Bombyx mori* N cell (BmN cell), etc. is used. Examples of the Sf cell which can be used are Sf9 cell (ATCC CRL1711), Sf21 cell (both cells are described in Vaughn, J. L. et al., In Vivo, 13, 213-217 (1977)), etc.

As the insect, for example, a larva of *Bombyx mori* can be used [Maeda et al., Nature, 315, 592 (1985)].

Examples of animal cells include monkey cell COS-7, Vero, Chinese hamster cell CHO (hereinafter referred to as CHO cell), dhfr gene-deficient Chinese hamster cell CHO (hereinafter simply referred to as CHO ($dhfr^-$) cell), mouse L cell, mouse AtT-20, mouse myeloma cell, mouse ATDC5 cell, rat GH3, human FL cell, etc.

Bacteria belonging to the genus *Escherichia* can be transformed, for example, by the method described in Proc. Natl. Acad. Sci. U.S.A., 69, 2110 (1972), Gene, 17, 107 (1982), etc.

Bacteria belonging to the genus *Bacillus* can be transformed, for example, by the method described in Molecular & General Genetics, 168, 111 (1979), etc.

Yeast can be transformed, for example, by the method described in Methods in Enzymology, 194, 182-187 (1991), Proc. Natl. Acad. Sci. U.S.A., 75, 1929 (1978), etc.

Insect cells or insects can be transformed, for example, according to the method described in Bio/Technology, 6, 47-55(1988), etc.

Animal cells can be transformed, for example, according to the method described in Saibo Kogaku (Cell Engineering), extra issue 8, Shin Saibo Kogaku Jikken Protocol (New Cell Engineering Experimental Protocol), 263-267 (1995) (published by Shujunsha), or Virology, 52, 456 (1973).

Thus, the transformants transformed with the expression vectors containing the DNAs encoding the protein can be obtained.

Where the host is bacteria belonging to the genus *Escherichia* or the genus *Bacillus*, the transformant can be appropriately cultured in a liquid medium which contains materials required for growth of the transformant such as carbon sources, nitrogen sources, inorganic materials, and the like. Examples of the carbon sources include glucose, dextrin, soluble starch, sucrose, etc.; examples of the nitrogen sources include inorganic or organic materials such as ammonium salts, nitrate salts, corn steep liquor, peptone, casein, meat extract, soybean cake, potato extract, etc.; and, examples of the inorganic materials are calcium chloride, sodium dihydrogenphosphate, magnesium chloride, etc. In addition, yeast extracts, vitamins, growth promoting factors etc. may also be added to the medium. Preferably, pH of the medium is adjusted to about 5 to about 8.

A preferred example of the medium for culturing the bacteria belonging to the genus *Escherichia* is M9 medium supplemented with glucose and Casamino acids [Miller, Journal of Experiments in Molecular Genetics, 431-433, Cold Spring Harbor Laboratory, New York, 1972]. If necessary, a chemical such as 3β-indolylacrylic acid can be added to the medium thereby to activate the promoter efficiently.

Where the bacteria belonging to the genus *Escherichia* are used as the host, the transformant is usually cultivated at about 15 to 43° C. for about 3 to 24 hours. If necessary, the culture may be aerated or agitated.

Where the bacteria belonging to the genus *Bacillus* are used as the host, the transformant is cultured generally at about 30 to 40° C. for about 6 to 24 hours. If necessary, the culture can be aerated or agitated.

Where yeast is used as the host, the transformant is cultivated, for example, in Burkholder's minimal medium [Bostian, K. L. et al., Proc. Natl. Acad. Sci. U.S.A., 77, 4505 (1980)] or in SD medium supplemented with 0.5% Casamino acids [Bitter, G. A. et al., Proc. Natl. Acad. Sci. U.S.A., 81, 5330 (1984)]. Preferably, pH of the medium is adjusted to about 5 to 8. In general, the transformant is cultivated at about 20 to 35° C. for about 24 to 72 hours. If necessary, the culture can be aerated or agitated.

Where insect cells or insects are used as the host, the transformant is cultivated in, for example, Grace's Insect Medium (Grace, T. C. C., Nature), 195, 788 (1962)) to which an appropriate additive such as immobilized 10% bovine serum is added. Preferably, pH of the medium is adjusted to about 6.2 to about 6.4. Normally, the transformant is cultivated at about 27° C. for about 3 days to about 5 days and, if necessary, the culture can be aerated or agitated.

Where animal cells are employed as the host, the transformant is cultured in, for example, MEM medium containing about 5 to 20% fetal bovine serum [Science, 122, 501 (1952)], DMEM medium [Virology, 8, 396 (1959)], RPMI 1640 medium [The Journal of the American Medical Association, 199, 519 (1967)], 199 medium [Proceeding of the Society for the Biological Medicine, 73, 1 (1950)], etc. Preferably, pH of the medium is adjusted to about 6 to about 8. The transformant is usually cultivated at about 30° C. to about 40° C. for about 15 to 60 hours and, if necessary, the culture can be aerated or agitated.

As described above, the protein of the present invention can be produced in the transformant, on the cell membrane of the transformant, or outside of the transformant.

The protein of the present invention can be separated and purified from the culture described above by the following procedures.

When the protein of the present invention is extracted from the bacteria or cells, the bacteria or cell is collected after culturing by a publicly known method and suspended in an appropriate buffer. The bacteria or cell is then disrupted by publicly known methods such as ultrasonication, a treatment with lysozyme and/or freeze-thaw cycling, followed by centrifugation, filtration, etc to produce crude extract of the protein. Thus, the crude extract of the protein can be obtained. The buffer used for the procedures may contain a protein modifier such as urea or guanidine hydrochloride, or a surfactant such as Triton X-100™, etc. When the protein is secreted in the culture broth, the supernatant can be separated, after completion of the cultivation, from the bacteria or cell to collect the supernatant by a publicly known method.

The protein contained in the supernatant or the extract thus obtained can be purified by appropriately combining the publicly known methods for separation and purification. Such publicly known methods for separation and purification include a method utilizing difference in solubility such as salting out, solvent precipitation, etc.; a method mainly utilizing difference in molecular weight such as dialysis, ultrafiltration, gel filtration, SDS-polyacrylamide gel electrophoresis, etc.; a method utilizing difference in electric charge such as ion exchange chromatography, etc.; a method utilizing difference in specific affinity such as affinity chromatography, etc.; a method utilizing difference in hydrophobicity such as reverse phase high performance liquid chromatography, etc.; a method utilizing difference in isoelectric point such as isoelectrofocusing electrophoresis; and the like.

When the protein thus obtained is in a free form, the protein can be converted into the salt by publicly known methods or modifications thereof. On the other hand, when the protein is obtained in the form of a salt, it can be converted into the free form or in the form of a different salt by publicly known methods or modifications thereof.

The protein produced by the recombinant can be treated, prior to or after the purification, with an appropriate protein-modifying enzyme so that the protein can be subjected to addition of an appropriate modification or removal of a partial polypeptide. Examples of the protein-modifying enzyme include trypsin, chymotrypsin, arginyl endopeptidase, protein kinase, glycosidase and the like.

The presence of the thus produced protein of the present invention can be determined by an enzyme immunoassay or western blotting using a specific antibody.

The antibodies to the protein or partial peptide used in the present invention, or its salts may be any of polyclonal and monoclonal antibodies, as long as they are capable of recognizing the protein or partial peptide used in the present invention, or its salts.

The antibodies to the protein or partial peptide used in the present invention, or its salts (hereinafter they are sometimes collectively referred to as the protein of the present invention in the description of the antibodies) can be produced by a publicly known method of producing an antibody or antiserum, using the protein of the present invention as an antigen.

[Preparation of Monoclonal Antibody]

(a) Preparation of Monoclonal Antibody-Producing Cells

The protein of the present invention is administered to warm-blooded animals either solely or together with carriers or diluents to the site where the production of antibody is possible by the administration. In order to potentiate the antibody productivity upon the administration, complete Freund's adjuvants or incomplete Freund's adjuvants may be administered. The administration is usually carried out once every about 2 to about 6 weeks and about 2 to about 10 times in total. Examples of the applicable warm-blooded animals are monkeys, rabbits, dogs, guinea pigs, mice, rats, sheep, goats and fowl, with the use of mice and rats being preferred.

In the preparation of monoclonal antibody-producing cells, a warm-blooded animal, e.g., mice, immunized with an antigen wherein the antibody titer is noted is selected, then spleen or lymph node is collected after 2 to 5 days from the final immunization and antibody-producing cells contained therein are fused with myeloma cells from homozoic or heterozoic animal to give monoclonal antibody-producing hybridomas. Measurement of the antibody titer in antisera may be carried out, for example, by reacting a labeled protein, which will be described later, with the antiserum followed by assaying the binding activity of the labeling agent bound to the antibody. The fusion may be carried out, for example, by the known method by Koehler and Milstein [Nature, 256, 495, and (1975)]. Examples of the fusion accelerator are polyethylene glycol (PEG), *Sendai virus*, etc., of which PEG is preferably employed.

Examples of the myeloma cells are those collected from warm-blooded animals such as NS-1, P3U1, SP2/0, AP-1, etc. In particular, P3U1 is preferably employed. A preferred ratio of the count of the antibody-producing cells used (spleen cells) to the count of myeloma cells is within a range of approximately 1:1 to 20:1. When PEG (preferably, PEG 1000 to PEG 6000) is added in a concentration of approximately 10 to 80% followed by incubation at 20 to 40° C., preferably at 30 to 37° C. for 1 to 10 minutes, an efficient cell fusion can be carried out.

Various methods can be used for screening of monoclonal antibody-producing hybridomas. Examples of such methods include a method which comprises adding the supernatant of a hybridoma to a solid phase (e.g., a microplate) adsorbed with the protein as an antigen directly or together with a carrier, adding an anti-immunoglobulin antibody (where mouse cells are used for the cell fusion, anti-mouse immunoglobulin antibody is used) labeled with a radioactive substance or an enzyme or Protein A and detecting the monoclonal antibody bound to the solid phase, and a method which comprises adding the supernatant of hybridoma to a solid phase adsorbed with an anti-immunoglobulin antibody or Protein A, adding the protein labeled with a radioactive substance or an enzyme and detecting the monoclonal antibody bound to the solid phase, or the like.

The monoclonal antibody can be screened according to publicly known methods or their modifications. In general, the screening can be performed in a medium for animal cells supplemented with HAT (hypoxanthine, aminopterin and thymidine). Any screening and growth medium can be employed as far as the hybridoma can grow there. For example, RPMI 1640 medium containing 1 to 20%, preferably 10 to 20% fetal bovine serum, GIT medium (Wako Pure Chemical Industries, Ltd.) containing 1 to 10% fetal bovine serum, a serum free medium for cultivation of a hybridoma (SFM-101, Nissui Seiyaku Co., Ltd.) And the like, can be used for the screening and growth medium. The culture is carried out generally at 20 to 40° C., preferably at 37° C., for about 5 days to about 3 weeks, preferably 1 to 2 weeks, normally in 5% $CO_2$. The antibody titer of the culture supernatant of a hybridoma can be determined as in the assay for the antibody titer in antisera described above.

(b) Purification of Monoclonal Antibody

Separation and purification of a monoclonal antibody can be carried out by publicly known methods, such as separation and purification of immunoglobulins [for example, salting-out, alcohol precipitation, isoelectric point precipitation, electrophoresis, adsorption and desorption with ion exchangers (e.g., DEAE), ultracentrifugation, gel filtration, or a specific purification method which comprises collecting only an antibody with an activated adsorbent such as an antigen-binding solid phase, Protein A or Protein G and dissociating the binding to obtain the antibody.]

[Preparation of Polyclonal Antibody]

The polyclonal antibody of the present invention can be manufactured by publicly known methods or modifications thereof. For example, a warm-blooded animal is immunized with an immunogen (protein antigen) per se, or with a complex of immunogen and a carrier protein formed in a manner similar to the method described above for the manufacture of monoclonal antibodies. The product containing the antibody to the protein of the present invention is collected from the immunized animal followed by separation and purification of the antibody.

In the complex of immunogen and carrier protein used to immunize a warm-blooded animal, the type of carrier protein and the mixing ratio of carrier to hapten may be any type and in any ratio, as long as the antibody is efficiently produced to the hapten immunized by crosslinking to the carrier. For example, bovine serum albumin, bovine thyroglobulin or hemocyanin is coupled to hapten in a carrier-to-hapten weight ratio of approximately 0.1 to 20, preferably about 1 to 5.

A variety of condensation agents can be used for the coupling of carrier to hapten. Glutaraldehyde, carbodiimide, maleimide activated ester and activated ester reagents containing thiol group or dithiopyridyl group are used for the coupling.

The condensation product is administered to warm-blooded animals either solely or together with carriers or diluents to the site that can produce the antibody by the administration. In order to potentiate the antibody productivity upon the administration, complete Freund's adjuvant or incomplete Freund's adjuvant may be administered. The administration is usually made once every about 2 to 6 weeks and about 3 to 10 times in total.

The polyclonal antibody can be collected from the blood, ascites, etc., preferably from the blood of warm-blooded animal immunized by the method described above.

The polyclonal antibody titer in antiserum can be assayed by the same procedure as that for the determination of serum antibody titer described above. The separation and purification of the polyclonal antibody can be carried out, following the method for the separation and purification of immunoglobulins performed as in the separation and purification of monoclonal antibodies described hereinabove.

The antisense polynucleotide having a complementary or substantially complementary base sequence to the base sequence of a polynucleotide encoding the protein or partial peptide used in the present invention (e.g., DNA (hereinafter these DNAs are sometimes collectively referred to as the DNA of the present invention in the description of antisense polynucleotide)) can be any antisense polynucleotide, so long as it possesses a base sequence complementary or substantially complementary to the base sequence of the polynucleotide (e.g., DNA) of the present invention and capable of suppressing the expression of said DNA, but antisense DNA is preferred.

The base sequence substantially complementary to the DNA of the present invention may include, for example, a base sequence having at least about 70% homology, preferably at least about 80% homology, more preferably at least about 90% homology and most preferably at least about 95% homology, to the entire base sequence or to its partial base sequence (i.e., complementary strand to the DNA of the present invention), and the like. Especially in the entire base sequence of the complementary strand to the DNA of the present invention, preferred are (a) An antisense polynucleotide having at least about 70% homology, preferably at least about 80% homology, more preferably at least about 90% homology and most preferably at least about 95% homology, to the complementary strand of the base sequence which encodes the N-terminal region of the protein of the present invention (e.g., the base sequence around the initiation codon) in the case of antisense polynucleotide directed to translation inhibition and (b) An antisense polynucleotide having at least about 70% homology, preferably at least about 80% homology, more preferably at least about 90% homology and most preferably at least about 95% homology, to the complementary strand of the entire base sequence of the DNA of the present invention having intron, in the case of antisense polynucleotide directed to RNA degradation by RNaseH, respectively.

Specific examples include an antisense polynucleotide containing the entire or part of a base sequence complementary or substantially complementary to a base sequence of DNA containing the base sequence represented by SEQ ID NO: 2, SEQ ID NO: 5, SEQ ID NO: 8, SEQ ID NO: 11, SEQ ID NO: 16, SEQ ID NO: 18, SEQ ID NO: 21, SEQ ID NO: 23, SEQ ID NO: 26 or SEQ ID NO: 28, preferably an antisense polynucleotide containing the entire or part of a base sequence complementary to a base sequence of DNA containing the base sequence represented by SEQ ID NO: 2, SEQ ID NO: 5, SEQ ID NO: 8, SEQ ID NO: 11, SEQ ID NO: 16, SEQ ID NO: 18, SEQ ID NO: 21, SEQ ID NO: 23, SEQ ID NO: 26 or SEQ ID NO: 28, etc.

The antisense polynucleotide is generally constituted by bases of about 10 to about 40, preferably about 15 to about 30.

To prevent digestion with a hydrolase such as nuclease, etc., the phosphoric acid residue (phosphate) of each nucleotide that constitutes the antisense DNA may be substituted with chemically modified phosphoric acid residues, e.g., phosphorothioate, methyl phosphonate, phosphorodithionate, etc. Also, the sugar (deoxyribose) in each nucleotide may be replaced by a chemically modified structure such as 2'-O-methylation, etc. The base part (pyrimidine, purine) may also be chemically modified and may be any one which hybridizes to a DNA containing the base sequence represented by SEQ ID NO: 2. These antisense polynucleotides may be synthesized using a publicly known DNA synthesizer, etc.

According to the present invention, the antisense polynucleotide (nucleic acid) capable of inhibiting the replication or expression of a gene for the protein of the present invention can be designed and synthesized based on the base sequence information of cloned or identified protein-encoding DNA. Such a polynucleotide (nucleic acid) is hybridizable to RNA of a gene for the protein of the present invention to inhibit the synthesis or function of said RNA or is capable of modulating and/or controlling the expression of a gene for the protein of the present invention via interaction with RNA associated with the protein of the present invention. Polynucleotides complementary to the selected sequences of RNA associated with the protein of the present invention and polynucleotides specifically hybridizable to RNA associated with the protein of the present invention are useful in modulating/controlling the in vivo and in vitro expression of the protein gene of the present invention, and are useful for the treatment or diagnosis of diseases, etc. The term “corresponding” is used to mean homologous to or complementary to a particular sequence of the nucleotide including the gene, base sequence or nucleic acid. The term “corresponding” between nucleotides, base sequences or nucleic acids and peptides (proteins) usually refer to amino acids of a peptide (protein) under the order derived from the sequence of nucleotides (nucleic acids) or their complements. In the protein genes, the 5' end hairpin loop, 5' end 6-base-pair repeats, 5' end untranslated region, polypeptide translation initiation codon, protein coding region, ORF translation termination codon, 3' end untranslated region, 3' end palindrome region, and 3' end hairpin loop, may be selected as preferred target regions, though any other region may be selected as a target in the protein genes.

The relationship between the targeted nucleic acids and the polynucleotides complementary to at least a part of the target region, specifically the relationship between the target nucleic acids and the polynucleotides hybridizable to the target region, can be denoted to be “antisense.” Examples of the antisense polynucleotides include polynucleotides containing 2-deoxy-D-ribose, polynucleotides containing D-ribose, any other type of polynucleotides which are N-glycosides of a purine or pyrimidine base, or other polymers containing non-nucleotide backbones (e.g., commercially available protein nucleic acids and synthetic sequence-specific nucleic acid polymers) or other polymers containing nonstandard linkages (provided that the polymers contain nucleotides having such a configuration that allows base pairing or base stacking, as is found in DNA or RNA), etc. The antisense polynucleotides may be double-stranded DNA, single-stranded DNA, double-stranded RNA, single-stranded RNA or a DNA:RNA hybrid, and may further include unmodified polynucleotides (or unmodified oligonucleotides), those with publicly known types of modifications, for example, those with labels known in the art, those with caps, methylated polynucleotides, those with substitution of one or more naturally occurring nucleotides by their analogue, those with intramolecular modifications of nucleotides such as those with uncharged linkages (e.g., methyl phosphonates, phosphotriesters, phosphoramidates, carbamates, etc.) And those with charged linkages or sulfur-containing linkages (e.g., phosphorothioates, phosphorodithioates, etc.), those having side chain groups such as proteins (nucleases, nuclease inhibitors, toxins, antibodies, signal peptides, poly-L-lysine, etc.), saccharides (e.g., monosaccharides, etc.), those with intercalators (e.g., acridine, psoralen, etc.), those containing chelators (e.g., metals, radioactive metals, boron, oxidative metals, etc.), those containing alkylating agents, those with modified linkages (e.g., α anomeric nucleic acids, etc.), and the like. Herein the terms “nucleoside”, “nucleotide” and “nucleic acid” are used to refer to moieties that contain not only the purine and pyrimidine bases, but also other heterocyclic bases, which have been modified. Such modifications may include methylated purines and pyrimidines, acylated purines and pyrimidines and other heterocyclic rings. Modified nucleotides and modified nucleotides also include modifications on the sugar moiety, wherein, for example, one or more hydroxyl groups may optionally be substituted with a halogen atom(s), an aliphatic group(s), etc., or may be converted into the corresponding functional groups such as ethers, amines, or the like.

The antisense polynucleotide (nucleic acid) of the present invention is RNA, DNA or a modified nucleic acid (RNA, DNA). Specific examples of the modified nucleic acid are, but not limited to, sulfur and thiophosphate derivatives of nucleic acids and those resistant to degradation of polynucleoside amides or oligonucleoside amides. The antisense nucleic acids of the present invention can be modified preferably based on the following design, that is, by increasing the intracellular stability of the antisense nucleic acid, enhancing the cell permeability of the antisense nucleic acid, increasing the affinity of the nucleic acid to the targeted sense strand to a higher level, or minimizing the toxicity, if any, of the antisense nucleic acid.

Most of such modifications are known in the art, as disclosed in J. Kawakami, et al., Pharm. Tech. Japan, Vol. 8, pp. 247, 1992; Vol. 8, pp. 395, 1992; S. T. Crooke, et al. ed., Antisense Research and Applications, CRC Press, 1993; etc.

The antisense nucleic acid of the present invention may contain altered or modified sugars, bases or linkages. The antisense nucleic acid may also be provided in a specialized form such as liposomes, microspheres, or may be applied to gene therapy, or may be provided in combination with attached moieties. Such attached moieties include polycations such as polylysine that act as charge neutralizers of the phosphate backbone, or hydrophobic moieties such as lipids (e.g., phospholipids, cholesterols, etc.) that enhance the interaction with cell membranes or increase uptake of the nucleic acid. Preferred examples of the lipids to be attached are cholesterols or derivatives thereof (e.g., cholesteryl chloroformate, cholic acid, etc.). These moieties may be attached to the nucleic acid at the 3' or 5' ends thereof and may also be attached thereto through a base, sugar, or intramolecular nucleoside linkage. Other moieties may be capping groups specifically placed at the 3' or 5' ends of the nucleic acid to prevent degradation by nucleases such as exonuclease, RNase, etc. Such capping groups include, but are not limited to, hydroxyl protecting groups known in the art, including glycols such as polyethylene glycol, tetraethylene glycol and the like.

The inhibitory action of the antisense nucleic acid can be examined using the transformant of the present invention, the gene expression system of the present invention in vivo and in vitro, or the translation system for the protein of the present invention in vivo and in vitro. The nucleic acid can be applied to cells by a variety of publicly known methods.

Hereinafter, the protein of the present invention, its partial peptides, or salts thereof (hereinafter sometimes merely referred to as the protein of the present invention), the DNA encoding the protein of the present invention or its partial peptides (hereinafter sometimes merely referred to as the DNA of the present invention), the antibodies to the protein of the present invention, its partial peptides, or salts thereof (hereinafter sometimes merely referred to as the antibody of the present invention) And the antisense polynucleotides to the DNA of the present invention (hereinafter sometimes merely referred to as the antisense polynucleotide of the present invention) are specifically described for their applications.

The protein of the present invention is increasingly expressed in cancer tissues and is thus available as a disease marker. That is, the protein is useful as a marker for early diagnosis in cancer tissues, for judgment of severity in conditions, or for predicted development of these diseases. Therefore, the pharmaceuticals comprising the antisense polynucleotide to the polynucleotide encoding the protein of the present invention, the compound or its salts that inhibits the activity of the protein of the present invention, the compound or its salts that inhibits the expression of a gene for the protein of the present invention, or the antibody to the protein of the present invention can be used as prophylactic/therapeutic agents for cancer such as colon cancer, breast cancer, lung cancer, prostate cancer, esophageal cancer, gastric cancer, liver cancer, biliary tract cancer, spleen cancer, renal cancer, bladder cancer, uterine cancer, testicular cancer, thyroid cancer, pancreatic cancer, brain tumor, blood tumor, etc. (preferably prophylactic/therapeutic agents for breast cancer, lung cancer, etc.), and as apoptosis promoters of cancer cells.

(1) Screening of Drug Candidate Compounds for Disease

The protein of the present invention shows increased expression in cancer tissues. In addition, when the activity (e.g., the chloroperoxidase activity) of the protein of the present invention is inhibited, cancer cells induce apoptosis. Thus, the compound or its salts inhibiting the activity of the protein of the present invention can be used as a prophylactic/therapeutic agents for cancer, including colon cancer, breast cancer, lung cancer, prostate cancer, esophageal cancer, gastric cancer, liver cancer, biliary tract cancer, spleen cancer, renal cancer, bladder cancer, uterine cancer, testicular cancer, thyroid cancer, pancreatic cancer, brain tumor, blood tumor, etc. Preferably, the compound or its salts can be used as a prophylactic/therapeutic agent for breast cancer, lung cancer, etc. Moreover, the compound or its salts inhibiting the activity (e.g., the chloroperoxidase activity) of the protein of the present invention can be used as, e.g., apoptosis promoters of cancer cells.

Accordingly, the protein of the present invention is useful as a reagent for screening the compound or its salts that inhibit the activity of the protein of the present invention.

That is, the present invention provides a method of screening the compound or its salts that inhibit the activity of the protein of the present invention, which comprises using the protein of the present invention.

Specifically, there is employed the method of screening the compound or its salts inhibiting the activity, which comprises comparing (i) the chloroperoxidase activity of a cell capable of producing the protein of the present invention with (ii) the chloroperoxidase activity of a mixture of the cell capable of producing the protein of the present invention and a test compound.

In the screening method described above, for example, in the cases (i) And (ii), the chloroperoxidase activity is assayed and the activity of forming dichlorodimedone by adding chlorine to monochlorodimedone is compared as an indicator.

The chloroperoxidase activity is assayed by publicly known methods, e.g., by the method described in Journal of Biological Chemistry (J. Biol. Chem.), 241, 1763-1768 (1966).

As the cells capable of producing the protein of the present invention, there are used, for example, the aforesaid host (transformant) transformed with a vector containing the DNA encoding the protein of the present invention. Preferably, animal cells such as COS7 cells, CHO cells, HEK293 cells, MCF-7 cells, etc. are used as the host. For the screening, the transformant, in which the protein of the present invention has been expressed in the cells, e.g., by culturing through the procedure described above, is preferably employed. The procedure for incubating the cells capable of expressing the protein of the present invention is similar to the incubation procedure for the transformant of the present invention described above.

Examples of the test compound include peptides, proteins, non-peptide compounds, synthetic compounds, fermentation products, cell extracts, plant extracts, animal tissue extracts, etc.

For example, when a test compound inhibits the chloroperoxidase activity in the case (ii) described above by at least about 20%, preferably at least 30% and more preferably at least about 50%, as compared to the case (i) above, the test compound can be selected as the compound that inhibits the activity of the protein of the present invention.

The compound having the activity of inhibiting the activity of the protein of the present invention is useful as a safe and low toxic pharmaceutical for suppressing the physiological activities of the protein of the present invention.

The compound or its salt obtained using the screening method or screening kit of the present invention is the compound selected from, for example, peptides, proteins, non-peptide compounds, synthetic compounds, fermentation products, cell extracts, plant extracts, animal tissue extracts, plasma, etc. The salts of these compounds used are those given above as the salts of the peptide of the present invention.

Furthermore, the gene for the protein of the present invention also shows an increased expression in cancer tissues. Accordingly, the compound or its salts inhibiting the expression of the gene for the protein of the present invention can also be used as a prophylactic/therapeutic agent for cancer, e.g., breast cancer, colon cancer, lung cancer, prostate cancer, esophageal cancer, gastric cancer, liver cancer, biliary tract cancer, spleen cancer, renal cancer, bladder cancer, uterine cancer, testicular cancer, thyroid cancer, pancreatic cancer, brain tumor, blood tumor, etc. Preferably, the compound or its salts are used as a prophylactic/therapeutic agent for breast cancer, lung cancer, etc. Furthermore, the compound or its salts inhibiting the expression of the gene for the protein of the present invention can be used as, e.g., apoptosis promoters of cancer cells.

Therefore, the polynucleotide (e.g., DNA) of the present invention is useful as a reagent for screening the compound or its salts inhibiting the expression of the gene for the protein of the present invention.

For the screening, there is a method of screening which comprises comparing (iii) the case that a cell capable of producing the protein of the present invention is incubated and (iv) the case that a cell capable of producing the protein used in the present invention is incubated in the presence of a test compound.

In the screening method described above, the expression level of the gene described above (specifically, the level of the protein of the present invention or the level of mRNA encoding the said protein) is determined in the cases of (iii) And (iv), followed by comparison.

Examples of the test compound and the cells capable of producing the protein of the present invention are the same as described above.

The level of the protein can be determined by publicly known methods, e.g., by measuring the aforesaid protein present in the cell extract, etc., using an antibody capable of recognizing the protein of the present invention, in accordance with methods like western blot analysis, ELISA, etc., or their modifications.

The mRNA level can be determined by publicly known methods, e.g., in accordance with methods such as Northern hybridization using a nucleic acid containing the entire or a part of SEQ ID NO: 2, SEQ ID NO: 5, SEQ ID NO: 8, SEQ ID NO: 11, SEQ ID NO: 16, SEQ ID NO: 18, SEQ ID NO: 21, SEQ ID NO: 23, SEQ ID NO: 26 or SEQ ID NO: 28 as a probe, or PCR using a nucleic acid containing the entire or a part of SEQ ID NO: 2, SEQ ID NO: 5, SEQ ID NO: 8, SEQ ID NO: 11, SEQ ID NO: 16, SEQ ID NO: 18, SEQ ID NO: 21, SEQ ID NO: 23, SEQ ID NO: 26 or SEQ ID NO: 28 as a primer, or modifications thereof.

For example, when a test compound inhibits the expression of the gene in the case (iv) described above by at least about 20%, preferably at least 30% and more preferably at least about 50%, as compared to the case (iii) above, the test compound can be selected to be the compound capable of inhibiting the expression of the gene for the protein of the present invention.

The screening kit of the present invention comprises the protein used in the present invention, its partial peptide or salts thereof, or the cell capable of producing the protein used in the present invention, or its partial peptide.

The compound or its salts obtained by using the screening method or screening kit of the present invention is the test compound described above, e.g., a compound selected from peptides, proteins, non-peptide compounds, synthetic compounds, fermentation products, cell extracts, plant extracts, animal tissue extracts, plasma, etc., or its salt, which is a compound or its salt inhibiting the activity of the protein of the present invention, a compound or its salt inhibiting the expression of the gene for the protein of the present invention.

The salts of these compounds used are those given above as the salts of the protein of the present invention.

The compound or its salts inhibiting the activity of the protein of the present invention and the compound or its salts inhibiting the expression of the gene for the protein of the present invention are useful as pharmaceuticals, respectively, for example, as therapeutic/prophylactic agents for cancer, e.g., colon cancer, breast cancer, lung cancer, prostate cancer, esophageal cancer, gastric cancer, liver cancer, biliary tract cancer, spleen cancer, renal cancer, bladder cancer, uterine cancer, testicular cancer, thyroid cancer, pancreatic cancer, brain tumor, blood tumor, etc. (preferably as prophylactic/therapeutic agents for breast cancer, lung cancer, etc.), or as apoptosis promoters of cancer cells.

Where the compound or its salt obtained by using the screening method or screening kit of the present invention is used as the prophylactic/therapeutic agent described above, these compounds can be converted into pharmaceutical preparations in a conventional manner.

For example, the composition for oral administration includes solid or liquid preparations, specifically, tablets (including dragees and film-coated tablets), pills, granules, powdery preparations, capsules (including soft capsules), syrup, emulsions, suspensions, etc. Such a composition is manufactured by publicly known methods and contains a vehicle, a diluent or excipient conventionally used in the field of pharmaceutical preparations. Examples of the vehicle or excipient for tablets are lactose, starch, sucrose, magnesium stearate, etc.

Examples of the composition for parenteral administration are injectable preparations, suppositories, etc. The injectable preparations may include dosage forms such as intravenous, subcutaneous, intracutaneous and intramuscular injections, drip infusions, intraarticular injections, etc. These injectable preparations may be prepared by methods publicly known. For example, the injectable preparations may be prepared by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mols) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is usually filled in an appropriate ampoule. The suppository used for rectal administration may be prepared by blending the aforesaid antibody or its salt with conventional bases for suppositories.

Advantageously, the pharmaceutical compositions for oral or parenteral use described above are prepared into pharmaceutical preparations with a unit dose suited to fit a dose of the active ingredients. Such unit dose preparations include, for example, tablets, pills, capsules, injections (ampoules), suppositories, etc. The amount of the aforesaid compound contained is generally 5 to 500 mg per dosage unit form; it is preferred that the aforesaid antibody is contained in about 5 to about 100 mg especially in the form of injection, and in 10 to 250 mg for the other forms.

Each composition described above may further contain other active components unless formulation causes any adverse interaction with the compound described above.

Since the pharmaceutical preparations thus obtained are safe and low toxic, they can be administered to human or warm-blooded animal (e.g., mouse, rat, rabbit, sheep, swine, bovine, horse, fowl, cat, dog, monkey, chimpanzee, etc.) orally or parenterally.

The dose of the above compound or its salts may vary depending upon its action, target disease, subject to be administered, route of administration, etc. For example, when the compound or its salt inhibiting the expression of the gene for the protein of the present invention is orally administered for the purpose of treating, e.g., breast cancer, the compound or its salt is generally administered to an adult (as 60 kg body weight) in a daily dose of about 0.1 to about 100 mg, preferably about 1.0 to about 50 mg and more preferably about 1.0 to about 20 mg. In parenteral administration, a single dose of the said compound or its salt may vary depending upon subject to be administered, target disease, etc. When the compound or its salts inhibiting the expression of the gene for the protein of the present invention is administered to an adult (as 60 kg body weight) in the form of an injectable preparation for the purpose of treating, e.g., breast cancer, it is advantageous to administer the compound or its salt at cancerous lesions by way of injection in a daily dose of about 0.01 to about 30 mg, preferably about 0.1 to about 20 mg, and more preferably about 0.1 to about 10 mg. For other animal species, the corresponding dose as converted per 60 kg weight can be administered.

(2) Quantification for the Protein of the Present Invention

The antibody of the present invention is capable of specifically recognizing the protein of the present invention and therefore can be used for quantification of the protein of the present invention in a test sample fluid, in particular, for quantification by sandwich immunoassay; etc.

That is, the present invention provides:

(i) a method of quantifying the protein of the present invention in a test sample fluid, which comprises competitively reacting the antibody of the present invention, a test sample fluid and a labeled form of the protein of the present invention, and measuring the ratio of the labeled form of the protein of the present invention bound to said antibody; and, (ii) a method of quantifying the protein of the present invention in a test sample fluid, which comprises reacting a test sample fluid simultaneously or continuously with the antibody of the present invention immobilized on a carrier and another labeled antibody of the present invention, and then measuring the activity of the labeling agent on the insoluble carrier.

In the quantification method (ii) described above, it is preferred that one antibody is capable of recognizing the N-terminal region of the protein of the present invention, while another antibody is capable of reacting with the C-terminal region of the protein of the present invention.

The monoclonal antibody to the protein of the present invention (hereinafter sometimes referred to as the monoclonal antibody of the present invention) can be used to quantify the protein of the present invention. In addition, the protein can be detected by means of a tissue staining as well. For these purposes, the antibody molecule per se may be used or F $(ab')_2$, Fab' or Fab fractions of the antibody molecule may also be used.

The method of quantifying the protein of the present invention using the antibody of the present invention is not particularly limited. Any quantification method can be used, so long as the amount of antibody, antigen or antibody-antigen complex corresponding to the amount of antigen (e.g., the amount of the protein) in a test sample fluid can be detected by chemical or physical means and the amount of the antigen can be calculated from a standard curve prepared from standard solutions containing known amounts of the antigen. For such an assay method, for example, nephrometry, the competitive method, the immunometric method, the sandwich method, etc. are suitably used and in terms of sensitivity and specificity, it is particularly preferred to use the sandwich method described hereinafter.

Examples of the labeling agent used in the assay method using the labeling substance are radioisotopes, enzymes, fluorescent substances, luminescent substances, and the like. As the radioisotopes, there are used, e.g., $[^{125}I]$, $[^{131}I]$, $[^{3}H]$, $[^{14}C]$, etc. The enzymes described above are preferably enzymes, which are stable and have a high specific activity, and include, e.g., β-galactosidase, β-glucosidase, alkaline phosphatase, peroxidase, malate dehydrogenase, etc. As the fluorescent substances, there are used, e.g., fluorescamine, fluorescein isothiocyanate, etc. As the luminescent substances described above there are used, e.g., luminol, a luminol derivative, luciferin, lucigenin, etc. Furthermore, the biotin-avidin system may be used as well for binding of an antibody or antigen to a labeling agent.

For immobilization of the antigen or antibody, physical adsorption may be used. Chemical binding techniques conventionally used for insolubilization or immobilization of proteins, enzymes, etc. may also be used. For carriers, there are used, e.g., insoluble polysaccharides such as agarose, dextran, cellulose, etc.; synthetic resin such as polystyrene, polyacrylamide, silicon, etc., and glass or the like.

In the sandwich method, the immobilized monoclonal antibody of the present invention is reacted with a test fluid (primary reaction), then with a labeled form of another monoclonal antibody of the present invention (secondary reaction), and the activity of the label on the immobilizing carrier is measured, whereby the amount of the protein of the present invention in the test fluid can be quantified. The order of the primary and secondary reactions may be reversed, and the reactions may be performed simultaneously or with an interval. The methods of labeling and immobilization can be performed by the methods described above. In the immunoassay by the sandwich method, the antibody used for immobilized or labeled antibodies is not necessarily one species, but a mixture of two or more species of antibody may be used to increase the measurement sensitivity.

In the methods of assaying the protein of the present invention by the sandwich method of the present invention, antibodies that bind to different sites of the protein of the present invention are preferably used as the monoclonal antibodies of the present invention used for the primary and secondary reactions. That is, in the antibodies used for the primary and secondary reactions are, for example, when the antibody used in the secondary reaction recognizes the C-terminal region of the protein of the present invention, it is preferable to use the antibody recognizing the region other than the C-terminal region for the primary reaction, e.g., the antibody recognizing the N-terminal region.

The monoclonal antibodies of the present invention can be used for the assay systems other than the sandwich method, for example, the competitive method, the immunometric method, nephrometry, etc.

In the competitive method, antigen in a test fluid and the labeled antigen are competitively reacted with antibody, and the unreacted labeled antigen (F) And the labeled antigen bound to the antibody (B) are separated (B/F separation). The amount of the label in B or F is measured, and the amount of the antigen in the test fluid is quantified. This reaction method includes a liquid phase method using a soluble antibody as an antibody, polyethylene glycol for B/F separation and a secondary antibody to the soluble antibody, and an immobilized method either using an immobilized antibody as the primary antibody, or using a soluble antibody as the primary antibody and immobilized antibody as the secondary antibody.

In the immunometric method, antigen in a test fluid and immobilized antigen are competitively reacted with a definite amount of labeled antibody, the immobilized phase is separated from the liquid phase, or antigen in a test fluid and an excess amount of labeled antibody are reacted, immobilized antigen is then added to bind the unreacted labeled antibody to the immobilized phase, and the immobilized phase is separated from the liquid phase. Then, the amount of the label in either phase is measured to quantify the antigen in the test fluid.

In the nephrometry, insoluble precipitate produced after the antigen-antibody reaction in gel or solution is quantified. When the amount of antigen in the test fluid is small and only a small amount of precipitate is obtained, laser nephrometry using scattering of laser is advantageously employed.

For applying each of these immunological methods to the quantification method of the present invention, any particular conditions or procedures are not required. Quantification system for the protein of the present invention or its salts is constructed by adding the usual technical consideration in the art to the conventional conditions and procedures. For the details of these general technical means, reference can be made to the following reviews and texts.

For example, Hiroshi Irie, ed. "Radioimmunoassay" (Kodansha, published in 1974), Hiroshi Irie, ed. "Sequel to the Radioimmunoassay" (Kodansha, published in 1979), Eiji Ishikawa, et al. ed. "Enzyme immunoassay" (Igakushoin, published in 1978), Eiji Ishikawa, et al. ed. "Immunoenzyme assay" (2nd ed.) (Igakushoin, published in 1982), Eiji Ishikawa, et al. ed. "Immunoenzyme assay" (3rd ed.) (Igakushoin, published in 1987), Methods in ENZYMOLOGY, Vol. 70 (Immunochemical Techniques (Part A)), ibid., Vol. 73 (Immunochemical Techniques (Part B)), ibid., Vol. 74 (Immunochemical Techniques (Part C)), ibid., Vol. 84 (Immunochemical Techniques (Part D: Selected Immunoassays)), ibid., Vol. 92 (Immunochemical Techniques (Part E: Monoclonal Antibodies and General Immunoassay Methods)), ibid., Vol. 121 (Immunochemical Techniques (Part I: Hybridoma Technology and Monoclonal Antibodies))(all published by Academic Press Publishing), etc.

As described above, the protein of the present invention can be quantified with high sensitivity, using the antibody of the present invention.

Furthermore, when an increased level of the protein of the present invention is detected by quantifying the level of the protein of the present invention using the antibody of the present invention, it can be diagnosed that one suffers from cancer, for example, colon cancer, breast cancer, lung cancer, prostate cancer, esophageal cancer, gastric cancer, liver cancer, biliary tract cancer, spleen cancer, renal cancer, bladder cancer, uterine cancer, testicular cancer, thyroid cancer, pancreatic cancer, brain tumor, blood tumor or the like; or it is highly likely to suffer from these disease in the future.

Moreover, the antibody of the present invention can be used to detect the protein of the present invention, which is present in a test sample such as a body fluid, a tissue, etc. The antibody can also be used to prepare an antibody column for purification of the protein of the present invention, detect the protein of the present invention in each fraction upon purification, analyze the behavior of the protein of the present invention in the cells under investigation; etc.

(3) Gene Diagnostic Agent

By using the DNA of the present invention, e.g., as a probe, an abnormality (gene abnormality) of the DNA or mRNA encoding the protein of the present invention or its partial peptide in human or warm-blooded animal (e.g., rat, mouse, guinea pig, rabbit, fowl, sheep, swine, bovine, horse, cat, dog, monkey, chimpanzee, etc.) can be detected. Therefore, the DNA of the present invention is useful as a gene diagnostic agent for detecting damages to the DNA or mRNA, its mutation, or decreased expression, increased expression, overexpression, etc. of the DNA or mRNA, and so on.

The gene diagnosis described above using the DNA of the present invention can be performed by, for example, the publicly known Northern hybridization assay or the PCR-SSCP assay (Genomics, 5, 874-879 (1989); Proceedings of the National Academy of Sciences of the United States of America, 86, 2766-2770 (1989)), etc.

When overexpression is detected by, e.g., Northern hybridization or DNA mutation is detected by the PCR-SSCP assay, it can be diagnosed that it is highly likely to suffer from cancer, for example, colon cancer, breast cancer, lung cancer, prostate cancer, esophageal cancer, gastric cancer, liver cancer, biliary tract cancer, spleen cancer, renal cancer, bladder cancer, uterine cancer, testicular cancer, thyroid cancer, pancreatic cancer, brain tumor, blood tumor, etc.

(4) Pharmaceutical Comprising the Antisense Polynucleotide

The antisense polynucleotide of the present invention that binds to the DNA of the present invention complementarily to inhibit expression of the DNA is low toxic and can suppress the functions or effects of the protein of the present invention or the DNA of the present invention in vivo. Thus, the antisense polynucleotide can be used as a prophylactic/therapeutic agent for cancer, e.g., colon cancer, breast cancer, lung cancer, prostate cancer, esophageal cancer, gastric cancer, liver cancer, biliary tract cancer, spleen cancer, renal cancer, bladder cancer, uterine cancer, testicular cancer, thyroid cancer, pancreatic cancer, brain tumor, blood tumor, etc. Preferably, the antisense polynucleotide is used as a prophylactic/therapeutic agent for breast cancer, lung cancer, etc. The antisense polynucleotide of the present invention promotes apoptosis of cancer cells and can thus be used as, e.g., an apoptosis promoter of cancer cells.

Where the antisense polynucleotide described above is used as the aforesaid prophylactic/therapeutic agent or as the promoter, it can be prepared into pharmaceutical preparations by publicly known methods, which are provided for administration.

For example, when the antisense polynucleotide described above is used, the antisense polynucleotide alone is administered directly, or the antisense polynucleotide is inserted into an appropriate vector such as retrovirus vector, adenovirus vector, adenovirus-associated virus vector, etc., followed by treating in a conventional manner. The antisense polynucleotide may then be administered orally or parenterally to human or a mammal (e.g., rat, rabbit, sheep, swine, bovine, cat, dog, monkey, etc.) in a conventional manner. The antisense polynucleotide may also be administered as it stands, or may be prepared in pharmaceutical preparations together with a physiologically acceptable carrier to assist its uptake, which are then administered by gene gun or through a catheter such as a catheter with a hydrogel. Alternatively, the antisense polynucleotide may be prepared into an aerosol, which is topically administered into the trachea as an inhaler.

Further for the purposes of improving pharmacokinetics, prolonging a half-life and improving intracellular uptake efficiency, the antisense polynucleotide described above is prepared into pharmaceutical preparations (injectable preparations) alone or together with a carrier such as liposome, etc. and the preparations may be administered intravenously, subcutaneously, etc.

A dose of the antisense polynucleotide may vary depending on target disease, subject to be administered, route for administration, etc. For example, where the antisense polynucleotide of the present invention is administered for the purpose of treating breast cancer, the antisense polynucleotide is generally administered to an adult (60 kg body weight) in a daily dose of about 0.1 to 100 mg.

In addition, the antisense polynucleotide may also be used as an oligonucleotide probe for diagnosis to examine the presence of the DNA of the present invention in tissues or cells and states of its expression.

As the antisense polynucleotide described above can, the double-stranded RNA containing a part of RNA encoding the protein of the present invention, ribozyme containing a part of RNA encoding the protein of the present invention, etc. can also prevent expression of the gene of the present invention to suppress the in vivo function of the protein used in the present invention or the DNA used in the present invention and thus can be used as a prophylactic/therapeutic agent for cancer, e.g., colon cancer, breast cancer, lung cancer, prostate cancer, esophageal cancer, gastric cancer, liver cancer, biliary tract cancer, spleen cancer, renal cancer, bladder cancer, uterine cancer, testicular cancer, thyroid cancer, pancreatic cancer, brain tumor, blood tumor, etc. (preferably, prophylactic/therapeutic agents for breast cancer, lung cancer, etc.), or as apoptosis promoters of cancer cells, etc.

The double-stranded RNA can be designed based on a sequence of the polynucleotide of the present invention and manufactured by modifications of publicly known methods (e.g., Nature, 411, 494, 2001).

The ribozyme can be designed based on a sequence of the polynucleotide of the present invention and manufactured by modifications of publicly known methods (e.g., TRENDS in Molecular Medicine, 7, 221, 2001). For example, the ribozyme can be manufactured by ligating a publicly known ribozyme to a part of the RNA encoding the protein of the present invention. A part of the RNA encoding the protein of the present invention includes a portion proximal to a cleavage site on the RNA of the present invention, which may be cleaved by a publicly known ribozyme (RNA fragment).

Where the double-stranded RNA or ribozyme described above is used as the prophylactic/therapeutic agent described above, the double-stranded RNA or ribozyme is prepared into pharmaceutical preparations as in the antisense polynucleotide, and the preparations can be provided for administration.

(5) Pharmaceutical Comprising the Antibody of the Present Invention

The antibody of the present invention can be used as a prophylactic/therapeutic agent (e.g., vaccine, etc.) for cancer, for example, colon cancer, breast cancer, lung cancer, prostate cancer, esophageal cancer, gastric cancer, liver cancer, biliary tract cancer, spleen cancer, renal cancer, bladder cancer, uterine cancer, testicular cancer, thyroid cancer, pancreatic cancer, brain tumor, blood tumor, etc. Preferably, the antibody is used as a prophylactic/therapeutic agent for breast cancer, lung cancer, etc. Also, the antibody of the present invention can also be used as, e.g., an apoptosis promoter of cancer cells.

Since the aforesaid prophylactic/therapeutic agent for diseases and promoters comprising the antibody of the present invention are safe and low toxic, they can be administered to human or a mammal (e.g., rat, rabbit, sheep, swine, bovine, cat, dog, monkey, etc.) orally or parenterally (e.g., intravascularly, subcutaneously, etc.) either as liquid preparations as they are or as pharmaceutical compositions of adequate dosage form. Preferably, they can be administered in the form of vaccine in a conventional manner.

The antibody of the present invention may be administered in itself or as an appropriate pharmaceutical composition. The pharmaceutical composition used for the administration may contain a pharmacologically acceptable carrier with the aforesaid antibody or its salts, a diluent or excipient. Such a composition is provided in the form of pharmaceutical preparations suitable for oral or parenteral administration.

Examples of the composition for parenteral administration are injectable preparations, suppositories, vaccine, etc. The injectable preparations may include dosage forms such as intravenous, subcutaneous, intracutaneous and intramuscular injections, drip infusions, etc. These injectable preparations may be prepared by methods publicly known. The injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mols) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule. The suppository used for rectal administration may be prepared by blending the aforesaid antibody or its salt with conventional bases for suppositories.

Examples of the composition for oral administration include solid or liquid preparations, specifically, tablets (including dragees and film-coated tablets), pills, granules, powdery preparations, capsules (including soft capsules), syrup, emulsions, suspensions, etc. Such a composition is manufactured by publicly known methods and contains a vehicle, a diluent or an excipient conventionally used in the field of pharmaceutical preparations. Examples of the vehicle or excipient for tablets are lactose, starch, sucrose, magnesium stearate, etc.

Advantageously, the pharmaceutical compositions for oral or parenteral use described above are prepared into pharmaceutical preparations in a unit dose suited to fit a dose of the active ingredients. Such unit dose preparations include, for example, tablets, pills, capsules, injections (ampoules), suppositories, etc. The amount of the aforesaid antibody contained is generally about 5 to 500 mg per dosage unit form; especially in the form of injection, it is preferred that the aforesaid antibody is contained in about 5 to 100 mg and in about 10 to 250 mg for the other forms.

The dose of the aforesaid prophylactic/therapeutic agent or regulator comprising the antibody of the present invention may vary depending upon subject to be administered, target disease, conditions, route of administration, etc. For example, when it is used for the purpose of treating/preventing, e.g., breast cancer in an adult, it is advantageous to intravenously administer the antibody of the present invention in a single dose of about 0.01 to about 20 mg/kg body weight, preferably about 0.1 to about 10 mg/kg body weight and more preferably about 0.1 to about 5 mg/kg body weight in approximately 1 to 5 times a day, preferably in approximately 1 to 3 times a day. In other parenteral administration and oral administration, the prophylactic/therapeutic agent or regulator can be administered in a dose corresponding to the dose given above. When the condition is especially severe, the dose may be increased according to the condition.

The antibody of the present invention may be administered in itself or in the form of an appropriate pharmaceutical composition. The pharmaceutical composition used for the administration may contain a pharmacologically acceptable carrier with the aforesaid antibody or its salts, a diluent or excipient. Such a composition is provided in the form of pharmaceutical preparations suitable for oral or parenteral administration (e.g., intravascular injection, subcutaneous injection, etc.).

Each composition described above may further contain other active components unless formulation causes any adverse interaction with the antibody described above.

(6) Pharmaceutical Comprising the Protein of the Present Invention

Since the protein of the present invention is overexpressed in cancers, the protein of the present invention can be used as a cancer vaccine to activate the immune system in patients with cancer.

For example, the so-called adoptive immunotherapy, which involves culturing potent antigen presenting cells (e.g., dendritic cells) in the presence of the protein of the present invention to engulf the protein and putting the cells back into the body, can preferably be used. The dendritic cells, returned back into the body, can induce and activate cytotoxic T cells specific to a cancer antigen whereby to kill cancer cells.

The protein of the present invention can also be administered to a mammal (e.g. human, monkey, mouse, rat, rabbit, swine) safely as a vaccine preparation to prevent or treat a cancer, e.g., colon cancer, breast cancer, lung cancer, prostate cancer, esophageal cancer, gastric cancer, liver cancer, biliary tract cancer, spleen cancer, renal cancer, bladder cancer, uterine cancer, testicular cancer, thyroid cancer, pancreatic cancer, brain tumor, blood tumor, etc.

The vaccine preparation usually contains the protein of the present invention and a physiologically acceptable carrier. Such a carrier includes a liquid carrier such as water, saline (including physiological saline), buffer (e.g., phosphate buffer), an alcohol (e.g., ethanol), etc.

The vaccine preparation can be prepared according to a conventional method of manufacturing a vaccine preparation.

In general, the protein of the present invention is dissolved or suspended in a physiologically acceptable carrier. Alternatively, the protein of the present invention and the physiologically acceptable carrier may be separately prepared and then mixed at use.

The vaccine preparation may be further formulated with, for example, an adjuvant (e.g., aluminum hydroxide gel, serum albumin, etc.), a preservative (e.g., thimerosal, etc.), a soothing agent (e.g., glucose, benzyl alcohol, etc.), in addition to the protein of the present invention and the physiologically acceptable carrier. Furthermore, the vaccine preparation may also be formulated with, for example, a cytokine (e.g., an interleukin such as interleukin-2, an interferon such as interferon-γ) to enhance the production of the antibody to the protein of the present invention.

When used as a vaccine preparation, the protein of the present invention may be used in its active form, or may be denatured to enhance the antigenicity. The protein of the present invention can be denatured usually by heating or treating with a protein-denaturing agent (e.g., formalin, guanidine hydrochloride and urea).

The thus obtained vaccine preparation is low toxic and may usually be administered in an injectable form, e.g., subcutaneously, intracutaneously, intramuscularly, or topically into or near a mass of cancer cells.

The dose of the protein of the present invention varies depending on a target disease, a subject to be administered, a route for administration, etc. For example, for subcutaneous administration of the protein of the present invention to an adult cancer patient (60 kg body weight) in an injectable form, the single dose is normally about 0.1 mg to about 300 mg, preferably about 100 mg to about 300 mg. The administration of the vaccine preparation may be carried out once, or 2 to 4 times in total approximately in every 2 weeks to 6 months to increase the production of the antibody.

(7) DNA Transgenic Animal

The present invention provides a non-human mammal bearing a DNA encoding the protein of the present invention, which is exogenous (hereinafter abbreviated as the exogenous DNA of the present invention) or its variant DNA (sometimes simply referred to as the exogenous variant DNA of the present invention).

That is, the present invention provides:

(1) A non-human mammal bearing the exogenous DNA of the present invention or its variant DNA;

(2) The mammal according to (1), wherein the non-human mammal is a rodent;

(3) The mammal according to (2), wherein the rodent is mouse or rat; and, (4) A recombinant vector containing the exogenous DNA of the present invention or its variant DNA and capable of expressing in a mammal; etc.

The non-human mammal bearing the exogenous DNA of the present invention or its variant DNA (hereinafter simply referred to as the DNA transgenic animal of the present invention) can be prepared by transfecting a desired DNA into an unfertilized egg, a fertilized egg, a spermatozoon, a germinal cell containing a primordial germinal cell thereof, or the like, preferably in the embryogenic stage in the development of a non-human mammal (more preferably in the single cell or fertilized cell stage and generally before the 8-cell phase), by standard means, such as the calcium phosphate method, the electric pulse method, the lipofection method, the agglutination method, the microinjection method, the particle gun method, the DEAE-dextran method, etc. Also, it is possible to transfect the exogenous DNA of the present invention into a somatic cell, a living organ, a tissue cell, or the like by the DNA transfection methods, and utilize the transformant for cell culture, tissue culture, etc. In addition, these cells may be fused with the above-described germinal cell by a publicly known cell fusion method to prepare the DNA transgenic animal of the present invention.

Examples of the non-human mammal that can be used include bovine, swine, sheep, goat, rabbits, dogs, cats, guinea pigs, hamsters, mice, rats, etc. Above all, preferred are rodents, especially mice (e.g., C57B1/6 strain, DBA2 strain, etc. for a pure line and for a cross line, $B6C3F_1$ strain, $BDF_1$ strain $B6D2F_1$ strain, BALB/c strain, ICR strain, etc.), rats (Wistar, SD, etc.) or the like, since they are relatively short in ontogeny and life cycle from a standpoint of creating model animals for human disease.

"Mammals" in a recombinant vector that can be expressed in the mammals include the aforesaid non-human mammals, human, etc.

The exogenous DNA of the present invention refers to the DNA of the present invention that is once isolated and extracted from mammals, not the DNA of the present invention inherently possessed by the non-human mammals.

The mutant DNA of the present invention includes mutants resulting from variation (e.g., mutation, etc.) in the base sequence of the original DNA of the present invention, specifically DNAs resulting from base addition, deletion, substitution with other bases, etc. and further including abnormal DNA.

The abnormal DNA is intended to mean DNA that expresses the abnormal protein of the present invention and exemplified by the DNA that expresses a protein for suppressing the function of the normal protein of the present invention.

The exogenous DNA of the present invention may be any one of those derived from a mammal of the same species as, or a different species from, the mammal as the target animal. In transfecting the DNA of the present invention into the target animal, it is generally advantageous to use the DNA as a DNA construct in which the DNA is ligated downstream a promoter capable of expressing the DNA in the target animal. For example, in the case of transfecting the human DNA of the present invention, a DNA transgenic mammal that expresses the DNA of the present invention to a high level, can be prepared by microinjecting a DNA construct (e.g., vector, etc.) ligated with the human DNA of the present invention into a fertilized egg of the target non-human mammal downstream various promoters which are capable of expressing the DNA derived from various mammals (e.g., rabbits, dogs, cats, guinea pigs, hamsters, rats, mice, etc.) bearing the DNA of the present invention highly homologous to the human DNA.

As expression vectors for the protein of the present invention, there are *Escherichia coli-derived* plasmids, *Bacillus subtilis-derived* plasmids, yeast-derived plasmids, bacteriophages such as λ phage, retroviruses such as Moloney leukemia virus, etc., and animal viruses such as vaccinia virus, baculovirus, etc. Of these vectors, *Escherichia coli-derived* plasmids, *Bacillus subtilis-derived* plasmids, or yeast-derived plasmids, etc. are preferably used.

Examples of these promoters for regulating the DNA expression described above include (i) promoters for DNA derived from viruses (e.g., simian virus, cytomegalovirus, Moloney leukemia virus, JC virus, breast cancer virus, poliovirus, etc.), and (ii) promoters derived from various mammals (human, rabbits, dogs, cats, guinea pigs, hamsters, rats, mice, etc.), for example, promoters of albumin, insulin II, uroplakin II, elastase, erythropoietin, endothelin, muscular creatine kinase, glial fibrillary acidic protein, glutathione S-transferase, platelet-derived growth factor β, keratins K1, K10 and K14, collagen types I and II, cyclic AMP-dependent protein kinase βI subunit, dystrophin, tartarate-resistant alkaline phosphatase, atrial natriuretic factor, endothelial receptor tyrosine kinase (generally abbreviated as Tie2), sodium-potassium adenosine triphosphorylase (Na,K-ATPase), neurofilament light chain, metallothioneins I and IIA, metalloproteinase I tissue inhibitor, MHC class I antigen (H-2L), H-ras, renin, dopamine β-hydroxylase, thyroid peroxidase (TPO), peptide chain elongation factor 1α (EF-1α), β actin, α and β myosin heavy chains, myosin light chains 1 and 2, myelin base protein, thyroglobulins, Thy-1, immunoglobulins, H-chain variable region (VNP), serum amyloid component P, myoglobin, troponin C, smooth muscle a actin, preproencephalin A, vasopressin, etc. Among them, cytomegalovirus promoters, human peptide chain elongation factor 1α (EF-1α) promoters, human and chicken β actin promoters, etc., which are capable of high expression in the whole body are preferred.

Preferably, the vectors described above have a sequence that terminates the transcription of the desired messenger RNA in the DNA transgenic animal (generally termed a terminator); for example, a sequence of each DNA derived from viruses and various mammals, and SV40 terminator of the simian virus and the like are preferably used.

In addition, for the purpose of increasing the expression of the desired exogenous DNA to a higher level, the splicing signal and enhancer region of each DNA, a portion of the intron of an eukaryotic DNA may also be ligated at the 5' upstream of the promoter region, or between the promoter region and the translational region, or at the 3' downstream of the translational region, depending upon purposes.

The translational region for the normal protein of the present invention can be obtained using as a starting material the entire genomic DNA or its portion of liver, kidney, thyroid cell or fibroblast origin from human or various mammals (e.g., rabbits, dogs, cats, guinea pigs, hamsters, rats, mice, etc.) or of various commercially available genomic DNA libraries, or using cDNA prepared by a publicly known method from RNA of liver, kidney, thyroid cell or fibroblast origin as a starting material. Also, an exogenous abnormal DNA can produce the translational region through variation of the translational region of normal protein obtained from the cells or tissues described above by point mutagenesis.

The translational region can be prepared by a conventional DNA engineering technique, in which the DNA is ligated downstream the aforesaid promoter and if desired, upstream the translation termination site, as a DNA construct capable of being expressed in the transgenic animal.

The exogenous DNA of the present invention is transfected at the fertilized egg cell stage in a manner such that the DNA is certainly present in all the germinal cells and somatic cells of the target mammal. The fact that the exogenous DNA of the present invention is present in the germinal cells of the animal prepared by DNA transfection means that all offspring of the prepared animal will maintain the exogenous DNA of the present invention in all of the germinal cells and somatic cells thereof. The offspring of the animal that inherits the exogenous DNA of the present invention also have the exogenous DNA of the present invention in all of the germinal cells and somatic cells thereof.

The non-human mammal in which the normal exogenous DNA of the present invention has been transfected can be passaged as the DNA-bearing animal under ordinary rearing environment, by confirming that the exogenous DNA is stably retained by crossing.

By the transfection of the exogenous DNA of the present invention at the fertilized egg cell stage, the DNA is retained to be excess in all of the germinal and somatic cells. The fact that the exogenous DNA of the present invention is excessively present in the germinal cells of the prepared animal after transfection means that the exogenous DNA of the present invention is excessively present in all of the germinal cells and somatic cells thereof. The offspring of the animal that inherits the exogenous DNA of the present invention have excessively the exogenous DNA of the present invention in all of the germinal cells and somatic cells thereof.

It is possible to obtain homozygous animals having the transfected DNA in both homologous chromosomes and breed male and female of the animal so that all the progeny have this DNA in excess.

In a non-human mammal bearing the normal DNA of the present invention, the normal DNA of the present invention has expressed at a high level, and may eventually develop hyperfunction in the function of the protein of the present invention by accelerating the function of endogenous normal DNA. Therefore, the animal can be utilized as a pathologic model animal for such a disease. For example, using the normal DNA transgenic animal of the present invention, it is possible to elucidate the mechanism of hyperfunction in the function of the protein of the present invention and the pathological mechanism of the disease associated with the protein of the present invention and to investigate how to treat these diseases.

Furthermore, since a mammal transfected with the exogenous normal DNA of the present invention exhibits an increasing symptom of the protein of the present invention liberated, the animal is usable for screening test of prophylactic/therapeutic agents for diseases associated with the protein of the present invention, for example, the prophylactic/therapeutic agent for a cancer such as colon cancer, breast cancer, lung cancer, prostate cancer, esophageal cancer, gastric cancer, liver cancer, biliary tract cancer, spleen cancer, renal cancer, bladder cancer, uterine cancer, testicular cancer, thyroid cancer, pancreatic cancer, brain tumor, blood tumor, etc.

On the other hand, a non-human mammal having the exogenous abnormal DNA of the present invention can be passaged under normal breeding conditions as the DNA-bearing animal by confirming stable retention of the exogenous DNA via crossing. Furthermore, the exogenous DNA of interest can be utilized as a starting material by inserting the DNA into the plasmid described above. The DNA construct with a promoter can be prepared by conventional DNA engineering techniques. The transfection of the abnormal DNA of the present invention at the fertilized egg cell stage is preserved to be present in all of the germinal and somatic cells of the target mammal. The fact that the abnormal DNA of the present invention is present in the germinal cells of the animal after DNA transfection means that all of the offspring of the prepared animal have the abnormal DNA of the present invention in all of the germinal and somatic cells. Such an offspring that passaged the exogenous DNA of the present invention will have the abnormal DNA of the present invention in all of the germinal and somatic cells. A homozygous animal having the introduced DNA on both of homologous chromosomes can be acquired, and by crossing these male and female animals, all the offspring can be bred to retain the DNA.

In a non-human mammal bearing the abnormal DNA of the present invention, the abnormal DNA of the present invention has expressed to a high level, and may eventually develop the function inactive type inadaptability to the protein of the present invention by inhibiting the functions of endogenous normal DNA. Therefore, the animal can be utilized as a pathologic model animal for such a disease. For example, using the abnormal DNA transgenic animal of the present invention, it is possible to elucidate the mechanism of the function inactive type inadaptability to the protein of the present invention and the pathological mechanism of the disease associated with the protein of the present invention and to investigate how to treat the disease.

More specifically, the transgenic animal of the present invention expressing the abnormal DNA of the present invention at a high level is expected to serve as an experimental model to elucidate the mechanism of the functional inhibition (dominant negative effect) of a normal protein by the abnormal protein of the present invention in the function inactive type inadaptability of the protein of the present invention.

Since a mammal bearing the abnormal exogenous DNA of the present invention shows an increased symptom of the protein of the present invention liberated, the animal is also expected to serve for screening test of prophylactic/therapeutic agents for the function inactive type inadaptability of the protein of the present invention, e.g., prophylactic/therapeutic agents for a cancer such as colon cancer, breast cancer, lung cancer, prostate cancer, esophageal cancer, gastric cancer, liver cancer, biliary tract cancer, spleen cancer, renal cancer, bladder cancer, uterine cancer, testicular cancer, thyroid cancer, pancreatic cancer, brain tumor, blood tumor, etc.

Other potential applications of two kinds of the DNA transgenic animals of the present invention described above further include:

(i) Use as a cell source for tissue culture;

(ii) Elucidation of the relation to a peptide that is specifically expressed or activated by the protein of the present invention, by direct analysis of DNA or RNA in tissues of the DNA transgenic animal of the present invention or by analysis of the peptide tissues expressed by the DNA;

(iii) Research on the function of cells derived from tissues that are usually cultured only with difficulty, using cells in tissues bearing the DNA cultured by a standard tissue culture technique;

(iv) Screening a drug that enhances the functions of cells using the cells described in (iii) above; and, (v) Isolation and purification of the variant protein of the present invention and preparation of an antibody thereto.

Furthermore, clinical conditions of a disease associated wit the protein of the present invention, including the function inactive type inadaptability to the protein of the present invention can be determined by using the DNA transgenic animal of the present invention. Also, pathological findings on each organ in a disease model associated with the protein of the present invention can be obtained in more detail, leading to the development of a new method for treatment as well as the research and therapy of any secondary diseases associated with the disease.

It is also possible to obtain a free DNA-transfected cell by withdrawing each organ from the DNA transgenic animal of the present invention, mincing the organ and degrading with a proteinase such as trypsin, etc., followed by establishing the line of culturing or cultured cells. Furthermore, the DNA transgenic animal of the present invention can serve to identify cells capable of producing the protein of the present invention, and to study in association with apoptosis, differentiation or propagation or on the mechanism of signal transduction in these properties to inspect any abnormality therein. Thus, the DNA transgenic animal can provide an effective research material for the protein of the present invention and for investigation of the function and effect thereof.

To develop a drug for the treatment of diseases associated with the protein of the present invention, including the function inactive type inadaptability to the protein of the present invention, using the DNA transgenic animal of the present invention, an effective and rapid method for screening can be provided by using the method for inspection and the method for quantification, etc. described above. It is also possible to investigate and develop a method for DNA therapy for the treatment of diseases associated with the protein of the present invention, using the DNA transgenic animal of the present invention or a vector capable of expressing the exogenous DNA of the present invention.

(8) Knockout Animal

The present invention provides a non-human mammal embryonic stem cell bearing the DNA of the present invention inactivated and a non-human mammal deficient in expressing the DNA of the present invention.

Thus, the present invention provides:

(1) A non-human mammal embryonic stem cell in which the DNA of the present invention is inactivated;

(2) The embryonic stem cell according to (1), wherein the DNA is inactivated by introducing a reporter gene (e.g., β-galactosidase gene derived from *Escherichia coli*);

(3) The embryonic stem cell according to (1), which is resistant to neomycin;

(4) The embryonic stem cell according to (1), wherein the non-human mammal is a rodent;

(5) The embryonic stem cell according to (4), wherein the rodent is mouse;

(6) A non-human mammal deficient in expressing the DNA of the present invention, wherein the DNA is inactivated;

(7) The non-human mammal according to (6), wherein the DNA is inactivated by inserting a reporter gene (e.g., β-galactosidase derived from *Escherichia coli*) therein and the reporter gene is capable of being expressed under control of a promoter for the DNA of the present invention;

(8) The non-human mammal according to (6), which is a rodent;

(9) The non-human mammal according to (8), wherein the rodent is mouse; and,

(10) A method of screening a compound that promotes or inhibits (preferably inhibits) the promoter activity to the DNA of the present invention, which comprises administering a test compound to the mammal of (7) And detecting expression of the reporter gene.

The non-human mammal embryonic stem cell in which the DNA of the present invention is inactivated refers to a non-human mammal embryonic stem cell that suppresses the ability of the non-human mammal to express the DNA by artificially mutating the DNA of the present invention, or the DNA has no substantial ability to express the protein of the present invention (hereinafter sometimes referred to as the knockout DNA of the present invention) by substantially inactivating the activities of the protein of the present invention encoded by the DNA (hereinafter merely referred to as ES cell).

As the non-human mammal, the same examples as described above apply.

Techniques for artificially mutating the DNA of the present invention include deletion of a part or all of the DNA sequence and insertion of or substitution with other DNA, by genetic engineering. By these variations, the knockout DNA of the present invention may be prepared, for example, by shifting the reading frame of a codon or by disrupting the function of a promoter or exon.

Specifically, the non-human mammal embryonic stem cell in which the DNA of the present invention is inactivated (hereinafter merely referred to as the ES cell with the DNA of the present invention inactivated or the knockout ES cell of the present invention) can be obtained by, for example, isolating the DNA of the present invention that the desired non-human mammal possesses, inserting a DNA fragment having a DNA sequence constructed by inserting a drug resistant gene such as a neomycin resistant gene or a hygromycin resistant gene, or a reporter gene such as lacZ (β-galactosidase gene) or cat (chloramphenicol acetyltransferase gene), etc. into its exon site thereby to disable the functions of exon, or integrating to a chromosome of the target animal by, e.g., homologous recombination, a DNA sequence that terminates gene transcription (e.g., polyA additional signal, etc.) in the intron between exons, thus inhibiting the synthesis of complete messenger RNA and eventually destroying the gene (hereinafter simply referred to as a targeting vector). The thus-obtained ES cells to the southern hybridization analysis with a DNA sequence on or near the DNA of the present invention as a probe, or to PCR analysis with a DNA sequence on the targeting vector and another DNA sequence near the DNA of the present invention which is not included in the targeting vector as primers, to select the knockout ES cell of the present invention.

The parent ES cells to inactivate the DNA of the present invention by homologous recombination, etc. may be of a strain already established as described above, or may originally be established in accordance with a modification of the known method by Evans and Kaufman described above. For example, in the case of mouse ES cells, currently it is common practice to use ES cells of the 129 strain. However, since their immunological background is obscure, the C57BL/6 mouse or the $BDF_1$ mouse ($F_1$ hybrid between C57BL/6 and DBA/2), wherein the low ovum availability per C57BL/6 in the C57BL/6 mouse has been improved by crossing with DBA/2, may be preferably used, instead of obtaining a pure line of ES cells with the clear immunological genetic background and for other purposes. The $BDF_1$ mouse is advantageous in that, when a pathologic model mouse is generated using ES cells obtained therefrom, the genetic background can be changed to that of the C57BL/6 mouse by back-crossing with the C57BL/6 mouse, since its background is of the C57BL/6 mouse, as well as being advantageous in that ovum availability per animal is high and ova are robust.

In establishing ES cells, blastocytes at 3.5 days after fertilization are commonly used. In the present invention, embryos are preferably collected at the 8-cell stage, after culturing until the blastocyte stage, the embryos are used to efficiently obtain a large number of early stage embryos.

Although the ES cells used may be of either sex, male ES cells are generally more convenient for generation of a germ cell line chimera. It is also desirable that sexes are identified as soon as possible to save painstaking culture time.

Methods for sex identification of the ES cell include the method in which a gene in the sex-determining region on the Y-chromosome is amplified by the PCR process and detected. When this method is used, one colony of ES cells (about 50 cells) is sufficient for sex-determination analysis, which karyotype analysis, for example G-banding method, requires about $10^6$ cells; therefore, the first selection of ES cells at the early stage of culture can be based on sex identification, and male cells can be selected early, which saves a significant amount of time at the early stage of culture.

Also, second selection can be achieved by, for example, confirmation of the number of chromosomes by the G-banding method. It is usually desirable that the chromosome number of the obtained ES cells be 100% of the normal number. However, when it is difficult to obtain the cells having the normal number of chromosomes due to physical operations, etc. in the cell establishment, it is desirable that the ES cell is again cloned to a normal cell (e.g., in a mouse cell having the number of chromosomes being 2n=40) after knockout of the gene of the ES cells.

Although the embryonic stem cell line thus obtained shows a very high growth potential, it must be subcultured with great care, since it tends to lose its ontogenic capability. For example, the embryonic stem cell line is cultured at about 37° C. in a carbon dioxide incubator (preferably 5% carbon dioxide and 95% air, or 5% oxygen, 5% carbon dioxide and 90% air) in the presence of LIF (1 to 10000 U/ml) on appropriate feeder cells such as STO fibroblasts, treated with a trypsin/EDTA solution (normally 0.001 to 0.5% trypsin/0.1 to about 5 mM EDTA, preferably about 0.1% trypsin/1 mM EDTA) at the time of passage to obtain separate single cells, which are then plated on freshly prepared feeder cells. This passage is normally conducted every 1 to 3 days; it is desirable that cells be observed at the passage and cells found to be morphologically abnormal in culture, if any, be abandoned.

Where ES cells are allowed to reach a high density in mono-layers or to form cell aggregates in suspension under appropriate conditions, it is possible to differentiate the ES cells to various cell types, for example, pariental and visceral muscles, cardiac muscle or the like [M. J. Evans and M. H. Kaufman, Nature, 292, 154, 1981; G. R. Martin, Proc. Natl. Acad. Sci. U.S.A., 78, 7634, 1981; T. C. Doetschman et al., Journal of Embryology Experimental Morphology, 87, 27, 1985]. The cells deficient in expression of the DNA of the present invention, which are obtained from the differentiated ES cells of the present invention, are useful for studying the function of the protein of the present invention cytologically.

The non-human mammal deficient in expression of the DNA of the present invention can be identified from a normal animal by measuring the mRNA level in the subject animal by a publicly known method, and indirectly comparing the degrees of expression.

As the non-human mammal, the same examples given above apply.

With respect to the non-human mammal deficient in expression of the DNA of the present invention, the DNA of the present invention can be knockout by transfecting a targeting vector, prepared as described above, to mouse embryonic stem cells or mouse oocytes, and conducting homologous recombination in which a targeting vector DNA sequence, wherein the DNA of the present invention is inactivated by the transfection, is replaced with the DNA of the present invention on a chromosome of a mouse embryonic stem cell or mouse embryo.

The knockout cells with the disrupted DNA of the present invention can be identified by the southern hybridization analysis using as a probe a DNA fragment on or near the DNA of the present invention, or by the PCR analysis using as primers a DNA sequence on the targeting vector and another DNA sequence at the proximal region of other than the DNA of the present invention derived from mouse used in the targeting vector. When non-human mammal stem cells are used, a cell line wherein the DNA of the present invention is inactivated by homologous recombination is cloned; the resulting clones are injected to, e.g., a non-human mammalian embryo or blastocyst, at an appropriate stage such as the 8-cell stage. The resulting chimeric embryos are transplanted to the uterus of the pseudopregnant non-human mammal. The resulting animal is a chimeric animal constructed with both cells having the normal locus of the DNA of the present invention and those having an artificially mutated locus of the DNA of the present invention.

When some germ cells of the chimeric animal have a mutated locus of the DNA of the present invention, an individual, which entire tissue is composed of cells having a mutated locus of the DNA of the present invention can be selected from a series of offspring obtained by crossing between such a chimeric animal and a normal animal, e.g., by coat color identification, etc. The individuals thus obtained are normally deficient in heterozygous expression of the protein of the present invention. The individuals deficient in homozygous expression of the protein of the present invention can be obtained from offspring of the intercross between those deficient in heterozygous expression of the protein of the present invention.

When an oocyte is used, a DNA solution may be injected, e.g., into the prenucleus by microinjection thereby to obtain a transgenic non-human mammal having a targeting vector introduced in its chromosome. From such transgenic non-human mammals, those having a mutation at the locus of the DNA of the present invention can be obtained by selection based on homologous recombination.

As described above, the individuals in which the DNA of the present invention is knockout permit passage rearing under ordinary rearing conditions, after the individuals obtained by their crossing have proven to have been knockout.

Furthermore, the genital system may be obtained and retained by conventional methods. That is, by crossing male and female animals each having the inactivated DNA, homozygous animals having the inactivated DNA in both loci can be obtained. The homozygotes thus obtained may be reared so that one normal animal and two or more homozygotes are produced from a mother animal to efficiently obtain such homozygotes. By crossing male and female heterozygotes, homozygotes and heterozygotes having the inactivated DNA are proliferated and passaged.

The non-human mammal embryonic stem cell, in which the DNA of the present invention is inactivated, is very useful for preparing a non-human mammal deficient in expression of the DNA of the present invention.

Since the non-human mammal deficient in expression of the DNA of the present invention lacks various biological activities derived from the protein of the present invention, such an animal can be a disease model suspected of inactivated biological activities of the protein of the present invention and thus, offers an effective study to investigate the causes for and therapy for these diseases.

(8a) Method of Screening the Compound Having a Therapeutic/Prophylactic Effect on Diseases Caused by Deficiency, Damages, etc. of the DNA of the Present Invention The non-human mammal deficient in expression of the DNA of the present invention can be employed for screening the compound having a therapeutic/prophylactic effect on diseases caused by deficiency, damages, etc. of the DNA of the present invention.

That is, the present invention provides a method of screening the compound having a therapeutic/prophylactic effect on diseases, e.g., cancer, caused by deficiency, damages, etc. of the DNA of the present invention, which comprises administering a test compound to a non-human mammal deficient in expression of the DNA of the present invention and, observing and measuring a change occurred in the animal.

As the non-human mammal deficient in expression of the DNA of the present invention, which can be employed for the screening method, the same examples as described above apply.

Examples of the test compound include peptides, proteins, non-peptide compounds, synthetic compounds, fermentation products, cell extracts, plant extracts, animal tissue extracts, blood plasma, etc. These compounds may be novel compounds or publicly known compounds.

Specifically, the non-human mammal deficient in expression of the DNA of the present invention is treated with a test compound, comparison is made with an intact animal for control and a change in each organ, tissue, disease conditions, etc. of the animal is used as an indicator to assess the therapeutic/prophylactic effects of the test compound.

For treating an animal to be tested with a test compound, for example, oral administration, intravenous injection, etc. are applied, and the treatment can be appropriately selected depending on conditions of the test animal, properties of the test compound, etc. Furthermore, a dose of the test compound to be administered can be appropriately chosen depending on the administration route, nature of the test compound, etc.

For screening of the compound having a therapeutic/prophylactic effect on a cancer, e.g., colon cancer, breast cancer, lung cancer, prostate cancer, esophageal cancer, gastric cancer, liver cancer, biliary tract cancer, spleen cancer, renal cancer, bladder cancer, uterine cancer, testicular cancer, thyroid cancer, pancreatic cancer, brain tumor, blood tumor, etc., a test compound is administered to the non-human mammal deficient in expression of the DNA of the present invention. Differences in incidence of cancer or differences in degree of healing from the group administered with no test compound are observed in the tissues described above with passage of time.

In the screening method, when a test compound is administered to a test animal and the disease conditions of the test animal are improved by at least about 10%, preferably at least about 30% and more preferably at least about 50%, the test compound can be selected as the compound having the therapeutic/prophylactic effect on the diseases described above.

The compound obtained using the above screening method is a compound selected from the test compounds described above and exhibits a therapeutic/prophylactic effect on diseases caused by deficiencies, damages, etc. of the protein of the present invention. Therefore, the compound can be employed as a safe and low toxic drug for the prevention/treatment of the diseases. Furthermore, compounds derived from the compound obtained by the screening described above may also be used as well.

The compound obtained by the screening method above may form salts, and may be used in the form of salts with physiologically acceptable acids (e.g., inorganic acids, organic acids, etc.) or bases (e.g., alkali metal salts), preferably in the form of physiologically acceptable acid addition salts. Examples of such salts are salts with inorganic acids (e.g., hydrochloric acid, phosphoric acid, hydrobromic acid, sulfuric acid, etc.), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid, etc.) And the like.

A pharmaceutical comprising the compound obtained by the above screening method or salts thereof can be manufactured in a manner similar to the method for preparing the pharmaceutical comprising the protein of the present invention described hereinabove.

Since the pharmaceutical preparation thus obtained is safe and low toxic, it can be administered to human or a mammal (e.g., rat, mouse, guinea pig, rabbit, sheep, swine, bovine, horse, cat, dog, monkey, etc.).

The dose of the compound or its salt may vary depending upon target disease, subject to be administered, route of administration, etc. For example, when the compound is orally administered, the compound is administered to the adult patient with breast cancer (as 60 kg body weight) generally in a dose of about 0.1 to 100 mg, preferably about 1.0 to 50 mg and more preferably about 1.0 to 20 mg. In parenteral administration, a single dose of the compound may vary depending upon subject to be administered, target disease, etc. When the compound is administered to the adult patient with breast cancer (as 60 kg body weight) in the form of an injectable preparation, it is advantageous to administer the compound in a single dose of about 0.01 to about 30 mg, preferably about 0.1 to about 20 mg and more preferably about 0.01 to about 10 mg a day. For other animal species, the corresponding dose as converted per 60 kg weight can be administered.

(8b) Method of Screening a Compound that Promotes or Inhibits the Activity of a Promoter to the DNA of the Present Invention The present invention provides a method of screening a compound or its salts that promote or inhibit the activity of a promoter to the DNA of the present invention, which comprises administering a test compound to a non-human mammal deficient in expression of the DNA of the present invention and detecting the expression of a reporter gene.

In the screening method described above, an animal in which the DNA of the present invention is inactivated by introducing a reporter gene and the reporter gene is expressed under control of a promoter to the DNA of the present invention is used as the non-human mammal deficient in expression of the DNA of the present invention, which is selected from the aforesaid non-human mammals deficient in expression of the DNA of the present invention.

The same examples of the test compound apply to specific compounds described above.

As the reporter gene, the same specific examples apply to this screening method. Preferably, there are used β-galactosidase (lacZ), soluble alkaline phosphatase gene, luciferase gene and the like.

Since the reporter gene is present under control of a promoter to the DNA of the present invention in the non-human mammal deficient in expression of the DNA of the present invention wherein the DNA of the present invention is substituted with the reporter gene, the activity of the promoter can be detected by tracing the expression of a substance encoded by the reporter gene.

When a part of the DNA region encoding the protein of the present invention is substituted with, e.g., β-galactosidase gene (lacZ) derived from *Escherichia coli*, β-galactosidase is expressed in a tissue where the protein of the present invention should originally be expressed, instead of the protein of the present invention. Thus, the state of expression of the protein of the present invention can be readily observed in vivo of an animal by staining with a reagent, e.g., 5-bromo-4-chloro-3-indolyl-β-galactopyranoside (X-gal) which is substrate for β-galactosidase. Specifically, a mouse deficient in the protein of the present invention, or its tissue section is fixed with glutaraldehyde, etc. After washing with phosphate buffered saline (PBS), the system is reacted with a staining solution containing X-gal at room temperature or about 37° C. for approximately 30 minutes to an hour. After the β-galactosidase reaction is terminated by washing the tissue preparation with 1 mM EDTA/PBS solution, the color formed is observed. Alternatively, mRNA encoding lacZ may be detected in a conventional manner.

The compound or salts thereof obtained using the screening method described above are compounds that are selected from the test compounds described above and that promote or inhibit the promoter activity to the DNA of the present invention.

The compound obtained by the screening method above may form salts, and may be used in the form of salts with physiologically acceptable acids (e.g., inorganic acids, etc.) or bases (e.g., alkali metals, etc.) or the like, especially in the form of physiologically acceptable acid addition salts. Examples of such salts are salts with inorganic acids (e.g., hydrochloric acid, phosphoric acid, hydrobromic acid, sulfuric acid, etc.), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid, etc.) And the like.

The compound or its salts inhibiting the promoter activity to the DNA of the present invention can inhibit expression of the protein of the present invention to inhibit the functions of the protein. Thus, the compound or its salt is useful as prophylactic/therapeutic agents for cancer, e.g., colon cancer, breast cancer, lung cancer, prostate cancer, esophageal cancer, gastric cancer, liver cancer, biliary tract cancer, spleen cancer, renal cancer, bladder cancer, uterine cancer, testicular cancer, thyroid cancer, pancreatic cancer, brain tumor, blood tumor, etc.

In addition, compounds derived from the compound obtained by the screening described above may also be used as well.

A pharmaceutical comprising the compound obtained by the above screening method or salts thereof can be manufactured in a manner similar to the method for preparing the pharmaceutical comprising the protein of the present invention described above.

Since the pharmaceutical preparation thus obtained is safe and low toxic, it can be administered to human or a mammal (e.g., rat, mouse, guinea pig, rabbit, sheep, swine, bovine, horse, cat, dog, monkey, etc.).

A dose of the compound or salts thereof may vary depending on target disease, subject to be administered, route for administration, etc.; when the compound that inhibits the promoter activity to the DNA of the present invention is orally administered, the compound is administered to the adult patient with breast cancer (as 60 kg body weight) normally in a daily dose of about 0.1 to 100 mg, preferably about 1.0 to 50 mg and more preferably about 1.0 to 20 mg. In parenteral administration, a single dose of the compound varies depending on subject to be administered, target disease, etc. but when the compound of inhibiting the promoter activity to the DNA of the present invention is administered to the adult patient with breast cancer (as 60 kg body weight) in the form of injectable preparation, it is advantageous to administer the compound intravenously to the patient in a daily dose of about 0.01 to about 30 mg, preferably about 0.1 to about 20 mg and more preferably about 0.1 to about 10 mg. For other animal species, the corresponding dose as converted per 60 kg weight can be administered.

As stated above, the non-human mammal deficient in expression of the DNA of the present invention is extremely useful for screening the compound or its salt that promotes or inhibits the promoter activity to the DNA of the present invention and, can greatly contribute to elucidation of causes for various diseases suspected of deficiency in expression of the DNA of the present invention and for the development of prophylactic/therapeutic agents for these diseases.

In addition, a so-called transgenic animal (gene transferred animal) can be prepared by using a DNA containing the promoter region of the protein of the present invention, ligating genes encoding various proteins at the downstream and injecting the same into oocyte of an animal. It is thus possible to synthesize the protein therein specifically and study its activity in vivo. When an appropriate reporter gene is ligated to the promoter site described above and a cell line that expresses the gene is established, the resulting system can be utilized as the search system for a low molecular compound having the action of specifically promoting or inhibiting the in vivo productivity of the protein itself of the present invention.

In the specification and drawings, the codes of bases, amino acids, etc. are denoted in accordance with the IUPAC-IUB Commission on Biochemical Nomenclature or by the common codes in the art, examples of which are shown below. For amino acids that may have the optical isomer, L form is presented unless otherwise indicated.

DNA: deoxyribonucleic acid
cDNA: complementary deoxyribonucleic acid
A: adenine
T thymine
G: guanine
C: cytosine
RNA: ribonucleic acid
mRNA: messenger ribonucleic acid
dATP: deoxyadenosine triphosphate
dTTP: deoxythymidine triphosphate
dGTP: deoxyguanosine triphosphate
dCTP deoxycytidine triphosphate
ATP: adenosine triphosphate
EDTA: ethylenediaminetetraacetic acid
EGTA: ethyleneglycol-bis-(beta-aminoethyl ether) tetraacetic acid
SDS: sodium dodecyl sulfate
Gly: glycine
Ala: alanine
Val: valine
Leu: leucine
Ile: isoleucine
Ser: serine
Thr: threonine
Cys: cysteine
Met: methionine
Glu: glutamic acid
Asp: aspartic acid
Lys lysine
Arg: arginine
His: histidine
Phe: phenylalanine
Tyr: tyrosine
Trp: tryptophan
Pro: proline
Asn: asparagine
Gln: glutamine
pGlu: pyroglutamic acid
Sec: selenocysteine Substituents, protecting groups and reagents generally used in this specification are presented as the codes below.

Me: methyl group
Et: ethyl group
Bu: butyl group
Ph: phenyl group
TC: thiazolidine-4(R)-carboxamido group
Tos: p-toluenesulfonyl
CHO: formyl
Bzl: benzyl
$Cl_2$-Bzl: 2,6-dichlorobenzyl
Bom: benzyloxymethyl
Z: benzyloxycarbonyl
Cl-Z: 2-chlorobenzyloxycarbonyl
Br-Z: 2-bromobenzyl oxycarbonyl
Boc: t-butoxycarbonyl
DNP: dinitrophenol
Trt: trityl
Bum: t-butoxymethyl
Fmoc: N-9-fluorenyl methoxycarbonyl
HOBt: 1-hydroxybenztriazole
HOOBt: 3,4-dihydro-3-hydroxy-4-oxo-1,2,3-benzotriazine
HONB: 1-hydroxy-5-norbornene-2,3-dicarboxyimide
DCC: N,N'-dicyclohexylcarbodiimide The sequence identification numbers in the sequence listing of the specification indicate the following sequences.

[SEQ ID NO: 1]

This shows the amino acid sequence of FLJ20539.

[SEQ ID NO: 2]

This shows the base sequence of DNA encoding FLJ20539 having the amino acid sequence represented by SEQ ID NO: 1.

[SEQ ID NO: 3]

This shows the base sequence of DNA containing the full-length gene encoding FLJ20539.

[SEQ ID NO: 4]

This shows the amino acid sequence of hCP50177.

[SEQ ID NO: 5]

This shows the base sequence of DNA for hCP50177 having the amino acid sequence represented by SEQ ID NO: 4.

[SEQ ID NO: 6]

This shows the base sequence of DNA containing the full-length gene encoding hCP50177.

[SEQ ID NO: 7]

This shows the amino acid sequence of hCP 1762319.

[SEQ ID NO: 8]

This shows the base sequence of DNA for hCP 1762319 having the amino acid sequence represented by SEQ ID NO: 7.

[SEQ ID NO: 9]

This shows the base sequence of DNA containing the full-length gene encoding hCP 1762319.

[SEQ ID NO: 10]

This shows the amino acid sequence of FLJ13515.

[SEQ ID NO: 11]

This shows the base sequence of DNA encoding FLJ13515 having the amino acid sequence represented by SEQ ID NO: 10.

[SEQ ID NO: 12]

This shows the base sequence of DNA containing the full-length gene encoding FLJ13515.

[SEQ ID NO: 13]

This shows the base sequence of antisense polynucleotide used in EXAMPLES 2, 19, 20 and 21.

[SEQ ID NO: 14]

This shows the base sequence of antisense polynucleotide used in EXAMPLES 2, 19, 20 and 21.

[SEQ ID NO: 15]

This shows the amino acid sequence of TACT427-A.

[SEQ ID NO: 16]

This shows the base sequence of DNA encoding TACT427-A having the amino acid sequence represented by SEQ ID NO: 15.

[SEQ ID NO: 17]

This shows the amino acid sequence of TACT427-A2.

[SEQ ID NO: 18]

This shows the base sequence of DNA encoding TACT427-A2 having the amino acid sequence represented by SEQ ID NO: 17.

[SEQ ID NO: 19]

This shows the base sequence of DNA containing the full-length gene encoding TACT427-A and TACT427-A2.

[SEQ ID NO: 20]

This shows the amino acid sequence of TACT427-B.

[SEQ ID NO: 21]

This shows the base sequence of DNA encoding TACT427-B having the amino acid sequence represented by SEQ ID NO: 20.

[SEQ ID NO: 22]

This shows the amino acid sequence of TACT427-B2.

[SEQ ID NO: 23]

This shows the base sequence of DNA encoding TACT427-B2 having the amino acid sequence represented by SEQ ID NO: 22.

[SEQ ID NO: 24]

This shows the base sequence of DNA containing the full-length gene encoding TACT427-B and TACT427-B2.

[SEQ ID NO: 25]

This shows the amino acid sequence of TACT427-C.

[SEQ ID NO: 26]

This shows the base sequence of DNA encoding TACT427-C having the amino acid sequence represented by SEQ ID NO: 25.

[SEQ ID NO: 27]

This shows the amino acid sequence of TACT427-C2.

[SEQ ID NO: 28]

This shows the base sequence of DNA encoding TACT427-C2 having the amino acid sequence represented by SEQ ID NO: 27.

[SEQ ID NO: 29]

This shows the base sequence of DNA containing the full-length gene encoding TACT427-C and TACT427-C2.

[SEQ ID NO: 30]

This shows the base sequence of primer 1 used in EXAMPLE 3.

[SEQ ID NO: 31]

This shows the base sequence of primer 2 used in EXAMPLE 3.

[SEQ ID NO: 32]

This shows the base sequence of primer 3 used in EXAMPLE 4.

[SEQ ID NO: 33]

This shows the base sequence of primer 4 used in EXAMPLE 4.

[SEQ ID NO: 34]

This shows the base sequence of primer 5 used in EXAMPLE 5.

[SEQ ID NO: 35]

This shows the base sequence of primer 6 used in EXAMPLE 5.

[SEQ ID NO: 36]

This shows the base sequence of primer 7 used in EXAMPLES 6, 7, 8 and 20.

[SEQ ID NO: 37]

This shows the base sequence of primer 8 used in EXAMPLES 6, 7, 8 and 20.

[SEQ ID NO: 38]

This shows the base sequence of TaqMan probe 1 used in EXAMPLES 6, 7, 8 and 20.

[SEQ ID NO: 39]

This shows the base sequence of primer 9 used in EXAMPLE 10.

[SEQ ID NO: 40]

This shows the base sequence of primer 10 used in EXAMPLE 10.

[SEQ ID NO: 41]

This shows the amino acid sequence of peptide 1 used in EXAMPLE 11.

[SEQ ID NO: 42]

This shows the amino acid sequence of peptide 2 used in EXAMPLE 11.

[SEQ ID NO: 43]

This shows the amino acid sequence of peptide 3 used in EXAMPLE 11.

[SEQ ID NO: 44]

This shows the base sequence of sense oligonucleotide used in EXAMPLES 19, 20 and 21.

The transformant, *Escherichia coli* TOP10/47427A/pCR-BluntII-TOPO obtained in EXAMPLE 4 later described has been on deposit since Dec. 3, 2002 under the Accession Number FERM BP-8253 at the National Institute of Advanced Industrial Science and Technology, International Patent Organism Depositary, located at Central 6, 1-1-1 Higashi, Tsukuba, Ibaraki, Japan (postal code 305-8566).

The transformant, *Escherichia coli* TOP10/47427B/pCR-BluntII-TOPO obtained in EXAMPLE 4 later described has been on deposit since Dec. 3, 2002 under the Accession Number FERM BP-8254 at the National Institute of Advanced Industrial Science and Technology, International Patent Organism 110 Depositary, located at Central 6, 1-1-1 Higashi, Tsukuba, Ibaraki, Japan (postal code 305-8566).

The transformant, *Escherichia coli* TOP10/47427C/pCR-BluntII-TOPO obtained in EXAMPLE 5 later described has been on deposit since Dec. 3, 2002 under the Accession Number FERM BP-8255 at the National Institute of Advanced Industrial Science and Technology, International Patent Organism Depositary, located at Central 6, 1-1-1 Higashi, Tsukuba, Ibaraki, Japan (postal code 305-8566).

Hereinafter, the present invention is described in more detail with reference to EXAMPLES, but is not deemed to limit the scope of the present invention thereto.

Genetic manipulation using *Escherichia coli* was carried out, following the procedures described in Molecular Cloning, $2^{nd}$, Cold Spring Harbor Lab. Press, 1989).

EXAMPLE 1

Gene Expression Analysis

In order to reveal a group of genes with their expression enhanced specifically in breast cancer and lung cancer tissues, gene expression analysis was performed by oligonucleotide microarray (Human Genome U95A, U95B, U95C, U95D, U95E; Affymetrix) on total RNAs extracted from 8 breast cancer tissues and 4 normal breast tissues (TABLE 1) And total RNAs extracted from 4 lung cancer tissues and 5 normal lung tissues (TABLE 3) as samples.

The experimental procedures were performed in accordance with the Affymetrix Corp. manual (Expression Analysis Technical Manual). As a result, the enhanced expression was detected on (1) FLJ20539 gene (SEQ ID NO: 2), hCP50177 gene (SEQ ID NO: 5), which was a FLJ20539-associated gene, hCP1762319 gene (SEQ ID NO: 8), which was a FLJ20539-associated gene as well as FLJ13515 gene (SEQ ID NO: 11), and (2) TACT427-A gene (SEQ ID NO: 16), TACT427-A2 gene (SEQ ID NO: 18), TACT427-B gene (SEQ ID NO: 21), TACT427-B2 gene (SEQ ID NO: 23), TACT427-C gene (SEQ ID NO: 26) as well as TACT427-C2 gene (SEQ ID NO: 28) obtained in EXAMPLE 4 or EXAMPLE 5 later described, in breast cancer tissues (lot. 0009-192-00101, lot. 0009-192-00120, lot. 0009-192-00153, lot. 0009-192-00178) And lung cancer tissues (lot. 0009-192-00122, lot. 0011-192-01293, lot. 0011-192-01297), respectively, when compared to normal breast tissues and normal lung tissues (TABLES 2 and 4).

TABLE 1

| RNA-extracted Tissue | Distribution Source |
|---|---|
| Breast cancer tissue (lot. 0009-192-00101) | BioClinical Partners, Inc. |
| Breast cancer tissue (lot. 0009-192-00120) | BioClinical Partners, Inc. |
| Breast cancer tissue (lot. 0009-192-00153) | BioClinical Partners, Inc. |
| Breast cancer tissue (lot. 0009-192-00155) | BioClinical Partners, Inc. |
| Breast cancer tissue (lot. 0009-192-00157) | BioClinical Partners, Inc. |
| Breast cancer tissue (lot. 0009-192-00178) | BioClinical Partners, Inc. |
| Breast cancer tissue (lot. 0011-192-01284) | BioClinical Partners, Inc. |
| Breast cancer tissue (lot. 0011-192-01287) | BioClinical Partners, Inc. |
| Normal breast tissue (lot. 0008-192-00404) | BioClinical Partners, Inc. |
| Normal breast tissue (lot. 0008-192-00422) | BioClinical Partners, Inc. |
| Normal breast tissue (lot. 0009-192-00153) | BioClinical Partners, Inc. |
| Normal breast tissue (lot. 0011-192-01286) | BioClinical Partners. Inc. |

TABLE 2

| Tissue | Gene Expression Level |
|---|---|
| Breast cancer tissue (lot. 0009-192-00101) | 3.7 |
| Breast cancer tissue (lot. 0009-192-00120) | 9.0 |
| Breast cancer tissue (lot. 0009-192-00153) | 2.1 |
| Breast cancer tissue (lot. 0009-192-00155) | ND |
| Breast cancer tissue (lot. 0009-192-00157) | 0.54 |
| Breast cancer tissue (lot. 0009-192-00178) | 2.1 |
| Breast cancer tissue (lot. 0011-192-01284) | ND |
| Breast cancer tissue (lot. 0011-192-01287) | ND |
| Normal breast tissue (lot. 0008-192-00404) | ND |
| Normal breast tissue (lot. 0008-192-00422) | ND |
| Normal breast tissue (lot. 0009-192-00153) | 1.6 |
| Normal breast tissue (lot. 0011-192-01286) | 1.2 |

The gene expression level was normalized by taking as 1 the median value of the expression levels of all genes that the expression was detected with the oligonucleotide microarray.

ND: not detected

TABLE 3

| RNA-extracted Tissue | Distribution Source |
|---|---|
| Lung cancer tissue (lot. 0009-192-00122) | BioClinical Partners, Inc. |
| Lung cancer tissue (lot. 0011-192-01285) | BioClinical Partners, Inc. |
| Lung cancer tissue (lot. 0011-192-01293) | BioClinical Partners, Inc. |
| Lung cancer tissue (lot. 0011-192-01297) | BioClinical Partners, Inc. |
| Normal lung tissue (lot. 0009-192-00150) | BioClinical Partners, Inc. |
| Normal lung tissue (lot. 0009-192-00168) | BioClinical Partners, Inc. |
| Normal lung tissue (lot. 0011-192-01283) | BioClinical Partners, Inc. |
| Normal lung tissue (lot. 0011-192-01285) | BioClinical Partners, Inc. |
| Normal lung tissue (lot. 0011-192-01297) | BioClinical Partners. Inc. |

TABLE 4

| Tissue | Gene Expression Level |
|---|---|
| Lung cancer tissue (lot. 0009-192-00122) | 2.8 |
| Lung cancer tissue (lot. 0011-192-01285) | 0.67 |
| Lung cancer tissue (lot. 0011-192-01293) | 1.3 |
| Lung cancer tissue (lot. 0011-192-01297) | 1.5 |
| Normal lung tissue (lot. 0009-192-00150) | ND |
| Normal lung tissue (lot. 0009-192-00168) | 0.38 |
| Normal lung tissue (lot. 0011-192-01283) | ND |
| Normal lung tissue (lot. 0011-192-01285) | ND |
| Normal lung tissue (lot. 0011-192-01297) | ND |

The gene expression level was normalized by taking as 1 the median value of the expression levels of all genes that the expression was detected with the oligonucleotide microarray.

ND: not detected

EXAMPLE 2

Apoptosis Induction in Human Lung Cancer Cell Line

The expression of a gene for the protein of the present invention was suppressed to see if apoptosis was induced in human lung cancer cell line.

First, human non-small-cell lung cancer cell line NCI-H460 purchased from American Type Culture Collection (ATCC) was suspended in RPMI-1640 medium (containing 25 mM HEPES) (Invitrogen) supplemented with 10% fetal bovine serum (ATCC), and plated on a 96-well flat bottomed tissue culture plate (BD Falcon) at a cell density of 4000 cells/well and then incubated overnight at 37° C. in a 5% carbon dioxide gas flow, followed by transfection of the antisense oligonucleotide.

Specifically, following the design of an antisense oligonucleotide sequence (SEQ ID NO: 13) hybridizable to the protein coding region sequence or the 3' untranslated region of (1) FLJ20539 gene (SEQ ID NO: 2), hCP50177 gene (SEQ ID NO: 5), which was a FLJ20539-associated gene, hCP1762319 gene (SEQ ID NO: 8), which was a FLJ20539-associated gene as well as FLJ13515 gene (SEQ ID NO: 11), and (2) TACT427-A gene (SEQ ID NO: 16), TACT427-A2 gene (SEQ ID NO: 18), TACT427-B gene (SEQ ID NO: 21), TACT427-B2 gene (SEQ ID NO: 23), TACT427-C gene (SEQ ID NO: 26) And TACT427-C2 gene (SEQ ID NO: 28) obtained in EXAMPLE 4 or EXAMPLE 5 later described, the phosphorothioated oligonucleotide was synthesized, purified on HPLC and provided for use in transfection experiment (hereinafter merely referred to as antisense oligonucleotide).

For control, reverse sequence (SEQ ID NO: 14) of the base sequence shown by SEQ ID NO: 13 was similarly phosphorothioated, purified on HPLC and provided for use (hereinafter merely referred to as the control oligonucleotide).

The antisense oligonucleotide or the control oligonucleotide was diluted in Opti-MEM (Invitrogen) And FuGENE6 reagent (Roche Diagnostics) was further added to the dilution in a 4-fold volume (4 μL/μg oligonucleotide). The resulting mixture was allowed to stand at room temperature for 30 minutes. This oligonucleotide solution was dispensed in 40 μL/well. The final concentration of the oligonucleotide was adjusted to become 140 nM. After incubation was continued for further 3 days under the conditions described above, the apoptosis induction activity of the oligonucleotide above was assayed with Cell Death Detection ELISA$^{PLUS}$ Kit (Roche Diagnostics) in accordance with the protocol attached thereto.

The results revealed that the antisense oligonucleotide showed the apoptosis induction activity of approximately 2.8 times higher than the control oligonucleotide used as a negative control, indicating that there was a statistically significant difference (P=0.0005) (TABLE 5).

TABLE 5

| | Apoptosis Induction Activity ($A_{405}$-$A_{492}$) | |
|---|---|---|
| | Mean Value | Standard Deviation |
| Blank | 0.297 | 0.053 |
| Control oligonucleotide (SEQ ID NO: 14) | 0.764 | 0.096 |
| Antisense oligonucleotide (SEQ ID NO: 13) | 1.57 | 0.093 |

EXAMPLE 3

Apoptosis Induction of NCI-H460 by Antisense Oligonucleotide Transfection

It was examined if the expression level of (1) FLJ20539 gene (SEQ ID NO: 2), hCP50177 gene (SEQ ID NO: 5), which was a FLJ20539-associated gene, hCP1762319 gene (SEQ ID NO: 8), which was a FLJ20539-associated gene as well as FLJ13515 gene (SEQ ID NO: 11), and (2) TACT427-A gene (SEQ ID NO: 16), TACT427-A2 gene (SEQ ID NO: 18), TACT427-B gene (SEQ ID NO: 21), TACT427-B2 gene (SEQ ID NO: 23), TACT427-C gene (SEQ ID NO: 26) And TACT427-C2 gene (SEQ ID NO: 28) obtained in EXAMPLE 4 or EXAMPLE 5 later described, was reduced by providing the antisense oligonucleotide.

Human non-small-cell lung cancer cell line NCI-H460 used in EXAMPLE 2 was suspended in the same medium as in EXAMPLE 2, and plated on a 24-well flat bottomed tissue culture plate (BD Falcon) at a cell density of 24,000 cells/well. The cells were incubated overnight at 37° C. in a 5% carbon dioxide gas flow, followed by transfection of the antisense oligonucleotide and the control oligonucleotide. A volume of the oligonucleotide solution added was made 390 μL/well and the final concentration of the oligonucleotide was adjusted to be 200 nM. Following the transfection, incubation was continued at 37° C. for further 24 hours in a 5% carbon dioxide gas flow and the total RNA was extracted by RNeasy Mini Total RNA Kit (QIAGEN). Using as a template about 400 ng of the total RNA, reverse transcription was carried out on TaqMan Reverse Transcription Reagents (Applied Biosystems) in accordance with the protocol attached thereto. Using as a template cDNA in an amount of corresponding to 10 ng when converted into the total RNA, the number of expressed copies of (1) FLJ20539 gene (SEQ ID NO: 2), hCP50177 gene (SEQ ID NO: 5) as a FLJ20539-associated gene, hCP1762319 gene (SEQ ID NO: 8) as a FLJ20539-associated gene as well as FLJ13515 gene (SEQ ID NO: 11), and (2) TACT427-A gene (SEQ ID NO: 16), TACT427-A2 gene (SEQ ID NO: 18), TACT427-B gene (SEQ ID NO: 21), TACT427-B2 gene (SEQ ID NO: 23), TACT427-C gene (SEQ ID NO: 26) And TACT427-C2 gene (SEQ ID NO: 28) obtained in EXAMPLE 4 later described, was determined using two primers [primer 1 (SEQ ID NO: 30) And primer 2 (SEQ ID NO: 31)] and SYBR Green PCR Master Mix (Applied Biosystems).

The expression level of a gene for α-actin contained in the same amount of template cDNA was assayed on TaqMan α-actin Control Reagents (Applied Biosystems), which was used as internal standard. Where no antisense oligonucleotide was transfected, the expression level of the ten genes identified above was 0.10% of the gene expression level of β-actin, whereas the expression level was 0.046% in the group given with the antisense oligonucleotide represented by SEQ ID NO: 13, indicating that a statistically significant ($P \leqq 0.05$) reduction in the expression level was observed. On the other hand, the expression level was 0.088% in the group given with the control oligonucleotide (SEQ ID NO: 14), indicating that any statistically significant reduction in the expression level was not observed when compared to the non-transfection group. These results revealed that apoptosis of the human lung cancer cell line was induced by decreasing the expression level of the ten genes described above.

EXAMPLE 4

Cloning and Base Sequencing of cDNAS Encoding Human Brain-Derived Proteins TACT427-A, TACT427-A2, TACT427-B and TACT427-B2

Using Human Brain Marathon-Ready cDNA (CLONTECH) as a template, PCR was carried out by using two primers [primer 3 (SEQ ID NO: 32) And primer 4 (SEQ ID NO: 33)]. In the reaction solution for the PCR, 1 μl of the above cDNA was used as a template; 6.25 U of PfuTurbo DNA Polymerase (STRATAGENE), 1.0 μM each of primer 3 (SEQ ID NO: 32) And primer 4 (SEQ ID NO: 33), 200 μM of dNTPs and 5 μl of Pfu Buffer (STRATAGENE) were added to the cDNA to make the volume of the solution 50 μl. PCR was carried out by reacting at 95° C. for 1 minute and then repeating 40 times the cycle set to include 95° C. for 10 seconds, 55° C. for 30 seconds, 72° C. for 6 minutes and 60° C. for 1 minute. The PCR product was purified using PCR Purification Kit (QIAGEN). The purified product was subcloned to plasmid vector pCR-BluntII-TOPO (Invitrogen) according to the protocol of Zero Blunt TOPO PCR Cloning Kit (Invitrogen). The clones were transfected to *Escherichia coli* TOP10 and the clones bearing cDNA were selected in kanamycin-containing LB agar medium. The sequences of individual clones were analyzed to give the base sequences of cDNAs represented by SEQ ID NO: 16 and SEQ ID NO: 21, respectively.

The base sequence in which the 1-160 base sequence and the 2483-2755 base sequence in the FLJ20539 full-length gene base sequence represented by SEQ ID NO: 3 are added to the base sequence represented by SEQ ID NO: 16 at the 5' and 3' ends thereof, respectively, is shown by SEQ ID NO: 19.

The base sequence in which the 1-160 base sequence and the 2483-2755 base sequence in the FLJ20539 full-length gene base sequence represented by SEQ ID NO: 3 are added to the base sequence represented by SEQ ID NO: 21 at the 5' and 3' ends thereof, respectively, is shown by SEQ ID NO: 24.

The plasmid bearing the DNA fragment having the base sequence represented by SEQ ID NO: 16 and the plasmid bearing the DNA fragment having the base sequence represented by SEQ ID NO: 21 were named TACT427-A/pCR-BluntII-TOPO and TACT427-B/pCR-BluntII-TOPO, respectively.

The protein containing the amino acid sequence (SEQ ID NO: 15) encoded by the base sequence represented by SEQ ID NO: 16 was named TACT427-A.

The protein containing the amino acid sequence (SEQ ID NO: 20) encoded by the base sequence represented by SEQ ID NO: 21 was named TACT427-B.

Furthermore, the transformant bearing plasmid TACT427-A/pCR-BluntII-TOPO introduced and the transformant bearing plasmid TACT427-B/pCR-BluntII-TOPO introduced were named *Escherichia coli* TOP10/47427A/pCR-BluntII-TOPO and *Escherichia coli* TOP 110/47427B/pCR-BluntII-TOPO, respectively.

In the amino acid sequence (SEQ ID NO: 20) of TACT427-B, Arg at the 278 position, Glu at the 825 position, Ala at the 826 position and Val at the 970 position in the amino acid sequence (SEQ ID NO: 15) of TACT427-A are replaced by Gln, Lys, Pro and Ala, respectively and Ser at the 340 position is deleted.

In the base sequence (SEQ ID NO: 21) of DNA encoding TACT427-B, g at the 833 position, g at the 1482 position, a at the 1590 position, g at the 2473 position, g at the 2476 position and t at the 2909 position in the base sequence (SEQ ID NO: 16) of DNA encoding TACT427-B are replaced by a, c, g, a, c and c, respectively and agc at the 1015-1017 positions are deleted.

The sequence, of which the 1-4 amino acid sequence in the amino acid sequence of TACT427-A is deleted, is represented by SEQ ID NO: 17. The protein containing the amino acid sequence represented by SEQ ID NO: 17 is named TACT427-A2. The base sequence of DNA encoding TACT427-A2 is shown by SEQ ID NO: 18.

The sequence, of which the 1-4 amino acid sequence in the amino acid sequence of TACT427-B is deleted, is represented by SEQ ID NO: 22. The protein containing the amino acid sequence represented by SEQ ID NO: 22 is named TACT427-B2. The base sequence of DNA encoding TACT427-B2 is shown by SEQ ID NO: 23.

In human, the base sequence (SEQ ID NO: 16) of DNA encoding TACT427-A showed the highest homology to the base sequence (SEQ ID NO: 2) of DNA encoding FLJ20539. The 1-138 and 139-2322 sequences in the base sequence represented by SEQ ID NO: 2 correspond to the 1-138 and 889-3072 sequences in the base sequence represented by SEQ ID NO: 16, and the respective partial sequences showed homology of 99.3% and 100%, respectively. The base sequence (SEQ ID NO: 2) of DNA encoding FLJ20539 is deleted of the base sequence corresponding to the 139-888 sequence in the base sequence (SEQ ID NO: 16) of DNA encoding TACT427-A and for this reason, it is a sequence specific to TACT427-A.

TACT427-A2, TACT427-B and TACT427-B2 showed the highest homology to FLJ20539, as in TACT427-A, and involved similar base replacement and base sequence deletion.

The amino acid sequence from 735 to 792 in the amino acid sequence (SEQ ID NO: 15) of TACT427-A, the amino acid sequence from 731 to 788 in the amino acid sequence (SEQ ID NO: 17) of TACT427-A2, the amino acid sequence from 734 to 791 in the amino acid sequence (SEQ ID NO: 20) of TACT427-B, and the amino acid sequence from 730 to 787 in the amino acid sequence (SEQ ID NO: 22) of TACT427-B2 are all considered to have a chloroperoxidase activity since they contain a chloroperoxidase motif by search on SMART, which is amino acid domain motif search site.

Hydrophobic plotting for TACT427-A, TACT427-A2, TACT427-B and TACT427-B2 are illustrated in FIGS. 1, 2, 3 and 4, respectively.

EXAMPLE 5

Cloning and Base Sequencing of cDNAS Encoding Human Lung Cancer Cell Line NCI-H522-Derived Proteins TACT427-C and TACT427-C2

Human non-small-cell lung cancer cell line NCI-H522 (purchased from ATCC) was incubated in RPMI-1640 medium (containing 25 mM HEPES) (Invitrogen) supplemented with 10% fetal bovine serum, and the total RNA was extracted by RNeasy Mini Total RNA Kit (QIAGEN). Using the total RNA as a template, reverse transcription was carried out on TaqMan Reverse Transcription Reagents (Applied Biosystems) in accordance with the protocol attached thereto to acquire cDNA. Using the thus acquired cDNA as a template, PCR was carried out with two primers [primer 5 (SEQ ID NO: 34) And primer 6 (SEQ ID NO: 35)]. In the reaction solution for the PCR, the above cDNA was used as a template; 2.5 U of PfuTurbo Hotstart DNA Polymerase (STRATAGENE), 1.0 μM each of primer 5 (SEQ ID NO: 34) And primer 6 (SEQ ID NO: 35), 200 μM of dNTPs and 10 μl of GC Buffer I (TaKaRa) were added to the cDNA to make the volume of the solution 20 μl. PCR was carried out by reacting at 95° C. for 1 minute and then repeating 35 times the cycle set to include 95° C. for 30 seconds, 60° C. for 20 seconds and 72° C. for 3 minutes. The PCR product was electrophoresed on agarose gel and then purified using MinElute Gel Extraction Kit (QIAGEN). The purified product was subcloned to plasmid vector pCR-BluntII-TOPO (Invitrogen) according to the protocol of Zero Blunt TOPO PCR Cloning Kit (Invitrogen). The clones were transfected to *Escherichia coli* TOP10 and the clones bearing cDNA were selected in kanamycin-containing LB agar medium. The sequences of individual clones were analyzed to give the base sequence of cDNA represented by SEQ ID NO: 26.

The base sequence in which the 1-160 base sequence and the 2483-2755 base sequence in the FLJ20539 full-length gene base sequence represented by SEQ ID NO: 3 are added to the base sequence represented by SEQ ID NO: 26 at the 5' and 3' ends thereof, respectively, is shown by SEQ ID NO: 29.

The plasmid bearing the DNA fragment having the base sequence represented by SEQ ID NO: 26, was named TACT427-C/pCR-BluntII-TOPO.

The protein containing the amino acid sequence (SEQ ID NO: 25) encoded by the base sequence of DNA represented by SEQ ID NO: 26 was named TACT427-C.

The transformant bearing plasmid TACT427-C/pCR-BluntII-TOPO introduced was named *Escherichia coli Escherichia coli* TOP10/47427C/pCR-BluntII-TOPO.

In the amino acid sequence (SEQ ID NO: 25) of TACT427-C, Val at the 491 position, Glu at the 825 position, Ala at the 826 position and Val at the 970 position in the amino acid sequence (SEQ ID NO: 15) of TACT427-A are replaced by Met, Lys, Pro and Ala, respectively and Ser at the 340 position is deleted.

In the base sequence (SEQ ID NO: 26) of DNA encoding TACT427-C, a at the 504 position, a at the 939 position, g at the 1471 position, g at the 1482 position, a at the 1590 position, g at the 2473 position, g at the 2476 position and t at the 2909 position in the base sequence (SEQ ID NO: 16) of DNA encoding TACT427-A are replaced by c, g, a, c, g, a, c and c, respectively and agc at the 1015-1017 positions are deleted.

The sequence, of which the 1-4 amino acid sequence in the amino acid sequence of TACT427-C is deleted, is represented by SEQ ID NO: 27. The protein containing the amino acid sequence represented by SEQ ID NO: 27 is named TACT427-C2. The base sequence of DNA encoding TACT427-C2 is shown by SEQ ID NO: 28.

In human, the base sequence (SEQ ID NO: 26) of DNA encoding TACT427-C showed the highest homology to the base sequence (SEQ ID NO: 2) of DNA encoding FLJ20539. The 1-138 and 886-3069 sequences in the base sequence represented by SEQ ID NO: 26 correspond to the 1-138 and 139-2322 sequences in the base sequence represented by SEQ ID NO: 2, and the respective partial sequences showed homology of 99.3% and 99.5%, respectively. The base sequence (SEQ ID NO: 2) of DNA encoding FLJ20539 is deleted of the base sequence of DNA corresponding to the 139-885 sequence, which is represented by TACT427-C (SEQ ID NO: 26) And thus, it is a sequence specific to TACT427-C. TACT427-C2 also showed the highest homology to FLJ20539, as in TACT427-C, and involved similar sequence deletion.

The sequence from 734 to 791 in the amino acid sequence (SEQ ID NO: 25) of TACT427-C and the sequence from 730 to 787 in the amino acid sequence (SEQ ID NO: 27) of TACT427-C are both considered to have a chloroperoxidase activity since they contain a chloroperoxidase motif by search on SMART, which is amino acid domain motif search site.

Figure 5:
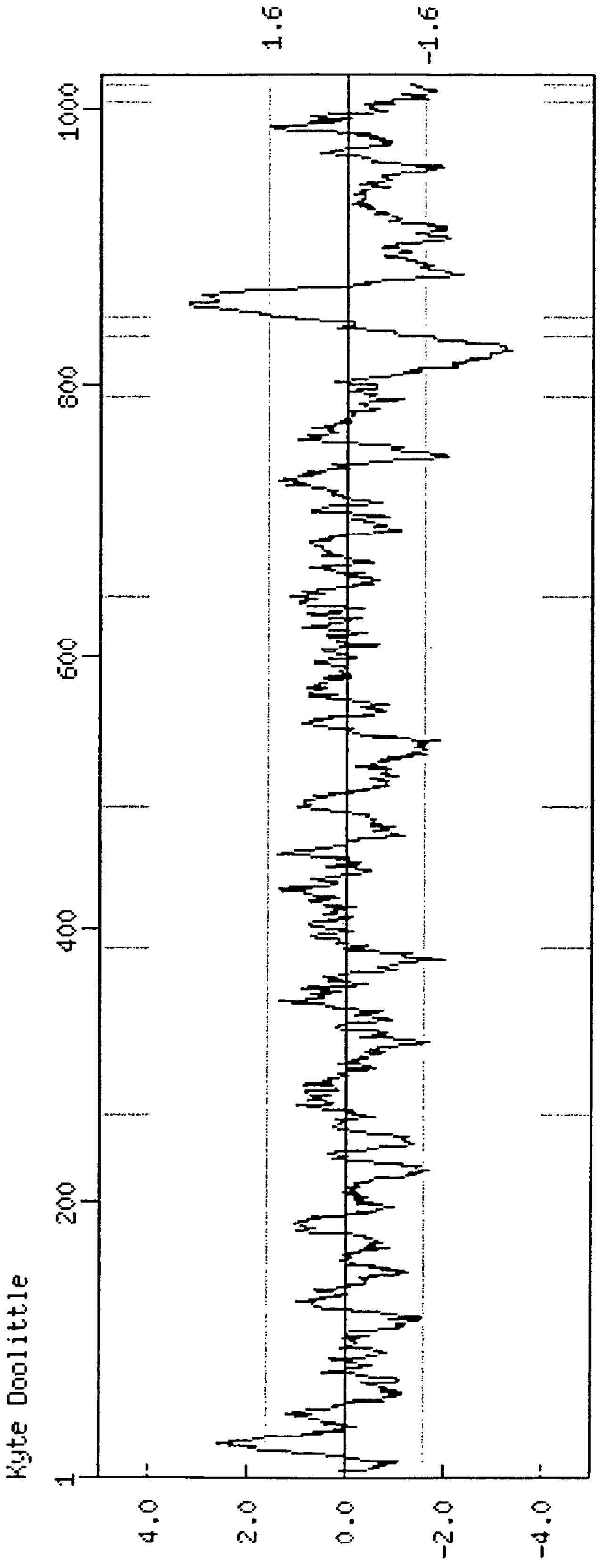
FIG. 5 is a graph illustrating the hydrophobic plot of TACT427-C.
Figure 6:
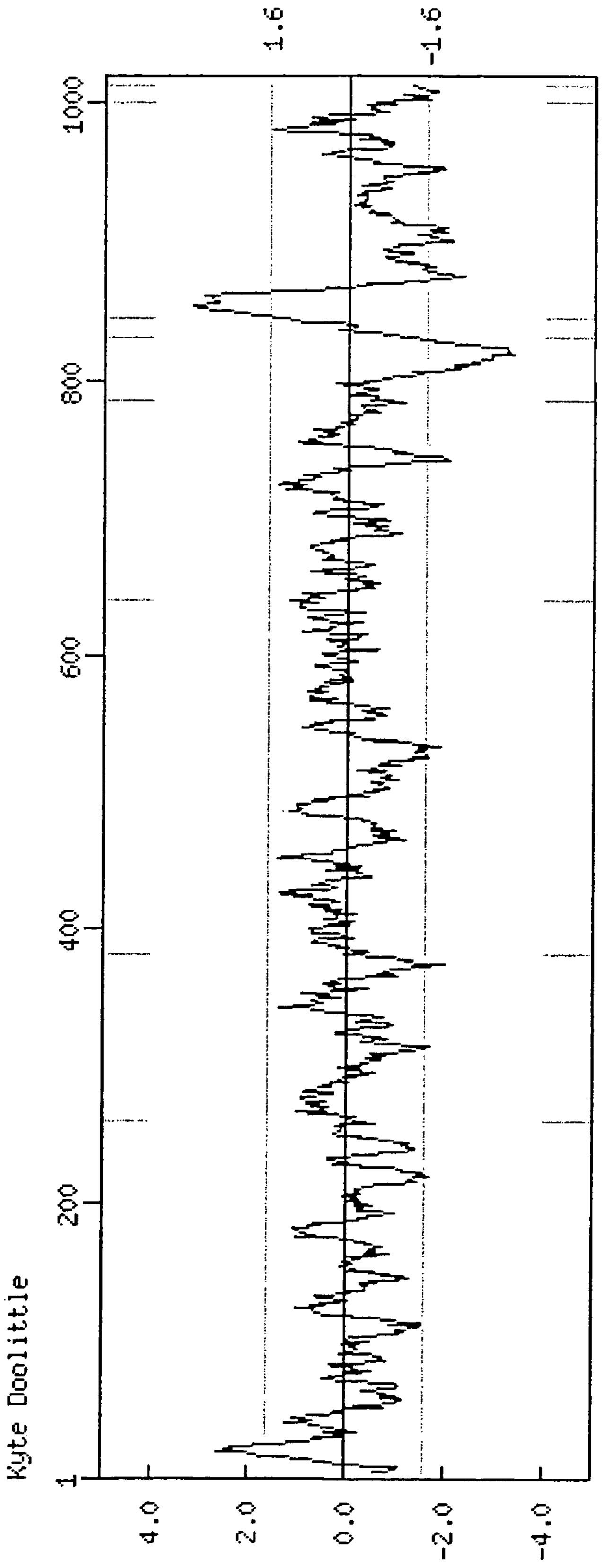
FIG. 6 is a graph illustrating the hydrophobic plot of TACT427-C2.

Hydrophobic plotting for TACT427-C and TACT427-C are illustrated in FIGS. 5 and 6, respectively.

EXAMPLE 6

In EXAMPLES below, TACT427-A gene (SEQ ID NO: 16), TACT427-A2 gene (SEQ ID NO: 18), TACT427-B gene (SEQ ID NO: 21), TACT427-B2 gene (SEQ ID NO: 23), TACT427-C gene (SEQ ID NO: 26) And TACT427-C2 gene (SEQ ID NO: 28) are sometimes collectively referred to asTACT427 gene.

TACT427-A protein (SEQ ID NO: 15), TACT427-A2 protein (SEQ ID NO: 17), TACT427-B protein (SEQ ID NO: 20), TACT427-B2 protein (SEQ ID NO: 22), TACT427-C protein (SEQ ID NO: 25) And TACT427-C2 protein (SEQ ID NO: 27) are sometimes collectively referred to as TACT427 protein.

Study of Gene Expression Level in Human Cancer Tissue (1)

Using Matched Tumor/Normal cDNA Pair (CLONTECH) derived from human tissue of patients with cancer (breast cancer, lung cancer, colon cancer, rectal cancer and ovarian cancer) as a template, quantitative PCR was carried out using FAM-labeled TaqMan probe to assay the expression levels of FLJ20539 gene (SEQ ID NO: 2), hCP50177 gene (SEQ ID NO: 5), hCP1762319 gene (SEQ ID NO: 8) And FLJ13515 gene (SEQ ID NO: 11) in cancer tissues and normal tissues, as well as TACT427 gene obtained in EXAMPLE 4 or EXAMPLE 5.

In the reaction solution for the PCR, 1 μl of the above cDNA was used as a template; 7.5 μl of TaqMan™ Universal PCR Master Mix (Applied Biosystems) And 0.5 μM each of primer 7 (SEQ ID NO: 36) And primer 8 (SEQ ID NO: 37) were added to the cDNA and 100 nM of TaqMan probe 1 (SEQ ID NO: 38) to make the volume of the solution 15 μl. PCR was carried out by reacting at 50° C. for 2 minutes and 95° C. for 10 minutes, and then repeating 40 times the cycle set to include 95° C. for 15 seconds and 60° C. for 1 minute.

Thus, the total level of each gene above showed the following expression level: in 2 out of 4 cases in human breast cancer tissues, higher by about 7 times and about 16 times than the peripheral normal tissues; in 2 out of 3 cases in human lung cancer tissues, higher by about 3 times and about 2 times than the peripheral normal tissues; in 4 out of 5 cases in human colon cancer tissues, higher by about 2 times, about 8 times, about 3 times and about 4 times than the peripheral normal tissues; and in 2 out of 5 cases in human ovarian cancer tissues, higher by about 3 times and about 20 times than the peripheral normal tissues;

The results reveal that the total levels of the above genes markedly enhanced in the cancer tissues.

EXAMPLE 7

Study of Gene Expression Level in Human Cancer Tissue (2)

Using cDNA prepared from human lung cancer tissue (purchased from Direct Clinical Access and BioClinical Partners) as a template, the genes used in EXAMPLE 6 were compared in cancer and normal tissues by the same procedures as in EXAMPLE 6, in terms of the expression level.

In the reaction solution for the reaction, 1 μl of the above cDNA was used as a template and PCR was carried out under the same conditions as in EXAMPLE 6. In parallel, the copy number of the gene for β-actin contained in 1 μl of the above cDNA was calculated using TaqMan™ Human β-actin Control Reagents (Applied Biosystems) And used as an internal standard. When normalized by the gene expression level of β-actin, the total level of the above gene from the Direct Clinical Access samples increased by about 144, about 3, about 5, about 4, about 4, about 13, about 3 and about 19 times in 8 out of 10 cases in human lung cancer tissues, when compared to normal lung tissue, indicating that markedly enhanced expression was noted in human lung cancer tissues.

In the BioClinical Partners samples, the case where the total level of the above gene exceeded 1% of the gene expression level of β-actin was observed in 1 out of 7 samples in normal lung tissues, whereas in human lung cancer tissues the case exceeding 1% was observed as frequently as 5 out of 11 samples.

The foregoing results revealed that expression of the gene described above was markedly enhanced in human lung cancer tissues.

EXAMPLE 8

Study of Gene Expression Level in Human Culture Cell Line

The 86 strains used below were purchased from ATCC: brain tumor cell lines SK-N-MC, SK-N-AS, SK-N-BE, SK-N-DZ, SK-N-FI, SK-N-SH, D341 Med, Daoy, DBTRG-05MG, U-118 MG, U-87 MC, CCF-STTG1 and SW 1088; human breast cancer cell linesHCC1937, ZR-75-1, AU565, MCF-7 and MDA-MB-231; human colon cancer cell lines-Caco-2, COLO 201, COLO 205, COLO 320DM, HCT-8, HT-29, LoVo, LS123, SNU-C1, SK-CO-1, SW 403, SW 48, SW 480, SW 620, SW 837 and SW 948; human embryonic kidney cell line HEK293; human small cell lung cancer cell lines NCI-H187, NCI-H378, NCI-H526, NCI-H889, NCI-H1672, NCI-H1836, NCI-H2227, NCI-N417 and SHP-77; human non-small cell lung cancer cell lines A549, NCI-H23, NCI-H226, NCI-H358, NCI-H460, NCI-H522, NCI-H661, NCI-H810, NCI-H1155, NCI-H1299, NCI-H1395, NCI- H1417, NCI-H1435, NCI-H1581, NCI-H1651, NCI-H1703, NCI-H1793, NCI-H1963, NCI-H2073, NCI-H2085, NCI-H2106, NCI-H2228, NCI-H2342 and NCI-H2347; human ovarian cancer cell lines ES-2, Caov-3, MDAH2774, NIH: OVCAR3, OV-90, SK-OV-3, TOV-112D and TOV-21G; human pancreas cancer cell lines PANC-1, MIA-PaCa-2, AsPC-1, BxPC-3, Capan-1 and Capan-2; human prostate cancer cell line DU 145; human retinoblastoma cell lines WERI-Rb-1 and Y79; and human testicular cancer cell line Cates-1B. Human normal small airway epithelial cells SAEC and human normal prostate epithelial cells HPrEC were purchased from Clonetics. Human colon cancer cell line COCM1, human non-small cell lung cancer cell line VMRC-LCD and human prostate cancer cell line PC3 was purchased from JCRB. These cell lines are sometimes used also in EXAMPLES subsequent to EXAMPLE 9.

Total RNA was prepared from the 91 cell lines described above using RNeasy Mini Total RNA Kit (QIAGEN). Reverse transcription was performed on the total RNA as a template using a random primer, in accordance with the attached protocol of TaqMan Reverse Transcription Reagents (Applied Biosystems) to prepare cDNA. Using this cDNA as a template, quantitative PCR was carried out to examine the expression levels of FLJ20539 gene (SEQ ID NO: 2), hCP50177 gene (SEQ ID NO: 5), hCP1762319 gene (SEQ ID NO: 8), FLJ13515 gene (SEQ ID NO: 111), and TACT427 gene.

The reaction above was carried out by the same procedures as in EXAMPLE 6, using cDNA generated from 5 ng of the total RNA described above as the template. In parallel, the copy number of the gene for β-actin contained in 1 ng of the total RNA above was calculated using TaqMan™ Human β-actin Control Reagents (Applied Biosystems) And used as an internal standard.

A relative expression rate obtained by normalizing the total gene expression level with the gene expression level of β-actin is shown in [TABLE 6].

The cancer cell lines in which the total gene expression level exceeds 1% of the gene expression level of β-actin were found to be 13 strains, indicating that enhanced expression of the genes above was noted in the cancer cell lines.

TABLE 6

| Cell Line | % of β-actin | Cell Line | % of β-actin | Cell Line | % of β-actin |
|---|---|---|---|---|---|
| SK-N-MC | 0.47 | COLO 201 | 0.15 | NCI-H889 | 0.63 |
| SK-N-AS | 0.8 | COLO 205 | 0.07 | NCI-H1672 | 1.61 |
| SK-N-BE | 1.14 | COLO 320 DM | 0.97 | NCI-H1836 | 0.58 |
| SK-N-DZ | 1.69 | HCT-8 | 0.66 | NCI-H2227 | 1.28 |
| SK-N-FI | 0.85 | HT-29 | 0.21 | NCI-N417 | 0.42 |
| SK-N-SH | 0.34 | LoVo | 0.56 | SHP-77 | 0.46 |
| D341 Med | 0.91 | LS123 | 0.23 | A549 | 0.45 |
| Daoy | 0.17 | SNU-C1 | 0.03 | NCI-H23 | 0.2 |
| DBTRG-05 MG | 0.63 | SK-CO-1 | 0.45 | NCI-H226 | 1.93 |
| U-118 MG | 0.07 | SW 403 | 0.04 | NCI-H358 | 0.16 |
| U-87 MG | 1.51 | SW 48 | 0.44 | NCI-H460 | 0.33 |
| CCF-STTG1 | 0.27 | SW 480 | 0.16 | NCI-H522 | 0.77 |
| SW 1088 | 0.36 | SW 620 | 1.1 | NCI-H661 | 0.27 |
| HCC1937 | 0.43 | SW 837 | 0.34 | NCI-H810 | 0.5 |
| ZR-75-1 | 2.55 | SW 948 | 0.07 | NCI-H1155 | 0.24 |
| AU565 | 2.59 | HEK293 | 0.32 | NCH-1299 | 0.29 |
| MCF-7 | 0.56 | SAEC | 0.96 | NCI-H1395 | 0.27 |
| MDA-MB-231 | 0.71 | NCI-H187 | 3.12 | NCI-H1417 | 1.58 |
| Caco-2 | 0.22 | NCI-H378 | 0.77 | NCI-H1435 | 0.13 |
| COCM1 | 0.23 | NCI-H526 | 0.89 | NCI-H1581 | 0.54 |
| NCI-H1651 | 0.14 | ES-2 | 0.26 | BxPC-3 | 0.25 |
| NCI-H1703 | 0.33 | Caov-3 | 0.15 | Capan-1 | 0.15 |

TABLE 6-continued

| Cell Line | % of β-actin | Cell Line | % of β-actin | Cell Line | % of β-actin |
|---|---|---|---|---|---|
| NCI-H1793 | 0 | MDAH2774 | 0.31 | Capan-2 | 0.08 |
| NCI-H1963 | 1.25 | NIH:OVCAR3 | 1.04 | HPrEC | 0.55 |
| NCI-H2073 | 0.08 | OV-90 | 0.4 | DU 145 | 0.84 |
| NCI-H2085 | 0.22 | SK-OV-3 | 0.26 | PC3 | 0.23 |
| NCI-H2106 | 0.82 | TOV-112D | 0.88 | WERI-Rb-1 | 0.89 |
| NCI-H2228 | 0.2 | TOV-21G | 0.53 | Y79 | 0.81 |
| NCI-H2342 | 0.48 | PANC-1 | 0.34 | Cates-1B | 0.31 |
| NCI-H2347 | 0.21 | MIA-PaCa-2 | 0.03 | | |
| VMRC-LCD | 0.74 | AsPC-1 | 0.06 | | |

EXAMPLE 9

Construction of Animal Cell Expression Vectors for Recombinant Full-Length Protein (1)

Expression vectors for animal cells capable of expressing TACT427-A and TACT427-B proteins tagged with 3xFLAG at the C termini were constructed.

TACT427-A/pCR-BluntII-TOPO and TACT427-B/pCR-BluntII-TOPO obtained in EXAMPLE 4 and p3xFLAG-CMV-14 (Sigma) were treated with restriction enzymes EcoRI and XbaI. After separation by agarose gel electrophoresis, the DNA fragments corresponding to TACT427-A, TACT427-B and p3xFLAG-CMV-14 were recovered and purified using Gel Extraction Kit (QIAGEN). The respective DNA fragments were subjected to ligation using DNA Ligation Kit ver. 2 (Takara Bio), followed by transfection to *Escherichia coli* TOP10 and selection in ampicillin-containing LB agar medium. As a result of the sequence analysis of individual clones, animal cell expression vectors p3xFLAG-TACT427-A and p3xFLAG-TACT427-B having cDNA sequences encoding TACT427-A protein (SEQ ID NO: 15) And TACT427-B protein (SEQ ID NO: 20) were acquired.

EXAMPLE 10

Construction of Animal Cell Expression Vectors for Recombinant Full-Length Protein (2)

Expression vector for animal cells capable of expressing TACT427-A protein (SEQ ID NO: 15) was constructed.

Using p3xFLAG-TACT427-A obtained in EXAMPLE 9 as a template, PCR was carried out using primer 9 (SEQ ID NO: 39) And primer 10 (SEQ ID NO: 40). In the reaction solution for the reaction, 200 ng of p3xFLAG-TACT427-A was used as a template; 2.5 U of PfuTurbo Hotstart DNA Polymerase (STRATAGENE), 1 μM each of primer 9 (SEQ ID NO: 39) And primer 10 (SEQ ID NO: 40), 200 μM of dNTPs and 25 μl of GC Buffer I (Takara Bio) were added to make the volume of the solution 50 μl. PCR was carried out by reacting at 95° C. for 1 minute and then repeating 25 times the cycle set to include 95° C. for 15 seconds, 60° C. for 15 seconds and 72° C. for 3 minutes. Next, the PCR product was purified with PCR Purification Kit (QIAGEN) followed by treatment with restriction enzymes XbaI and EcoRI. Furthermore, pcDNA3.1 (+) (Invitrogen) was treated with restriction enzymes XbaI and EcoRI. After they were separated by agarose gel electrophoresis, the DNA fragment having the base sequence encoding TACT427-A protein and the DNA fragment corresponding to pcDNA3.1 (+) were recovered, respectively, and purified using Gel Extraction Kit (QIAGEN, Inc.). After the respective DNA fragments were subjected to ligation using DNA Ligation Kit ver. 2 (Takara Bio), the ligation products were transfected to *Escherichia coli* TOP 10, followed by selection in ampicillin-containing LB agar medium. As a result of the sequence analysis of individual clones, animal cell expression vector pcDNA3.1 (+)-TACT427-A having cDNA sequence encoding TACT427-A protein was acquired.

EXAMPLE 11

Production and Purification of Peptide Antibodies

Based on the amino acid sequence of TACT427 protein, the following 3 peptides (peptides 1 to 3) composed of 15 amino acids were synthesized by Fmoc solid phase synthesis.

The amino acid sequence of peptide 1 [Gly-Ser-Gly-Glu-Glu-Asn-Asp-Pro-Gly-Glu-Gln-Ala-Leu-Pro-Cys (SEQ ID NO: 41)] is a sequence of the 220-233 amino acid sequence in TACT427-A protein (SEQ ID NO: 15), in which Cys is added to the amino acid sequence at the C terminus.

The amino acid sequence of peptide 2 [Gly-Pro-Ala-Glu-Gly-Pro-Ala-Glu-Pro-Ala-Ala-Glu-Ala-Ser-Cys (SEQ ID NO: 42)] is a sequence of the 517-530 amino acid sequence in TACT427-A protein (SEQ ID NO: 15), in which Cys is added to the amino acid sequence at the C terminus.

The amino acid sequence of peptide 3 [Gly-Ser-Val-Gly-Gly-Asn-Thr-Gly-Val-Arg-Gly-Lys-Phe-Glu-Cys (SEQ ID NO: 43)] is a sequence of the 800-813 amino acid sequence in TACT427-A protein (SEQ ID NO: 15), in which Cys is added to the amino acid sequence at the C terminus.

Keyhole limpet hemocyanin (KLH) as a carrier protein was coupled to the respective peptides of the peptides 1, 2 and 3, which were used as antigens to produce rabbit polyclonal antibodies, as described below.

One male rabbit KBL:JW (11 weeks old, Oriental Yeast Co., Ltd.) was used as an immunized animal. Complete Freund's adjuvant (Difco Laboratories) suspension was used for primary sensitization and incomplete adjuvant (Difco Laboratories) suspension for the second sensitization and thereafter. The sensitization was performed by subcutaneous injection at the back and 0.5 mg of each antigen was used per sensitization. After the primary sensitization, it was repeated 3 times every 14 days. On day 52 after the primary sensitization, blood was collected through the carotid artery under anesthesia to give about 50 ml of serum. The serum thus obtained was concentrated by means of ammonium sulfate salting out. The total amount of the crude IgG fractions obtained were purified on protein A-affinity column (Amersham-Bioscience) to give about 223 mg, about 495 mg and about 390 mg of purified IgG from peptides 1, 2 and 3, respectively. Further using 111 mg of the purified IgG to peptide 1, 248 mg of the purified IgG to peptide 2 and 195 mg of the purified IgG to peptide 3 as materials, the IgG fraction bound to the column where each of the immunogenic peptides was immobilized was acquired. For immobilization, the C-terminal Cys of each peptide was utilized and the peptide was coupled to Sepharose column (Amersham-Bioscience) using borate buffer. For elution from the column, 8M urea/phosphate buffered saline (PBS) was used. The eluate was dialyzed to PBS to remove urea, which was followed by ultraconcentration and sterilization by filtering. Thus, affinity-purified antibodies AS-2480, AS-2481 and AS-2482 to peptides 1, 2 and 3, were acquired in about 3.7 mg, about 0.69 mg and about 17 mg, respectively.

EXAMPLE 12

Western Blotting Using Rabbit Peptide Antibodies

TACT427-A protein (SEQ ID NO: 15) was detected with rabbit sera containing the peptide antibodies prepared in EXAMPLE 11. Human embryonic kidney-derived HEK293 cells were suspended in 9 ml of Dulbecco's Modified Eagle's Minimal Medium (Invitrogen) containing 10% fetal bovine serum (JRH) at a concentration of $1.0\times10^6$ and plated on a Petri dish of 10 cm in diameter. After incubation at 37° C. overnight in a 5% carbon dioxide flow, 6 μg of p3xFLAG-TACT427-A, which had been previously mixed with 18 μl of FuGene6 transfection reagent (Roche Diagnostics) And OPTI-MEM I (Invitrogen) followed by allowing to stand at room temperature for 15 minutes, was added to the medium. Incubation was continued under the same conditions. Two days after, the cells were washed with PBS and 800 μl of ice-chilled RIPA buffer [50 mM Tris-hydrochloride buffer, pH 7.5, 150 mM sodium chloride, 1% Triton X-100, 0.1% SDS, 1% deoxycholic acid, Complete™ Tablet (Roche Diagnostics) And Phosphatase Inhibitor Cocktail-2 (Sigma)] was added to the cells. The mixture was allowed to stand at 4° C. for 15 minutes. This RIPA buffer was recovered and centrifuged at 15,000 rpm for 20 minutes. The supernatant separated was used as the cell-free extract, 20 μl of which was provided for SDS-PAGE on 7.5% acrylamide gel. The protein electrophoresed and then isolated was transferred onto Clear Blotting P Membrane (ATTO) in a conventional manner, which was then allowed to stand in a blocking buffer (Tris-buffered saline, 0.1% Tween-20, 5% skimmed milk) at room temperature for an hour. Next, 3 kinds of rabbit sera containing the peptide antibody AS-2480, AS-2481 or AS-2482 produced in EXAMPLE 11 were diluted in the blocking buffer to 100-fold, respectively, followed by addition of each dilution. After incubation at 4° C. overnight, the system was allowed to stand for an hour in a secondary antibody solution, which was prepared by diluting HRP-labeled anti-rabbit IgG antibody (Amersham-Bioscience) in the blocking buffer to 100,000-fold. Detection was performed following the protocol attached to ECL plus (Amersham-Bioscience).

Even when any of the three rabbit sera containing the peptide antibodies AS-2480, AS-2481 and AS-2482, respectively, was used, a specific band attributed to the TACT427-A protein was noted at the position near 150 kD molecular weight.

EXAMPLE 13

Immunoprecipitation Using Peptide Antibodies

Using the peptide antibodies produced in EXAMPLE 11, immunoprecipitation was performed on the TACT427-A protein under non-denaturing conditions.

Using p3xFLAG-TACT427-A acquired in EXAMPLE 9, 50 μl of Protein G-Sepharose 4FF (Amersham-Bioscience) suspension (suspended in an equal volume of RIPA buffer) And 3 μl of rabbit serum were added to 1 ml of the cell-free extract prepared by the same procedures as in EXAMPLE 12. The mixture was agitated at 4° C. overnight. As the rabbit serum, any one of the three rabbit serum containing the peptide antibody AS-2480, AS-2481 or AS-2482 prepared in EXAMPLE 11. After the Protein G-Sepharose 4FF co-precipitated fraction was washed with RIPA buffer, the fraction was suspended in 50 μl of SDS-PAGE sample buffer (Bio-Rad Laboratories) containing 1% 2-mercaptoethanol. The mixture was heated at 95° C. for 5 minutes and then, 20 μl of the mixture was provided for SDS-PAGE on 7.5% acrylamide gel. Detection was performed by the same procedures as in EXAMPLE 12, except that mouse anti-FLAG M2 antibody (Sigma) diluted with the blocking buffer to 10 μg/ml was used HRP-labeled anti-mouse IgG antibody (Amersham-Bioscience) diluted with the blocking buffer to 50,000-fold was used as the primary antibody and as the secondary antibody. Even when immunoprecipitation was performed using any of the three rabbit sera containing the peptide antibodies AS-2480, AS-2481 and AS-2482, respectively, a specific band attributed to the TACT427-A protein was noted at the position near 150 kD molecular weight.

The foregoing results reveal that the peptide antibodies AS-2480, AS-2481 and AS-2482 bind to the non-denaturing TACT427-A protein.

EXAMPLE 14

Study of Expression of TACT427 Protein in Cancer Cell Lines

Lung cancer cell lines A549, NCI-H226 and NCI-H522 as well as breast cancer cell line ZR-75-1 plated, respectively, on a Petri dish of 10 cm in diameter, were washed with PBS and cell-free extracts were prepared by the procedures described in EXAMPLE 12. To 1 ml each of the cell-free extracts of A549, NCI-H226, NCI-H522 and ZR-75-1, 50 μl of Protein G-Sepharose 4FF (Amersham-Bioscience) suspension (suspended in an equal volume of RIPA buffer) and 3 μg of peptide antibody AS-2482 produced in EXAMPLE 11 were added, followed by agitation at 4° C. overnight. After washing the Protein G-Sepharose 4FF co-precipitated fraction with RIPA buffer, the fraction was suspended in 50 μl of SDS-PAGE sample buffer (Bio-Rad Laboratories) containing 1% 2-mercaptoethanol and the suspension was heated at 95° C. for 5 minutes, 20 μl of which was provided for SDS-PAGE on 7.5% acrylamide gel. Using the peptide antibody AS-2482, detection was performed in a manner similar to EXAMPLE 12.

Even with any of A549, NCI-H226, NCI-H522 and ZR-75-1, a specific band attributed to the TACT427 protein was noted at the position near 150 kD molecular weight.

The foregoing results reveal that the protein described above is expressed in the five cancer cell lines described above.

EXAMPLE 15

Study of Localization of the TACT427-A Protein (Cell Staining)

Human embryonic kidney-derived HEK293 cells were suspended in Dulbecco's Modified Eagle's Minimal Medium (Invitrogen) containing 10% fetal bovine serum (JRH) at a concentration of $1.0\times10^5$ and plated on a 2-well poly-D-lysine coated culture slide (BD Falcon). Similarly, human non-small cell lung cancer cell line NCI-H460 was suspended in RPMI 1640 Medium (Invitrogen) containing 10% fetal bovine serum (JRH) at a concentration of $5\times10^4$ and plated on a 2-well poly-D-lysine coated culture slide (BD Falcon). After incubation at 37° C. overnight in a 5% carbon dioxide flow, 1.33 μg of p3xFLAG-TACT427-A, which had been previously mixed with 5.3 μl of FuGene6 transfection reagent (Roche Diagnostics) And OPTI-MEM I (Invitrogen) followed by allowing to stand at room temperature for 15 minutes, was added to the medium. Incubation was continued under the same conditions. Two days after, the cells were washed with PBS and 10% neutral formalin buffer was added thereto to immobilize the cells at room temperature for 30 minutes. Subsequently, Triton X-100 diluted in PBS to 0.1% was added. The mixture was washed again with PBS and PBS containing 1% BSA was further added to the mixture. The mixture was allowed to stand at 4° C. for 24 hours to block non-specific binding sites of the antibody. Next, mouse anti-FLAG M2 antibody (Sigma) diluted in 1% BSA-containing PBS in 10 μg/ml was added to react them at room temperature for 45 minutes. The reaction mixture was then washed with PBS and Alexa488-labeled anti-mouse IgG antibody (Molecular Probes) diluted in 1% BSA-containing PBS to 10 μg/ml was added thereto. Again, the mixture was reacted at room temperature for 45 minutes. After washing with PBS, the mixture was observed under a fluorescence microscope.

The results revealed that the TACT427-A protein was expressed on the cytoplasmic membrane in any of HEK293 and NCI-H460.

Plasmid pcDNA3.1 (+)-TACT427-A was transfected to HEK293 cells in a similar manner, and localization of the TACT427-A protein was examined using 10 μg/ml of AS-2480, AS-2481 and AS-2482 as primary antibodies and 10 μg/ml of Alexa488-labeled anti-rabbit IgG antibody (Molecular Probes) as the secondary antibody. The results revealed that the protein was likewise expressed on the cytoplasmic membrane.

EXAMPLE 16

Study of Localization of TACT427-A Protein (Biotin Labeling)

In a manner similar to EXAMPLE 12, plasmid p3xFLAG-TACT427-A was transfected to HEK293 cells. The protein exposed onto the cell surface 48 hours after was labeled with biotin using Cellular Labeling and Immunoprecipitation Kit (Roche Diagnostics). Using 1 ml of the cell-free extract prepared as in EXAMPLE 12 and 3 μg of mouse anti-FLAG M2 antibody (Sigma), immunoprecipitation was carried out in accordance with the procedures of EXAMPLE 13, followed by SDS-PAGE. By detection with HRP-labeled streptoavidin (Amersham-Bioscience), a band attributed to the TACT427-A protein was observed near 150 kD molecular weight, which revealed that the TACT427-A protein was expressed on the cytoplasmic membrane.

EXAMPLE 17

Study of Localization of TACT427 Protein (Biotin Labeling)

The protein exposed on the cell surfaces of non-small cell lung cancer cell lines A549, NCI-H226 and NCI-H522 plated on a Petri dish of 10 cm in diameter was labeled with biotin using Cellular Labeling and Immunoprecipitation Kit (Roche Diagnostics). Using 1 ml of the cell-free extract prepared by the procedures of EXAMPLE 12 and 3 μg of rabbit peptide antibody AS-2482, immunoprecipitation was performed in accordance with the process of EXAMPLE 13, followed by SDS-PAGE. By detection with HRP-labeled streptoavidin (Amersham-Bioscience), bands attributed to the TACT427-A protein, TACT427-A2 protein, TACT427-B protein, TACT427-B2 protein, TACT427-C protein and TACT427-C2 protein were observed near 150 kD molecular weight, in all of A549, NCI-H226 and NCI-H522.

These results revealed that the TACT427 protein was expressed on the cytoplasmic membrane.

EXAMPLE 18

Study of Localization of TACT427 Protein (FACS Analysis)

Human non-small cell lung cancer cell line A549 plated in a Petri dish of 10 cm in diameter and cultured to be subconfluent was washed with PBS. Then 3% BSA and PBS containing 5 mM EDTA were added thereto. The mixture was allowed to stand at room temperature for 15 minutes to disperse A549 cells. Next, A549 cells were suspended in Buffer A [HBSS (Hanks' Balanced Salt Solutions, Invitrogen) containing 2% fetal bovine serum (JRH) And 0.1% sodium azide] in a concentration of $1\times10^6$/ml, and AS-2482 or non-immunized rabbit IgG (Jackson) was added to the suspension in a final concentration of 5 μg/ml. The mixture was allowed to stand on ice for 5 hours. Subsequently, the cells were washed with Buffer A and suspended in Buffer A containing 10 μg/ml of Alexa488-labeled anti-rabbit IgG antibody (Molecular Probes), followed by allowing to stand on ice for 1.5 hours. After washing again with Buffer A, the cells were analyzed by FACScan (BD Biosciences). As a result, A549 cells were stained specifically to rabbit peptide antibody AS-2482, which revealed that TACT427-A protein, TACT427-A2 protein, TACT427-B protein, TACT427-B2 protein, TACT427-C protein and TACT427-C2 protein were expressed on the cytoplasmic membrane.

EXAMPLE 19

Apoptosis Induction of Human Non-Small Cell Lung Cancer Cell Lines A549 and NCI-H226 by transfection of the antisense oligonucleotide It was examined whether or not apoptosis could be induced by transfection of the antisense oligonucleotide also into human non-small cell lung cancer cell lines other than NCI-H460 described in EXAMPLE 2.

Human non-small cell lung cancer cell lines A549 and NCI-H226 (both purchased from ATCC) were suspended in Kaighn's Modified F-12 Nutrient Mixture (Invitrogen) And 25 mM HEPES-containing RPMI-1640 medium (Invitrogen) supplemented with 10% fetal bovine serum (JRH), respectively. The cells were plated on a 96-well flat bottomed tissue culture plate (BD Falcon) at a cell density of $1\times10^4$/well. After incubation at 37° C. overnight in a 5% carbon dioxide gas flow, oligonucleotide was transfected.

The sense oligonucleotide (SEQ ID NO: 44) used in EXAMPLES 19, 20 and 21 described below was designed to have a complementary sequence to the antisense oligonucleotide (SEQ ID NO: 13) described in EXAMPLE 2. The sense oligonucleotide was phosphorothioated, purified on HPLC and provided for use (hereinafter simply referred to as the sense oligonucleotide).

Specifically referring to A549 cells, 0.05 μg of each of the antisense oligonucleotide (SEQ ID NO: 13) And the control oligonucleotide (SEQ ID NO: 14) obtained in EXAMPLE 2 and the sense oligonucleotide (SEQ ID NO: 44) was mixed with 50 μl of OPTI-MEM I (Invitrogen) together with 0.8 μl of Lipofectamine 2000 (Invitrogen). The mixture was then allowed to stand at room temperature for 20 minutes. The whole volume of the mixture was added to the A549 cells, which medium had previously been exchanged with 50 μl of OPTI-MEM I (Invitrogen). After incubation was continued for further 3 hours, the medium was exchanged with 100 μl of Kaighn's Modified F-12 Nutrient Mixture (Invitrogen) supplemented with 10% fetal bovine serum (JRH).

In the case of NCI-H226 cells, 0.13 μg of each of the antisense oligonucleotide (SEQ ID NO: 13), the control oligonucleotide (SEQ ID NO: 14) And the sense oligonucleotide (SEQ ID NO: 44) was mixed with 50 μl of OPTI-MEM I (Invitrogen) together with 0.8 μl of Oligofectamine (Invitrogen), followed by allowing to stand at room temperature for 20 minutes. The whole volume of the mixture was added to the NCI-H226 cells, which medium had previously been exchanged with 50 μl of OPTI-MEM I (Invitrogen). After incubation was continued for further 3 hours, 50 μl of 25 mM HEPES-containing RPMI-1640 medium (Invitrogen) supplemented with 30% fetal bovine serum (JRH) was added to the mixture.

After the oligonucleotide was transfected, incubation was continued for further 2 days. Following the protocol attached to Cell Death Detection ELISA$^{PLUS}$ (Roche Diagnostics), the oligonucleotide described above was assayed for its apoptosis induction activity.

As a result, the antisense oligonucleotide showed the apoptosis induction activity in the two cell lines as higher by 1.65 times and 3.03 times than the control oligonucleotide and sense oligonucleotide used as negative control, indicating that there was a statistically significant difference ($P\leqq0.01$).

EXAMPLE 20

Reduced mRNA Expression Level of FLJ20539 Gene (SEQ ID NO: 2), hCP50177 Gene (SEQ ID NO: 5), hCP1762319 Gene (SEQ ID NO: 8) And FLJ13515 Gene (SEQ ID NO: 11) in Human Non-Small Cell Lung Cancer Cell Lines A549 and NCI-H226, and TACT427 Gene by Transfection of the Antisense Oligonucleotide It was examined whether or not mRNA expression level of the genes described above could be reduced by administration of the antisense oligonucleotide also in human non-small cell lung cancer cell lines other than NCI-H460 described in EXAMPLE 3.

Human non-small cell lung cancer cell lines A549 and NCI-H226 were suspended, respectively, in the same medium as used in EXAMPLE 19. The cells were plated on a 24-well flat bottomed tissue culture plate (BD Falcon) at a cell density of $7.5\times10^4$/well in the A549 cell line and at a cell density of $5\times10^4$/well in the NCI-H226 cell line, respectively. After incubation at 37° C. overnight in a 5% carbon dioxide gas flow, transfection of oligonucleotide was performed.

Specifically referring to the A549 cell line, 0.84 μg of each of the antisense oligonucleotide (SEQ ID NO: 13), the control oligonucleotide (SEQ ID NO: 14) And the sense oligonucleotide (SEQ ID NO: 44) was mixed with 200 μl of OPTI-MEM I (Invitrogen) together with 3.2 μl of Lipofectamine 2000 (Invitrogen). The mixture was then allowed to stand at room temperature for 20 minutes. The whole volume of the mixture was added to the A549 cells, which medium had previously been exchanged with 200 μl of OPTI-MEM I (Invitrogen). After incubation was continued for further 3 hours, the medium was exchanged with 500 μl of Kaighn's Modified F-12 Nutrient Mixture (Invitrogen) supplemented with 10% fetal bovine serum (JRH).

In the NCI-H226 cells, 0.13 μg of each of the antisense oligonucleotide (SEQ ID NO: 13), the control oligonucleotide (SEQ ID NO: 14) And the sense oligonucleotide (SEQ ID NO: 44) was mixed with 125 μl of OPTI-MEM I (Invitrogen) together with 2 μl of Oligofectamine (Invitrogen), followed by allowing to stand at room temperature for 20 minutes. The whole volume of the mixture was added to the NCI-H226 cells, which medium had previously been exchanged with 125 μl of OPTI-MEM I. (Invitrogen). After incubation was continued for further 4 hours, 125 μl of 25 mM HEPES-containing RPMI-1640 medium (Invitrogen) supplemented with 30% fetal bovine serum (JRH) was added to the mixture.

After transfection of the oligonucleotide, incubation was continued for further 16 hours and then the total RNA was extracted from the A549 cells and NCI-H226 cells, using RNeasy Mini Total RNA Kit (QIAGEN). According to the protocol attached to TaqMan™ Reverse Transcription Reagents (Applied Biosystems), reverse transcription using a random primer was carried out to prepare cDNA from the total RNA. Using as a template cDNA prepared from about 5 ng of the total RNA, FLJ20539 gene (SEQ ID NO: 2), hCP50177 gene (SEQ ID NO: 5), hCP1762319 gene (SEQ ID NO: 8), FLJ13515 gene (SEQ ID NO: 11) And TACT427 gene were assayed for their expression levels in a manner similar to EXAMPLE 6. The expression level of a gene for β-actin contained in the same amount of template cDNA was assayed on TaqMan™ β-actin Control Reagents (Applied Biosystems), which was used as internal standard.

A relative expression level rate (%) of the gene to the expression level of β-actin gene was markedly reduced when the antisense oligonucleotide (SEQ ID NO: 13) was transfected, as compared to the case where the control oligonucleotide (SEQ ID NO: 14) or the sense oligonucleotide (SEQ ID NO: 44) was transfected as a negative control, indicating that there was a statistically significant reduction in the expression level ($P \leqq 0.01$) (TABLE 7).

The results reveal that apoptosis was induced also in human non-small cell lung cancer cell lines A549 and NCI-H226 by the reduced expression level of mRNA for FLJ20539 gene (SEQ ID NO: 2), hCP50177 gene (SEQ ID NO: 5), hCP1762319 gene (SEQ ID NO: 8) as well as FLJ13515 gene (SEQ ID NO: 11), and TACT427 gene.

TABLE 7

| | Relative Gene Expression Level (Rate to β-Actin expressed, %) | |
|---|---|---|
| | A549 | NCI-H226 |
| Control oligonucleotide (SEQ ID NO: 14) | 0.44 | 1.01 |
| Sense oligonucleotide (SEQ ID NO: 44) | 0.44 | 1.08 |
| Antisense oligonucleotide (SEQ ID NO: 13) | 0.09 | 0.22 |

EXAMPLE 21

Reduction in Expression Level of TACT427 Protein in A549 and NCI-H226 by Transfection of Antisense Oligonucleotide Human non-small cell lung cancer cell lines A549 and NCI-H226 were suspended, respectively, in the same medium as used in EXAMPLE 19. The cells were plated on a Petri dish of 10 cm in diameter (BD Falcon) at a cell density of $2.25\times10^6$/well in the A549 cell line and at a cell density of $1.45\times10^6$/well in the NCI-H226 cell line, respectively. After incubation at 37° C. overnight in a 5% carbon dioxide gas flow the oligonucleotide was transfected.

Specifically referring to the A549 cell line, 5.8 μg of each of the antisense oligonucleotide (SEQ ID NO: 13), the control oligonucleotide (SEQ ID NO: 14) And the sense oligonucleotide (SEQ ID NO: 44) was mixed with 6 ml of OPTI-MEM I (Invitrogen) together with 96 μl of Lipofectamine 2000 (Invitrogen). The mixture was then allowed to stand at room temperature for 20 minutes. The whole volume of the mixture was added to the A549 cells, which medium had previously been exchanged with 6 ml of OPTI-MEM I (Invitrogen). After incubation was continued for further 3 hours, the medium was exchanged with 15 ml of Kaighn's Modified F-12 Nutrient Mixture (Invitrogen) supplemented with 10% fetal bovine serum (JRH).

In the NCI-H226 cell line, 9.7 μg of each of the antisense oligonucleotide (SEQ ID NO: 13), the control oligonucleotide (SEQ ID NO: 14) And the sense oligonucleotide (SEQ ID NO: 44) was mixed with 3.75 ml of OPTI-MEM I (Invitrogen) together with 60 μl of Oligofectamine (Invitrogen), followed by allowing to stand at room temperature for 20 minutes. The whole volume of the mixture was added to the NCI-H226 cells, which medium had previously been exchanged with 3.75 ml of OPTI-MEM I (Invitrogen). After incubation was continued for further 4 hours, the medium was exchanged with 3.75 ml of 25 mM HEPES-containing RPMI-1640 medium (Invitrogen) supplemented with 30% fetal bovine serum (JRH) was added to the mixture. After transfection, incubation was continued for further 24, 48 and 72 hours and then the cell-free extract was prepared by the procedures in EXAMPLE 12. The protein level of the cell-free extract obtained was assayed with BCA Protein Assay Kit (Pierce) to make the protein level uniform. According to the procedures of EXAMPLE 12 with modifications, 100 μg of the cell-free extract from the A549 cell line and 140 μg of the cell-free extract from the NCI-H226 cell line were subjected to SDS-PAGE and western blotting. As a primary antibody, AS-2482 prepared in EXAMPLE 11 was used in a concentration of 3 μg/ml and HRP-labeled anti-rabbit IgG antibody (Amersham-Bioscience) was used as a secondary antibody. Detection was made in accordance with the manual attached to Super Signal™ West Femto Maximum Sensitivity Substrate (Pierce).

As a result, it was confirmed that the TACT427 almost disappeared in both of the cell lines only when the antisense oligonucleotide was transfected, and the protein disappearance was noted in 24 hours. At the same time, the expression level of cytokeratin 8 protein was examined by western blotting using anti-human cytokeratin 8 antibody (Oncogene). No reduction in expression level was noted in any oligonucleotide treatment. It was demonstrated from these results that apoptosis of the human lung cancer cell line was induced by specific reduction in the expression level of TACT427 protein.

EXAMPLE 22

Establishment of the Cell Line Stably Expressing the Full-Length Recombinant Protein Mouse embryo-derived fibroblast cell line Balb3T3-A31 (hereinafter simply referred to as A31 cells) was used to establish a cell line constitutively expressing TACT427-A protein (SEQ ID NO: 15) carrying a C-terminal 3xFLAG tag. A31 cells were suspended in 2.5 ml of Dulbecco's Modified Eagle's Minimal Medium (Invitrogen) containing 10% fetal bovine serum (JRH) And 50 μg/ml of gentamycin (Invitrogen) in $1.25\times10^5$. After plating on one well of a 6-well plate, the cells were incubated at 37° C. overnight in a 5% carbon dioxide gas flow. The medium was exchanged with 2.5 ml of the same medium. After incubation was continued for 4 hours, 1.25 μg of plasmid p3xFLAG-TACT427-A, which had been previously mixed with 3.8 μl of FuGENE6 transfection reagent (Roche Diagnostics) And 93.3 μl of OPTI-MEM I (Invitrogen) followed by allowing to stand at room temperature for 15 minutes, was added to the cells and incubation was continued. On the following day, the cells were recovered by trypsin/EDTA (Invitrogen) And suspended in 10 ml of the medium described above (G418 selection medium) containing 0.5 mg/ml of G418 (Promega). The cells were then plated on aPetri dish of 10 cm in diameter. Incubation was continued in the G418 selection medium. After subculturing twice, a series of twelve 2-fold serious dilutions beginning with a rate of 100 cells per well (0.1 ml in medium volume) were prepared and plated on a 96-well plate, respectively. While exchanging the G418 selection medium every 3 other days, incubation was continued. Eleven days after the cells were recovered from the wells where 0.8-3.2 cells/well grew to form colonies and equally plated on 2 wells of a 24-well plate. After incubation was continued in the G418 selection medium to be confluent, the cells corresponding to one well were recovered with a scraper and suspended in 40 μl of SDS-PAGE sample buffer (Bio-Rad Laboratories) containing 1% 1% 2-mercaptoethanol. After heat treatment at 95° C. for 5 minutes, 12 μl of the suspension was provided for SDS-PAGE on 10% acrylamide gel. Using mouse anti-FLAG M2 antibody (Sigma, 1000-fold dilution), western blotting was performed by a modification of the procedures described in EXAMPLE 13 to give the TACT-1 cell line constitutively expressing TACT427-A protein (SEQ ID NO: 15) carrying a C-terminal 3xFLAG tag.

EXAMPLE 23

Assessment of Tolerance of TACT-1 to Apoptosis

TACT-1 and its parent strain A31 cells acquired in EXAMPLE 22 wee suspended in 0.1 ml of Dulbecco's Modified Eagle's Minimal Medium (Invitrogen) containing 10% fetal bovine serum (JRH) And 50 μg/ml of gentamycin (Invitrogen) and plated on a 96-well plate for tissue culture in $6\times10^3$/well, respectively. After incubation at 37° C. overnight in a 5% carbon dioxide gas flow, the medium was exchanged with the above medium supplemented with topoisomerase II inhibitor camptothecin (Wako Pure Chemical Industries) or protein synthesis inhibitor anisomycin (Wako Pure Chemical Industries) in various concentrations, and incubation was continued. Twenty four hours after, apoptosis was detected by Cell Death Detection ELISA$^{PLUS}$ (Roche Diagnostics). Apoptosis induced in TACT-1 by adding camptothecin in the final concentration of 1 μg/ml was only 56% of apoptosis noted in A31 under the same conditions. Apoptosis induced in TACT-1 by adding anisomycin in the final concentration of 1 μg/ml was only 69% of apoptosis noted in A31 under the same conditions. These results demonstrate that the TACT-1cells became tolerant to apoptosis induced by camptothecin or anisomycin, and revealed that the cells acquired apoptosis tolerance by forced expression of TACT427-A.

EXAMPLE 24

Enhanced Phosphorylation of ERK1/2 in TACT-1

As part of investigating the mechanism of a phenomenon of apoptosis tolerance in the TACT-1 cell line described in EXAMPLE 23, a MAP kinase associated with anti-apoptosis activity, namely, ERK1/2 protein was compared with the A31 cell line in terms of phosphorylation. The cells were cultured in at 37° C. in a 5% carbon dioxide gas flow in a Petri dish (BD Falcon) of 10 cm in diameter charged with Dulbecco's Modified Eagle's Minimal Medium (Invitrogen) containing 10% fetal bovine serum (JRH) And 50 μg/ml of gentamycin (Invitrogen) for the A31 cells and for the TACT-1 cells in the same medium further supplemented with 0.6 mg/ml of G418 (Promega). At the point when the cell density reached approximately 80% confluent, the medium was exchanged with the above medium supplemented with 1 μg/ml of anisomycin (Wako Pure Chemical Industries) And incubation was continued at 37° C. for 1, 4 and 8 hours. After these cells including the cells prior to the anisomycin treatment were washed twice with 10 ml of ice-chilled PBS (Ca, Mg-free), respectively, 0.5 ml of a cell lysis buffer [50 mM Tris-hydrochloride buffer containing 1% Triton X-100, 1% deoxycholic acid, 0.05% SDS, 5.25 mM EGTA, EDTA-free Complete™ Tablet (Roche Diagnostics), Phosphatase inhibitor cocktail-2 (Sigma) And 150 mM sodium chloride, pH7.5] was added to the cells. The mixture was allowed to stand at 4° C. for 20 minutes. The cell lysate was recovered with a scraper and centrifuged at 4° C. for 20 minutes at 15000 rpm to remove the precipitates. After 20 μl of 5-fold concentrated SDS/PAGE sample buffer (Bio Rad Laboratories) containing 10% 2-mercaptoethanol was added to 80 μl of the cell lysate, the mixture was heated at 95° C. for 5 minutes. The cell lysate, 5 μl, was diluted to 10-fold with distilled water and the protein level was determined by a modification of the formula of Micro BCA protein assay reagent (Pierce). The cell lysate was then appropriately diluted with SDS-PAGE sample buffer (Bio-Rad Laboratories) containing 2% 2-mercaptoethanol to make the protein level uniform. After 24 μg of the total protein was provided for SDS-PAGE on 7.5% polyacrylamide gel, the protein was transferred onto a PVDF membrane. After blocking with 5% skimmed milk-containing TTBS (TBS containing 0.1% Tween 20) at room temperature for an hour, the transferred membrane was washed twice with TTBS for 10 minutes. Using as a primary antibody solution a 5000-fold dilution of anti-ERK1/2 antibody (Cell Signaling Technology) or 1000-fold dilution of anti-phosphorylation ERK1/2 antibody (Cell Signaling Technology), which was obtained by diluting the antibody with TTBS containing 5% BSA (Sigma), the protein was reacted at 4° C. overnight followed by washing 4 times with TTBS for 10 minutes. Next, HRP-labeled anti-rabbit IgG antibody (Amersham-Bioscience) diluted to 10000-fold with 5% skimmed milk-containing TTBS was added to the reaction mixture and the mixture was kept warm at room temperature for an hour, followed by washing 4 times with TTBS for 10 minutes. Bands corresponding to the ERK1/2 protein and the ERK1/2 protein were detected using ECL plus reagent (Amersham-Bioscience). The results indicate that phosphorylation, i.e., activation of the ERK1/2 protein induced by the addition of anisomycin was enhanced in the TACT-1 cell line when compared to the A31 cell line. In order to determine the enhanced degree of ERK1/2 activation in TACT-1 cells, the developed films were read by LAS-1000$^{plus}$ Luminoimage analyzer (FUJI FILM) as images and the intensity of each band for phosphorylated ERK1 and phosphorylated ERK2 was digitized using Image Gauge software (Fuji Film) attached. Phosphorylation enhancing rate of TACT-1 cells was calculated every anisomycin treatment time (2, 4 and 8 hours) when the band intensity of A31 cells was made 100%. In TACT-1 cells, the phosphorylation enhancing rates of ERK1 were 164%, 150% and 158% and the phosphorylation enhancing rates of ERK2 were 130%, 137% and 172%.

These results reveal that one of mechanism for apoptosis tolerance phenomenon in the TACT-1 cell line is potentiated activation of ERK1/2.

EXAMPLE 25

Promoted Phosphorylation of p38MAPK in TACT-1

As part of investigating the mechanism of apoptosis tolerance phenomenon in the TACT-1 cell line described in EXAMPLE 23, p38MAPK was compared with the A31 cell line in terms of phosphorylation. A31 cells or TACT-1 cells of $8\times10^5$ were suspended in 5 ml of Dulbecco's Modified Eagle's Minimal Medium (Invitrogen) containing 10% fetal bovine serum (JRH) And 50 μg/ml of gentamycin (Invitrogen) And plated on a Petri dish (BD Falcon) of 6 cm in diameter. After incubation at 37° C. overnight in a 5% carbon dioxide gas, anisomycin (Wako Pure Chemical Industries)

was added in the final concentration of 1 μg/ml. Immediately thereafter, incubation was continued. The cells prior to or 15, 30 and 60 minutes after anisomycin addition were washed once with 5 ml of PBS containing 1 mM sodium orthovanadate (Wako Pure Chemical Industries). Then, 0.2 ml of the cell lysis buffer obtained by adding Phosphatase Inhibitor Cocktail-1 to RIPA buffer described in EXAMPLE 12 was added to the cells. The mixture was allowed to stand at 4° C. for 15 minutes. The cell lysate was recovered with a scraper and centrifuged at 4° C. for 5 minutes at 15000 rpm to remove the precipitates. After 20 μl of 5-fold concentrated SDS/PAGE sample buffer (Bio Rad Laboratories) containing 5% 2-mercaptoethanol was added to 80 μl of the cell lysate, the mixture was heated at 95° C. for 5 minutes. The above cell lysate, 15 μl, was diluted to 20-fold with distilled water and the protein level was determined by a modification of the formula of Micro BCA protein assay reagent (Pierce), confirming that the protein level was almost uniform. After approximately 14 μg of the total protein was provided for SDS-PAGE on 5%-20% polyacrylamide gradient gel, the protein was transferred onto a PVDF membrane. The transferred membrane was blocked with 5% skimmed milk-containing TTBS (TBS containing 0.1% Tween 20) at room temperature for an hour and washed thrice with TTBS for 5 minutes. Then, the reaction was carried out at 4° C. overnight using a primary antibody solution, which was obtained by diluting anti-p38MAPK2 antibody (Cell Signaling Technology) or anti-phosphorylation p38MAPK antibody (Cell Signaling Technology) with TTBS containing 5% BSA (Sigma) to 1000-fold. Subsequently, after washing thrice with TTBS for 5 minutes, HRP-labeled anti-rabbit IgG antibody (Amersham-Bioscience) diluted to 5000-fold with 5% skimmed milk-containing TTBS was added to the reaction mixture and the mixture was kept warm at room temperature for an hour. Again, the mixture was washed thrice with TTBS for 5 minutes to remove an excess amount of the antibody. Using ECL plus reagent (Amersham-Bioscience), the bands corresponding to p38MAPK protein and phosphorylated p38MAPK protein were detected. The phosphorylation of p38MAPK protein in A31 cells was barely slightly observed 30 minutes after anisomycin addition, whereas in TACT-1 cells the phosphorylation was obviously intensely observed in 15 minutes after anisomycin addition, indicating that the phosphorylation or activation of p38MAPK protein was rapidly induced.

From these results it is suggested that the effect of enhancing the activation of p38MAPK will be responsible for one part of the mechanism of apoptosis tolerance phenomenon in the TACT-1 cell line.

INDUSTRIAL APPLICABILITY

The protein used in the present invention is specifically expressed in cancer cells and is a diagnosis marker for cancer. Therefore, the compound or its salt that inhibits the activity of the protein, and the compound or its salt that inhibit the expression of a gene for the protein can be safely used as prophylactic/therapeutic agents for cancer, e.g., colon cancer, breast cancer, lung cancer, prostate cancer, esophageal cancer, gastric cancer, liver cancer, biliary tract cancer, spleen cancer, renal cancer, bladder cancer, uterine cancer, testicular cancer, thyroid cancer, pancreatic cancer, brain tumor, blood tumor, etc. Preferably, these compounds are prophylactic/therapeutic agents for breast cancer, lung cancer, etc. Furthermore, the compound or its salt that inhibits the activity of the compound and the compound or its salt that inhibits the expression of a gene for the protein can also be safely used, e.g., as apoptosis promoters for cancer cells.

The antisense polynucleotide or antibody of the present invention can inhibit the expression or activity of the protein used in the present invention and can be safely used as a prophylactic/therapeutic agent for cancer, e.g., colon cancer, breast cancer, lung cancer, prostate cancer, esophageal cancer, gastric cancer, liver cancer, biliary tract cancer, spleen cancer, renal cancer, bladder cancer, uterine cancer, testicular cancer, thyroid cancer, pancreatic cancer, brain tumor, blood tumor, etc., preferably as a prophylactic/therapeutic agent for breast cancer, lung cancer, etc.; or an apoptosis promoter for cancer cells.

The invention claimed is:

1. An isolated polynucleotide comprising the polynucleotide of SEQ ID NO:16.

2. The polynucleotide according to claim 1, which is a DNA.

3. An isolated polynucleotide consisting of the sequence of SEQ ID NO: 16.

4. An isolated recombinant vector comprising the polynucleotide according to claim 1.

5. An isolated transformant transformed by the recombinant vector according to claim 4.

6. A composition comprising the polynucleotide according to claim 1 and a pharmaceutically acceptable carrier.

7. A diagnostic agent comprising the polynucleotide according to claim 1.

8. A kit for screening a compound or its salt, comprising the polynucleotide according to claim 1.

9. A kit for screening a prophylactic/therapeutic agent for a cancer, comprising an isolated polynucleotide comprising the polynucleotide of SEQ ID NO:16.

* * * * *

```
                         SEQUENCE LISTING

<160> NUMBER OF SEQ ID NOS: 44

<210> SEQ ID NO 1
<211> LENGTH: 774
<212> TYPE: PRT
<213> ORGANISM: Homo sapiens

<400> SEQUENCE: 1

Met Cys Ala Arg Met Ala Gly Arg Thr Arg Ala Ala Pro Arg Gly Pro
                 5                  10                  15

Tyr Gly Pro Trp Leu Cys Leu Leu Val Ala Leu Ala Leu Asp Val Val
            20                  25                  30

Arg Val Asp Cys Gly Gln Ala Pro Leu Asp Pro Val Tyr Leu His Val
        35                  40                  45

Thr Ala Ala Arg Pro Ala Gln Pro Thr Leu Trp Thr Ala Lys Leu Asp
    50                  55                  60

Arg Phe Lys Gly Ser Arg His His Thr Thr Leu Ile Thr Cys His Arg
65                  70                  75                  80

Ala Gly Leu Thr Glu Pro Asp Ser Ser Ser Pro Leu Glu Leu Ser Glu
                85                  90                  95
```

-continued

```
Phe Leu Trp Val Asp Phe Val Val Glu Asn Ser Thr Gly Gly Gly Val
            100                 105                 110

Ala Val Thr Arg Pro Val Thr Trp Gln Leu Glu Tyr Pro Gly Gln Ala
        115                 120                 125

Pro Glu Ala Glu Lys Asp Lys Met Val Trp Glu Ile Leu Val Ser Glu
    130                 135                 140

Arg Asp Ile Arg Ala Leu Ile Pro Leu Ala Lys Ala Glu Glu Leu Val
145                 150                 155                 160

Asn Thr Ala Pro Leu Thr Gly Val Pro Gln His Val Pro Val Arg Leu
                165                 170                 175

Val Thr Val Asp Gly Gly Gly Ala Leu Val Glu Val Thr Glu His Val
            180                 185                 190

Gly Cys Glu Ser Ala Asn Thr Gln Val Leu Gln Val Ser Glu Ala Cys
        195                 200                 205

Asp Ala Val Phe Val Ala Gly Lys Glu Ser Arg Gly Ala Arg Gly Val
    210                 215                 220

Arg Val Asp Phe Trp Trp Arg Arg Leu Arg Ala Ser Leu Arg Leu Thr
225                 230                 235                 240

Val Trp Ala Pro Leu Leu Pro Leu Arg Ile Glu Leu Thr Asp Thr Thr
                245                 250                 255

Leu Glu Gln Val Arg Gly Trp Arg Val Pro Gly Pro Ala Glu Gly Pro
            260                 265                 270

Ala Glu Pro Ala Ala Glu Ala Ser Asp Glu Ala Glu Arg Arg Ala Arg
        275                 280                 285

Gly Cys His Leu Gln Tyr Gln Arg Ala Gly Val Arg Phe Leu Ala Pro
    290                 295                 300

Phe Ala Ala His Pro Leu Asp Gly Gly Arg Arg Leu Thr His Leu Leu
305                 310                 315                 320

Gly Pro Asp Trp Leu Leu Asp Val Ser His Leu Val Ala Pro His Ala
                325                 330                 335

Arg Val Leu Asp Ser Arg Val Ala Ser Leu Glu Gly Gly Arg Val Val
            340                 345                 350

Val Gly Arg Glu Pro Gly Val Thr Ser Ile Glu Val Arg Ser Pro Leu
        355                 360                 365

Ser Asp Ser Ile Leu Gly Glu Gln Ala Leu Ala Val Thr Asp Asp Lys
    370                 375                 380

Val Ser Val Leu Glu Leu Arg Val Gln Pro Val Met Gly Ile Ser Leu
385                 390                 395                 400

Thr Leu Ser Arg Gly Thr Ala His Pro Gly Glu Val Thr Ala Thr Cys
                405                 410                 415

Trp Ala Gln Ser Ala Leu Pro Ala Pro Lys Gln Glu Val Ala Leu Ser
            420                 425                 430

Leu Trp Leu Ser Phe Ser Asp His Thr Val Ala Pro Ala Glu Leu Tyr
        435                 440                 445

Asp Arg Arg Asp Leu Gly Leu Ser Val Ser Ala Glu Glu Pro Gly Ala
    450                 455                 460

Ile Leu Pro Ala Glu Glu Gln Gly Ala Gln Leu Gly Val Val Val Ser
465                 470                 475                 480

Gly Ala Gly Ala Glu Gly Leu Pro Leu His Val Ala Leu His Pro Pro
                485                 490                 495

Glu Pro Cys Arg Arg Gly Arg His Arg Val Pro Leu Ala Ser Gly Thr
            500                 505                 510
```

-continued

```
Ala Trp Leu Gly Leu Pro Pro Ala Ser Thr Pro Ala Pro Ala Leu Pro
        515                 520                 525

Ser Ser Pro Ala Trp Ser Pro Pro Ala Thr Glu Ala Thr Met Gly Gly
    530                 535                 540

Lys Arg Gln Val Ala Gly Ser Val Gly Gly Asn Thr Gly Val Arg Gly
545                 550                 555                 560

Lys Phe Glu Arg Ala Glu Glu Glu Ala Arg Lys Glu Glu Thr Glu Ala
                565                 570                 575

Arg Glu Glu Glu Glu Glu Glu Glu Glu Glu Met Val Pro Ala Pro Gln
            580                 585                 590

His Val Thr Glu Leu Glu Leu Gly Met Tyr Ala Leu Leu Gly Val Phe
        595                 600                 605

Cys Val Ala Ile Phe Ile Phe Leu Val Asn Gly Val Val Phe Val Leu
    610                 615                 620

Arg Tyr Gln Arg Lys Glu Pro Pro Asp Ser Ala Thr Asp Pro Thr Ser
625                 630                 635                 640

Pro Gln Pro His Asn Trp Val Trp Leu Gly Thr Asp Gln Glu Glu Leu
                645                 650                 655

Ser Arg Gln Leu Asp Arg Gln Ser Pro Gly Pro Pro Lys Gly Glu Gly
            660                 665                 670

Ser Cys Pro Cys Glu Ser Gly Gly Gly Gly Glu Ala Pro Thr Leu Ala
        675                 680                 685

Pro Gly Pro Pro Gly Gly Thr Thr Ser Ser Ser Ser Thr Leu Ala Arg
    690                 695                 700

Lys Glu Ala Gly Gly Arg Arg Lys Arg Val Glu Phe Val Thr Phe Val
705                 710                 715                 720

Pro Ala Pro Pro Ala Gln Ser Pro Glu Glu Pro Val Gly Ala Pro Ala
                725                 730                 735

Val Gln Ser Ile Leu Val Ala Gly Glu Glu Asp Ile Arg Trp Val Cys
            740                 745                 750

Glu Asp Met Gly Leu Lys Asp Pro Glu Glu Leu Arg Asn Tyr Met Glu
        755                 760                 765

Arg Ile Arg Gly Ser Ser
    770
```

<210> SEQ ID NO 2
<211> LENGTH: 2322
<212> TYPE: DNA
<213> ORGANISM: Homo sapiens

<400> SEQUENCE: 2

```
atgtgcgcgc ggatggccgg tcgcacaaga gcggcccctc gggggcccta cggcccctgg      60

ctctgcctcc tggtggccct cgccctggac gtcgtgagag tggactgtgg ccaggctccc     120

ctggaccctg tctacctgca tgtgacagcc gcccgcccag cccagcccac actctggact     180

gccaagctag accgcttcaa gggctccagg caccacacca ccctcatcac ctgccaccgt     240

gctgggctca cagagccaga ttccagcagt ccccttgaac tgtctgagtt cctatgggtg     300

gactttgtgg tggagaatag cactggtggg ggcgtagcgg tcactcgccc cgtcacgtgg     360

cagctggagt acccaggcca ggcccctgaa gcagagaagg acaaaatggt gtgggaaatc     420

ctggtgtctg agcgggacat cagagccctt atcccactgg ccaaggctga ggagctggtg     480

aatacagcac cactgactgg agtgccccag catgtccccg tgcgccttgt cactgtggac     540

ggcggggggg ccttggtgga ggtgacagag catgtcggct gcgagtctgc caacacacag     600
```

-continued

```
gtcctgcagg tgtctgaggc ctgtgatgcc gtgttcgtgg ctggcaagga gagccggggc    660

gcccgggggg tgcgagtgga cttctggtgg cgccggctcc gcgcctcgct gcggctgacc    720

gtgtgggccc cgctgctacc gctgcgtatc gagctcaccg acaccaccct cgagcaggtc    780

cgcggctgga gggtacctgg ccctgctgaa gggcctgcgg aacccgctgc agaggcgtca    840

gatgaggccg agcggcgcgc ccgtggctgc cacctgcagt accagcgggc cggtgtgcgc    900

ttcctcgccc ccttcgcggc ccacccgctg gacggcggcc gccgcctcac gcacctgctt    960

ggccccgact ggctgctaga cgtgtcccac ctcgtggcgc cacacgcccg cgtgctggac   1020

tcgcgtgtag cctctctgga gggtggccgt gtcgtggtgg gccgggagcc cggtgtcacc   1080

tccattgagg tgcgttcccc actgtctgac tccatcctgg gggagcaggc gctggctgtg   1140

acggacgaca aggtctcagt gctggagctg agggtgcagc cagtgatggg catctcgctg   1200

accttgagcc ggggcactgc ccaccccggg gaggtcacag ctacgtgctg ggcacagtca   1260

gcccttcccg ccccaaagca ggaggtggcc ctctccctat ggctgtcctt ctctgatcac   1320

actgtggccc cagctgagct ctacgaccgc cgtgacctgg gactgtccgt ctcagccgag   1380

gagcctggtg ccatcctgcc agctgaggag cagggtgccc agctcggggt ggtggtgagt   1440

ggggcaggcg ccgaggggct gccgctgcat gtggctctgc acccgcccga gccctgccgc   1500

cggggccgcc accgtgtgcc tctggcctct ggcaccgcct ggctggggct gccccctgcc   1560

tccactccag cccctgctct cccatccagc cctgcttgga gcccaccagc cacagaagcc   1620

accatgggtg gtaaacggca ggtggcaggc agtgtcgggg gcaacacagg tgtgaggggc   1680

aagtttgagc gggcagagga ggaggccagg aaggaggaga ccgaagccag ggaggaggag   1740

gaggaagagg aggaggagat ggtccctgcc cctcagcatg tcactgagct agagctgggc   1800

atgtacgccc tgctgggagt cttctgcgtg gccatcttca tcttcttggt caatggtgtg   1860

gtcttcgtcc tgcgctatca gcgcaaagaa cctcccgaca gtgccactga ccccacctcc   1920

ccccagcccc acaactgggt ctggctgggc actgaccagg aggaactgag ccgccagctg   1980

gaccggcagt cccctggccc gcccaagggg gaggggagct gcccctgtga gagtggggga   2040

ggaggggagg cccctaccct ggcccctggc cctcctgggg gcaccaccag ctcctcaagc   2100

accctggccc gaaaggaggc tgggggcgg cggaagcgag tagagtttgt gacatttgtg   2160

ccagcccctc cagcccagtc acctgaggag cctgtagggg cccctgctgt gcagtccatc   2220

cttgtggcag gcgaggagga catccgctgg gtgtgtgagg acatggggct gaaggaccct   2280

gaggagcttc gcaactacat ggagaggatc cggggcagct cc                      2322
```

<210> SEQ ID NO 3
<211> LENGTH: 2755
<212> TYPE: DNA
<213> ORGANISM: Homo sapiens

<400> SEQUENCE: 3

```
attgtctggg aattgcagcc gcggggcggg cggcggcggc ggcggcggcg gccgggaccc     60

agcgggccag gtggggacgg cgcggagcgg gtgcgggaga tgccgtgcgg gactggggcc    120

acctgagccg cccgcctcgt ccccgccttc tgtgggaagg atgtgcgcgc ggatggccgg    180

tcgcacaaga gcggcccctc gggggcccta cggcccctgg ctctgcctcc tggtggccct    240

cgccctggac gtcgtgagag tggactgtgg ccaggctccc ctggaccctg tctacctgca    300

tgtgacagcc gcccgcccag cccagcccac actctggact gccaagctag accgcttcaa    360

gggctccagg caccacacca ccctcatcac ctgccaccgt gctgggctca cagagccaga    420
```

-continued

```
ttccagcagt ccccttgaac tgtctgagtt cctatgggtg gactttgtgg tggagaatag    480
cactggtggg ggcgtagcgg tcactcgccc cgtcacgtgg cagctggagt acccaggcca    540
ggcccctgaa gcagagaagg acaaaatggt gtgggaaatc ctggtgtctg agcgggacat    600
cagagccctt atcccactgg ccaaggctga ggagctggtg aatacagcac cactgactgg    660
agtgccccag catgtccccg tgcgccttgt cactgtggac ggcggggggg ccttggtgga    720
ggtgacagag catgtcggct gcgagtctgc caacacacag gtcctgcagg tgtctgaggc    780
ctgtgatgcc gtgttcgtgg ctggcaagga gagccggggc gcccgggggg tgcgagtgga    840
cttctggtgg cgccggctcc gcgcctcgct gcggctgacc gtgtgggccc cgctgctacc    900
gctgcgtatc gagctcaccg acaccaccct cgagcaggtc cgcggctgga gggtacctgg    960
ccctgctgaa gggcctgcgg aacccgctgc agaggcgtca gatgaggccg agcggcgcgc   1020
ccgtggctgc cacctgcagt accagcgggc cggtgtgcgc ttcctcgccc ccttcgcggc   1080
ccacccgctg gacggcggcc gccgcctcac gcacctgctt ggccccgact ggctgctaga   1140
cgtgtcccac ctcgtggcgc cacacgcccg cgtgctggac tcgcgtgtag cctctctgga   1200
gggtggccgt gtcgtggtgg gccgggagcc cggtgtcacc tccattgagg tgcgttcccc   1260
actgtctgac tccatcctgg gggagcaggc gctggctgtg acggacgaca aggtctcagt   1320
gctggagctg agggtgcagc cagtgatggg catctcgctg accttgagcc ggggcactgc   1380
ccaccccggg gaggtcacag ctacgtgctg ggcacagtca gcccttcccg ccccaaagca   1440
ggaggtggcc ctctccctat ggctgtcctt ctctgatcac actgtggccc cagctgagct   1500
ctacgaccgc cgtgacctgg gactgtccgt ctcagccgag gagcctggtg ccatcctgcc   1560
agctgaggag cagggtgccc agctcggggt ggtggtgagt ggggcaggcg ccgaggggct   1620
gccgctgcat gtggctctgc acccgcccga gccctgccgc cggggccgcc accgtgtgcc   1680
tctggcctct ggcaccgcct ggctggggct gccccctgcc tccactccag cccctgctct   1740
cccatccagc cctgcttgga gcccaccagc cacagaagcc accatgggtg gtaaacggca   1800
ggtggcaggc agtgtcgggg gcaacacagg tgtgaggggc aagtttgagc gggcagagga   1860
ggaggccagg aaggaggaga ccgaagccag ggaggaggag gaggaagagg aggaggagat   1920
ggtccctgcc cctcagcatg tcactgagct agagctgggc atgtacgccc tgctgggagt   1980
cttctgcgtg gccatcttca tcttcttggt caatggtgtg gtcttcgtcc tgcgctatca   2040
gcgcaaagaa cctcccgaca gtgccactga ccccacctcc ccccagcccc acaactgggt   2100
ctggctgggc actgaccagg aggaactgag ccgccagctg gaccggcagt cccctggccc   2160
gcccaagggg gaggggagct gcccctgtga gagtggggga ggaggggagg cccctacccct   2220
ggcccctggc cctcctgggg gcaccaccag ctcctcaagc accctggccc gaaaggaggc   2280
tggggggcgg cggaagcgag tagagtttgt gacatttgtg ccagcccctc cagcccagtc   2340
acctgaggag cctgtagggg cccctgctgt gcagtccatc cttgtggcag gcgaggagga   2400
catccgctgg gtgtgtgagg acatggggct gaaggaccct gaggagcttc gcaactacat   2460
ggagaggatc cggggcagct cctgaccctc cacagccacc tggtcagcca ccagctgggg   2520
caacgagggt ggaggtccca ctgagcctct cgcctgcccc cgccactcgt ctggtgcttg   2580
ttgatccaag tcccctgcct ggtcccccac aaggactccc atccaggccc cctctgccct   2640
gccccttgtc atggaccatg gtcgtgagga agggctcatg ccccttattt atgggaacca   2700
tctcattcta acagaataaa ccgagaagga aaccagaaaa aaaaaaaaaa aaaaa        2755
```

-continued

<210> SEQ ID NO 4
<211> LENGTH: 909
<212> TYPE: PRT
<213> ORGANISM: Homo sapiens

<400> SEQUENCE: 4

```
Met Cys Ala Arg Met Ala Gly Arg Thr Thr Ala Ala Pro Arg Gly Pro
                5                   10                  15

Tyr Gly Pro Trp Leu Cys Leu Leu Val Ala Leu Ala Leu Asp Val Val
            20                  25                  30

Arg Val Asp Cys Gly Gln Ala Pro Leu Asp Pro Val Tyr Leu Pro Ala
        35                  40                  45

Ala Leu Glu Leu Leu Asp Ala Pro Glu His Phe Arg Val Gln Gln Val
    50                  55                  60

Gly His Tyr Pro Pro Ala Asn Ser Ser Leu Ser Ser Arg Ser Glu Thr
65                  70                  75                  80

Phe Leu Leu Leu Gln Pro Trp Pro Arg Ala Gln Pro Leu Leu Arg Ala
                85                  90                  95

Ser Tyr Pro Pro Phe Ala Thr Gln Gln Val Val Pro Pro Arg Val Thr
            100                 105                 110

Glu Pro His Gln Arg Pro Val Pro Trp Asp Val Arg Ala Val Ser Val
        115                 120                 125

Glu Ala Ala Val Thr Pro Ala Glu Pro Tyr Ala Arg Val Leu Phe His
    130                 135                 140

Leu Lys Gly Gln Asp Trp Pro Pro Gly Ser Gly Ser Leu Pro Cys Ala
145                 150                 155                 160

Arg Leu His Ala Thr His Pro Ala Gly Thr Ala His Gln Ala Cys Arg
                165                 170                 175

Phe Gln Pro Ser Leu Gly Ala Cys Val Val Glu Leu Glu Leu Pro Ser
            180                 185                 190

His Trp Phe Ser Gln Ala Ser Thr Thr Arg Ala Glu Leu Ala Tyr Thr
        195                 200                 205

Leu Glu Pro Ala Ala Glu Gly Pro Gly Gly Cys Gly Ser Gly Glu Glu
    210                 215                 220

Asn Asp Pro Gly Glu Gln Ala Leu Pro Val Gly Gly Val Glu Leu Arg
225                 230                 235                 240

Pro Ala Asp Pro Pro Gln Tyr Gln Glu Val Pro Leu Asp Glu Ala Val
                245                 250                 255

Thr Leu Arg Val Pro Asp Met Pro Val Arg Pro Gly Gln Leu Phe Ser
            260                 265                 270

Ala Thr Leu Leu Leu Arg His Asn Phe Thr Ala Ser Leu Leu Thr Leu
        275                 280                 285

Arg Ile Lys Val Lys Lys Gly Leu His Val Thr Ala Ala Arg Pro Ala
    290                 295                 300

Gln Pro Thr Leu Trp Thr Ala Lys Leu Asp Arg Phe Lys Gly Ser Arg
305                 310                 315                 320

His His Thr Thr Leu Ile Thr Cys His Arg Ala Gly Leu Thr Glu Pro
                325                 330                 335

Asp Ser Ser Pro Leu Glu Leu Ser Glu Phe Leu Trp Val Asp Phe Val
            340                 345                 350

Val Glu Asn Ser Thr Gly Gly Gly Val Ala Val Thr Arg Pro Val Thr
        355                 360                 365

Trp Gln Leu Glu Tyr Pro Gly Gln Ala Pro Glu Ala Glu Lys Asp Lys
    370                 375                 380
```

-continued

Met Val Trp Glu Ile Leu Val Ser Glu Arg Asp Ile Arg Ala Leu Ile
385 390 395 400

Pro Leu Ala Lys Ala Glu Glu Leu Val Asn Thr Ala Pro Leu Thr Gly
405 410 415

Val Pro Gln His Val Pro Val Arg Leu Val Thr Val Asp Gly Gly Gly
420 425 430

Ala Leu Val Glu Val Thr Glu His Val Gly Cys Glu Ser Ala Asn Thr
435 440 445

Gln Val Leu Gln Val Ser Glu Ala Cys Asp Ala Val Phe Val Ala Gly
450 455 460

Lys Glu Ser Arg Gly Ala Arg Gly Val Arg Val Asp Phe Trp Trp Arg
465 470 475 480

Arg Leu Arg Ala Ser Leu Arg Leu Thr Val Trp Ala Pro Leu Leu Pro
485 490 495

Leu Arg Ile Glu Leu Thr Asp Thr Thr Leu Glu Gln Val Arg Gly Trp
500 505 510

Arg Val Pro Gly Pro Ala Glu Gly Pro Ala Glu Pro Ala Ala Glu Ala
515 520 525

Ser Asp Glu Ala Glu Arg Arg Ala Arg Gly Cys His Leu Gln Tyr Gln
530 535 540

Arg Ala Gly Val Arg Phe Leu Ala Pro Phe Ala Ala His Pro Leu Asp
545 550 555 560

Gly Gly Arg Arg Leu Thr His Leu Leu Gly Pro Asp Trp Leu Leu Asp
565 570 575

Val Ser His Leu Val Ala Pro His Ala Arg Val Leu Asp Ser Arg Val
580 585 590

Ala Ser Leu Glu Gly Gly Arg Val Val Val Gly Arg Glu Pro Gly Val
595 600 605

Thr Ser Ile Glu Val Arg Ser Pro Leu Ser Asp Ser Ile Leu Gly Glu
610 615 620

Gln Ala Leu Ala Val Thr Asp Asp Lys Val Ser Val Leu Glu Leu Arg
625 630 635 640

Val Gln Pro Val Met Gly Ile Ser Leu Thr Leu Ser Arg Gly Thr Ala
645 650 655

His Pro Gly Glu Val Thr Ala Thr Cys Trp Ala Gln Ser Ala Leu Pro
660 665 670

Ala Pro Lys Gln Glu Val Ala Leu Ser Leu Trp Leu Ser Phe Ser Asp
675 680 685

His Thr Val Ala Pro Ala Glu Leu Tyr Asp Arg Arg Asp Leu Gly Leu
690 695 700

Ser Val Ser Ala Glu Glu Pro Gly Ala Ile Leu Pro Ala Glu Glu Gln
705 710 715 720

Gly Ala Gln Leu Gly Val Val His Val Thr Glu Leu Glu Leu Gly Met
725 730 735

Tyr Ala Leu Leu Gly Val Phe Cys Val Ala Ile Phe Ile Phe Leu Val
740 745 750

Asn Gly Val Val Phe Val Leu Arg Tyr Gln Arg Lys Glu Pro Pro Asp
755 760 765

Ser Ala Thr Asp Pro Thr Ser Pro Gln Pro His Asn Trp Val Trp Leu
770 775 780

Gly Thr Asp Gln Glu Glu Leu Ser Arg Gln Leu Asp Arg Gln Ser Pro
785 790 795 800

-continued

```
Gly Pro Pro Lys Gly Glu Gly Ser Cys Pro Cys Glu Ser Gly Gly Gly
                805                 810                 815

Gly Glu Ala Pro Thr Leu Ala Pro Gly Pro Pro Gly Gly Thr Thr Ser
            820                 825                 830

Ser Ser Ser Thr Leu Ala Arg Lys Glu Ala Gly Gly Arg Arg Lys Arg
        835                 840                 845

Val Glu Phe Val Thr Phe Ala Pro Ala Pro Pro Ala Gln Ser Pro Glu
    850                 855                 860

Glu Pro Val Gly Ala Pro Ala Val Gln Ser Ile Leu Val Ala Gly Glu
865                 870                 875                 880

Glu Asp Ile Arg Trp Val Cys Glu Asp Met Gly Leu Lys Asp Pro Glu
                885                 890                 895

Glu Leu Arg Asn Tyr Met Glu Arg Ile Arg Gly Ser Ser
            900                 905


<210> SEQ ID NO 5
<211> LENGTH: 2727
<212> TYPE: DNA
<213> ORGANISM: Homo sapiens

<400> SEQUENCE: 5

atgtgcgcgc ggatggccgg tcgcacaaca gcggcccctc gggggcccta cggcccctgg      60

ctctgcctcc tggtggccct cgccctggac gtcgtgagag tggactgtgg ccaggctccc     120

ctggaccctg tctacctgcc ggcagccctg gagctcctag acgcccctga acacttccgt     180

gtgcagcagg tgggccacta cccacctgcc aactcctctc tgagctcccg atctgagacc     240

tttctgctcc tacagccctg gcccagggcc cagccacttc tccgggcctc ctacccacct     300

tttgccactc agcaggtggt ccccccctcga gtcactgagc cccaccaacg gccagtccca     360

tgggacgtgc gggccgtttc agtggaagcg gctgtgactc cagcagagcc ctacgcccgg     420

gttctcttcc acctcaaagg gcaggattgg ccaccagggt ctggcagcct gccctgtgcc     480

cggctccatg ccacacaccc tgccggcact gctcaccaag cctgccgctt ccagccatcc     540

ctgggcgcct gcgtggtgga gctggagctt ccctcgcact ggttctcaca ggcctccacc     600

acacgggccg agctggccta cacgcttgag cctgcagctg agggccctgg gggctgtggc     660

tccggcgagg agaacgaccc tggggagcag gccctcccag tgggggggtgt ggagctgcgc     720

ccagcagacc ccccgcagta ccaggaggta cctctggacg aggctgtgac tctgcgggtg     780

cctgacatgc cagtgcggcc cggccagctc tttagtgcta ccctcctgct tcggcacaac     840

ttcacagcca gcctcctgac cctgcggatc aaggtgaaga aggggctgca tgtgacagcc     900

gcccgcccag cccagcccac actctggact gccaagctgg accgcttcaa gggctccagg     960

caccacacca ccctcatcac ctgccaccgt gctgggctca cagagccaga ttccagtccc    1020

cttgaactgt ctgagttcct atgggtggac tttgtggtgg agaatagcac tggtgggggc    1080

gtagcggtca ctcgccccgt cacgtggcag ctggagtacc caggccaggc ccctgaagca    1140

gagaaggaca aaatggtgtg ggaaatcctg gtgtctgagc gggacatcag agcccttatc    1200

ccactggcca aggctgagga gctggtgaat acagcaccac tgactggagt gccccagcat    1260

gtccccgtgc gccttgtcac tgtggacggc ggggggggcct tggtggaggt gacagagcat    1320

gtcggctgcg agtctgccaa cacacaggtc ctgcaggtgt ctgaggcctg tgatgccgtg    1380

ttcgtggctg gcaaggagag ccggggcgcc cgggggggtgc gagtggactt ctggtggcgc    1440

cggctccgcg cctcgctgcg gctgaccgtg tgggcccccc tgctaccgct gcgtatcgag    1500
```

-continued

```
ctcaccgaca ccaccctcga gcaggtccgc ggctggaggg tacctggccc tgctgaaggg   1560

cctgcggaac ccgctgcaga ggcgtcggat gaggccgagc ggcgcgcccg tggctgccac   1620

ctgcagtacc agcgggccgg tgtgcgcttc ctcgccccct tcgcggccca cccgctggac   1680

ggcggccgcc gcctcacgca cctgcttggc cccgactggc tgctagacgt gtcccacctc   1740

gtggcgccac acgcccgcgt gctggactcg cgtgtagcct ctctggaggg tggccgtgtc   1800

gtggtgggcc gggagcccgg tgtcacctcc attgaggtgc gttccccact gtctgactcc   1860

atcctggggg agcaggcgct ggctgtgacg gacgacaagg tctcagtgct ggagctgagg   1920

gtgcagccag tgatgggcat ctcgctgacc ttgagccggg gcactgccca ccccggggag   1980

gtcacagcta cgtgctgggc acagtcagcc cttcccgccc caaagcagga ggtggccctc   2040

tccctatggc tgtccttctc tgatcacact gtggccccag ctgagctcta cgaccgccgt   2100

gacctgggac tgtccgtctc agccgaggag cctggtgcca tcctgccagc tgaggagcag   2160

ggtgcccagc tcggggtggt gcatgtcact gagctagagc tgggcatgta cgccctgctg   2220

ggagtcttct gcgtggccat cttcatcttc ttggtcaatg gtgtggtctt cgtcctgcgc   2280

tatcagcgca aagaacctcc cgacagtgcc actgacccca cctcccccca gccccacaac   2340

tgggtctggc tgggcactga ccaggaggaa ctgagccgcc agctggaccg gcagtcccct   2400

ggcccgccca agggggaggg gagctgcccc tgtgagagtg gggaggaggg ggaggcccct   2460

accctggccc ctggccctcc tgggggcacc accagctcct caagcaccct ggcccgaaag   2520

gaggctgggg ggcggcggaa gcgagtagag tttgtgacat ttgcgccagc ccctccagcc   2580

cagtcacctg aggagcctgt aggggcccct gctgtgcagt ccatccttgt ggcaggcgag   2640

gaggacatcc gctgggtgtg tgaggacatg ggctgaaggg accctgagga gcttcgcaac   2700

tacatggaga ggatccgggg cagctcc                                       2727
```

<210> SEQ ID NO 6
<211> LENGTH: 2778
<212> TYPE: DNA
<213> ORGANISM: Homo sapiens

<400> SEQUENCE: 6

```
ctggggccac ctgagccgcc cgcctcgtcc ccgccttctg tgggaaggat gtgcgcgcgg     60

atggccggtc gcacaacagc ggcccctcgg gggccctacg gcccctggct ctgcctcctg    120

gtggccctcg ccctggacgt cgtgagagtg gactgtggcc aggctcccct ggaccctgtc    180

tacctgccgg cagccctgga gctcctagac gcccctgaac acttccgtgt gcagcaggtg    240

ggccactacc cacctgccaa ctcctctctg agctcccgat ctgagacctt tctgctccta    300

cagccctggc ccagggccca gccacttctc cgggcctcct acccaccttt tgccactcag    360

caggtggtcc cccctcgagt cactgagccc caccaacggc cagtcccatg ggacgtgcgg    420

gccgtttcag tggaagcggc tgtgactcca gcagagccct acgcccgggt tctcttccac    480

ctcaaagggc aggattggcc accagggtct ggcagcctgc cctgtgcccg gctccatgcc    540

acacaccctg ccggcactgc tcaccaagcc tgccgcttcc agccatccct gggcgcctgc    600

gtggtggagc tggagcttcc ctcgcactgg ttctcacagg cctccaccac acgggccgag    660

ctggcctaca cgcttgagcc tgcagctgag ggccctgggg gctgtggctc cggcgaggag    720

aacgaccctg gggagcaggc cctcccagtg gggggtgtgg agctgcgccc agcagacccc    780

ccgcagtacc aggaggtacc tctggacgag gctgtgactc tgcgggtgcc tgacatgcca    840

gtgcggcccg gccagctctt tagtgctacc ctcctgcttc ggcacaactt cacagccagc    900
```

-continued

```
ctcctgaccc tgcggatcaa ggtgaagaag gggctgcatg tgacagccgc ccgcccagcc    960

cagcccacac tctggactgc caagctggac cgcttcaagg gctccaggca ccacaccacc   1020

ctcatcacct gccaccgtgc tgggctcaca gagccagatt ccagtcccct tgaactgtct   1080

gagttcctat gggtggactt tgtggtggag aatagcactg gtgggggcgt agcggtcact   1140

cgccccgtca cgtggcagct ggagtaccca ggccaggccc ctgaagcaga gaaggacaaa   1200

atggtgtggg aaatcctggt gtctgagcgg gacatcagag ccccttatccc actggccaag   1260

gctgaggagc tggtgaatac agcaccactg actggagtgc cccagcatgt ccccgtgcgc   1320

cttgtcactg tggacggcgg gggggccttg gtggaggtga cagagcatgt cggctgcgag   1380

tctgccaaca cacaggtcct gcaggtgtct gaggcctgtg atgccgtgtt cgtggctggc   1440

aaggagagcc ggggcgcccg gggggtgcga gtggacttct ggtggcgccg gctccgcgcc   1500

tcgctgcggc tgaccgtgtg ggccccccctg ctaccgctgc gtatcgagct caccgacacc   1560

accctcgagc aggtccgcgg ctggagggta cctggccctg ctgaagggcc tgcggaaccc   1620

gctgcagagg cgtcggatga ggccgagcgg cgcgcccgtg gctgccacct gcagtaccag   1680

cgggccggtg tgcgcttcct cgccccccttc gcggcccacc cgctggacgg cggccgccgc   1740

ctcacgcacc tgcttggccc cgactggctg ctagacgtgt cccacctcgt ggcgccacac   1800

gcccgcgtgc tggactcgcg tgtagcctct ctggagggtg gccgtgtcgt ggtgggccgg   1860

gagcccggtg tcacctccat tgaggtgcgt tccccactgt ctgactccat cctgggggag   1920

caggcgctgg ctgtgacgga cgacaaggtc tcagtgctgg agctgagggt gcagccagtg   1980

atgggcatct cgctgacctt gagccggggc actgcccacc ccggggaggt cacagctacg   2040

tgctgggcac agtcagccct tcccgcccca aagcaggagg tggccctctc cctatggctg   2100

tccttctctg atcacactgt ggccccagct gagctctacg accgccgtga cctgggactg   2160

tccgtctcag ccgaggagcc tggtgccatc ctgccagctg aggagcaggg tgcccagctc   2220

ggggtggtgc atgtcactga gctagagctg ggcatgtacg ccctgctggg agtcttctgc   2280

gtggccatct tcatcttctt ggtcaatggt gtggtcttcg tcctgcgcta tcagcgcaaa   2340

gaacctcccg acagtgccac tgaccccacc tccccccagc cccacaactg ggtctggctg   2400

ggcactgacc aggaggaact gagccgccag ctggaccggc agtcccctgg cccgcccaag   2460

ggggagggga gctgcccctg tgagagtggg ggaggagggg aggcccctac cctggcccct   2520

ggccctcctg gggcaccac cagctcctca agcaccctgg cccgaaagga ggctgggggg   2580

cggcggaagc gagtagagtt tgtgacattt gcgccagccc ctccagccca gtcacctgag   2640

gagcctgtag gggcccctgc tgtgcagtcc atccttgtgg caggcgagga ggacatccgc   2700

tgggtgtgtg aggacatggg gctgaaggac cctgaggagc ttcgcaacta catggagagg   2760

atccggggca gctcctga                                                 2778
```

<210> SEQ ID NO 7
<211> LENGTH: 594
<212> TYPE: PRT
<213> ORGANISM: Homo sapiens

<400> SEQUENCE: 7

```
Met Cys Ala Arg Met Ala Gly Arg Thr Thr Ala Ala Pro Arg Gly Pro
                5                   10                  15

Tyr Gly Pro Trp Leu Cys Leu Leu Val Ala Leu Ala Leu Asp Val Val
            20                  25                  30
```

-continued

```
Arg Val Asp Cys Gly Gln Ala Pro Leu Asp Pro Gly Leu His Val Thr
        35                  40                  45

Ala Ala Arg Pro Ala Gln Pro Thr Leu Trp Thr Ala Lys Leu Asp Arg
    50                  55                  60

Phe Lys Gly Ser Arg His His Thr Thr Leu Ile Thr Cys His Arg Ala
65                  70                  75                  80

Gly Leu Thr Glu Pro Asp Ser Ser Ser Pro Leu Glu Leu Ser Glu Phe
                85                  90                  95

Leu Trp Val Asp Phe Val Val Glu Asn Ser Thr Gly Gly Gly Val Ala
            100                 105                 110

Val Thr Arg Pro Val Thr Trp Gln Leu Glu Tyr Pro Gly Gln Ala Pro
        115                 120                 125

Glu Ala Glu Lys Asp Lys Met Val Trp Glu Ile Leu Val Ser Glu Arg
    130                 135                 140

Asp Ile Arg Ala Leu Ile Pro Leu Ala Lys Ala Glu Glu Leu Val Asn
145                 150                 155                 160

Thr Ala Pro Leu Thr Gly Val Pro Gln His Val Pro Val Arg Leu Val
                165                 170                 175

Thr Val Asp Gly Gly Gly Ala Leu Val Glu Val Thr Glu His Val Gly
            180                 185                 190

Cys Glu Ser Ala Asn Thr Gln Val Leu Gln Val Ser Glu Ala Cys Asp
        195                 200                 205

Ala Val Phe Val Ala Gly Lys Glu Ser Arg Gly Ala Arg Gly Val Arg
    210                 215                 220

Val Asp Phe Trp Trp Arg Arg Leu Arg Ala Ser Leu Arg Leu Thr Val
225                 230                 235                 240

Trp Ala Pro Leu Leu Pro Leu Arg Ile Glu Leu Thr Asp Thr Thr Leu
                245                 250                 255

Glu Gln Val Arg Gly Trp Arg Val Pro Gly Pro Ala Glu Gly Pro Ala
            260                 265                 270

Glu Pro Ala Ala Glu Ala Ser Asp Glu Ala Glu Arg Arg Ala Arg Gly
        275                 280                 285

Cys His Leu Gln Tyr Gln Arg Ala Gly Val Arg Phe Leu Ala Pro Phe
    290                 295                 300

Ala Ala His Pro Leu Asp Gly Gly Arg Arg Leu Thr His Leu Leu Gly
305                 310                 315                 320

Pro Asp Trp Leu Leu Asp Val Ser His Leu Val Ala Pro His Ala Arg
                325                 330                 335

Val Leu Asp Ser Arg Val Ala Ser Leu Glu Gly Gly Arg Val Val Val
            340                 345                 350

Gly Arg Glu Pro Gly Val Thr Ser Ile Glu Val Arg Ser Pro Leu Ser
        355                 360                 365

Asp Ser Ile Leu Gly Glu Gln Ala Leu Ala Val Thr Asp Asp Lys Val
    370                 375                 380

Ser Val Leu Glu Leu Arg Val Gln Pro Val Met Gly Ile Ser Leu Thr
385                 390                 395                 400

Leu Ser Arg Gly Thr Ala His Pro Gly Glu Val Thr Ala Thr Cys Trp
                405                 410                 415

Ala Gln Ser Ala Leu Pro Ala Pro Lys Gln Glu Val Ala Leu Ser Leu
            420                 425                 430

Trp Leu Ser Phe Ser Asp His Thr Val Ala Pro Ala Glu Leu Tyr Asp
        435                 440                 445
```

-continued

```
Arg Arg Asp Leu Gly Leu Ser Val Ser Ala Glu Glu Pro Gly Ala Ile
    450                 455                 460

Leu Pro Ala Glu Glu Gln Gly Ala Gln Leu Gly Val Val Val Ser Gly
465                 470                 475                 480

Ala Gly Ala Glu Gly Leu Pro Leu His Val Ala Leu His Pro Pro Glu
                485                 490                 495

Pro Cys Arg Arg Gly Arg His Arg Val Pro Leu Ala Ser Gly Thr Ala
            500                 505                 510

Trp Leu Gly Leu Pro Pro Ala Ser Thr Pro Ala Pro Ala Leu Pro Ser
        515                 520                 525

Ser Pro Ala Trp Ser Pro Pro Ala Thr Glu Ala Thr Met Gly Gly Lys
    530                 535                 540

Arg Gln Val Ala Gly Ser Val Gly Gly Asn Thr Gly Val Arg Gly Lys
545                 550                 555                 560

Phe Glu Arg Ala Glu Glu Glu Ala Arg Lys Glu Glu Thr Glu Ala Arg
                565                 570                 575

Asp Gly Gly Gly Gly Arg Gly Gly Gly Asp Gly Pro Cys Pro Ser Ala
            580                 585                 590

Cys His


<210> SEQ ID NO 8
<211> LENGTH: 1782
<212> TYPE: DNA
<213> ORGANISM: Homo sapiens

<400> SEQUENCE: 8

atgtgcgcgc ggatggccgg tcgcacaaca gcggcccctc gggggcccta cggcccctgg     60

ctctgcctcc tggtggccct cgccctggac gtcgtgagag tggactgtgg ccaggctccc    120

ctggaccctg ggctgcatgt gacagccgcc cgcccagccc agcccacact ctggactgcc    180

aagctggacc gcttcaaggg ctccaggcac cacaccaccc tcatcacctg ccaccgtgct    240

gggctcacag agccagattc cagcagtccc cttgaactgt ctgagttcct atgggtggac    300

tttgtggtgg agaatagcac tggtgggggc gtagcggtca ctcgccccgt cacgtggcag    360

ctggagtacc caggccaggc ccctgaagca gagaaggaca aaatggtgtg ggaaatcctg    420

gtgtctgagc gggacatcag agcccttatc ccactggcca aggctgagga gctggtgaat    480

acagcaccac tgactggagt gccccagcat gtccccgtgc gccttgtcac tgtggacggc    540

ggggggccct tggtggaggt gacagagcat gtcggctgcg agtctgccaa cacacaggtc    600

ctgcaggtgt ctgaggcctg tgatgccgtg ttcgtggctg gcaaggagag ccggggcgcc    660

cggggggtgc gagtggactt ctggtggcgc cggctccgcg cctcgctgcg gctgaccgtg    720

tgggcccccc tgctaccgct gcgtatcgag ctcaccgaca ccaccctcga gcaggtccgc    780

ggctggaggg tacctggccc tgctgaaggg cctgcggaac ccgctgcaga ggcgtcggat    840

gaggccgagc ggcgcgcccg tggctgccac ctgcagtacc agcgggccgg tgtgcgcttc    900

ctcgcccccct tcgcggccca cccgctggac ggcggccgcc gcctcacgca cctgcttggc    960

cccgactggc tgctagacgt gtcccacctc gtggcgccac acgcccgcgt gctggactcg   1020

cgtgtagcct ctctggaggg tggccgtgtc gtggtgggcc gggagcccgg tgtcacctcc   1080

attgaggtgc gttccccact gtctgactcc atcctggggg agcaggcgct ggctgtgacg   1140

gacgacaagg tctcagtgct ggagctgagg gtgcagccag tgatgggcat ctcgctgacc   1200

ttgagccggg gcactgccca ccccggggag gtcacagcta cgtgctgggc acagtcagcc   1260
```

-continued

```
cttcccgccc caaagcagga ggtggccctc tccctatggc tgtccttctc tgatcacact   1320

gtggccccag ctgagctcta cgaccgccgt gacctgggac tgtccgtctc agccgaggag   1380

cctggtgcca tcctgccagc tgaggagcag ggtgcccagc tcggggtggt ggtgagtggg   1440

gcaggcgccg aggggctgcc gctgcatgtg gctctgcacc cgcccgagcc ctgccgccgg   1500

ggccgccacc gtgtgcctct ggcctctggc accgcctggc tggggctgcc ccctgcctcc   1560

actccagccc ctgctctccc atccagccct gcttggagcc caccagccac agaagccacc   1620

atgggtggta aacggcaggt ggcaggcagt gtcgggggca acacaggtgt gaggggcaag   1680

tttgagcggg cagaggagga ggccaggaag gaggagaccg aagccaggga cggaggagga   1740

ggaagaggag gaggagatgg tccctgcccc tcagcatgtc ac                      1782
```

<210> SEQ ID NO 9
<211> LENGTH: 2735
<212> TYPE: DNA
<213> ORGANISM: Homo sapiens

<400> SEQUENCE: 9

```
attgtctggg aattgcagcc gcggggcggg cggcggcggc ggcggcggcg gccgggaccc     60

agcgggccag gtggggacgg cgcggagcgg gtgcgggaga tgccgtgcgg gactggggcc    120

acctgagccg cccgcctcgt ccccgccttc tgtgggaagg atgtgcgcgc ggatggccgg    180

tcgcacaaca gcggcccctc gggggcccta cggcccctgg ctctgcctcc tggtggccct    240

cgccctggac gtcgtgagag tggactgtgg ccaggctccc ctggaccctg ggctgcatgt    300

gacagccgcc cgcccagccc agcccacact ctggactgcc aagctggacc gcttcaaggg    360

ctccaggcac cacaccaccc tcatcacctg ccaccgtgct gggctcacag agccagattc    420

cagcagtccc cttgaactgt ctgagttcct atgggtggac tttgtggtgg agaatagcac    480

tggtgggggc gtagcggtca ctcgccccgt cacgtggcag ctggagtacc caggccaggc    540

ccctgaagca gagaaggaca aaatggtgtg ggaaatcctg gtgtctgagc gggacatcag    600

agcccttatc ccactggcca aggctgagga gctggtgaat acagcaccac tgactggagt    660

gccccagcat gtccccgtgc gccttgtcac tgtggacggc ggggggggcct tggtggaggt    720

gacagagcat gtcggctgcg agtctgccaa cacacaggtc ctgcaggtgt ctgaggcctg    780

tgatgccgtg ttcgtggctg gcaaggagag ccggggcgcc cggggggtgc gagtggactt    840

ctggtggcgc cggctccgcg cctcgctgcg gctgaccgtg tgggcccccc tgctaccgct    900

gcgtatcgag ctcaccgaca ccaccctcga gcaggtccgc ggctggaggg tacctggccc    960

tgctgaaggg cctgcggaac ccgctgcaga ggcgtcggat gaggccgagc ggcgcgcccg   1020

tggctgccac ctgcagtacc agcgggccgg tgtgcgcttc ctcgcccccct tcgcggccca   1080

cccgctggac ggcggccgcc gcctcacgca cctgcttggc cccgactggc tgctagacgt   1140

gtcccacctc gtggcgccac acgcccgcgt gctggactcg cgtgtagcct ctctggaggg   1200

tggccgtgtc gtggtgggcc gggagcccgg tgtcacctcc attgaggtgc gttccccact   1260

gtctgactcc atcctggggg agcaggcgct ggctgtgacg gacgacaagg tctcagtgct   1320

ggagctgagg gtgcagccag tgatgggcat ctcgctgacc ttgagccggg gcactgccca   1380

ccccggggag gtcacagcta cgtgctgggc acagtcagcc cttcccgccc caaagcagga   1440

ggtggccctc tccctatggc tgtccttctc tgatcacact gtggccccag ctgagctcta   1500

cgaccgccgt gacctgggac tgtccgtctc agccgaggag cctggtgcca tcctgccagc   1560

tgaggagcag ggtgcccagc tcggggtggt ggtgagtggg gcaggcgccg aggggctgcc   1620
```

-continued

```
gctgcatgtg gctctgcacc cgcccgagcc ctgccgccgg ggccgccacc gtgtgcctct   1680

ggcctctggc accgcctggc tggggctgcc ccctgcctcc actccagccc ctgctctccc   1740

atccagccct gcttggagcc caccagccac agaagccacc atgggtggta aacggcaggt   1800

ggcaggcagt gtcgggggca acacaggtgt gaggggcaag tttgagcggg cagaggagga   1860

ggccaggaag gaggagaccg aagccaggga cggaggagga ggaagaggag gaggagatgg   1920

tccctgcccc tcagcatgtc actgagctag agctgggcat gtacgccctg ctgggagtct   1980

tctgcgtggc catcttcatc ttcttggtca atggtgtggt cttcgtcctg cgctatcagc   2040

gcaaagaacc tcccgacagt gccactgacc ccacctcccc ccagccccac aactgggtct   2100

ggctgggcac tgaccaggag gaactgagcc gccagctgga ccggcagtcc cctggcccgc   2160

ccaaggggga ggggagctgc ccctgtgaga gtgggggagg aggggaggcc cctaccctgg   2220

cccctggccc tcctgggggc accaccagct cctcaagcac cctggcccga aaggaggctg   2280

gggggcggcg gaagcgagta gagtttgtga catttgcgcc agcccctcca gcccagtcac   2340

ctgaggagcc tgtaggggcc cctgctgtgc agtccatcct tgtggcaggc gaggaggaca   2400

tccgctgggt gtgtgaggac atggggctga aggaccctga ggagcttcgc aactacatgg   2460

agaggatccg gggcagctcc tgaccctcca cagccacctg gtcagccacc agctggggca   2520

acgagggtgg aggtcccact gagcctctcg cctgccccg ccactcgtct ggtgcttgtt   2580

gatccaagtc ccctgcctgg tcccccacaa ggactcccat ccaggccccc tctgccctgc   2640

cccttgtcat ggaccatggt cgtgaggaag ggctcatgcc ccttatttat gggaaccatt   2700

tcattctaac agaataaacc gagaaggaaa ccaga                              2735
```

<210> SEQ ID NO 10
<211> LENGTH: 639
<212> TYPE: PRT
<213> ORGANISM: Homo sapiens

<400> SEQUENCE: 10

```
Met Val Trp Glu Ile Leu Val Ser Glu Arg Asp Ile Arg Ala Leu Ile
                5                   10                  15

Pro Leu Ala Lys Ala Glu Glu Leu Val Asn Thr Ala Pro Leu Thr Gly
            20                  25                  30

Val Pro Gln His Val Pro Val Arg Leu Val Thr Val Asp Gly Gly Gly
        35                  40                  45

Ala Leu Val Glu Val Thr Glu His Val Gly Cys Glu Ser Ala Asn Thr
    50                  55                  60

Gln Val Leu Gln Val Ser Glu Ala Cys Asp Ala Val Phe Val Ala Gly
65                  70                  75                  80

Lys Glu Ser Arg Gly Ala Arg Gly Val Arg Val Asp Phe Trp Trp Arg
                85                  90                  95

Arg Leu Arg Ala Ser Leu Arg Leu Thr Val Trp Ala Pro Leu Leu Pro
            100                 105                 110

Leu Arg Ile Glu Leu Thr Asp Thr Thr Leu Glu Gln Val Arg Gly Trp
        115                 120                 125

Arg Val Pro Gly Pro Ala Glu Gly Pro Ala Glu Pro Ala Ala Glu Ala
    130                 135                 140

Ser Asp Glu Ala Glu Arg Arg Ala Arg Gly Cys His Leu Gln Tyr Gln
145                 150                 155                 160

Arg Ala Gly Val Arg Phe Leu Ala Pro Phe Ala Ala His Pro Leu Asp
                165                 170                 175
```

-continued

```
Gly Gly Arg Arg Leu Thr His Leu Leu Gly Pro Asp Trp Leu Leu Asp
            180                 185                 190

Val Ser His Leu Val Ala Pro His Ala Arg Val Leu Asp Ser Arg Val
        195                 200                 205

Ala Ser Leu Glu Gly Gly Arg Val Val Val Gly Arg Glu Pro Gly Val
    210                 215                 220

Thr Ser Ile Glu Val Arg Ser Pro Leu Ser Asp Ser Ile Leu Gly Glu
225                 230                 235                 240

Gln Ala Leu Ala Val Thr Asp Asp Lys Val Ser Val Leu Glu Leu Arg
                245                 250                 255

Val Gln Pro Val Met Gly Ile Ser Leu Thr Leu Ser Arg Gly Thr Ala
            260                 265                 270

His Pro Gly Glu Val Thr Ala Thr Cys Trp Ala Gln Ser Ala Leu Pro
        275                 280                 285

Ala Pro Lys Gln Glu Val Ala Leu Ser Leu Trp Leu Ser Phe Ser Asp
    290                 295                 300

His Thr Val Ala Pro Ala Glu Leu Tyr Asp Arg Arg Asp Leu Gly Leu
305                 310                 315                 320

Ser Val Ser Ala Glu Glu Pro Gly Ala Ile Leu Pro Ala Glu Glu Gln
                325                 330                 335

Gly Ala Gln Leu Gly Val Val Val Ser Gly Ala Gly Ala Glu Gly Leu
            340                 345                 350

Pro Leu His Val Ala Leu His Pro Pro Glu Pro Cys Arg Arg Gly Arg
        355                 360                 365

His Arg Val Pro Leu Ala Ser Gly Thr Ala Trp Leu Gly Leu Pro Pro
    370                 375                 380

Ala Ser Thr Pro Ala Pro Ala Leu Pro Ser Ser Pro Ala Trp Ser Pro
385                 390                 395                 400

Pro Ala Thr Glu Ala Thr Met Gly Gly Lys Arg Gln Val Ala Gly Ser
                405                 410                 415

Val Gly Gly Asn Thr Gly Val Arg Gly Lys Phe Glu Arg Ala Glu Glu
            420                 425                 430

Glu Ala Arg Lys Glu Glu Thr Lys Ala Arg Glu Glu Glu Glu Glu Glu
        435                 440                 445

Glu Glu Glu Met Val Pro Ala Pro Gln His Val Thr Glu Leu Glu Leu
    450                 455                 460

Gly Met Tyr Ala Leu Leu Gly Val Phe Cys Val Ala Ile Phe Ile Phe
465                 470                 475                 480

Leu Val Asn Gly Val Val Phe Val Leu Arg Tyr Gln Arg Lys Glu Pro
                485                 490                 495

Pro Asp Ser Ala Thr Asp Pro Thr Ser Pro Gln Pro His Asn Trp Val
            500                 505                 510

Trp Leu Gly Thr Asp Gln Glu Glu Leu Ser Arg Gln Leu Asp Arg Gln
        515                 520                 525

Ser Pro Gly Pro Pro Lys Gly Glu Gly Ser Cys Pro Cys Glu Ser Gly
    530                 535                 540

Gly Gly Gly Glu Ala Pro Thr Leu Ala Pro Gly Pro Pro Gly Gly Thr
545                 550                 555                 560

Thr Ser Ser Ser Ser Thr Leu Ala Arg Lys Glu Ala Gly Gly Arg Arg
                565                 570                 575

Lys Arg Val Glu Phe Val Thr Phe Ala Pro Ala Pro Pro Ala Gln Ser
            580                 585                 590
```

-continued

```
Pro Glu Glu Pro Val Gly Ala Pro Ala Val Gln Ser Ile Leu Val Ala
        595                 600                 605

Gly Glu Glu Asp Ile Arg Trp Val Cys Glu Asp Met Gly Leu Lys Asp
    610                 615                 620

Pro Glu Glu Leu Arg Asn Tyr Met Glu Arg Ile Arg Gly Ser Ser
625                 630                 635


<210> SEQ ID NO 11
<211> LENGTH: 1917
<212> TYPE: DNA
<213> ORGANISM: Homo sapiens

<400> SEQUENCE: 11

atggtgtggg aaatcctggt gtctgagcgg gacatcagag cccttatccc actggccaag      60

gctgaggagc tggtgaatac agcaccactg actggagtgc cccagcatgt ccccgtgcgc     120

cttgtcactg tggacggcgg gggggccttg gtggaggtga cagagcatgt cggctgcgag     180

tctgccaaca cacaggtcct gcaggtgtct gaggcctgtg atgccgtgtt cgtggctggc     240

aaggagagcc ggggcgcccg gggggtgcga gtggacttct ggtggcgccg gctccgcgcc     300

tcgctgcggc tgaccgtgtg ggccccccctg ctaccgctgc gtatcgagct caccgacacc     360

accctcgagc aggtccgcgg ctggagggta cctggccctg ctgaagggcc tgcggaaccc     420

gctgcagagg cgtcggatga ggccgagcgg cgcgcccgtg gctgccacct gcagtaccag     480

cgggccggtg tgcgcttcct cgccccccttc gcggcccacc cgctggacgg cggccgccgc     540

ctcacgcacc tgcttggccc cgactggctg ctagacgtgt cccacctcgt ggcgccacac     600

gcccgcgtgc tggactcgcg tgtagcctct ctggagggtg gccgtgtcgt ggtgggccgg     660

gagcccggtg tcacctccat tgaggtgcgt tccccactgt ctgactccat cctgggggag     720

caggcgctgg ctgtgacgga cgacaaggtc tcagtgctgg agctgagggt gcagccagtg     780

atgggcatct cgctgacctt gagccggggc actgcccacc ccggggaggt cacagctacg     840

tgctgggcac agtcagccct tcccgcccca aagcaggagg tggccctctc cctatggctg     900

tccttctctg atcacactgt ggccccagct gagctctacg accgccgtga cctgggactg     960

tccgtctcag ccgaggagcc tggtgccatc ctgccagctg aggagcaggg tgcccagctc    1020

ggggtggtgg tgagtggggc aggcgccgag gggctgccgc tgcatgtggc tctgcacccg    1080

cccgagccct gccgccgggg ccgccaccgt gtgcctctgg cctctggcac cgcctggctg    1140

gggctgcccc ctgcctccac tccagcccct gctctcccat ccagccctgc ttggagccca    1200

ccagccacag aagccaccat gggtggtaaa cggcaggtgg caggcagtgt cgggggcaac    1260

acaggtgtga ggggcaagtt tgagcgggca gaggaggagg ccaggaagga ggagaccaaa    1320

gccagggagg aggaggagga agaggaggag gagatggtcc ctgcccctca gcatgtcact    1380

gagctagagc tgggcatgta cgccctgctg ggagtcttct gcgtggccat cttcatcttc    1440

ttggtcaatg gtgtggtctt cgtcctgcgc tatcagcgca aagaacctcc cgacagtgcc    1500

actgacccca cctcccccca gccccacaac tgggtctggc tgggcactga ccaggaggaa    1560

ctgagccgcc agctggaccg gcagtcccct ggcccgccca agggggaggg gagctgcccc    1620

tgtgagagtg ggggaggagg ggaggcccct accctggccc ctggccctcc tgggggcacc    1680

accagctcct caagcaccct ggcccgaaag gaggctgggg ggcggcggaa gcgagtagag    1740

tttgtgacat ttgcgccagc ccctccagcc cagtcacctg aggagcctgt aggggcccct    1800
```

-continued gctgtgcagt ccatccttgt ggcaggcgag gaggacatcc gctgggtgtg tgaggacatg 1860
gggctgaagg accctgagga gcttcgcaac tacatggaga ggatccgggg cagctcc 1917

<210> SEQ ID NO 12
<211> LENGTH: 2235
<212> TYPE: DNA
<213> ORGANISM: Homo sapiens

<400> SEQUENCE: 12
cactcgcccc gtcacgtggc agctggagta cccaggccag gcccctgaag cagagaagga 60
caaaatggtg tgggaaatcc tggtgtctga gcgggacatc agagccctta tcccactggc 120
caaggctgag gagctggtga atacagcacc actgactgga gtgccccagc atgtccccgt 180
gcgccttgtc actgtggacg gcgggggggc cttggtggag gtgacagagc atgtcggctg 240
cgagtctgcc aacacacagg tcctgcaggt gtctgaggcc tgtgatgccg tgttcgtggc 300
tggcaaggag agccggggcg cccggggggt gcgagtggac ttctggtggc gccggctccg 360
cgcctcgctg cggctgaccg tgtgggcccc cctgctaccg ctgcgtatcg agctcaccga 420
caccaccctc gagcaggtcc gcggctggag ggtacctggc cctgctgaag ggcctgcgga 480
acccgctgca gaggcgtcgg atgaggccga gcggcgcgcc cgtggctgcc acctgcagta 540
ccagcgggcc ggtgtgcgct tcctcgcccc cttcgcggcc cacccgctgg acggcggccg 600
ccgcctcacg cacctgcttg gccccgactg gctgctagac gtgtcccacc tcgtggcgcc 660
acacgcccgc gtgctggact cgcgtgtagc ctctctggag ggtggccgtg tcgtggtggg 720
ccgggagccc ggtgtcacct ccattgaggt gcgttcccca ctgtctgact ccatcctggg 780
ggagcaggcg ctggctgtga cggacgacaa ggtctcagtg ctggagctga gggtgcagcc 840
agtgatgggc atctcgctga ccttgagccg ggcactgcc caccccgggg aggtcacagc 900
tacgtgctgg gcacagtcag cccttcccgc cccaaagcag gaggtggccc tctccctatg 960
gctgtccttc tctgatcaca ctgtggcccc agctgagctc tacgaccgcc gtgacctggg 1020
actgtccgtc tcagccgagg agcctggtgc catcctgcca gctgaggagc agggtgccca 1080
gctcggggtg gtggtgagtg gggcaggcgc cgaggggctg ccgctgcatg tggctctgca 1140
cccgcccgag ccctgccgcc ggggccgcca ccgtgtgcct ctggcctctg gcaccgcctg 1200
gctggggctg ccccctgcct ccactccagc ccctgctctc ccatccagcc ctgcttggag 1260
cccaccagcc acagaagcca ccatgggtgg taaacggcag gtggcaggca gtgtcggggg 1320
caacacaggt gtgaggggca agtttgagcg ggcagaggag gaggccagga aggaggagac 1380
caaagccagg gaggaggagg aggaagagga ggaggagatg gtccctgccc ctcagcatgt 1440
cactgagcta gagctgggca tgtacgccct gctgggagtc ttctgcgtgg ccatcttcat 1500
cttcttggtc aatggtgtgg tcttcgtcct gcgctatcag cgcaaagaac ctcccgacag 1560
tgccactgac cccacctccc cccagcccca caactgggtc tggctgggca ctgaccagga 1620
ggaactgagc cgccagctgg accggcagtc ccctggcccg cccaaggggg aggggagctg 1680
cccctgtgag agtgggggag gaggggaggc ccctaccctg gcccctggcc ctcctggggg 1740
caccaccagc tcctcaagca ccctggcccg aaaggaggct ggggggcggc ggaagcgagt 1800
agagtttgtg acatttgcgc cagcccctcc agcccagtca cctgaggagc ctgtaggggc 1860
ccctgctgtg cagtccatcc ttgtggcagg cgaggaggac atccgctggg tgtgtgagga 1920
catggggctg aaggaccctg aggagcttcg caactacatg gagaggatcc ggggcagctc 1980
ctgaccctcc acagccacct ggtcagccac cagctggggc aacgagggtg gaggtcccac 2040

-continued tgagcctctc gcctgccccc gccactcgtc tggtgcttgt tgatccaagt cccctgcctg 2100
gtcccccaca aggactccca tccaggcccc ctctgccctg ccccttgtca tggaccatgg 2160
tcgtgaggaa gggctcatgc cccttattta tgggaaccat ttcattctaa cagaataaac 2220
cgagaaggaa accag 2235

<210> SEQ ID NO 13
<211> LENGTH: 20
<212> TYPE: DNA
<213> ORGANISM: Artificial Sequence
<220> FEATURE:
<223> OTHER INFORMATION: Designed oligonucleotide

<400> SEQUENCE: 13
agaccacacc attgaccaag 20

<210> SEQ ID NO 14
<211> LENGTH: 20
<212> TYPE: DNA
<213> ORGANISM: Artificial Sequence
<220> FEATURE:
<223> OTHER INFORMATION: Designed oligonucleotide

<400> SEQUENCE: 14
gaaccagtta ccacaccaga 20

<210> SEQ ID NO 15
<211> LENGTH: 1024
<212> TYPE: PRT
<213> ORGANISM: Homo sapiens

<400> SEQUENCE: 15

Met Cys Ala Arg Met Ala Gly Arg Thr Thr Ala Ala Pro Arg Gly Pro
1 5 10 15

Tyr Gly Pro Trp Leu Cys Leu Leu Val Ala Leu Ala Leu Asp Val Val
20 25 30

Arg Val Asp Cys Gly Gln Ala Pro Leu Asp Pro Val Tyr Leu Pro Ala
35 40 45

Ala Leu Glu Leu Leu Asp Ala Pro Glu His Phe Arg Val Gln Gln Val
50 55 60

Gly His Tyr Pro Pro Ala Asn Ser Ser Leu Ser Ser Arg Ser Glu Thr
65 70 75 80

Phe Leu Leu Leu Gln Pro Trp Pro Arg Ala Gln Pro Leu Leu Arg Ala
85 90 95

Ser Tyr Pro Pro Phe Ala Thr Gln Gln Val Val Pro Pro Arg Val Thr
100 105 110

Glu Pro His Gln Arg Pro Val Pro Trp Asp Val Arg Ala Val Ser Val
115 120 125

Glu Ala Ala Val Thr Pro Ala Glu Pro Tyr Ala Arg Val Leu Phe His
130 135 140

Leu Lys Gly Gln Asp Trp Pro Pro Gly Ser Gly Ser Leu Pro Cys Ala
145 150 155 160

Arg Leu His Ala Thr His Pro Ala Gly Thr Ala His Gln Ala Cys Arg
165 170 175

Phe Gln Pro Ser Leu Gly Ala Cys Val Val Glu Leu Glu Leu Pro Ser
180 185 190

His Trp Phe Ser Gln Ala Ser Thr Thr Arg Ala Glu Leu Ala Tyr Thr
195 200 205

-continued

```
Leu Glu Pro Ala Ala Glu Gly Pro Gly Gly Cys Gly Ser Gly Glu Glu
    210                 215                 220

Asn Asp Pro Gly Glu Gln Ala Leu Pro Val Gly Gly Val Glu Leu Arg
225                 230                 235                 240

Pro Ala Asp Pro Pro Gln Tyr Gln Glu Val Pro Leu Asp Glu Ala Val
                245                 250                 255

Thr Leu Arg Val Pro Asp Met Pro Val Arg Pro Gly Gln Leu Phe Ser
            260                 265                 270

Ala Thr Leu Leu Leu Arg His Asn Phe Thr Ala Ser Leu Leu Thr Leu
        275                 280                 285

Arg Ile Lys Val Lys Lys Gly Leu His Val Thr Ala Ala Arg Pro Ala
    290                 295                 300

Gln Pro Thr Leu Trp Thr Ala Lys Leu Asp Arg Phe Lys Gly Ser Arg
305                 310                 315                 320

His His Thr Thr Leu Ile Thr Cys His Arg Ala Gly Leu Thr Glu Pro
                325                 330                 335

Asp Ser Ser Ser Pro Leu Glu Leu Ser Glu Phe Leu Trp Val Asp Phe
            340                 345                 350

Val Val Glu Asn Ser Thr Gly Gly Gly Val Ala Val Thr Arg Pro Val
        355                 360                 365

Thr Trp Gln Leu Glu Tyr Pro Gly Gln Ala Pro Glu Ala Glu Lys Asp
    370                 375                 380

Lys Met Val Trp Glu Ile Leu Val Ser Glu Arg Asp Ile Arg Ala Leu
385                 390                 395                 400

Ile Pro Leu Ala Lys Ala Glu Glu Leu Val Asn Thr Ala Pro Leu Thr
                405                 410                 415

Gly Val Pro Gln His Val Pro Val Arg Leu Val Thr Val Asp Gly Gly
            420                 425                 430

Gly Ala Leu Val Glu Val Thr Glu His Val Gly Cys Glu Ser Ala Asn
        435                 440                 445

Thr Gln Val Leu Gln Val Ser Glu Ala Cys Asp Ala Val Phe Val Ala
    450                 455                 460

Gly Lys Glu Ser Arg Gly Ala Arg Gly Val Arg Val Asp Phe Trp Trp
465                 470                 475                 480

Arg Arg Leu Arg Ala Ser Leu Arg Leu Thr Val Trp Ala Pro Leu Leu
                485                 490                 495

Pro Leu Arg Ile Glu Leu Thr Asp Thr Thr Leu Glu Gln Val Arg Gly
            500                 505                 510

Trp Arg Val Pro Gly Pro Ala Glu Gly Pro Ala Glu Pro Ala Ala Glu
        515                 520                 525

Ala Ser Asp Glu Ala Glu Arg Arg Ala Arg Gly Cys His Leu Gln Tyr
    530                 535                 540

Gln Arg Ala Gly Val Arg Phe Leu Ala Pro Phe Ala Ala His Pro Leu
545                 550                 555                 560

Asp Gly Gly Arg Arg Leu Thr His Leu Leu Gly Pro Asp Trp Leu Leu
                565                 570                 575

Asp Val Ser His Leu Val Ala Pro His Ala Arg Val Leu Asp Ser Arg
            580                 585                 590

Val Ala Ser Leu Glu Gly Gly Arg Val Val Val Gly Arg Glu Pro Gly
        595                 600                 605

Val Thr Ser Ile Glu Val Arg Ser Pro Leu Ser Asp Ser Ile Leu Gly
    610                 615                 620
```

-continued

```
Glu Gln Ala Leu Ala Val Thr Asp Asp Lys Val Ser Val Leu Glu Leu
625                 630                 635                 640

Arg Val Gln Pro Val Met Gly Ile Ser Leu Thr Leu Ser Arg Gly Thr
                645                 650                 655

Ala His Pro Gly Glu Val Thr Ala Thr Cys Trp Ala Gln Ser Ala Leu
            660                 665                 670

Pro Ala Pro Lys Gln Glu Val Ala Leu Ser Leu Trp Leu Ser Phe Ser
        675                 680                 685

Asp His Thr Val Ala Pro Ala Glu Leu Tyr Asp Arg Arg Asp Leu Gly
    690                 695                 700

Leu Ser Val Ser Ala Glu Glu Pro Gly Ala Ile Leu Pro Ala Glu Glu
705                 710                 715                 720

Gln Gly Ala Gln Leu Gly Val Val Val Ser Gly Ala Gly Ala Glu Gly
                725                 730                 735

Leu Pro Leu His Val Ala Leu His Pro Pro Glu Pro Cys Arg Arg Gly
            740                 745                 750

Arg His Arg Val Pro Leu Ala Ser Gly Thr Ala Trp Leu Gly Leu Pro
        755                 760                 765

Pro Ala Ser Thr Pro Ala Pro Ala Leu Pro Ser Ser Pro Ala Trp Ser
    770                 775                 780

Pro Pro Ala Thr Glu Ala Thr Met Gly Gly Lys Arg Gln Val Ala Gly
785                 790                 795                 800

Ser Val Gly Gly Asn Thr Gly Val Arg Gly Lys Phe Glu Arg Ala Glu
                805                 810                 815

Glu Glu Ala Arg Lys Glu Glu Thr Glu Ala Arg Glu Glu Glu Glu Glu
            820                 825                 830

Glu Glu Glu Glu Met Val Pro Ala Pro Gln His Val Thr Glu Leu Glu
        835                 840                 845

Leu Gly Met Tyr Ala Leu Leu Gly Val Phe Cys Val Ala Ile Phe Ile
    850                 855                 860

Phe Leu Val Asn Gly Val Val Phe Val Leu Arg Tyr Gln Arg Lys Glu
865                 870                 875                 880

Pro Pro Asp Ser Ala Thr Asp Pro Thr Ser Pro Gln Pro His Asn Trp
                885                 890                 895

Val Trp Leu Gly Thr Asp Gln Glu Glu Leu Ser Arg Gln Leu Asp Arg
            900                 905                 910

Gln Ser Pro Gly Pro Pro Lys Gly Glu Gly Ser Cys Pro Cys Glu Ser
        915                 920                 925

Gly Gly Gly Gly Glu Ala Pro Thr Leu Ala Pro Gly Pro Pro Gly Gly
    930                 935                 940

Thr Thr Ser Ser Ser Ser Thr Leu Ala Arg Lys Glu Ala Gly Gly Arg
945                 950                 955                 960

Arg Lys Arg Val Glu Phe Val Thr Phe Val Pro Ala Pro Pro Ala Gln
                965                 970                 975

Ser Pro Glu Glu Pro Val Gly Ala Pro Ala Val Gln Ser Ile Leu Val
            980                 985                 990

Ala Gly Glu Glu Asp Ile Arg Trp Val Cys Glu Asp Met Gly Leu Lys
        995                 1000                1005

Asp Pro Glu Glu Leu Arg Asn Tyr Met Glu Arg Ile Arg Gly Ser Ser
   1010                 1015                1020
```

-continued

<210> SEQ ID NO 16
<211> LENGTH: 3072
<212> TYPE: DNA
<213> ORGANISM: Homo sapiens

<400> SEQUENCE: 16
atgtgcgcgc ggatggccgg tcgcacaaca gcggcccctc gggggcccta cggcccctgg 60
ctctgcctcc tggtggccct cgccctggac gtcgtgagag tggactgtgg ccaggctccc 120
ctggaccctg tctacctgcc ggcagccctg gagctcctag acgcccctga acacttccgt 180
gtgcagcagg tgggccacta cccacctgcc aactcctctc tgagctcccg atctgagacc 240
tttctgctcc tacagccctg gcccagggcc cagccacttc tccgggcctc ctacccacct 300
tttgccactc agcaggtggt cccccctcga gtcactgagc cccaccaacg gccagtccca 360
tgggacgtgc gggccgtttc agtggaagcg gctgtgactc cagcagagcc ctacgcccgg 420
gttctcttcc acctcaaagg gcaggattgg ccaccagggt ctggcagcct gccctgtgcc 480
cggctccatg ccacacaccc tgcaggcact gctcaccaag cctgccgctt ccagccatcc 540
ctgggcgcct gcgtggtgga gctggagctt ccctcgcact ggttctcaca ggcctccacc 600
acacgggccg agctggccta cacgcttgag cctgcagctg agggccctgg gggctgtggc 660
tccggcgagg agaacgaccc tggggagcag gccctcccag tgggggggtgt ggagctgcgc 720 ccagcagacc ccccgcagta ccaggaggta cctctggacg aggctgtgac tctgcgggtg 780
cctgacatgc cagtgcggcc cggccagctc tttagtgcta ccctcctgct tcggcacaac 840
ttcacagcca gcctcctgac cctgcggatc aaggtgaaga aggggctgca tgtgacagcc 900
gcccgcccag cccagcccac actctggact gccaagctag accgcttcaa gggctccagg 960
caccacacca ccctcatcac ctgccaccgt gctgggctca cagagccaga ttccagcagt 1020
ccccttgaac tgtctgagtt cctatgggtg gactttgtgg tggagaatag cactggtggg 1080
ggcgtagcgg tcactcgccc cgtcacgtgg cagctggagt acccaggcca ggcccctgaa 1140
gcagagaagg acaaaatggt gtgggaaatc ctggtgtctg agcgggacat cagagccctt 1200
atcccactgg ccaaggctga ggagctggtg aatacagcac cactgactgg agtgccccag 1260
catgtccccg tgcgccttgt cactgtggac ggcggggggg ccttggtgga ggtgacagag 1320
catgtcggct gcgagtctgc caacacacag gtcctgcagg tgtctgaggc ctgtgatgcc 1380
gtgttcgtgg ctggcaagga gagccggggc gcccgggggg tgcgagtgga cttctggtgg 1440
cgccggctcc gcgcctcgct gcggctgacc gtgtgggccc cgctgctacc gctgcgtatc 1500
gagctcaccg acaccaccct cgagcaggtc cgcggctgga gggtacctgg ccctgctgaa 1560
gggcctgcgg aacccgctgc agaggcgtca gatgaggccg agcggcgcgc ccgtggctgc 1620
cacctgcagt accagcgggc cggtgtgcgc ttcctcgccc ccttcgcggc ccacccgctg 1680
gacggcggcc gccgcctcac gcacctgctt ggccccgact ggctgctaga cgtgtcccac 1740
ctcgtggcgc cacacgcccg cgtgctggac tcgcgtgtag cctctctgga gggtggccgt 1800
gtcgtggtgg gccgggagcc cggtgtcacc tccattgagg tgcgttcccc actgtctgac 1860
tccatcctgg gggagcaggc gctggctgtg acggacgaca aggtctcagt gctggagctg 1920
agggtgcagc cagtgatggg catctcgctg accttgagcc ggggcactgc ccaccccggg 1980
gaggtcacag ctacgtgctg ggcacagtca gcccttcccg ccccaaagca ggaggtggcc 2040
ctctccctat ggctgtcctt ctctgatcac actgtggccc cagctgagct ctacgaccgc 2100
cgtgacctgg gactgtccgt ctcagccgag gagcctggtg ccatcctgcc agctgaggag 2160

-continued

```
cagggtgccc agctcggggt ggtggtgagt ggggcaggcg ccgaggggct gccgctgcat   2220

gtggctctgc acccgcccga gccctgccgc cggggccgcc accgtgtgcc tctggcctct   2280

ggcaccgcct ggctggggct gccccctgcc tccactccag cccctgctct cccatccagc   2340

cctgcttgga gcccaccagc cacagaagcc accatgggtg gtaaacggca ggtggcaggc   2400

agtgtcgggg gcaacacagg tgtgaggggc aagtttgagc gggcagagga ggaggccagg   2460

aaggaggaga ccgaagccag ggaggaggag gaggaagagg aggaggagat ggtccctgcc   2520

cctcagcatg tcactgagct agagctgggc atgtacgccc tgctgggagt cttctgcgtg   2580

gccatcttca tcttcttggt caatggtgtg gtcttcgtcc tgcgctatca gcgcaaagaa   2640

cctcccgaca gtgccactga ccccacctcc ccccagcccc acaactgggt ctggctgggc   2700

actgaccagg aggaactgag ccgccagctg gaccggcagt cccctggccc gcccaagggg   2760

gaggggagct gcccctgtga gagtggggga ggaggggagg cccctaccct ggcccctggc   2820

cctcctgggg gcaccaccag ctcctcaagc accctggccc gaaaggaggc tgggggggcgg   2880

cggaagcgag tagagtttgt gacatttgtg ccagcccctc cagcccagtc acctgaggag   2940

cctgtagggg cccctgctgt gcagtccatc cttgtggcag gcgaggagga catccgctgg   3000

gtgtgtgagg acatggggct gaaggaccct gaggagcttc gcaactacat ggagaggatc   3060

cggggcagct cc                                                       3072
```

<210> SEQ ID NO 17
<211> LENGTH: 1020
<212> TYPE: PRT
<213> ORGANISM: Homo sapiens

<400> SEQUENCE: 17

```
Met Ala Gly Arg Thr Thr Ala Ala Pro Arg Gly Pro Tyr Gly Pro Trp
1               5                   10                  15

Leu Cys Leu Leu Val Ala Leu Ala Leu Asp Val Val Arg Val Asp Cys
            20                  25                  30

Gly Gln Ala Pro Leu Asp Pro Val Tyr Leu Pro Ala Ala Leu Glu Leu
        35                  40                  45

Leu Asp Ala Pro Glu His Phe Arg Val Gln Gln Val Gly His Tyr Pro
    50                  55                  60

Pro Ala Asn Ser Ser Leu Ser Ser Arg Ser Glu Thr Phe Leu Leu Leu
65                  70                  75                  80

Gln Pro Trp Pro Arg Ala Gln Pro Leu Leu Arg Ala Ser Tyr Pro Pro
                85                  90                  95

Phe Ala Thr Gln Gln Val Val Pro Pro Arg Val Thr Glu Pro His Gln
            100                 105                 110

Arg Pro Val Pro Trp Asp Val Arg Ala Val Ser Val Glu Ala Ala Val
        115                 120                 125

Thr Pro Ala Glu Pro Tyr Ala Arg Val Leu Phe His Leu Lys Gly Gln
    130                 135                 140

Asp Trp Pro Pro Gly Ser Gly Ser Leu Pro Cys Ala Arg Leu His Ala
145                 150                 155                 160

Thr His Pro Ala Gly Thr Ala His Gln Ala Cys Arg Phe Gln Pro Ser
                165                 170                 175

Leu Gly Ala Cys Val Val Glu Leu Glu Leu Pro Ser His Trp Phe Ser
            180                 185                 190

Gln Ala Ser Thr Thr Arg Ala Glu Leu Ala Tyr Thr Leu Glu Pro Ala
        195                 200                 205
```

-continued

```
Ala Glu Gly Pro Gly Gly Cys Gly Ser Gly Glu Glu Asn Asp Pro Gly
    210                 215                 220

Glu Gln Ala Leu Pro Val Gly Gly Val Glu Leu Arg Pro Ala Asp Pro
225                 230                 235                 240

Pro Gln Tyr Gln Glu Val Pro Leu Asp Glu Ala Val Thr Leu Arg Val
                245                 250                 255

Pro Asp Met Pro Val Arg Pro Gly Gln Leu Phe Ser Ala Thr Leu Leu
            260                 265                 270

Leu Arg His Asn Phe Thr Ala Ser Leu Leu Thr Leu Arg Ile Lys Val
        275                 280                 285

Lys Lys Gly Leu His Val Thr Ala Ala Arg Pro Ala Gln Pro Thr Leu
    290                 295                 300

Trp Thr Ala Lys Leu Asp Arg Phe Lys Gly Ser Arg His His Thr Thr
305                 310                 315                 320

Leu Ile Thr Cys His Arg Ala Gly Leu Thr Glu Pro Asp Ser Ser Ser
                325                 330                 335

Pro Leu Glu Leu Ser Glu Phe Leu Trp Val Asp Phe Val Val Glu Asn
            340                 345                 350

Ser Thr Gly Gly Gly Val Ala Val Thr Arg Pro Val Thr Trp Gln Leu
        355                 360                 365

Glu Tyr Pro Gly Gln Ala Pro Glu Ala Glu Lys Asp Lys Met Val Trp
    370                 375                 380

Glu Ile Leu Val Ser Glu Arg Asp Ile Arg Ala Leu Ile Pro Leu Ala
385                 390                 395                 400

Lys Ala Glu Glu Leu Val Asn Thr Ala Pro Leu Thr Gly Val Pro Gln
                405                 410                 415

His Val Pro Val Arg Leu Val Thr Val Asp Gly Gly Gly Ala Leu Val
            420                 425                 430

Glu Val Thr Glu His Val Gly Cys Glu Ser Ala Asn Thr Gln Val Leu
        435                 440                 445

Gln Val Ser Glu Ala Cys Asp Ala Val Phe Val Ala Gly Lys Glu Ser
    450                 455                 460

Arg Gly Ala Arg Gly Val Arg Val Asp Phe Trp Trp Arg Arg Leu Arg
465                 470                 475                 480

Ala Ser Leu Arg Leu Thr Val Trp Ala Pro Leu Leu Pro Leu Arg Ile
                485                 490                 495

Glu Leu Thr Asp Thr Thr Leu Glu Gln Val Arg Gly Trp Arg Val Pro
            500                 505                 510

Gly Pro Ala Glu Gly Pro Ala Glu Pro Ala Ala Glu Ala Ser Asp Glu
        515                 520                 525

Ala Glu Arg Arg Ala Arg Gly Cys His Leu Gln Tyr Gln Arg Ala Gly
    530                 535                 540

Val Arg Phe Leu Ala Pro Phe Ala Ala His Pro Leu Asp Gly Gly Arg
545                 550                 555                 560

Arg Leu Thr His Leu Leu Gly Pro Asp Trp Leu Leu Asp Val Ser His
                565                 570                 575

Leu Val Ala Pro His Ala Arg Val Leu Asp Ser Arg Val Ala Ser Leu
            580                 585                 590

Glu Gly Gly Arg Val Val Val Gly Arg Glu Pro Gly Val Thr Ser Ile
        595                 600                 605

Glu Val Arg Ser Pro Leu Ser Asp Ser Ile Leu Gly Glu Gln Ala Leu
    610                 615                 620
```

-continued

Ala Val Thr Asp Asp Lys Val Ser Val Leu Glu Leu Arg Val Gln Pro
625 630 635 640

Val Met Gly Ile Ser Leu Thr Leu Ser Arg Gly Thr Ala His Pro Gly
645 650 655

Glu Val Thr Ala Thr Cys Trp Ala Gln Ser Ala Leu Pro Ala Pro Lys
660 665 670

Gln Glu Val Ala Leu Ser Leu Trp Leu Ser Phe Ser Asp His Thr Val
675 680 685

Ala Pro Ala Glu Leu Tyr Asp Arg Arg Asp Leu Gly Leu Ser Val Ser
690 695 700

Ala Glu Glu Pro Gly Ala Ile Leu Pro Ala Glu Glu Gln Gly Ala Gln
705 710 715 720

Leu Gly Val Val Val Ser Gly Ala Gly Ala Glu Gly Leu Pro Leu His
725 730 735

Val Ala Leu His Pro Pro Glu Pro Cys Arg Arg Gly Arg His Arg Val
740 745 750

Pro Leu Ala Ser Gly Thr Ala Trp Leu Gly Leu Pro Pro Ala Ser Thr
755 760 765

Pro Ala Pro Ala Leu Pro Ser Ser Pro Ala Trp Ser Pro Pro Ala Thr
770 775 780

Glu Ala Thr Met Gly Gly Lys Arg Gln Val Ala Gly Ser Val Gly Gly
785 790 795 800

Asn Thr Gly Val Arg Gly Lys Phe Glu Arg Ala Glu Glu Glu Ala Arg
805 810 815

Lys Glu Glu Thr Glu Ala Arg Glu Glu Glu Glu Glu Glu Glu Glu Glu
820 825 830

Met Val Pro Ala Pro Gln His Val Thr Glu Leu Glu Leu Gly Met Tyr
835 840 845

Ala Leu Leu Gly Val Phe Cys Val Ala Ile Phe Ile Phe Leu Val Asn
850 855 860

Gly Val Val Phe Val Leu Arg Tyr Gln Arg Lys Glu Pro Pro Asp Ser
865 870 875 880

Ala Thr Asp Pro Thr Ser Pro Gln Pro His Asn Trp Val Trp Leu Gly
885 890 895

Thr Asp Gln Glu Glu Leu Ser Arg Gln Leu Asp Arg Gln Ser Pro Gly
900 905 910

Pro Pro Lys Gly Glu Gly Ser Cys Pro Cys Glu Ser Gly Gly Gly Gly
915 920 925

Glu Ala Pro Thr Leu Ala Pro Gly Pro Pro Gly Gly Thr Thr Ser Ser
930 935 940

Ser Ser Thr Leu Ala Arg Lys Glu Ala Gly Gly Arg Arg Lys Arg Val
945 950 955 960

Glu Phe Val Thr Phe Val Pro Ala Pro Pro Ala Gln Ser Pro Glu Glu
965 970 975

Pro Val Gly Ala Pro Ala Val Gln Ser Ile Leu Val Ala Gly Glu Glu
980 985 990

Asp Ile Arg Trp Val Cys Glu Asp Met Gly Leu Lys Asp Pro Glu Glu
995 1000 1005

Leu Arg Asn Tyr Met Glu Arg Ile Arg Gly Ser Ser
1010 1015 1020

-continued

<210> SEQ ID NO 18
<211> LENGTH: 3060
<212> TYPE: DNA
<213> ORGANISM: Homo sapiens

<400> SEQUENCE: 18
atggccggtc gcacaacagc ggcccctcgg gggccctacg gcccctggct ctgcctcctg 60
gtggccctcg ccctggacgt cgtgagagtg gactgtggcc aggctcccct ggaccctgtc 120
tacctgccgg cagccctgga gctcctagac gcccctgaac acttccgtgt gcagcaggtg 180
ggccactacc cacctgccaa ctcctctctg agctcccgat ctgagacctt tctgctccta 240
cagccctggc ccagggccca gccacttctc cgggcctcct acccaccttt tgccactcag 300
caggtggtcc cccctcgagt cactgagccc caccaacggc cagtcccatg ggacgtgcgg 360
gccgtttcag tggaagcggc tgtgactcca gcagagccct acgcccgggt tctcttccac 420
ctcaaagggc aggattggcc accagggtct ggcagcctgc cctgtgcccg gctccatgcc 480
acacaccctg caggcactgc tcaccaagcc tgccgcttcc agccatccct gggcgcctgc 540
gtggtggagc tggagcttcc ctcgcactgg ttctcacagg cctccaccac acgggccgag 600
ctggcctaca cgcttgagcc tgcagctgag ggccctgggg gctgtggctc cggcgaggag 660
aacgaccctg gggagcaggc cctcccagtg gggggtgtgg agctgcgccc agcagacccc 720
ccgcagtacc aggaggtacc tctggacgag gctgtgactc tgcgggtgcc tgacatgcca 780
gtgcggcccg gccagctctt tagtgctacc ctcctgcttc ggcacaactt cacagccagc 840
ctcctgaccc tgcggatcaa ggtgaagaag gggctgcatg tgacagccgc ccgcccagcc 900
cagcccacac tctggactgc caagctagac cgcttcaagg gctccaggca ccacaccacc 960
ctcatcacct gccaccgtgc tgggctcaca gagccagatt ccagcagtcc ccttgaactg 1020
tctgagttcc tatgggtgga ctttgtggtg gagaatagca ctggtggggg cgtagcggtc 1080
actcgccccg tcacgtggca gctggagtac ccaggccagg cccctgaagc agagaaggac 1140
aaaatggtgt gggaaatcct ggtgtctgag cgggacatca gagcccttat cccactggcc 1200
aaggctgagg agctggtgaa tacagcacca ctgactggag tgccccagca tgtccccgtg 1260
cgccttgtca ctgtggacgg cgggggggcc ttggtggagg tgacagagca tgtcggctgc 1320
gagtctgcca acacacaggt cctgcaggtg tctgaggcct gtgatgccgt gttcgtggct 1380
ggcaaggaga gccggggcgc ccgggggggtg cgagtggact tctggtggcg ccggctccgc 1440
gcctcgctgc ggctgaccgt gtgggccccg ctgctaccgc tgcgtatcga gctcaccgac 1500
accaccctcg agcaggtccg cggctggagg gtacctggcc ctgctgaagg gcctgcggaa 1560
cccgctgcag aggcgtcaga tgaggccgag cggcgcgccc gtggctgcca cctgcagtac 1620
cagcgggccg gtgtgcgctt cctcgccccc ttcgcggccc acccgctgga cggcggccgc 1680
cgcctcacgc acctgcttgg ccccgactgg ctgctagacg tgtcccacct cgtggcgcca 1740
cacgcccgcg tgctggactc gcgtgtagcc tctctggagg gtggccgtgt cgtggtgggc 1800
cgggagcccg gtgtcacctc cattgaggtg cgttccccac tgtctgactc catcctgggg 1860
gagcaggcgc tggctgtgac ggacgacaag gtctcagtgc tggagctgag ggtgcagcca 1920
gtgatgggca tctcgctgac cttgagccgg ggcactgccc accccgggga ggtcacagct 1980
acgtgctggg cacagtcagc ccttcccgcc ccaaagcagg aggtggccct ctccctatgg 2040
ctgtccttct ctgatcacac tgtggcccca gctgagctct acgaccgccg tgacctggga 2100
ctgtccgtct cagccgagga gcctggtgcc atcctgccag ctgaggagca gggtgcccag 2160

-continued

```
ctcggggtgg tggtgagtgg ggcaggcgcc gaggggctgc cgctgcatgt ggctctgcac   2220

ccgcccgagc cctgccgccg gggccgccac cgtgtgcctc tggcctctgg caccgcctgg   2280

ctggggctgc cccctgcctc cactccagcc cctgctctcc catccagccc tgcttggagc   2340

ccaccagcca cagaagccac catgggtggt aaacggcagg tggcaggcag tgtcgggggc   2400

aacacaggtg tgaggggcaa gtttgagcgg gcagaggagg aggccaggaa ggaggagacc   2460

gaagccaggg aggaggagga ggaagaggag gaggagatgg tccctgcccc tcagcatgtc   2520

actgagctag agctgggcat gtacgccctg ctgggagtct tctgcgtggc catcttcatc   2580

ttcttggtca atggtgtggt cttcgtcctg cgctatcagc gcaaagaacc tcccgacagt   2640

gccactgacc ccacctcccc ccagccccac aactgggtct ggctgggcac tgaccaggag   2700

gaactgagcc gccagctgga ccggcagtcc cctggcccgc ccaaggggga ggggagctgc   2760

ccctgtgaga gtgggggagg aggggaggcc cctaccctgg cccctggccc tcctgggggc   2820

accaccagct cctcaagcac cctggcccga aaggaggctg gggggcggcg gaagcgagta   2880

gagtttgtga catttgtgcc agcccctcca gcccagtcac ctgaggagcc tgtaggggcc   2940

cctgctgtgc agtccatcct tgtggcaggc gaggaggaca tccgctgggt gtgtgaggac   3000

atggggctga aggaccctga ggagcttcgc aactacatgg agaggatccg gggcagctcc   3060
```

<210> SEQ ID NO 19
<211> LENGTH: 3505
<212> TYPE: DNA
<213> ORGANISM: Homo sapiens

<400> SEQUENCE: 19

```
attgtctggg aattgcagcc gcggggcggg cggcggcggc ggcggcggcg gccgggaccc     60

agcgggccag gtggggacgg cgcggagcgg gtgcgggaga tgccgtgcgg gactggggcc    120

acctgagccg cccgcctcgt ccccgccttc tgtgggaagg atgtgcgcgc ggatggccgg    180

tcgcacaaca gcggcccctc gggggcccta cggcccctgg ctctgcctcc tggtggccct    240

cgccctggac gtcgtgagag tggactgtgg ccaggctccc ctggaccctg tctacctgcc    300

ggcagccctg gagctcctag acgcccctga acacttccgt gtgcagcagg tgggccacta    360

cccacctgcc aactcctctc tgagctcccg atctgagacc tttctgctcc tacagccctg    420

gcccagggcc cagccacttc tccgggcctc ctacccacct tttgccactc agcaggtggt    480

ccccccctcga gtcactgagc cccaccaacg gccagtccca tgggacgtgc gggccgtttc    540

agtggaagcg gctgtgactc cagcagagcc ctacgcccgg gttctcttcc acctcaaagg    600

gcaggattgg ccaccagggt ctggcagcct gccctgtgcc cggctccatg ccacacaccc    660

tgcaggcact gctcaccaag cctgccgctt ccagccatcc ctgggcgcct gcgtggtgga    720

gctggagctt ccctcgcact ggttctcaca ggcctccacc acacgggccg agctggccta    780

cacgcttgag cctgcagctg agggccctgg gggctgtggc tccggcgagg agaacgaccc    840

tggggagcag gccctcccag tggggggtgt ggagctgcgc ccagcagacc ccccgcagta    900

ccaggaggta cctctggacg aggctgtgac tctgcgggtg cctgacatgc cagtgcggcc    960

cggccagctc tttagtgcta ccctcctgct tcggcacaac ttcacagcca gcctcctgac   1020

cctgcggatc aaggtgaaga aggggctgca tgtgacagcc gcccgcccag cccagcccac   1080

actctggact gccaagctag accgcttcaa gggctccagg caccacacca ccctcatcac   1140

ctgccaccgt gctgggctca cagagccaga ttccagcagt cccccttgaac tgtctgagtt   1200
```

-continued

```
cctatgggtg gactttgtgg tggagaatag cactggtggg ggcgtagcgg tcactcgccc   1260
cgtcacgtgg cagctggagt acccaggcca ggcccctgaa gcagagaagg acaaaatggt   1320
gtgggaaatc ctggtgtctg agcgggacat cagagccctt atcccactgg ccaaggctga   1380
ggagctggtg aatacagcac cactgactgg agtgccccag catgtccccg tgcgccttgt   1440
cactgtggac ggcggggggg ccttggtgga ggtgacagag catgtcggct gcgagtctgc   1500
caacacacag gtcctgcagg tgtctgaggc ctgtgatgcc gtgttcgtgg ctggcaagga   1560
gagccggggc gcccgggggg tgcgagtgga cttctggtgg cgccggctcc gcgcctcgct   1620
gcggctgacc gtgtgggccc cgctgctacc gctgcgtatc gagctcaccg acaccaccct   1680
cgagcaggtc cgcggctgga gggtacctgg ccctgctgaa gggcctgcgg aacccgctgc   1740
agaggcgtca gatgaggccg agcggcgcgc ccgtggctgc cacctgcagt accagcgggc   1800
cggtgtgcgc ttcctcgccc ccttcgcggc ccacccgctg gacggcggcc gccgcctcac   1860
gcacctgctt ggccccgact ggctgctaga cgtgtcccac ctcgtggcgc cacacgcccg   1920
cgtgctggac tcgcgtgtag cctctctgga gggtggccgt gtcgtggtgg gccgggagcc   1980
cggtgtcacc tccattgagg tgcgttcccc actgtctgac tccatcctgg gggagcaggc   2040
gctggctgtg acggacgaca aggtctcagt gctggagctg agggtgcagc cagtgatggg   2100
catctcgctg accttgagcc ggggcactgc ccaccccggg gaggtcacag ctacgtgctg   2160
ggcacagtca gcccttcccg ccccaaagca ggaggtggcc ctctccctat ggctgtcctt   2220
ctctgatcac actgtggccc cagctgagct ctacgaccgc cgtgacctgg gactgtccgt   2280
ctcagccgag gagcctggtg ccatcctgcc agctgaggag cagggtgccc agctcggggt   2340
ggtggtgagt ggggcaggcg ccgaggggct gccgctgcat gtggctctgc acccgcccga   2400
gccctgccgc cggggccgcc accgtgtgcc tctggcctct ggcaccgcct ggctggggct   2460
gccccctgcc tccactccag cccctgctct cccatccagc cctgcttgga gcccaccagc   2520
cacagaagcc accatgggtg gtaaacggca ggtggcaggc agtgtcgggg gcaacacagg   2580
tgtgaggggc aagtttgagc gggcagagga ggaggccagg aaggaggaga ccgaagccag   2640
ggaggaggag gaggaagagg aggaggagat ggtccctgcc cctcagcatg tcactgagct   2700
agagctgggc atgtacgccc tgctgggagt cttctgcgtg gccatcttca tcttcttggt   2760
caatggtgtg gtcttcgtcc tgcgctatca gcgcaaagaa cctcccgaca gtgccactga   2820
ccccacctcc ccccagcccc acaactgggt ctggctgggc actgaccagg aggaactgag   2880
ccgccagctg gaccggcagt cccctggccc gcccaagggg gaggggagct gcccctgtga   2940
gagtggggga ggaggggagg cccctaccct ggcccctggc cctcctgggg gcaccaccag   3000
ctcctcaagc accctggccc gaaaggaggc tgggggggcgg cggaagcgag tagagtttgt   3060
gacatttgtg ccagcccctc cagcccagtc acctgaggag cctgtagggg cccctgctgt   3120
gcagtccatc cttgtggcag gcgaggagga catccgctgg gtgtgtgagg acatggggct   3180
gaaggaccct gaggagcttc gcaactacat ggagaggatc cggggcagct cctgaccctc   3240
cacagccacc tggtcagcca ccagctgggg caacgagggt ggaggtccca ctgagcctct   3300
cgcctgcccc cgccactcgt ctggtgcttg ttgatccaag tcccctgcct ggtcccccac   3360
aaggactccc atccaggccc cctctgccct gccccttgtc atggaccatg gtcgtgagga   3420
agggctcatg ccccttattt atgggaacca tctcattcta acagaataaa ccgagaagga   3480
aaccagaaaa aaaaaaaaaa aaaaa                                         3505
```

-continued

<210> SEQ ID NO 20
<211> LENGTH: 1023
<212> TYPE: PRT
<213> ORGANISM: Homo sapiens

<400> SEQUENCE: 20

```
Met Cys Ala Arg Met Ala Gly Arg Thr Thr Ala Ala Pro Arg Gly Pro
                5                   10                  15

Tyr Gly Pro Trp Leu Cys Leu Leu Val Ala Leu Ala Leu Asp Val Val
            20                  25                  30

Arg Val Asp Cys Gly Gln Ala Pro Leu Asp Pro Val Tyr Leu Pro Ala
        35                  40                  45

Ala Leu Glu Leu Leu Asp Ala Pro Glu His Phe Arg Val Gln Gln Val
    50                  55                  60

Gly His Tyr Pro Pro Ala Asn Ser Ser Leu Ser Ser Arg Ser Glu Thr
65                  70                  75                  80

Phe Leu Leu Leu Gln Pro Trp Pro Arg Ala Gln Pro Leu Leu Arg Ala
                85                  90                  95

Ser Tyr Pro Pro Phe Ala Thr Gln Gln Val Val Pro Pro Arg Val Thr
            100                 105                 110

Glu Pro His Gln Arg Pro Val Pro Trp Asp Val Arg Ala Val Ser Val
        115                 120                 125

Glu Ala Ala Val Thr Pro Ala Glu Pro Tyr Ala Arg Val Leu Phe His
    130                 135                 140

Leu Lys Gly Gln Asp Trp Pro Pro Gly Ser Gly Ser Leu Pro Cys Ala
145                 150                 155                 160

Arg Leu His Ala Thr His Pro Ala Gly Thr Ala His Gln Ala Cys Arg
                165                 170                 175

Phe Gln Pro Ser Leu Gly Ala Cys Val Val Glu Leu Glu Leu Pro Ser
            180                 185                 190

His Trp Phe Ser Gln Ala Ser Thr Thr Arg Ala Glu Leu Ala Tyr Thr
        195                 200                 205

Leu Glu Pro Ala Ala Glu Gly Pro Gly Gly Cys Gly Ser Gly Glu Glu
    210                 215                 220

Asn Asp Pro Gly Glu Gln Ala Leu Pro Val Gly Gly Val Glu Leu Arg
225                 230                 235                 240

Pro Ala Asp Pro Pro Gln Tyr Gln Glu Val Pro Leu Asp Glu Ala Val
                245                 250                 255

Thr Leu Arg Val Pro Asp Met Pro Val Arg Pro Gly Gln Leu Phe Ser
            260                 265                 270

Ala Thr Leu Leu Leu Gln His Asn Phe Thr Ala Ser Leu Leu Thr Leu
        275                 280                 285

Arg Ile Lys Val Lys Lys Gly Leu His Val Thr Ala Ala Arg Pro Ala
    290                 295                 300

Gln Pro Thr Leu Trp Thr Ala Lys Leu Asp Arg Phe Lys Gly Ser Arg
305                 310                 315                 320

His His Thr Thr Leu Ile Thr Cys His Arg Ala Gly Leu Thr Glu Pro
                325                 330                 335

Asp Ser Ser Pro Leu Glu Leu Ser Glu Phe Leu Trp Val Asp Phe Val
            340                 345                 350

Val Glu Asn Ser Thr Gly Gly Gly Val Ala Val Thr Arg Pro Val Thr
        355                 360                 365

Trp Gln Leu Glu Tyr Pro Gly Gln Ala Pro Glu Ala Glu Lys Asp Lys
    370                 375                 380
```

-continued

```
Met Val Trp Glu Ile Leu Val Ser Glu Arg Asp Ile Arg Ala Leu Ile
385                 390                 395                 400

Pro Leu Ala Lys Ala Glu Glu Leu Val Asn Thr Ala Pro Leu Thr Gly
                405                 410                 415

Val Pro Gln His Val Pro Val Arg Leu Val Thr Val Asp Gly Gly Gly
            420                 425                 430

Ala Leu Val Glu Val Thr Glu His Val Gly Cys Glu Ser Ala Asn Thr
        435                 440                 445

Gln Val Leu Gln Val Ser Glu Ala Cys Asp Ala Val Phe Val Ala Gly
    450                 455                 460

Lys Glu Ser Arg Gly Ala Arg Gly Val Arg Val Asp Phe Trp Trp Arg
465                 470                 475                 480

Arg Leu Arg Ala Ser Leu Arg Leu Thr Val Trp Ala Pro Leu Leu Pro
                485                 490                 495

Leu Arg Ile Glu Leu Thr Asp Thr Thr Leu Glu Gln Val Arg Gly Trp
            500                 505                 510

Arg Val Pro Gly Pro Ala Glu Gly Pro Ala Glu Pro Ala Ala Glu Ala
        515                 520                 525

Ser Asp Glu Ala Glu Arg Arg Ala Arg Gly Cys His Leu Gln Tyr Gln
    530                 535                 540

Arg Ala Gly Val Arg Phe Leu Ala Pro Phe Ala Ala His Pro Leu Asp
545                 550                 555                 560

Gly Gly Arg Arg Leu Thr His Leu Leu Gly Pro Asp Trp Leu Leu Asp
                565                 570                 575

Val Ser His Leu Val Ala Pro His Ala Arg Val Leu Asp Ser Arg Val
            580                 585                 590

Ala Ser Leu Glu Gly Gly Arg Val Val Val Gly Arg Glu Pro Gly Val
        595                 600                 605

Thr Ser Ile Glu Val Arg Ser Pro Leu Ser Asp Ser Ile Leu Gly Glu
    610                 615                 620

Gln Ala Leu Ala Val Thr Asp Asp Lys Val Ser Val Leu Glu Leu Arg
625                 630                 635                 640

Val Gln Pro Val Met Gly Ile Ser Leu Thr Leu Ser Arg Gly Thr Ala
                645                 650                 655

His Pro Gly Glu Val Thr Ala Thr Cys Trp Ala Gln Ser Ala Leu Pro
            660                 665                 670

Ala Pro Lys Gln Glu Val Ala Leu Ser Leu Trp Leu Ser Phe Ser Asp
        675                 680                 685

His Thr Val Ala Pro Ala Glu Leu Tyr Asp Arg Arg Asp Leu Gly Leu
    690                 695                 700

Ser Val Ser Ala Glu Glu Pro Gly Ala Ile Leu Pro Ala Glu Glu Gln
705                 710                 715                 720

Gly Ala Gln Leu Gly Val Val Val Ser Gly Ala Gly Ala Glu Gly Leu
                725                 730                 735

Pro Leu His Val Ala Leu His Pro Pro Glu Pro Cys Arg Arg Gly Arg
            740                 745                 750

His Arg Val Pro Leu Ala Ser Gly Thr Ala Trp Leu Gly Leu Pro Pro
        755                 760                 765

Ala Ser Thr Pro Ala Pro Ala Leu Pro Ser Ser Pro Ala Trp Ser Pro
    770                 775                 780

Pro Ala Thr Glu Ala Thr Met Gly Gly Lys Arg Gln Val Ala Gly Ser
785                 790                 795                 800
```

-continued

```
Val Gly Gly Asn Thr Gly Val Arg Gly Lys Phe Glu Arg Ala Glu Glu
                805                 810                 815

Glu Ala Arg Lys Glu Glu Thr Lys Pro Arg Glu Glu Glu Glu Glu Glu
            820                 825                 830

Glu Glu Glu Met Val Pro Ala Pro Gln His Val Thr Glu Leu Glu Leu
        835                 840                 845

Gly Met Tyr Ala Leu Leu Gly Val Phe Cys Val Ala Ile Phe Ile Phe
    850                 855                 860

Leu Val Asn Gly Val Val Phe Val Leu Arg Tyr Gln Arg Lys Glu Pro
865                 870                 875                 880

Pro Asp Ser Ala Thr Asp Pro Thr Ser Pro Gln Pro His Asn Trp Val
                885                 890                 895

Trp Leu Gly Thr Asp Gln Glu Glu Leu Ser Arg Gln Leu Asp Arg Gln
            900                 905                 910

Ser Pro Gly Pro Pro Lys Gly Glu Gly Ser Cys Pro Cys Glu Ser Gly
        915                 920                 925

Gly Gly Gly Glu Ala Pro Thr Leu Ala Pro Gly Pro Pro Gly Gly Thr
    930                 935                 940

Thr Ser Ser Ser Ser Thr Leu Ala Arg Lys Glu Ala Gly Gly Arg Arg
945                 950                 955                 960

Lys Arg Val Glu Phe Val Thr Phe Ala Pro Ala Pro Pro Ala Gln Ser
                965                 970                 975

Pro Glu Glu Pro Val Gly Ala Pro Ala Val Gln Ser Ile Leu Val Ala
            980                 985                 990

Gly Glu Glu Asp Ile Arg Trp Val Cys Glu Asp Met Gly Leu Lys Asp
        995                 1000                1005

Pro Glu Glu Leu Arg Asn Tyr Met Glu Arg Ile Arg Gly Ser Ser
   1010                1015                1020


<210> SEQ ID NO 21
<211> LENGTH: 3069
<212> TYPE: DNA
<213> ORGANISM: Homo sapiens

<400> SEQUENCE: 21

atgtgcgcgc ggatggccgg tcgcacaaca gcggcccctc gggggcccta cggcccctgg      60

ctctgcctcc tggtggccct cgccctggac gtcgtgagag tggactgtgg ccaggctccc     120

ctggaccctg tctacctgcc ggcagccctg gagctcctag acgcccctga acacttccgt     180

gtgcagcagg tgggccacta cccacctgcc aactcctctc tgagctcccg atctgagacc     240

tttctgctcc tacagccctg gcccagggcc cagccacttc tccgggcctc ctacccacct     300

tttgccactc agcaggtggt cccccctcga gtcactgagc cccaccaacg gccagtccca     360

tgggacgtgc gggccgtttc agtggaagcg gctgtgactc cagcagagcc ctacgcccgg     420

gttctcttcc acctcaaagg gcaggattgg ccaccagggt ctggcagcct gccctgtgcc     480

cggctccatg ccacacaccc tgcaggcact gctcaccaag cctgccgctt ccagccatcc     540

ctgggcgcct gcgtggtgga gctggagctt ccctcgcact ggttctcaca ggcctccacc     600

acacgggccg agctggccta cacgcttgag cctgcagctg agggccctgg gggctgtggc     660

tccggcgagg agaacgaccc tggggagcag gccctcccag tgggggtgt ggagctgcgc      720

ccagcagacc ccccgcagta ccaggaggta cctctggacg aggctgtgac tctgcgggtg     780

cctgacatgc cagtgcggcc cggccagctc tttagtgcta ccctcctgct tcagcacaac     840

ttcacagcca gcctcctgac cctgcggatc aaggtgaaga aggggctgca tgtgacagcc     900
```

-continued

```
gcccgcccag cccagcccac actctggact gccaagctag accgcttcaa gggctccagg    960

caccacacca ccctcatcac ctgccaccgt gctgggctca cagagccaga ttccagtccc   1020

cttgaactgt ctgagttcct atgggtggac tttgtggtgg agaatagcac tggtgggggc   1080

gtagcggtca ctcgccccgt cacgtggcag ctggagtacc caggccaggc ccctgaagca   1140

gagaaggaca aaatggtgtg ggaaatcctg gtgtctgagc gggacatcag agcccttatc   1200

ccactggcca aggctgagga gctggtgaat acagcaccac tgactggagt gccccagcat   1260

gtccccgtgc gccttgtcac tgtggacggc ggggggcct tggtggaggt gacagagcat   1320

gtcggctgcg agtctgccaa cacacaggtc ctgcaggtgt ctgaggcctg tgatgccgtg   1380

ttcgtggctg gcaaggagag ccggggcgcc cgggggtgc gagtggactt ctggtggcgc   1440

cggctccgcg cctcgctgcg gctgaccgtg tgggcccccc tgctaccgct gcgtatcgag   1500

ctcaccgaca ccaccctcga gcaggtccgc ggctggaggg tacctggccc tgctgaaggg   1560

cctgcggaac ccgctgcaga ggcgtcggat gaggccgagc ggcgcgcccg tggctgccac   1620

ctgcagtacc agcgggccgg tgtgcgcttc ctcgcccct tcgcggccca cccgctggac   1680

ggcggccgcc gcctcacgca cctgcttggc cccgactggc tgctagacgt gtcccacctc   1740

gtggcgccac acgcccgcgt gctggactcg cgtgtagcct ctctggaggg tggccgtgtc   1800

gtggtgggcc gggagcccgg tgtcacctcc attgaggtgc gttccccact gtctgactcc   1860

atcctggggg agcaggcgct ggctgtgacg gacgacaagg tctcagtgct ggagctgagg   1920

gtgcagccag tgatgggcat ctcgctgacc ttgagccggg gcactgccca ccccggggag   1980

gtcacagcta cgtgctgggc acagtcagcc cttcccgccc caaagcagga ggtggccctc   2040

tccctatggc tgtccttctc tgatcacact gtggccccag ctgagctcta cgaccgccgt   2100

gacctgggac tgtccgtctc agccgaggag cctggtgcca tcctgccagc tgaggagcag   2160

ggtgcccagc tcggggtggt ggtgagtggg gcaggcgccg aggggctgcc gctgcatgtg   2220

gctctgcacc cgcccgagcc ctgccgccgg ggccgccacc gtgtgcctct ggcctctggc   2280

accgcctggc tggggctgcc ccctgcctcc actccagccc ctgctctccc atccagccct   2340

gcttggagcc caccagccac agaagccacc atgggtggta aacggcaggt ggcaggcagt   2400

gtcgggggca acacaggtgt gaggggcaag tttgagcggg cagaggagga ggccaggaag   2460

gaggagacca aacccaggga ggaggaggag gaagaggagg aggagatggt ccctgcccct   2520

cagcatgtca ctgagctaga gctgggcatg tacgccctgc tgggagtctt ctgcgtggcc   2580

atcttcatct tcttggtcaa tggtgtggtc ttcgtcctgc gctatcagcg caaagaacct   2640

cccgacagtg ccactgaccc cacctccccc cagccccaca actgggtctg gctgggcact   2700

gaccaggagg aactgagccg ccagctggac cggcagtccc ctggcccgcc caagggggag   2760

gggagctgcc cctgtgagag tgggggagga ggggaggccc ctaccctggc ccctggccct   2820

cctgggggca ccaccagctc ctcaagcacc ctggcccgaa aggaggctgg ggggcggcgg   2880

aagcgagtag agtttgtgac atttgcgcca gcccctccag cccagtcacc tgaggagcct   2940

gtaggggccc ctgctgtgca gtccatcctt gtggcaggcg aggaggacat ccgctgggtg   3000

tgtgaggaca tggggctgaa ggaccctgag gagcttcgca actacatgga gaggatccgg   3060

ggcagctcc                                                           3069
```

<210> SEQ ID NO 22
<211> LENGTH: 1019
<212> TYPE: PRT
<213> ORGANISM: Homo sapiens -continued

<400> SEQUENCE: 22

```
Met Ala Gly Arg Thr Thr Ala Ala Pro Arg Gly Pro Tyr Gly Pro Trp
                5                   10                  15

Leu Cys Leu Leu Val Ala Leu Ala Leu Asp Val Val Arg Val Asp Cys
            20                  25                  30

Gly Gln Ala Pro Leu Asp Pro Val Tyr Leu Pro Ala Ala Leu Glu Leu
        35                  40                  45

Leu Asp Ala Pro Glu His Phe Arg Val Gln Gln Val Gly His Tyr Pro
    50                  55                  60

Pro Ala Asn Ser Ser Leu Ser Ser Arg Ser Glu Thr Phe Leu Leu Leu
65                  70                  75                  80

Gln Pro Trp Pro Arg Ala Gln Pro Leu Leu Arg Ala Ser Tyr Pro Pro
                85                  90                  95

Phe Ala Thr Gln Gln Val Val Pro Pro Arg Val Thr Glu Pro His Gln
            100                 105                 110

Arg Pro Val Pro Trp Asp Val Arg Ala Val Ser Val Glu Ala Ala Val
        115                 120                 125

Thr Pro Ala Glu Pro Tyr Ala Arg Val Leu Phe His Leu Lys Gly Gln
    130                 135                 140

Asp Trp Pro Pro Gly Ser Gly Ser Leu Pro Cys Ala Arg Leu His Ala
145                 150                 155                 160

Thr His Pro Ala Gly Thr Ala His Gln Ala Cys Arg Phe Gln Pro Ser
                165                 170                 175

Leu Gly Ala Cys Val Val Glu Leu Glu Leu Pro Ser His Trp Phe Ser
            180                 185                 190

Gln Ala Ser Thr Thr Arg Ala Glu Leu Ala Tyr Thr Leu Glu Pro Ala
        195                 200                 205

Ala Glu Gly Pro Gly Gly Cys Gly Ser Gly Glu Glu Asn Asp Pro Gly
    210                 215                 220

Glu Gln Ala Leu Pro Val Gly Gly Val Glu Leu Arg Pro Ala Asp Pro
225                 230                 235                 240

Pro Gln Tyr Gln Glu Val Pro Leu Asp Glu Ala Val Thr Leu Arg Val
                245                 250                 255

Pro Asp Met Pro Val Arg Pro Gly Gln Leu Phe Ser Ala Thr Leu Leu
            260                 265                 270

Leu Gln His Asn Phe Thr Ala Ser Leu Leu Thr Leu Arg Ile Lys Val
        275                 280                 285

Lys Lys Gly Leu His Val Thr Ala Ala Arg Pro Ala Gln Pro Thr Leu
    290                 295                 300

Trp Thr Ala Lys Leu Asp Arg Phe Lys Gly Ser Arg His His Thr Thr
305                 310                 315                 320

Leu Ile Thr Cys His Arg Ala Gly Leu Thr Glu Pro Asp Ser Ser Pro
                325                 330                 335

Leu Glu Leu Ser Glu Phe Leu Trp Val Asp Phe Val Val Glu Asn Ser
            340                 345                 350

Thr Gly Gly Gly Val Ala Val Thr Arg Pro Val Thr Trp Gln Leu Glu
        355                 360                 365

Tyr Pro Gly Gln Ala Pro Glu Ala Glu Lys Asp Lys Met Val Trp Glu
    370                 375                 380

Ile Leu Val Ser Glu Arg Asp Ile Arg Ala Leu Ile Pro Leu Ala Lys
385                 390                 395                 400

Ala Glu Glu Leu Val Asn Thr Ala Pro Leu Thr Gly Val Pro Gln His
                405                 410                 415
```

-continued

```
Val Pro Val Arg Leu Val Thr Val Asp Gly Gly Gly Ala Leu Val Glu
            420                 425                 430

Val Thr Glu His Val Gly Cys Glu Ser Ala Asn Thr Gln Val Leu Gln
        435                 440                 445

Val Ser Glu Ala Cys Asp Ala Val Phe Val Ala Gly Lys Glu Ser Arg
    450                 455                 460

Gly Ala Arg Gly Val Arg Val Asp Phe Trp Trp Arg Arg Leu Arg Ala
465                 470                 475                 480

Ser Leu Arg Leu Thr Val Trp Ala Pro Leu Leu Pro Leu Arg Ile Glu
                485                 490                 495

Leu Thr Asp Thr Thr Leu Glu Gln Val Arg Gly Trp Arg Val Pro Gly
            500                 505                 510

Pro Ala Glu Gly Pro Ala Glu Pro Ala Ala Glu Ala Ser Asp Glu Ala
        515                 520                 525

Glu Arg Arg Ala Arg Gly Cys His Leu Gln Tyr Gln Arg Ala Gly Val
    530                 535                 540

Arg Phe Leu Ala Pro Phe Ala Ala His Pro Leu Asp Gly Gly Arg Arg
545                 550                 555                 560

Leu Thr His Leu Leu Gly Pro Asp Trp Leu Leu Asp Val Ser His Leu
                565                 570                 575

Val Ala Pro His Ala Arg Val Leu Asp Ser Arg Val Ala Ser Leu Glu
            580                 585                 590

Gly Gly Arg Val Val Val Gly Arg Glu Pro Gly Val Thr Ser Ile Glu
        595                 600                 605

Val Arg Ser Pro Leu Ser Asp Ser Ile Leu Gly Glu Gln Ala Leu Ala
    610                 615                 620

Val Thr Asp Asp Lys Val Ser Val Leu Glu Leu Arg Val Gln Pro Val
625                 630                 635                 640

Met Gly Ile Ser Leu Thr Leu Ser Arg Gly Thr Ala His Pro Gly Glu
                645                 650                 655

Val Thr Ala Thr Cys Trp Ala Gln Ser Ala Leu Pro Ala Pro Lys Gln
            660                 665                 670

Glu Val Ala Leu Ser Leu Trp Leu Ser Phe Ser Asp His Thr Val Ala
        675                 680                 685

Pro Ala Glu Leu Tyr Asp Arg Arg Asp Leu Gly Leu Ser Val Ser Ala
    690                 695                 700

Glu Glu Pro Gly Ala Ile Leu Pro Ala Glu Glu Gln Gly Ala Gln Leu
705                 710                 715                 720

Gly Val Val Val Ser Gly Ala Gly Ala Glu Gly Leu Pro Leu His Val
                725                 730                 735

Ala Leu His Pro Pro Glu Pro Cys Arg Arg Gly Arg His Arg Val Pro
            740                 745                 750

Leu Ala Ser Gly Thr Ala Trp Leu Gly Leu Pro Pro Ala Ser Thr Pro
        755                 760                 765

Ala Pro Ala Leu Pro Ser Ser Pro Ala Trp Ser Pro Pro Ala Thr Glu
    770                 775                 780

Ala Thr Met Gly Gly Lys Arg Gln Val Ala Gly Ser Val Gly Gly Asn
785                 790                 795                 800

Thr Gly Val Arg Gly Lys Phe Glu Arg Ala Glu Glu Glu Ala Arg Lys
                805                 810                 815

Glu Glu Thr Lys Pro Arg Glu Glu Glu Glu Glu Glu Glu Glu Glu Met
            820                 825                 830
```

-continued

```
Val Pro Ala Pro Gln His Val Thr Glu Leu Glu Leu Gly Met Tyr Ala
        835                 840                 845

Leu Leu Gly Val Phe Cys Val Ala Ile Phe Ile Phe Leu Val Asn Gly
    850                 855                 860

Val Val Phe Val Leu Arg Tyr Gln Arg Lys Glu Pro Pro Asp Ser Ala
865                 870                 875                 880

Thr Asp Pro Thr Ser Pro Gln Pro His Asn Trp Val Trp Leu Gly Thr
                885                 890                 895

Asp Gln Glu Glu Leu Ser Arg Gln Leu Asp Arg Gln Ser Pro Gly Pro
            900                 905                 910

Pro Lys Gly Glu Gly Ser Cys Pro Cys Glu Ser Gly Gly Gly Gly Glu
        915                 920                 925

Ala Pro Thr Leu Ala Pro Gly Pro Pro Gly Gly Thr Thr Ser Ser Ser
    930                 935                 940

Ser Thr Leu Ala Arg Lys Glu Ala Gly Gly Arg Arg Lys Arg Val Glu
945                 950                 955                 960

Phe Val Thr Phe Ala Pro Ala Pro Pro Ala Gln Ser Pro Glu Glu Pro
                965                 970                 975

Val Gly Ala Pro Ala Val Gln Ser Ile Leu Val Ala Gly Glu Glu Asp
            980                 985                 990

Ile Arg Trp Val Cys Glu Asp Met Gly Leu Lys Asp Pro Glu Glu Leu
        995                1000                1005

Arg Asn Tyr Met Glu Arg Ile Arg Gly Ser Ser
   1010                1015


<210> SEQ ID NO 23
<211> LENGTH: 3057
<212> TYPE: DNA
<213> ORGANISM: Homo sapiens

<400> SEQUENCE: 23

atggccggtc gcacaacagc ggcccctcgg gggccctacg gcccctggct ctgcctcctg      60

gtggccctcg ccctggacgt cgtgagagtg gactgtggcc aggctcccct ggaccctgtc     120

tacctgccgg cagccctgga gctcctagac gcccctgaac acttccgtgt gcagcaggtg     180

ggccactacc cacctgccaa ctcctctctg agctcccgat ctgagacctt tctgctccta     240

cagccctggc ccagggccca gccacttctc cgggcctcct acccaccttt tgccactcag     300

caggtggtcc cccctcgagt cactgagccc caccaacggc cagtcccatg ggacgtgcgg     360

gccgtttcag tggaagcggc tgtgactcca gcagagccct acgcccgggt tctcttccac     420

ctcaaagggc aggattggcc accagggtct ggcagcctgc cctgtgcccg gctccatgcc     480

acacaccctg caggcactgc tcaccaagcc tgccgcttcc agccatccct gggcgcctgc     540

gtggtggagc tggagcttcc ctcgcactgg ttctcacagg cctccaccac acgggccgag     600

ctggcctaca cgcttgagcc tgcagctgag ggccctgggg gctgtggctc cggcgaggag     660

aacgaccctg gggagcaggc cctcccagtg gggggtgtgg agctgcgccc agcagacccc     720

ccgcagtacc aggaggtacc tctggacgag gctgtgactc tgcgggtgcc tgacatgcca     780

gtgcggcccg gccagctctt tagtgctacc ctcctgcttc agcacaactt cacagccagc     840

ctcctgaccc tgcggatcaa ggtgaagaag gggctgcatg tgacagccgc ccgcccagcc     900

cagcccacac tctggactgc caagctagac cgcttcaagg gctccaggca ccacaccacc     960

ctcatcacct gccaccgtgc tgggctcaca gagccagatt ccagtcccct tgaactgtct    1020

gagttcctat gggtggactt tgtggtggag aatagcactg gtgggggcgt agcggtcact    1080
```

-continued

```
cgccccgtca cgtggcagct ggagtaccca ggccaggccc ctgaagcaga gaaggacaaa   1140

atggtgtggg aaatcctggt gtctgagcgg gacatcagag cccttatccc actggccaag   1200

gctgaggagc tggtgaatac agcaccactg actggagtgc cccagcatgt ccccgtgcgc   1260

cttgtcactg tggacggcgg gggggccttg gtggaggtga cagagcatgt cggctgcgag   1320

tctgccaaca cacaggtcct gcaggtgtct gaggcctgtg atgccgtgtt cgtggctggc   1380

aaggagagcc ggggcgcccg gggggtgcga gtggacttct ggtggcgccg gctccgcgcc   1440

tcgctgcggc tgaccgtgtg ggccccccctg ctaccgctgc gtatcgagct caccgacacc  1500

accctcgagc aggtccgcgg ctggagggta cctggccctg ctgaagggcc tgcggaaccc   1560

gctgcagagg cgtcggatga ggccgagcgg cgcgcccgtg gctgccacct gcagtaccag   1620

cgggccggtg tgcgcttcct cgcccccttc gcggcccacc cgctggacgg cggccgccgc   1680

ctcacgcacc tgcttggccc cgactggctg ctagacgtgt cccacctcgt ggcgccacac   1740

gcccgcgtgc tggactcgcg tgtagcctct ctggagggtg gccgtgtcgt ggtgggccgg   1800

gagcccggtg tcacctccat tgaggtgcgt tccccactgt ctgactccat cctgggggag   1860

caggcgctgg ctgtgacgga cgacaaggtc tcagtgctgg agctgagggt gcagccagtg   1920

atgggcatct cgctgacctt gagccggggc actgcccacc ccggggaggt cacagctacg   1980

tgctgggcac agtcagccct tcccgcccca aagcaggagg tggccctctc cctatggctg   2040

tccttctctg atcacactgt ggccccagct gagctctacg accgccgtga cctgggactg   2100

tccgtctcag ccgaggagcc tggtgccatc ctgccagctg aggagcaggg tgcccagctc   2160

ggggtggtgg tgagtggggc aggcgccgag gggctgccgc tgcatgtggc tctgcacccg   2220

cccgagccct gccgccgggg ccgccaccgt gtgcctctgg cctctggcac cgcctggctg   2280

gggctgcccc ctgcctccac tccagcccct gctctcccat ccagccctgc ttggagccca   2340

ccagccacag aagccaccat gggtggtaaa cggcaggtgg caggcagtgt cgggggcaac   2400

acaggtgtga ggggcaagtt tgagcgggca gaggaggagg ccaggaagga ggagaccaaa   2460

cccagggagg aggaggagga agaggaggag gagatggtcc ctgcccctca gcatgtcact   2520

gagctagagc tgggcatgta cgccctgctg ggagtcttct gcgtggccat cttcatcttc   2580

ttggtcaatg gtgtggtctt cgtcctgcgc tatcagcgca aagaacctcc cgacagtgcc   2640

actgacccca cctcccccca gccccacaac tgggtctggc tgggcactga ccaggaggaa   2700

ctgagccgcc agctggaccg gcagtcccct ggcccgccca agggggaggg gagctgcccc   2760

tgtgagagtg ggggaggagg ggaggcccct accctggccc ctggccctcc tgggggcacc   2820

accagctcct caagcaccct ggcccgaaag gaggctgggg ggcggcggaa gcgagtagag   2880

tttgtgacat ttgcgccagc ccctccagcc cagtcacctg aggagcctgt aggggcccct   2940

gctgtgcagt ccatccttgt ggcaggcgag gaggacatcc gctgggtgtg tgaggacatg   3000

gggctgaagg accctgagga gcttcgcaac tacatggaga ggatccgggg cagctcc      3057
```

<210> SEQ ID NO 24
<211> LENGTH: 3502
<212> TYPE: DNA
<213> ORGANISM: Homo sapiens

<400> SEQUENCE: 24

```
attgtctggg aattgcagcc gcggggcggg cggcggcggc ggcggcggcg gccgggaccc     60

agcgggccag gtggggacgg cgcggagcgg gtgcgggaga tgccgtgcgg gactggggcc    120

acctgagccg cccgcctcgt ccccgccttc tgtgggaagg atgtgcgcgc ggatggccgg    180
```

-continued

```
tcgcacaaca gcggcccctc gggggcccta cggcccctgg ctctgcctcc tggtggccct    240
cgccctggac gtcgtgagag tggactgtgg ccaggctccc ctggaccctg tctacctgcc    300
ggcagccctg gagctcctag acgcccctga acacttccgt gtgcagcagg tgggccacta    360
cccacctgcc aactcctctc tgagctcccg atctgagacc tttctgctcc tacagccctg    420
gcccagggcc cagccacttc tccgggcctc ctacccacct tttgccactc agcaggtggt    480
ccccccctcga gtcactgagc cccaccaacg gccagtccca tgggacgtgc gggccgtttc    540
agtggaagcg gctgtgactc cagcagagcc ctacgcccgg gttctcttcc acctcaaagg    600
gcaggattgg ccaccagggt ctggcagcct gccctgtgcc cggctccatg ccacacaccc    660
tgcaggcact gctcaccaag cctgccgctt ccagccatcc ctgggcgcct gcgtggtgga    720
gctggagctt ccctcgcact ggttctcaca ggcctccacc acacgggccg agctggccta    780
cacgcttgag cctgcagctg agggccctgg gggctgtggc tccggcgagg agaacgaccc    840
tggggagcag gccctcccag tggggggtgt ggagctgcgc ccagcagacc ccccgcagta    900
ccaggaggta cctctggacg aggctgtgac tctgcgggtg cctgacatgc cagtgcggcc    960
cggccagctc tttagtgcta ccctcctgct tcagcacaac ttcacagcca gcctcctgac   1020
cctgcggatc aaggtgaaga aggggctgca tgtgacagcc gcccgcccag cccagcccac   1080
actctggact gccaagctag accgcttcaa gggctccagg caccacacca ccctcatcac   1140
ctgccaccgt gctgggctca cagagccaga ttccagtccc cttgaactgt ctgagttcct   1200
atgggtggac tttgtggtgg agaatagcac tggtgggggc gtagcggtca ctcgccccgt   1260
cacgtggcag ctggagtacc caggccaggc ccctgaagca gagaaggaca aaatggtgtg   1320
ggaaatcctg gtgtctgagc gggacatcag agcccttatc ccactggcca aggctgagga   1380
gctggtgaat acagcaccac tgactggagt gccccagcat gtccccgtgc gccttgtcac   1440
tgtggacggc ggggggggcct tggtggaggt gacagagcat gtcggctgcg agtctgccaa   1500
cacacaggtc ctgcaggtgt ctgaggcctg tgatgccgtg ttcgtggctg gcaaggagag   1560
ccggggcgcc cggggggtgc gagtggactt ctggtggcgc cggctccgcg cctcgctgcg   1620
gctgaccgtg tgggcccccc tgctaccgct gcgtatcgag ctcaccgaca ccaccctcga   1680
gcaggtccgc ggctggaggg tacctggccc tgctgaaggg cctgcggaac ccgctgcaga   1740
ggcgtcggat gaggccgagc ggcgcgcccg tggctgccac ctgcagtacc agcgggccgg   1800
tgtgcgcttc ctcgccccct tcgcggccca cccgctggac ggcggccgcc gcctcacgca   1860
cctgcttggc cccgactggc tgctagacgt gtcccacctc gtggcgccac acgcccgcgt   1920
gctggactcg cgtgtagcct ctctggaggg tggccgtgtc gtggtgggcc gggagcccgg   1980
tgtcacctcc attgaggtgc gttccccact gtctgactcc atcctggggg agcaggcgct   2040
ggctgtgacg gacgacaagg tctcagtgct ggagctgagg gtgcagccag tgatgggcat   2100
ctcgctgacc ttgagccggg gcactgccca ccccggggag gtcacagcta cgtgctgggc   2160
acagtcagcc cttcccgccc caaagcagga ggtggccctc tccctatggc tgtccttctc   2220
tgatcacact gtggccccag ctgagctcta cgaccgccgt gacctgggac tgtccgtctc   2280
agccgaggag cctggtgcca tcctgccagc tgaggagcag ggtgcccagc tcggggtggt   2340
ggtgagtggg gcaggcgccg aggggctgcc gctgcatgtg gctctgcacc cgcccgagcc   2400
ctgccgccgg ggccgccacc gtgtgcctct ggcctctggc accgcctggc tggggctgcc   2460
ccctgcctcc actccagccc ctgctctccc atccagccct gcttggagcc caccagccac   2520
agaagccacc atgggtggta aacggcaggt ggcaggcagt gtcgggggca acacaggtgt   2580
```

-continued

```
gaggggcaag tttgagcggg cagaggagga ggccaggaag gaggagacca aacccaggga   2640

ggaggaggag gaagaggagg aggagatggt ccctgcccct cagcatgtca ctgagctaga   2700

gctgggcatg tacgccctgc tgggagtctt ctgcgtggcc atcttcatct tcttggtcaa   2760

tggtgtggtc ttcgtcctgc gctatcagcg caaagaacct cccgacagtg ccactgaccc   2820

cacctccccc cagccccaca actgggtctg gctgggcact gaccaggagg aactgagccg   2880

ccagctggac cggcagtccc ctggcccgcc caagggggag gggagctgcc cctgtgagag   2940

tgggggagga ggggaggccc ctaccctggc ccctggccct cctgggggca ccaccagctc   3000

ctcaagcacc ctggcccgaa aggaggctgg ggggcggcgg aagcgagtag agtttgtgac   3060

atttgcgcca gcccctccag cccagtcacc tgaggagcct gtaggggccc ctgctgtgca   3120

gtccatcctt gtggcaggcg aggaggacat ccgctgggtg tgtgaggaca tggggctgaa   3180

ggaccctgag gagcttcgca actacatgga gaggatccgg ggcagctcct gaccctccac   3240

agccacctgg tcagccacca gctggggcaa cgagggtgga ggtcccactg agcctctcgc   3300

ctgcccccgc cactcgtctg gtgcttgttg atccaagtcc cctgcctggt cccccacaag   3360

gactcccatc caggcccccct ctgccctgcc ccttgtcatg gaccatggtc gtgaggaagg   3420

gctcatgccc cttatttatg ggaaccatct cattctaaca gaataaaccg agaaggaaac   3480

cagaaaaaaa aaaaaaaaaa aa                                            3502


<210> SEQ ID NO 25
<211> LENGTH: 1023
<212> TYPE: PRT
<213> ORGANISM: Homo sapiens

<400> SEQUENCE: 25

Met Cys Ala Arg Met Ala Gly Arg Thr Thr Ala Ala Pro Arg Gly Pro
                5                   10                  15

Tyr Gly Pro Trp Leu Cys Leu Leu Val Ala Leu Ala Leu Asp Val Val
            20                  25                  30

Arg Val Asp Cys Gly Gln Ala Pro Leu Asp Pro Val Tyr Leu Pro Ala
        35                  40                  45

Ala Leu Glu Leu Leu Asp Ala Pro Glu His Phe Arg Val Gln Gln Val
    50                  55                  60

Gly His Tyr Pro Pro Ala Asn Ser Ser Leu Ser Ser Arg Ser Glu Thr
65                  70                  75                  80

Phe Leu Leu Leu Gln Pro Trp Pro Arg Ala Gln Pro Leu Leu Arg Ala
                85                  90                  95

Ser Tyr Pro Pro Phe Ala Thr Gln Gln Val Val Pro Pro Arg Val Thr
            100                 105                 110

Glu Pro His Gln Arg Pro Val Pro Trp Asp Val Arg Ala Val Ser Val
        115                 120                 125

Glu Ala Ala Val Thr Pro Ala Glu Pro Tyr Ala Arg Val Leu Phe His
    130                 135                 140

Leu Lys Gly Gln Asp Trp Pro Pro Gly Ser Gly Ser Leu Pro Cys Ala
145                 150                 155                 160

Arg Leu His Ala Thr His Pro Ala Gly Thr Ala His Gln Ala Cys Arg
                165                 170                 175

Phe Gln Pro Ser Leu Gly Ala Cys Val Val Glu Leu Glu Leu Pro Ser
            180                 185                 190

His Trp Phe Ser Gln Ala Ser Thr Thr Arg Ala Glu Leu Ala Tyr Thr
        195                 200                 205
```

-continued

```
Leu Glu Pro Ala Ala Glu Gly Pro Gly Gly Cys Gly Ser Gly Glu Glu
    210                 215                 220

Asn Asp Pro Gly Glu Gln Ala Leu Pro Val Gly Gly Val Glu Leu Arg
225                 230                 235                 240

Pro Ala Asp Pro Pro Gln Tyr Gln Glu Val Pro Leu Asp Glu Ala Val
                245                 250                 255

Thr Leu Arg Val Pro Asp Met Pro Val Arg Pro Gly Gln Leu Phe Ser
            260                 265                 270

Ala Thr Leu Leu Leu Arg His Asn Phe Thr Ala Ser Leu Leu Thr Leu
        275                 280                 285

Arg Ile Lys Val Lys Lys Gly Leu His Val Thr Ala Ala Arg Pro Ala
    290                 295                 300

Gln Pro Thr Leu Trp Thr Ala Lys Leu Asp Arg Phe Lys Gly Ser Arg
305                 310                 315                 320

His His Thr Thr Leu Ile Thr Cys His Arg Ala Gly Leu Thr Glu Pro
                325                 330                 335

Asp Ser Ser Pro Leu Glu Leu Ser Glu Phe Leu Trp Val Asp Phe Val
            340                 345                 350

Val Glu Asn Ser Thr Gly Gly Gly Val Ala Val Thr Arg Pro Val Thr
        355                 360                 365

Trp Gln Leu Glu Tyr Pro Gly Gln Ala Pro Glu Ala Glu Lys Asp Lys
    370                 375                 380

Met Val Trp Glu Ile Leu Val Ser Glu Arg Asp Ile Arg Ala Leu Ile
385                 390                 395                 400

Pro Leu Ala Lys Ala Glu Glu Leu Val Asn Thr Ala Pro Leu Thr Gly
                405                 410                 415

Val Pro Gln His Val Pro Val Arg Leu Val Thr Val Asp Gly Gly Gly
            420                 425                 430

Ala Leu Val Glu Val Thr Glu His Val Gly Cys Glu Ser Ala Asn Thr
        435                 440                 445

Gln Val Leu Gln Val Ser Glu Ala Cys Asp Ala Val Phe Val Ala Gly
    450                 455                 460

Lys Glu Ser Arg Gly Ala Arg Gly Val Arg Val Asp Phe Trp Trp Arg
465                 470                 475                 480

Arg Leu Arg Ala Ser Leu Arg Leu Thr Met Trp Ala Pro Leu Leu Pro
                485                 490                 495

Leu Arg Ile Glu Leu Thr Asp Thr Thr Leu Glu Gln Val Arg Gly Trp
            500                 505                 510

Arg Val Pro Gly Pro Ala Glu Gly Pro Ala Glu Pro Ala Ala Glu Ala
        515                 520                 525

Ser Asp Glu Ala Glu Arg Arg Ala Arg Gly Cys His Leu Gln Tyr Gln
    530                 535                 540

Arg Ala Gly Val Arg Phe Leu Ala Pro Phe Ala Ala His Pro Leu Asp
545                 550                 555                 560

Gly Gly Arg Arg Leu Thr His Leu Leu Gly Pro Asp Trp Leu Leu Asp
                565                 570                 575

Val Ser His Leu Val Ala Pro His Ala Arg Val Leu Asp Ser Arg Val
            580                 585                 590

Ala Ser Leu Glu Gly Gly Arg Val Val Val Gly Arg Glu Pro Gly Val
        595                 600                 605

Thr Ser Ile Glu Val Arg Ser Pro Leu Ser Asp Ser Ile Leu Gly Glu
    610                 615                 620
```

-continued

Gln Ala Leu Ala Val Thr Asp Asp Lys Val Ser Val Leu Glu Leu Arg
625 630 635 640

Val Gln Pro Val Met Gly Ile Ser Leu Thr Leu Ser Arg Gly Thr Ala
645 650 655

His Pro Gly Glu Val Thr Ala Thr Cys Trp Ala Gln Ser Ala Leu Pro
660 665 670

Ala Pro Lys Gln Glu Val Ala Leu Ser Leu Trp Leu Ser Phe Ser Asp
675 680 685

His Thr Val Ala Pro Ala Glu Leu Tyr Asp Arg Arg Asp Leu Gly Leu
690 695 700

Ser Val Ser Ala Glu Glu Pro Gly Ala Ile Leu Pro Ala Glu Glu Gln
705 710 715 720

Gly Ala Gln Leu Gly Val Val Val Ser Gly Ala Gly Ala Glu Gly Leu
725 730 735

Pro Leu His Val Ala Leu His Pro Pro Glu Pro Cys Arg Arg Gly Arg
740 745 750

His Arg Val Pro Leu Ala Ser Gly Thr Ala Trp Leu Gly Leu Pro Pro
755 760 765

Ala Ser Thr Pro Ala Pro Ala Leu Pro Ser Ser Pro Ala Trp Ser Pro
770 775 780

Pro Ala Thr Glu Ala Thr Met Gly Gly Lys Arg Gln Val Ala Gly Ser
785 790 795 800

Val Gly Gly Asn Thr Gly Val Arg Gly Lys Phe Glu Arg Ala Glu Glu
805 810 815

Glu Ala Arg Lys Glu Glu Thr Lys Pro Arg Glu Glu Glu Glu Glu Glu
820 825 830

Glu Glu Glu Met Val Pro Ala Pro Gln His Val Thr Glu Leu Glu Leu
835 840 845

Gly Met Tyr Ala Leu Leu Gly Val Phe Cys Val Ala Ile Phe Ile Phe
850 855 860

Leu Val Asn Gly Val Val Phe Val Leu Arg Tyr Gln Arg Lys Glu Pro
865 870 875 880

Pro Asp Ser Ala Thr Asp Pro Thr Ser Pro Gln Pro His Asn Trp Val
885 890 895

Trp Leu Gly Thr Asp Gln Glu Glu Leu Ser Arg Gln Leu Asp Arg Gln
900 905 910

Ser Pro Gly Pro Pro Lys Gly Glu Gly Ser Cys Pro Cys Glu Ser Gly
915 920 925

Gly Gly Gly Glu Ala Pro Thr Leu Ala Pro Gly Pro Pro Gly Gly Thr
930 935 940

Thr Ser Ser Ser Ser Thr Leu Ala Arg Lys Glu Ala Gly Gly Arg Arg
945 950 955 960

Lys Arg Val Glu Phe Val Thr Phe Ala Pro Ala Pro Pro Ala Gln Ser
965 970 975

Pro Glu Glu Pro Val Gly Ala Pro Ala Val Gln Ser Ile Leu Val Ala
980 985 990

Gly Glu Glu Asp Ile Arg Trp Val Cys Glu Asp Met Gly Leu Lys Asp
995 1000 1005

Pro Glu Glu Leu Arg Asn Tyr Met Glu Arg Ile Arg Gly Ser Ser
1010 1015 1020

-continued

<210> SEQ ID NO 26
<211> LENGTH: 3069
<212> TYPE: DNA
<213> ORGANISM: Homo sapiens

<400> SEQUENCE: 26
atgtgcgcgc ggatggccgg tcgcacaaca gcggcccctc gggggcccta cggcccctgg 60
ctctgcctcc tggtggccct cgccctggac gtcgtgagag tggactgtgg ccaggctccc 120
ctggaccctg tctacctgcc ggcagccctg gagctcctag acgcccctga acacttccgt 180
gtgcagcagg tgggccacta cccacctgcc aactcctctc tgagctcccg atctgagacc 240
tttctgctcc tacagccctg gcccagggcc cagccacttc tccgggcctc ctacccacct 300
tttgccactc agcaggtggt ccccccctcga gtcactgagc cccaccaacg gccagtccca 360
tgggacgtgc gggccgtttc agtggaagcg gctgtgactc cagcagagcc ctacgcccgg 420
gttctcttcc acctcaaagg gcaggattgg ccaccagggt ctggcagcct gccctgtgcc 480
cggctccatg ccacacaccc tgccggcact gctcaccaag cctgccgctt ccagccatcc 540
ctgggcgcct gcgtggtgga gctggagctt ccctcgcact ggttctcaca ggcctccacc 600
acacgggccg agctggccta cacgcttgag cctgcagctg agggccctgg gggctgtggc 660
tccggcgagg agaacgaccc tggggagcag gccctcccag tgggggggtgt ggagctgcgc 720 ccagcagacc ccccgcagta ccaggaggta cctctggacg aggctgtgac tctgcgggtg 780
cctgacatgc cagtgcggcc cggccagctc tttagtgcta ccctcctgct tcggcacaac 840
ttcacagcca gcctcctgac cctgcggatc aaggtgaaga aggggctgca tgtgacagcc 900
gcccgcccag cccagcccac actctggact gccaagctgg accgcttcaa gggctccagg 960
caccacacca ccctcatcac ctgccaccgt gctgggctca cagagccaga ttccagtccc 1020
cttgaactgt ctgagttcct atgggtggac tttgtggtgg agaatagcac tggtgggggc 1080
gtagcggtca ctcgccccgt cacgtggcag ctggagtacc caggccaggc ccctgaagca 1140
gagaaggaca aaatggtgtg ggaaatcctg gtgtctgagc gggacatcag agcccttatc 1200
ccactggcca aggctgagga gctggtgaat acagcaccac tgactggagt gccccagcat 1260
gtccccgtgc gccttgtcac tgtggacggc gggggggcct tggtggaggt gacagagcat 1320
gtcggctgcg agtctgccaa cacacaggtc ctgcaggtgt ctgaggcctg tgatgccgtg 1380
ttcgtggctg gcaaggagag ccggggcgcc cggggggtgc gagtggactt ctggtggcgc 1440
cggctccgcg cctcgctgcg gctgaccatg tgggcccccc tgctaccgct gcgtatcgag 1500
ctcaccgaca ccaccctcga gcaggtccgc ggctggaggg tacctggccc tgctgaaggg 1560
cctgcggaac ccgctgcaga ggcgtcggat gaggccgagc ggcgcgcccg tggctgccac 1620
ctgcagtacc agcgggccgg tgtgcgcttc ctcgccccct tcgcggccca cccgctggac 1680
ggcggccgcc gcctcacgca cctgcttggc cccgactggc tgctagacgt gtcccacctc 1740
gtggcgccac acgcccgcgt gctggactcg cgtgtagcct ctctggaggg tggccgtgtc 1800
gtggtgggcc gggagcccgg tgtcacctcc attgaggtgc gttccccact gtctgactcc 1860
atcctggggg agcaggcgct ggctgtgacg gacgacaagg tctcagtgct ggagctgagg 1920
gtgcagccag tgatgggcat ctcgctgacc ttgagccggg gcactgccca ccccggggag 1980
gtcacagcta cgtgctgggc acagtcagcc cttcccgccc caaagcagga ggtggccctc 2040
tccctatggc tgtccttctc tgatcacact gtggccccag ctgagctcta cgaccgccgt 2100
gacctgggac tgtccgtctc agccgaggag cctggtgcca tcctgccagc tgaggagcag 2160

-continued

```
ggtgcccagc tcggggtggt ggtgagtggg gcaggcgccg aggggctgcc gctgcatgtg   2220

gctctgcacc cgcccgagcc ctgccgccgg ggccgccacc gtgtgcctct ggcctctggc   2280

accgcctggc tggggctgcc ccctgcctcc actccagccc ctgctctccc atccagccct   2340

gcttggagcc caccagccac agaagccacc atgggtggta aacggcaggt ggcaggcagt   2400

gtcgggggca acacaggtgt gaggggcaag tttgagcggg cagaggagga ggccaggaag   2460

gaggagacca aacccaggga ggaggaggag gaagaggagg aggagatggt ccctgcccct   2520

cagcatgtca ctgagctaga gctgggcatg tacgccctgc tgggagtctt ctgcgtggcc   2580

atcttcatct tcttggtcaa tggtgtggtc ttcgtcctgc gctatcagcg caaagaacct   2640

cccgacagtg ccactgaccc cacctccccc cagccccaca actgggtctg gctgggcact   2700

gaccaggagg aactgagccg ccagctggac cggcagtccc ctggcccgcc caagggggag   2760

gggagctgcc cctgtgagag tgggggagga ggggaggccc ctaccctggc ccctggccct   2820

cctgggggca ccaccagctc ctcaagcacc ctggcccgaa aggaggctgg ggggcggcgg   2880

aagcgagtag agtttgtgac atttgcgcca gcccctccag cccagtcacc tgaggagcct   2940

gtaggggccc ctgctgtgca gtccatcctt gtggcaggcg aggaggacat ccgctgggtg   3000

tgtgaggaca tggggctgaa ggaccctgag gagcttcgca actacatgga gaggatccgg   3060

ggcagctcc                                                           3069
```

<210> SEQ ID NO 27
<211> LENGTH: 1019
<212> TYPE: PRT
<213> ORGANISM: Homo sapiens

<400> SEQUENCE: 27

```
Met Ala Gly Arg Thr Thr Ala Ala Pro Arg Gly Pro Tyr Gly Pro Trp
                5                   10                  15

Leu Cys Leu Leu Val Ala Leu Ala Leu Asp Val Val Arg Val Asp Cys
            20                  25                  30

Gly Gln Ala Pro Leu Asp Pro Val Tyr Leu Pro Ala Ala Leu Glu Leu
        35                  40                  45

Leu Asp Ala Pro Glu His Phe Arg Val Gln Gln Val Gly His Tyr Pro
    50                  55                  60

Pro Ala Asn Ser Ser Leu Ser Ser Arg Ser Glu Thr Phe Leu Leu Leu
65                  70                  75                  80

Gln Pro Trp Pro Arg Ala Gln Pro Leu Leu Arg Ala Ser Tyr Pro Pro
                85                  90                  95

Phe Ala Thr Gln Gln Val Val Pro Pro Arg Val Thr Glu Pro His Gln
            100                 105                 110

Arg Pro Val Pro Trp Asp Val Arg Ala Val Ser Val Glu Ala Ala Val
        115                 120                 125

Thr Pro Ala Glu Pro Tyr Ala Arg Val Leu Phe His Leu Lys Gly Gln
    130                 135                 140

Asp Trp Pro Pro Gly Ser Gly Ser Leu Pro Cys Ala Arg Leu His Ala
145                 150                 155                 160

Thr His Pro Ala Gly Thr Ala His Gln Ala Cys Arg Phe Gln Pro Ser
                165                 170                 175

Leu Gly Ala Cys Val Val Glu Leu Glu Leu Pro Ser His Trp Phe Ser
            180                 185                 190

Gln Ala Ser Thr Thr Arg Ala Glu Leu Ala Tyr Thr Leu Glu Pro Ala
        195                 200                 205
```

-continued

```
Ala Glu Gly Pro Gly Gly Cys Gly Ser Gly Glu Glu Asn Asp Pro Gly
    210                 215                 220

Glu Gln Ala Leu Pro Val Gly Gly Val Glu Leu Arg Pro Ala Asp Pro
225                 230                 235                 240

Pro Gln Tyr Gln Glu Val Pro Leu Asp Glu Ala Val Thr Leu Arg Val
                245                 250                 255

Pro Asp Met Pro Val Arg Pro Gly Gln Leu Phe Ser Ala Thr Leu Leu
            260                 265                 270

Leu Arg His Asn Phe Thr Ala Ser Leu Leu Thr Leu Arg Ile Lys Val
        275                 280                 285

Lys Lys Gly Leu His Val Thr Ala Ala Arg Pro Ala Gln Pro Thr Leu
    290                 295                 300

Trp Thr Ala Lys Leu Asp Arg Phe Lys Gly Ser Arg His His Thr Thr
305                 310                 315                 320

Leu Ile Thr Cys His Arg Ala Gly Leu Thr Glu Pro Asp Ser Ser Pro
                325                 330                 335

Leu Glu Leu Ser Glu Phe Leu Trp Val Asp Phe Val Val Glu Asn Ser
            340                 345                 350

Thr Gly Gly Gly Val Ala Val Thr Arg Pro Val Thr Trp Gln Leu Glu
        355                 360                 365

Tyr Pro Gly Gln Ala Pro Glu Ala Glu Lys Asp Lys Met Val Trp Glu
    370                 375                 380

Ile Leu Val Ser Glu Arg Asp Ile Arg Ala Leu Ile Pro Leu Ala Lys
385                 390                 395                 400

Ala Glu Glu Leu Val Asn Thr Ala Pro Leu Thr Gly Val Pro Gln His
                405                 410                 415

Val Pro Val Arg Leu Val Thr Val Asp Gly Gly Gly Ala Leu Val Glu
            420                 425                 430

Val Thr Glu His Val Gly Cys Glu Ser Ala Asn Thr Gln Val Leu Gln
        435                 440                 445

Val Ser Glu Ala Cys Asp Ala Val Phe Val Ala Gly Lys Glu Ser Arg
    450                 455                 460

Gly Ala Arg Gly Val Arg Val Asp Phe Trp Trp Arg Arg Leu Arg Ala
465                 470                 475                 480

Ser Leu Arg Leu Thr Met Trp Ala Pro Leu Leu Pro Leu Arg Ile Glu
                485                 490                 495

Leu Thr Asp Thr Thr Leu Glu Gln Val Arg Gly Trp Arg Val Pro Gly
            500                 505                 510

Pro Ala Glu Gly Pro Ala Glu Pro Ala Ala Glu Ala Ser Asp Glu Ala
        515                 520                 525

Glu Arg Arg Ala Arg Gly Cys His Leu Gln Tyr Gln Arg Ala Gly Val
    530                 535                 540

Arg Phe Leu Ala Pro Phe Ala Ala His Pro Leu Asp Gly Gly Arg Arg
545                 550                 555                 560

Leu Thr His Leu Leu Gly Pro Asp Trp Leu Leu Asp Val Ser His Leu
                565                 570                 575

Val Ala Pro His Ala Arg Val Leu Asp Ser Arg Val Ala Ser Leu Glu
            580                 585                 590

Gly Gly Arg Val Val Val Gly Arg Glu Pro Gly Val Thr Ser Ile Glu
        595                 600                 605

Val Arg Ser Pro Leu Ser Asp Ser Ile Leu Gly Glu Gln Ala Leu Ala
    610                 615                 620
```

-continued

```
Val Thr Asp Asp Lys Val Ser Val Leu Glu Leu Arg Val Gln Pro Val
625                 630                 635                 640

Met Gly Ile Ser Leu Thr Leu Ser Arg Gly Thr Ala His Pro Gly Glu
                645                 650                 655

Val Thr Ala Thr Cys Trp Ala Gln Ser Ala Leu Pro Ala Pro Lys Gln
            660                 665                 670

Glu Val Ala Leu Ser Leu Trp Leu Ser Phe Ser Asp His Thr Val Ala
        675                 680                 685

Pro Ala Glu Leu Tyr Asp Arg Arg Asp Leu Gly Leu Ser Val Ser Ala
    690                 695                 700

Glu Glu Pro Gly Ala Ile Leu Pro Ala Glu Glu Gln Gly Ala Gln Leu
705                 710                 715                 720

Gly Val Val Val Ser Gly Ala Gly Ala Glu Gly Leu Pro Leu His Val
                725                 730                 735

Ala Leu His Pro Pro Glu Pro Cys Arg Arg Gly Arg His Arg Val Pro
            740                 745                 750

Leu Ala Ser Gly Thr Ala Trp Leu Gly Leu Pro Pro Ala Ser Thr Pro
        755                 760                 765

Ala Pro Ala Leu Pro Ser Ser Pro Ala Trp Ser Pro Pro Ala Thr Glu
    770                 775                 780

Ala Thr Met Gly Gly Lys Arg Gln Val Ala Gly Ser Val Gly Gly Asn
785                 790                 795                 800

Thr Gly Val Arg Gly Lys Phe Glu Arg Ala Glu Glu Glu Ala Arg Lys
                805                 810                 815

Glu Glu Thr Lys Pro Arg Glu Glu Glu Glu Glu Glu Glu Glu Glu Met
            820                 825                 830

Val Pro Ala Pro Gln His Val Thr Glu Leu Glu Leu Gly Met Tyr Ala
        835                 840                 845

Leu Leu Gly Val Phe Cys Val Ala Ile Phe Ile Phe Leu Val Asn Gly
    850                 855                 860

Val Val Phe Val Leu Arg Tyr Gln Arg Lys Glu Pro Pro Asp Ser Ala
865                 870                 875                 880

Thr Asp Pro Thr Ser Pro Gln Pro His Asn Trp Val Trp Leu Gly Thr
                885                 890                 895

Asp Gln Glu Glu Leu Ser Arg Gln Leu Asp Arg Gln Ser Pro Gly Pro
            900                 905                 910

Pro Lys Gly Glu Gly Ser Cys Pro Cys Glu Ser Gly Gly Gly Gly Glu
        915                 920                 925

Ala Pro Thr Leu Ala Pro Gly Pro Pro Gly Gly Thr Thr Ser Ser Ser
    930                 935                 940

Ser Thr Leu Ala Arg Lys Glu Ala Gly Gly Arg Arg Lys Arg Val Glu
945                 950                 955                 960

Phe Val Thr Phe Ala Pro Ala Pro Pro Ala Gln Ser Pro Glu Glu Pro
                965                 970                 975

Val Gly Ala Pro Ala Val Gln Ser Ile Leu Val Ala Gly Glu Glu Asp
            980                 985                 990

Ile Arg Trp Val Cys Glu Asp Met Gly Leu Lys Asp Pro Glu Glu Leu
        995                 1000                1005

Arg Asn Tyr Met Glu Arg Ile Arg Gly Ser Ser
    1010                1015
```

-continued

<210> SEQ ID NO 28
<211> LENGTH: 3057
<212> TYPE: DNA
<213> ORGANISM: Homo sapiens

<400> SEQUENCE: 28
atggccggtc gcacaacagc ggcccctcgg gggccctacg gcccctggct ctgcctcctg 60
gtggccctcg ccctggacgt cgtgagagtg gactgtggcc aggctcccct ggaccctgtc 120
tacctgccgg cagccctgga gctcctagac gcccctgaac acttccgtgt gcagcaggtg 180
ggccactacc cacctgccaa ctcctctctg agctcccgat ctgagacctt tctgctccta 240
cagccctggc ccagggccca gccacttctc cgggcctcct acccaccttt tgccactcag 300
caggtggtcc cccctcgagt cactgagccc caccaacggc cagtcccatg ggacgtgcgg 360
gccgtttcag tggaagcggc tgtgactcca gcagagccct acgcccgggt tctcttccac 420
ctcaaagggc aggattggcc accagggtct ggcagcctgc cctgtgcccg gctccatgcc 480
acacaccctg ccggcactgc tcaccaagcc tgccgcttcc agccatccct gggcgcctgc 540
gtggtggagc tggagcttcc ctcgcactgg ttctcacagg cctccaccac acgggccgag 600
ctggcctaca cgcttgagcc tgcagctgag ggccctgggg gctgtggctc cggcgaggag 660
aacgaccctg gggagcaggc cctcccagtg gggggtgtgg agctgcgccc agcagacccc 720
ccgcagtacc aggaggtacc tctggacgag gctgtgactc tgcgggtgcc tgacatgcca 780
gtgcggcccg gccagctctt tagtgctacc ctcctgcttc ggcacaactt cacagccagc 840
ctcctgaccc tgcggatcaa ggtgaagaag gggctgcatg tgacagccgc ccgcccagcc 900
cagcccacac tctggactgc caagctggac cgcttcaagg gctccaggca ccacaccacc 960
ctcatcacct gccaccgtgc tgggctcaca gagccagatt ccagtcccct tgaactgtct 1020
gagttcctat gggtggactt tgtggtggag aatagcactg gtgggggcgt agcggtcact 1080
cgccccgtca cgtggcagct ggagtaccca ggccaggccc ctgaagcaga gaaggacaaa 1140
atggtgtggg aaatcctggt gtctgagcgg gacatcagag ccccttatccc actggccaag 1200 gctgaggagc tggtgaatac agcaccactg actggagtgc cccagcatgt ccccgtgcgc 1260
cttgtcactg tggacggcgg gggggccttg gtggaggtga cagagcatgt cggctgcgag 1320
tctgccaaca cacaggtcct gcaggtgtct gaggcctgtg atgccgtgtt cgtggctggc 1380
aaggagagcc ggggcgcccg gggggtgcga gtggacttct ggtggcgccg gctccgcgcc 1440
tcgctgcggc tgaccatgtg ggccccccctg ctaccgctgc gtatcgagct caccgacacc 1500
accctcgagc aggtccgcgg ctggagggta cctggccctg ctgaagggcc tgcggaaccc 1560
gctgcagagg cgtcggatga ggccgagcgg cgcgcccgtg gctgccacct gcagtaccag 1620
cgggccggtg tgcgcttcct cgccccccttc gcggcccacc cgctggacgg cggccgccgc 1680
ctcacgcacc tgcttggccc cgactggctg ctagacgtgt cccacctcgt ggcgccacac 1740
gcccgcgtgc tggactcgcg tgtagcctct ctggagggtg gccgtgtcgt ggtgggccgg 1800
gagcccggtg tcacctccat tgaggtgcgt tccccactgt ctgactccat cctgggggag 1860
caggcgctgg ctgtgacgga cgacaaggtc tcagtgctgg agctgagggt gcagccagtg 1920
atgggcatct cgctgacctt gagccggggc actgcccacc ccggggaggt cacagctacg 1980
tgctgggcac agtcagccct tcccgcccca aagcaggagg tggccctctc cctatggctg 2040
tccttctctg atcacactgt ggccccagct gagctctacg accgccgtga cctgggactg 2100
tccgtctcag ccgaggagcc tggtgccatc ctgccagctg aggagcaggg tgcccagctc 2160

-continued

```
ggggtggtgg tgagtggggc aggcgccgag gggctgccgc tgcatgtggc tctgcacccg   2220

cccgagccct gccgccgggg ccgccaccgt gtgcctctgg cctctggcac cgcctggctg   2280

gggctgcccc ctgcctccac tccagcccct gctctcccat ccagccctgc ttggagccca   2340

ccagccacag aagccaccat gggtggtaaa cggcaggtgg caggcagtgt cgggggcaac   2400

acaggtgtga ggggcaagtt tgagcgggca gaggaggagg ccaggaagga ggagaccaaa   2460

cccagggagg aggaggagga agaggaggag gagatggtcc ctgcccctca gcatgtcact   2520

gagctagagc tgggcatgta cgccctgctg ggagtcttct gcgtggccat cttcatcttc   2580

ttggtcaatg gtgtggtctt cgtcctgcgc tatcagcgca aagaacctcc cgacagtgcc   2640

actgacccca cctcccccca gccccacaac tgggtctggc tgggcactga ccaggaggaa   2700

ctgagccgcc agctggaccg gcagtcccct ggcccgccca agggggaggg gagctgcccc   2760

tgtgagagtg ggggaggagg ggaggcccct accctggccc ctggccctcc tgggggcacc   2820

accagctcct caagcaccct ggcccgaaag gaggctgggg ggcggcggaa gcgagtagag   2880

tttgtgacat ttgcgccagc ccctccagcc cagtcacctg aggagcctgt aggggcccct   2940

gctgtgcagt ccatccttgt ggcaggcgag gaggacatcc gctgggtgtg tgaggacatg   3000

gggctgaagg accctgagga gcttcgcaac tacatggaga ggatccgggg cagctcc      3057
```

<210> SEQ ID NO 29
<211> LENGTH: 3502
<212> TYPE: DNA
<213> ORGANISM: Homo sapiens

<400> SEQUENCE: 29

```
attgtctggg aattgcagcc gcggggcggg cggcggcggc ggcggcggcg gccgggaccc     60

agcgggccag gtggggacgg cgcggagcgg gtgcgggaga tgccgtgcgg gactggggcc    120

acctgagccg cccgcctcgt ccccgccttc tgtgggaagg atgtgcgcgc ggatggccgg    180

tcgcacaaca gcggcccctc gggggcccta cggcccctgg ctctgcctcc tggtggccct    240

cgccctggac gtcgtgagag tggactgtgg ccaggctccc ctggaccctg tctacctgcc    300

ggcagccctg gagctcctag acgcccctga acacttccgt gtgcagcagg tgggccacta    360

cccacctgcc aactcctctc tgagctcccg atctgagacc tttctgctcc tacagccctg    420

gcccagggcc cagccacttc tccgggcctc ctacccacct tttgccactc agcaggtggt    480

ccccccctcga gtcactgagc cccaccaacg gccagtccca tgggacgtgc gggccgtttc    540

agtggaagcg gctgtgactc cagcagagcc ctacgcccgg gttctcttcc acctcaaagg    600

gcaggattgg ccaccagggt ctggcagcct gccctgtgcc cggctccatg ccacacaccc    660

tgccggcact gctcaccaag cctgccgctt ccagccatcc ctgggcgcct gcgtggtgga    720

gctggagctt ccctcgcact ggttctcaca ggcctccacc acacgggccg agctggccta    780

cacgcttgag cctgcagctg agggccctgg gggctgtggc tccggcgagg agaacgaccc    840

tggggagcag gccctcccag tggggggtgt ggagctgcgc ccagcagacc ccccgcagta    900

ccaggaggta cctctggacg aggctgtgac tctgcgggtg cctgacatgc cagtgcggcc    960

cggccagctc tttagtgcta ccctcctgct tcggcacaac ttcacagcca gcctcctgac   1020

cctgcggatc aaggtgaaga aggggctgca tgtgacagcc gcccgcccag cccagcccac   1080

actctggact gccaagctgg accgcttcaa gggctccagg caccacacca ccctcatcac   1140

ctgccaccgt gctgggctca cagagccaga ttccagtccc cttgaactgt ctgagttcct   1200

atgggtggac tttgtggtgg agaatagcac tggtgggggc gtagcggtca ctcgccccgt   1260
```

-continued

```
cacgtggcag ctggagtacc caggccaggc ccctgaagca gagaaggaca aaatggtgtg   1320
ggaaatcctg gtgtctgagc gggacatcag agcccttatc ccactggcca aggctgagga   1380
gctggtgaat acagcaccac tgactggagt gccccagcat gtccccgtgc gccttgtcac   1440
tgtggacggc ggggggcct tggtggaggt gacagagcat gtcggctgcg agtctgccaa   1500
cacacaggtc ctgcaggtgt ctgaggcctg tgatgccgtg ttcgtggctg gcaaggagag   1560
ccggggcgcc cgggggtgc gagtggactt ctggtggcgc cggctccgcg cctcgctgcg   1620
gctgaccatg tgggccccc tgctaccgct gcgtatcgag ctcaccgaca ccaccctcga   1680
gcaggtccgc ggctggaggg tacctggccc tgctgaaggg cctgcggaac ccgctgcaga   1740
ggcgtcggat gaggccgagc ggcgcgcccg tggctgccac ctgcagtacc agcgggccgg   1800
tgtgcgcttc ctcgcccct tcgcggccca cccgctggac ggcggccgcc gcctcacgca   1860
cctgcttggc cccgactggc tgctagacgt gtcccacctc gtggcgccac acgcccgcgt   1920
gctggactcg cgtgtagcct ctctggaggg tggccgtgtc gtggtgggcc gggagcccgg   1980
tgtcacctcc attgaggtgc gttccccact gtctgactcc atcctggggg agcaggcgct   2040
ggctgtgacg gacgacaagg tctcagtgct ggagctgagg gtgcagccag tgatgggcat   2100
ctcgctgacc ttgagccggg gcactgccca ccccggggag gtcacagcta cgtgctgggc   2160
acagtcagcc cttcccgccc caaagcagga ggtggccctc tccctatggc tgtccttctc   2220
tgatcacact gtggccccag ctgagctcta cgaccgccgt gacctgggac tgtccgtctc   2280
agccgaggag cctggtgcca tcctgccagc tgaggagcag ggtgcccagc tcggggtggt   2340
ggtgagtggg gcaggcgccg aggggctgcc gctgcatgtg gctctgcacc cgcccgagcc   2400
ctgccgccgg ggccgccacc gtgtgcctct ggcctctggc accgcctggc tggggctgcc   2460
ccctgcctcc actccagccc ctgctctccc atccagccct gcttggagcc caccagccac   2520
agaagccacc atgggtggta aacggcaggt ggcaggcagt gtcgggggca acacaggtgt   2580
gaggggcaag tttgagcggg cagaggagga ggccaggaag gaggagacca aacccaggga   2640
ggaggaggag gaagaggagg aggagatggt ccctgcccct cagcatgtca ctgagctaga   2700
gctgggcatg tacgccctgc tgggagtctt ctgcgtggcc atcttcatct tcttggtcaa   2760
tggtgtggtc ttcgtcctgc gctatcagcg caaagaacct cccgacagtg ccactgaccc   2820
cacctccccc cagccccaca actgggtctg gctgggcact gaccaggagg aactgagccg   2880
ccagctggac cggcagtccc ctggcccgcc caagggggag gggagctgcc cctgtgagag   2940
tgggggagga ggggaggccc ctaccctggc ccctggccct cctgggggca ccaccagctc   3000
ctcaagcacc ctggcccgaa aggaggctgg ggggcggcgg aagcgagtag agtttgtgac   3060
atttgcgcca gcccctccag cccagtcacc tgaggagcct gtaggggccc ctgctgtgca   3120
gtccatcctt gtggcaggcg aggaggacat ccgctgggtg tgtgaggaca tggggctgaa   3180
ggaccctgag gagcttcgca actacatgga gaggatccgg ggcagctcct gaccctccac   3240
agccacctgg tcagccacca gctggggcaa cgagggtgga ggtcccactg agcctctcgc   3300
ctgcccccgc cactcgtctg gtgcttgttg atccaagtcc cctgcctggt cccccacaag   3360
gactcccatc caggcccccct ctgccctgcc ccttgtcatg gaccatggtc gtgaggaagg   3420
gctcatgccc cttatttatg ggaaccatct cattctaaca gaataaaccg agaaggaaac   3480
cagaaaaaaa aaaaaaaaaa aa                                            3502
```

-continued

<210> SEQ ID NO 30
<211> LENGTH: 20
<212> TYPE: DNA
<213> ORGANISM: Artificial Sequence
<220> FEATURE:
<223> OTHER INFORMATION: Primer

<400> SEQUENCE: 30
attgaggtgc gttccccact 20

<210> SEQ ID NO 31
<211> LENGTH: 22
<212> TYPE: DNA
<213> ORGANISM: Artificial Sequence
<220> FEATURE:
<223> OTHER INFORMATION: Primer

<400> SEQUENCE: 31
ccactcacca ccaccccgag ct 22

<210> SEQ ID NO 32
<211> LENGTH: 24
<212> TYPE: DNA
<213> ORGANISM: Artificial Sequence
<220> FEATURE:
<223> OTHER INFORMATION: Primer

<400> SEQUENCE: 32
tatgaattca tgtgcgcgcg gatg 24

<210> SEQ ID NO 33
<211> LENGTH: 29
<212> TYPE: DNA
<213> ORGANISM: Artificial Sequence
<220> FEATURE:
<223> OTHER INFORMATION: Primer

<400> SEQUENCE: 33
tattatctag aggagctgcc ccggatcct 29

<210> SEQ ID NO 34
<211> LENGTH: 20
<212> TYPE: DNA
<213> ORGANISM: Artificial Sequence
<220> FEATURE:
<223> OTHER INFORMATION: Primer

<400> SEQUENCE: 34
ccttctgtgg gaaggatgtg 20

<210> SEQ ID NO 35
<211> LENGTH: 22
<212> TYPE: DNA
<213> ORGANISM: Artificial Sequence
<220> FEATURE:
<223> OTHER INFORMATION: Primer

<400> SEQUENCE: 35
tggctgtgga gggtcaggag ct 22

<210> SEQ ID NO 36
<211> LENGTH: 17
<212> TYPE: DNA
<213> ORGANISM: Artificial Sequence
<220> FEATURE:
<223> OTHER INFORMATION: Primer -continued

<400> SEQUENCE: 36
tcggctgcga gtctgcc 17

<210> SEQ ID NO 37
<211> LENGTH: 18
<212> TYPE: DNA
<213> ORGANISM: Artificial Sequence
<220> FEATURE:
<223> OTHER INFORMATION: Primer

<400> SEQUENCE: 37
ctctccttgc cagccacg 18

<210> SEQ ID NO 38
<211> LENGTH: 23
<212> TYPE: DNA
<213> ORGANISM: Artificial Sequence
<220> FEATURE:
<223> OTHER INFORMATION: Primer

<400> SEQUENCE: 38
tgtctgaggc ctgtgatgcc gtg 23

<210> SEQ ID NO 39
<211> LENGTH: 24
<212> TYPE: DNA
<213> ORGANISM: Artificial Sequence
<220> FEATURE:
<223> OTHER INFORMATION: Primer

<400> SEQUENCE: 39
tatgaattca tgtgcgcgcg gatg 24

<210> SEQ ID NO 40
<211> LENGTH: 29
<212> TYPE: DNA
<213> ORGANISM: Artificial Sequence
<220> FEATURE:
<223> OTHER INFORMATION: Primer

<400> SEQUENCE: 40
tatttctaga tcaggagctg ccccggatc 29

<210> SEQ ID NO 41
<211> LENGTH: 15
<212> TYPE: PRT
<213> ORGANISM: Homo sapiens

<400> SEQUENCE: 41

Gly Ser Gly Glu Glu Asn Asp Pro Gly Glu Gln Ala Leu Pro Cys
5 10 15

<210> SEQ ID NO 42
<211> LENGTH: 15
<212> TYPE: PRT
<213> ORGANISM: Homo sapiens

<400> SEQUENCE: 42

Gly Pro Ala Glu Gly Pro Ala Glu Pro Ala Ala Glu Ala Ser Cys
5 10 15

<210> SEQ ID NO 43
<211> LENGTH: 15
<212> TYPE: PRT
<213> ORGANISM: Homo sapiens -continued

```
<400> SEQUENCE: 43

Gly Ser Val Gly Gly Asn Thr Gly Val Arg Gly Lys Phe Glu Cys
                5                   10                  15


<210> SEQ ID NO 44
<211> LENGTH: 20
<212> TYPE: DNA
<213> ORGANISM: Artificial Sequence
<220> FEATURE:
<223> OTHER INFORMATION: Sense oligonucleotide

<400> SEQUENCE: 44

cttggtcaat ggtgtggtct                                                20
```